US012585186B2

(12) United States Patent
Watanabe et al.

(10) Patent No.: US 12,585,186 B2
(45) Date of Patent: Mar. 24, 2026

(54) PHOTOACID GENERATOR, CHEMICALLY AMPLIFIED RESIST COMPOSITION, AND PATTERNING PROCESS

(71) Applicant: Shin-Etsu Chemical Co., Ltd., Tokyo (JP)

(72) Inventors: Tomomi Watanabe, Joetsu (JP); Takayuki Fujiwara, Joetsu (JP); Koji Hasegawa, Tokyo (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 568 days.

(21) Appl. No.: 17/965,388

(22) Filed: Oct. 13, 2022

(65) Prior Publication Data

US 2023/0123180 A1 Apr. 20, 2023

(30) Foreign Application Priority Data

Oct. 15, 2021 (JP) ................................ 2021-169695

(51) Int. Cl.

| | |
|---|---|
| ***G03F 7/038*** | (2006.01) |
| ***C07C 303/32*** | (2006.01) |
| ***C07C 381/12*** | (2006.01) |
| ***G03F 7/004*** | (2006.01) |
| ***G03F 7/039*** | (2006.01) |
| ***G03F 7/20*** | (2006.01) |

(Continued)

(52) U.S. Cl.

CPC .......... *G03F 7/0045* (2013.01); *C07C 303/32* (2013.01); *C07C 381/12* (2013.01); *G03F 7/0382* (2013.01); *G03F 7/0395* (2013.01); *G03F 7/0397* (2013.01); *G03F 7/2041* (2013.01); *G03F 7/30* (2013.01); *G03F 7/322* (2013.01); *G03F 7/325* (2013.01)

(58) Field of Classification Search

CPC .... G03F 7/0392; G03F 7/0397; G03F 7/0382; G03F 7/2041; G03F 7/30; C07C 303/32; C07C 381/12

See application file for complete search history.

(56) References Cited

U.S. PATENT DOCUMENTS

| | | |
|---|---|---|
| 6,037,098 A | 3/2000 | Aoai et al. |
| 9,366,958 B2 | 6/2016 | Ohashi et al. |

(Continued)

FOREIGN PATENT DOCUMENTS

| | | | |
|---|---|---|---|
| CN | 110058489 A * | 7/2019 | ............. G03F 7/004 |
| CN | 113801042 A * | 12/2021 | ........... C07C 309/12 |

(Continued)

OTHER PUBLICATIONS

Office Action dated Jan. 18, 2024, issued in counterpart KR Application No. 10-2022-0130838, with English translation. (17 pages).

*Primary Examiner* — John S. Chu
(74) *Attorney, Agent, or Firm* — WHDA, LLP

(57) ABSTRACT

An onium salt consisting of an anion containing an iodized aromatic group and two sulfonate groups and a sulfonium or iodonium cation is a useful photoacid generator. A chemically amplified resist composition comprising the photoacid generator forms a pattern of rectangular profile with a good balance of sensitivity, CDU, LWR, MEF, and DOF when it is processed by photolithography using high-energy radiation.

20 Claims, 10 Drawing Sheets

(51) Int. Cl.

| | |
|---|---|
| ***G03F 7/30*** | (2006.01) |
| ***G03F 7/32*** | (2006.01) |

(56) References Cited

U.S. PATENT DOCUMENTS

| | | | | |
|---|---|---|---|---|
| 2008/0044738 | A1* | 2/2008 | Harada | C07D 333/46 430/4 |
| 2009/0053652 | A1* | 2/2009 | Chakrapani | G03F 7/0397 430/311 |
| 2010/0062366 | A1* | 3/2010 | Nishi | G03F 7/0045 430/326 |
| 2013/0236833 | A1* | 9/2013 | Houlihan | G03F 7/0955 430/326 |
| 2023/0139891 | A1 | 5/2023 | Kojima et al. | |
| 2024/0351979 | A1* | 10/2024 | Fang | C07C 303/02 |

FOREIGN PATENT DOCUMENTS

| | | | | | |
|---|---|---|---|---|---|
| CN | 113820919 | A | * | 12/2021 | C07C 381/12 |
| JP | 3773139 | B2 | | 5/2006 | |
| JP | 2008-013551 | A | | 1/2008 | |
| JP | 2015-206932 | A | | 11/2015 | |
| JP | 2019-194178 | A | | 11/2019 | |
| KR | 20230009932 | A | | 1/2023 | |
| TW | 202142528 | A | * | 11/2021 | G03F 7/20 |
| WO | 2011/048919 | A1 | | 4/2011 | |

* cited by examiner

PHOTOACID GENERATOR, CHEMICALLY AMPLIFIED RESIST COMPOSITION, AND PATTERNING PROCESS

CROSS-REFERENCE TO RELATED APPLICATION

This non-provisional application claims priority under 35 U.S.C. § 119(a) on Patent Application No. 2021-169695 filed in Japan on Oct. 15, 2021, the entire contents of which are hereby incorporated by reference.

TECHNICAL FIELD

This invention relates to a photoacid generator, a chemically amplified resist composition, and a patterning process using the resist composition.

BACKGROUND ART

To meet the current demand for higher integration density and operating speed of LSIs, the effort to reduce the pattern rule is in rapid progress. In particular, logic devices are manufactured in a large scale using a multi-patterning lithography process involving a plurality of exposure steps by the ArF lithography. In order to form patterns of smaller feature size, studies are continued on resist compositions adapted for radiation of short wavelength such as EB or EUV. With the advance of pattern miniaturization, it is considered more important to improve lithographic performance factors such as pattern profile, contrast, LWR of line patterns, and CDU of hole patterns.

In resist compositions comprising a photoacid generator (PAG) adapted to generate an acid upon light exposure, the diffusion of the generated acid in a resist film has a substantial influence on the lithography performance toward degradation. It is an effective means for controlling acid diffusion to incorporate a bulky substituent group or polar group into a PAG or to increase the molecular weight of a PAG. Patent Documents 1 and 2 disclose PAGs having a bis-sulfonium cation. Patent Documents 3, 4 and 5 disclose PAGs in the form of a bis-sulfonium salt having a bis-sulfonate anion. Because of their low solvent solubility and low sensitivity, these bis-sulfonium salts are limited in addition amount and undesirably cause surface defects (to be described below).

In addition to the improvements in lithographic performance factors as mentioned above, it is also necessary to minimize defects in resist patterns. As used herein, the defects include scum, bubbles and dust left after development, and bridges between resist pattern features. Low solubility in the casting solvent and undissolved residues after development become causes for such defects.

In order to take advantage of the energy source of short wavelength and to improve lithographic performance, the key factor is to design a PAG of optimum structure so as to effectively control acid diffusion and increase solvent solubility.

CITATION LIST

Patent Document 1: JP 3773139

Patent Document 2: JP-A 2019-194178

Patent Document 3: JP-A 2008-013551

Patent Document 4: WO 2011/048919

Patent Document 5: JP-A 2015-206932 (U.S. Pat. No. 9,366,958)

SUMMARY OF INVENTION

While it is currently required to form a resist pattern with a high resolution, few prior art PAGs meet the requisite lithographic performance factors such as sensitivity, acid diffusion length, solvent solubility, and development contrast.

An object of the present invention is to provide a chemically amplified resist composition which forms a pattern of rectangular profile with a good balance of sensitivity, CDU, LWR, MEF, and DOF when it is processed by photolithography using high-energy radiation such as KrF excimer laser radiation, ArF excimer laser radiation, EB or EUV; a photoacid generator for use therein; and a pattern forming process using the resist composition.

The inventors have found that a chemically amplified resist composition comprising a photoacid generator in the form of an onium salt of specific structure has a good balance of lithographic performance factors including sensitivity, LWR, MEF, and CDU and is quite effective for precise micro-patterning.

In one aspect, the invention provides a photoacid generator in the form of an onium salt consisting of an anion containing an iodine-substituted aromatic group and two sulfonate groups and a sulfonium or iodonium cation.

In a preferred embodiment, the onium salt has the formula (1).

(1)

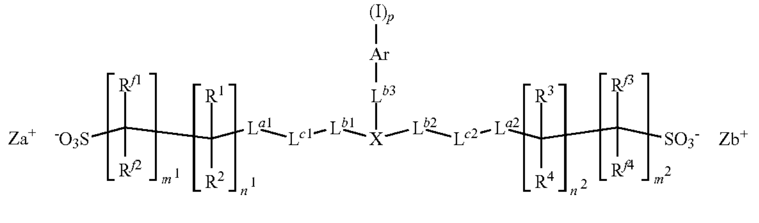

Herein X is a $C_1$-$C_{35}$ trivalent hydrocarbon group which may contain a heteroatom, $R^1$, $R^2$, $R^3$, and $R^4$ are each independently hydrogen or a $C_1$-$C_{10}$ hydrocarbyl group which may contain a heteroatom, $R^1$ and $R^2$ may bond together to form a ring with the carbon atom to which they are attached, $R^3$ and $R^4$ may bond together to form a ring with the carbon atom to which they are attached, $R^{f1}$, $R^{f2}$, $R^{f3}$, and $R^{f4}$ are each independently hydrogen, fluorine or trifluoromethyl, at least one of $R^{f1}$ and $R^{f2}$ is fluorine or trifluoromethyl, at least one of $R^{f3}$ and $R^{f4}$ is fluorine or trifluoromethyl, $m^1$ and $m^2$ are each independently an integer of 1 to 4, $n^1$ and $n^2$ are each independently an integer of 0 to 4, $L^{a1}$ and $L^{a2}$ are each independently an ether bond, ester bond, sulfonic ester bond or carbonate bond, $L^{c1}$ and $L^{c2}$ are each independently a single bond or a $C_1$-$C_{15}$ hydrocarbylene group in which some hydrogen may be substituted by a heteroatom-containing moiety and some constituent —$CH_2$— may be replaced by —O— or —C(=O)—, $L^{b1}$, $L^{b2}$ and $L^{b3}$ are each independently a single bond, ether bond, ester bond, sulfonic ester bond, carbonate bond or carbamate bond, Ar is a $C_3$-$C_{15}$ (p+1)-valent aromatic group in which some hydrogen may be substituted by fluorine, hydroxy or $C_1$-$C_{15}$ hydrocarbyl group, some hydrogen in the hydrocarbyl group may be substituted by a heteroatom-containing moiety and some constituent —$CH_2$— in the hydrocarbyl group may be replaced by —O—, —C(=O)— or —N($R^N$)—, $R^N$ is hydrogen or a $C_1$-$C_{10}$ hydrocarbyl group in which some hydrogen may be substituted by a heteroatom-containing moiety and some constituent —$CH_2$— may be replaced by —O—, —C(=O)— or —S(=O)$_2$—, p is an integer of 1 to 5, $Za^+$ and $Zb^+$ are each independently a sulfonium cation or iodonium cation.

In a more preferred embodiment, the onium salt has the formula (1a).

(1a)

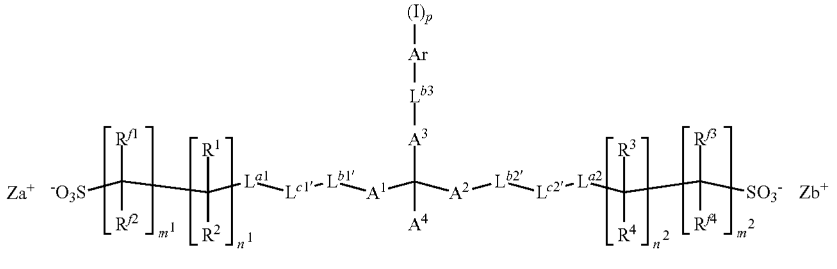

Herein $R^1$, $R^2$, $R^3$, $R^4$, $R^{f1}$, $R^{f2}$, $R^{f3}$, $R^{f4}$, $L^{a1}$, $L^{a2}$, $L^{b3}$, Ar, $m^1$, $m^2$, $n^1$, $n^2$, p, $Za^+$, and $Zb^+$ are as defined above, $A^1$, $A^2$, and $A^3$ are each independently a single bond or a $C_1$-$C_8$ hydrocarbylene group which may contain a heteroatom, in which some constituent —$CH_2$— may be replaced by —O— or —C(=O)—, $A^4$ is hydrogen, hydroxy, or a $C_1$-$C_{10}$ hydrocarbyl group which may contain a heteroatom, in which some constituent —$CH_2$— may be replaced by —O— or —C(=O)—, $L^{b1'}$ and $L^{b2'}$ are each independently an ether bond, ester bond, sulfonic ester bond, carbonate bond or carbamate bond, $L^{c1'}$ and $L^{c2'}$ are each independently a single bond or a $C_1$-$C_{10}$ hydrocarbylene group in which some hydrogen may be substituted by a heteroatom-containing moiety and some constituent —$CH_2$— may be replaced by —O— or —C(=O)—.

In a further preferred embodiment, the onium salt has the formula (1b).

(1b)

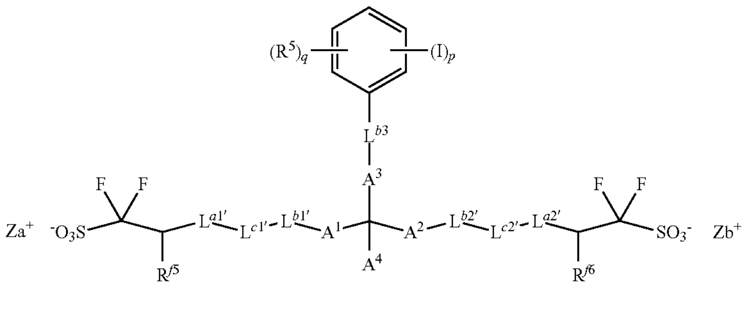

Herein $A^1$, $A^2$, $A^3$, $A^4$, $L^{b1'}$, $L^{b2'}$, $L^{b3'}$, $Za^+$, and $Zb^+$ are as defined above, p is an integer of 1 to 5, q is an integer of 0 to 4, the sum of p and q is from 1 to 5, $R^{f5}$ and $R^{f6}$ are each independently hydrogen or trifluoromethyl, $L^{a1'}$ and $L^{a2'}$ are each independently an ether bond or ester bond, $R^5$ is hydroxy, fluorine, or a $C_1$-$C_{15}$ hydrocarbyl group in which some hydrogen may be substituted by a heteroatom-containing moiety and some constituent —$CH_2$— may be replaced by —O—, —C(=O)— or —N($R^N$)—;

$R^N$ is hydrogen or a $C_1$-$C_{10}$ hydrocarbyl group in which some hydrogen may be substituted by a heteroatom-containing moiety and some constituent —$CH_2$— may be replaced by —O—, —C(=O)— or —S(=O)$_2$—, when q is 2 or more, a plurality of $R^5$ may be the same or different and two $R^5$ may bond together to form a ring with the carbon atoms on the benzene ring to which they are attached.

In a further preferred embodiment, the onium salt has the formula (1c).

(1c)

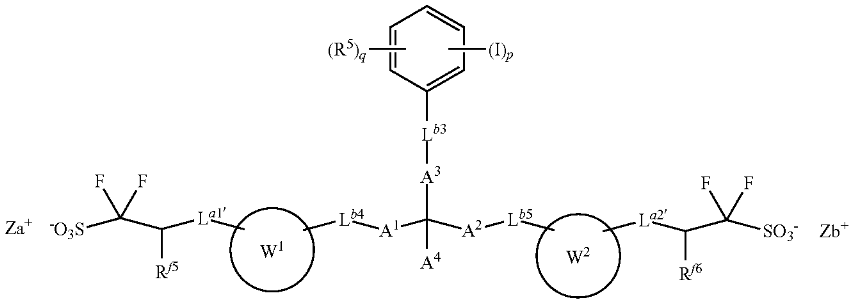

Herein $A^3$, $L^{a1'}$, $L^{a2'}$, $L^{b3}$, $R^5$, $R^{f5}$, $R^{f6}$, p, q, $Za^+$, and $Zb^+$ are as defined above, $L^{b4}$ and $L^{b5}$ are each independently an ether bond or ester bond, $A^5$ and $A^6$ are each independently a $C_1$-$C_4$ straight hydrocarbylene group, $A^7$ is hydrogen, hydroxy, or a $C_1$-$C_8$ alkyl group, the rings $W^1$ and $W^2$ are each independently a $C_3$-$C_{10}$ alicyclic hydrocarbon group which may contain a heteroatom.

Preferably, $Za^+$ and $Zb^+$ are each independently a cation having the formula (Z-1) or (Z-2).

(Z-1)

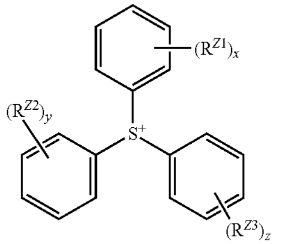

-continued (Z-2)

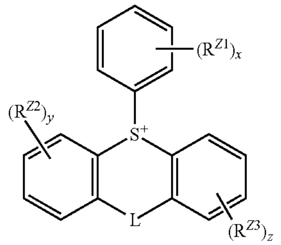

Herein $R^{Z1}$, $R^{Z2}$, and $R^{Z3}$ are each independently halogen, hydroxy or a $C_1$-$C_{15}$ hydrocarbyl group in which some hydrogen may be substituted by a heteroatom-containing moiety and some constituent —$CH_2$— may be replaced by —O—, —C(=O)—, —S—, —S(=O)—, —S(=O)$_2$—, or —N($R^N$)—;

L is a single bond, —$CH_2$—, —O—, —C(=O)—, —S—, —S(=O)—, —S(=O)$_2$—, or —N($R^N$)—;

$R^N$ is hydrogen or a $C_1$-$C_{10}$ hydrocarbyl group in which some hydrogen may be substituted by a heteroatom-containing moiety and some constituent —$CH_2$— may be replaced by —O—, —C(=O)— or —S(=O)$_2$—, x, y and z are each independently an integer of 0 to 5, when x is 2 or more, a plurality of $R^{Z1}$ may be the same or different and two $R^{Z1}$ may bond together to form a ring with the carbon atoms on the benzene ring to which they are attached, when y is 2 or more, a plurality of $R^{Z2}$ may be the same or different and two $R^{Z2}$ may bond together to form a ring with the carbon atoms on the benzene ring to which they are attached, when z is 2 or more, a plurality of $R^{Z3}$ may be the same or different and two $R^{Z3}$ may bond together to form a ring with the carbon atoms on the benzene ring to which they are attached.

More preferably, p is an integer of 1 to 3.

In another aspect, the invention provides a chemically amplified resist composition comprising (A) the photoacid generator defined above, (B) a base polymer adapted to change its solubility in a developer under the action of acid, and (C) an organic solvent.

In a preferred embodiment, the base polymer comprises repeat units having the formula (a) or repeat units having the formula (b).

(a)

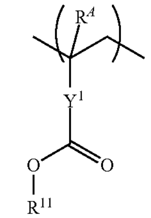

(b)

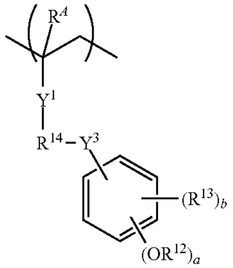

Herein $R^A$ is each independently hydrogen or methyl, $Y^1$ is a single bond, phenylene, naphthylene, or a $C_1$-$C_{12}$ linking group containing an ester bond and/or lactone ring, $Y^2$ is a single bond or ester bond, $Y^3$ is a single bond, ether bond or ester bond, $R^{11}$ and $R^{12}$ are each independently an acid labile group, $R^{13}$ is halogen, hydroxy, cyano, or a $C_1$-$C_6$ hydrocarbyl group in which some constituent —$CH_2$— may be replaced by —O— or —C(═O)—, $R^4$ is a single bond or a $C_1$-$C_6$ alkanediyl group in which some constituent —$CH_2$— may be replaced by an ether bond or ester bond, "a" is 1 or 2, "b" is an integer of 0 to 4, and the sum of a+b is from 1 to 5.

In a preferred embodiment, the base polymer further comprises repeat units of at least one type selected from repeat units having the formulae (g1) to (g3).

(g1)

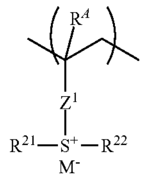

(g2)

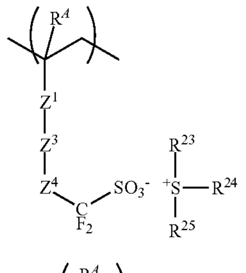

(g3)

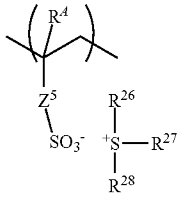

Herein $R^A$ is each independently hydrogen or methyl. $Z^1$ is a single bond, or a $C_1$-$C_6$ aliphatic hydrocarbylene group, phenylene group, naphthylene group, or a $C_7$-$C_{18}$ group obtained by combining the foregoing, or —O—$Z^{11}$—, —C(═O)—O—$Z^{11}$— or —C(═O)—NH—$Z^{11}$—, $Z^{11}$ is a $C_1$-$C_6$ aliphatic hydrocarbylene group, phenylene group, naphthylene group, or a $C_7$-$C_{18}$ group obtained by combining the foregoing, which may contain a carbonyl moiety, ester bond, ether bond or hydroxy moiety. $Z^2$ is a single bond or ester bond. $Z^3$ is a single bond, —$Z^{31}$—C(═O)—O—, —$Z^{31}$—O—, or —$Z^{31}$—O—C(═O)—, $Z^{31}$ is a $C_1$-$C_{12}$ aliphatic hydrocarbylene group, phenylene group or a $C_7$-$C_{18}$ group obtained by combining the foregoing, which may contain a carbonyl moiety, ester bond, ether bond, bromine or iodine. $Z^4$ is methylene, 2,2,2-trifluoro-1,1-ethanediyl or carbonyl. $Z^5$ is a single bond, methylene, ethylene, phenylene, fluorinated phenylene, trifluoromethyl-substituted phenylene group, —O—$Z^{51}$—, —C(═O)—O—$Z^{51}$— or —C(═O)—NH—$Z^{51}$—, $Z^{51}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond, halogen or hydroxy moiety. $R^{21}$ to $R^{28}$ are each independently halogen or a $C_1$-$C_{20}$ hydrocarbyl group which may contain a heteroatom, a pair of $R^{23}$ and $R^{24}$ or $R^{26}$ and $R^{27}$ may bond together to form a ring with the sulfur atom to which they are attached. $M^-$ is a non-nucleophilic counter ion.

The resist composition may further comprise a quencher, a photoacid generator other than the photoacid generator defined herein, and/or a surfactant.

In a further aspect, the invention provides a pattern forming process comprising the steps of applying the chemically amplified resist composition defined herein onto a substrate to form a resist film thereon, exposing a selected region of the resist film to high-energy radiation, and developing the exposed resist film in a developer.

In a preferred embodiment, the exposing step is carried out by the immersion lithography while a liquid having a refractive index of at least 1.0 is held between the resist film and a projection lens.

The process may further comprise the step of forming a protective film on the resist film prior to the exposure step, wherein the immersion lithography is carried out while the liquid is held between the protective film and the projection lens.

Typically, the high-energy radiation is KrF excimer laser radiation, ArF excimer laser radiation, EB, or EUV.

In a preferred embodiment, the developing step uses an aqueous alkaline solution as the developer to form a positive tone pattern wherein the exposed region of resist film is dissolved away and the unexposed region of resist film is not dissolved.

In another preferred embodiment, the developing step uses an organic solvent as the developer to form a negative tone pattern wherein the unexposed region of resist film is dissolved away and the exposed region of resist film is not dissolved. Preferably, the developer is at least one organic solvent selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, butenyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

Advantageous Effects of Invention

When processed by the lithography, the resist composition comprising the photoacid generator is improved in lithographic performance factors including sensitivity, LWR, and CDU and effective for forming a resist pattern having a small feature size.

DESCRIPTION OF EMBODIMENTS

Figure 1:
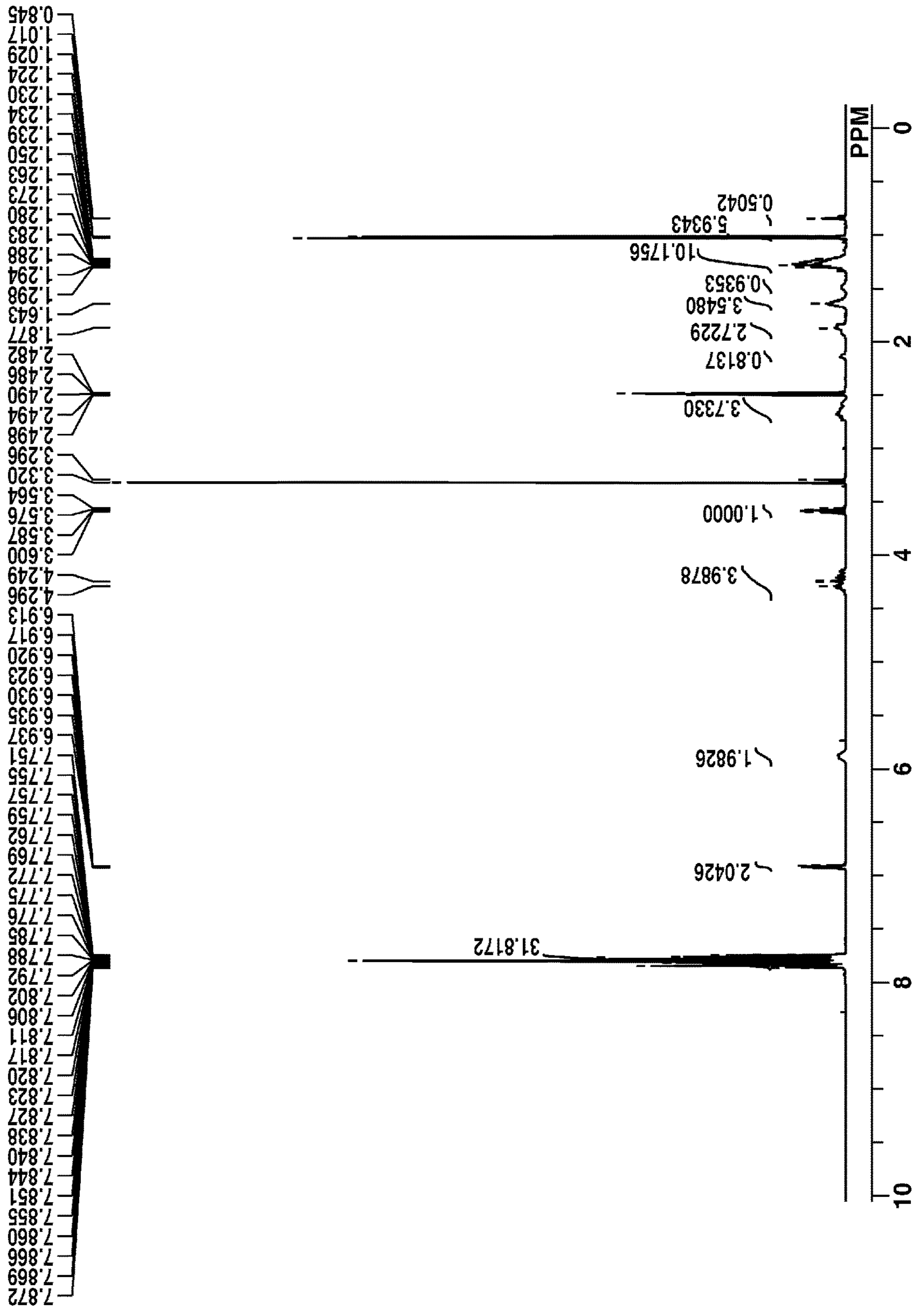
FIG. 1 is a $^1$H-NMR spectrum of PAG-1 synthesized in Example 1-1.

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. As used herein, the term "iodized" compound indicates a compound containing iodine or a compound substituted with iodine. In chemical formulae, Me stands for methyl, and Ac for acetyl.

The abbreviations and acronyms have the following meaning.

EB: electron beam

EUV: extreme ultraviolet

Mw: weight average molecular weight

Mn: number average molecular weight

Mw/Mn: molecular weight dispersity

GPC: gel permeation chromatography

PEB: post-exposure bake

PAG: photoacid generator

LWR: line width roughness

MEF: mask error factor

CDU: critical dimension uniformity

DOF: depth of focus

Photoacid Generator

One embodiment of the invention is a photoacid generator in the form of an onium salt compound consisting of an anion containing an iodine-substituted aromatic group and two sulfonate groups and a sulfonium or iodonium cation.

Preferably, the onium salt has the formula (1).

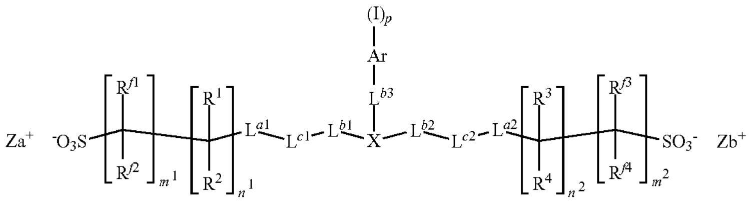

(1)

In formula (1), X is a $C_1$-$C_{35}$ trivalent hydrocarbon group which may contain a heteroatom. The trivalent hydrocarbon group may be saturated or unsaturated and straight, branched or cyclic. In the trivalent hydrocarbon group, some or all of the hydrogen atoms may be substituted by a moiety containing a heteroatom such as oxygen, sulfur, nitrogen or halogen, and some constituent —$CH_2$— may be replaced by a moiety containing a heteroatom such as oxygen, sulfur or nitrogen, so that the group may contain fluorine, chlorine, bromine, iodine, hydroxy, cyano, carbonyl, ether bond, ester bond, sulfonic ester bond, carbonate bond, lactone ring, sultone ring, carboxylic anhydride (—C(=O)—O—C(=O)—), or haloalkyl moiety.

Examples of X are shown below, but not limited thereto.

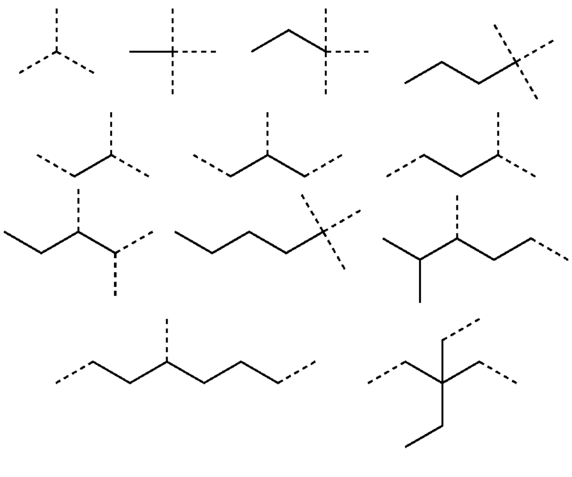

-continued
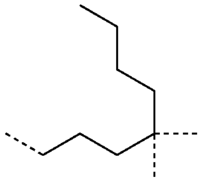
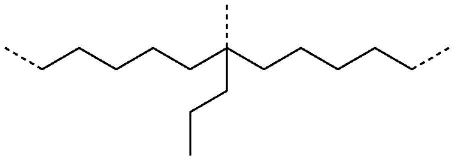
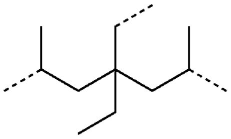
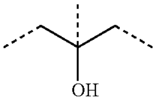
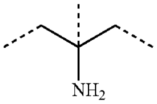
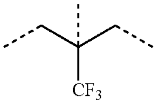
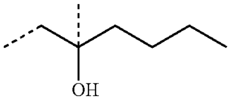
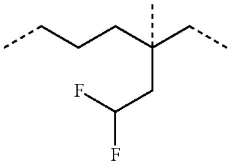
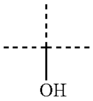
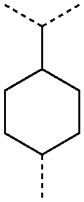
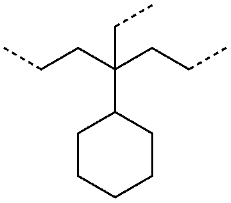
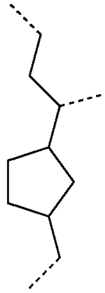
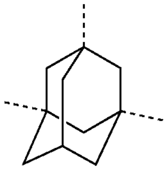
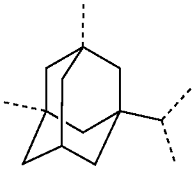
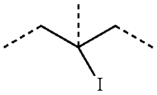
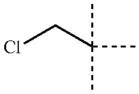
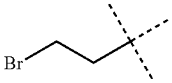
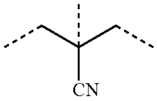
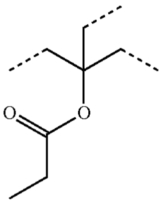
-continued
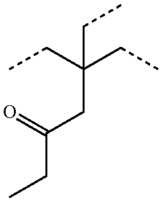
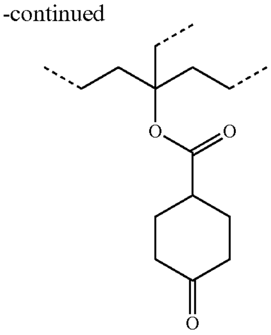
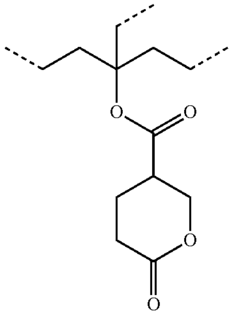
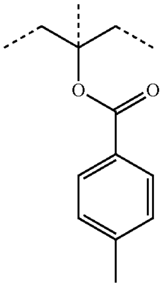
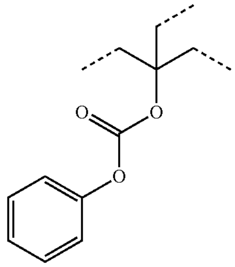
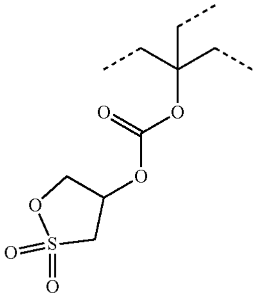
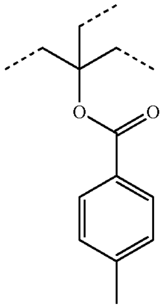
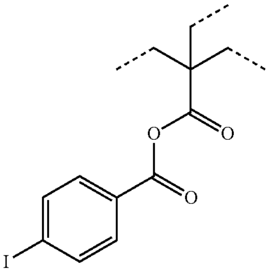
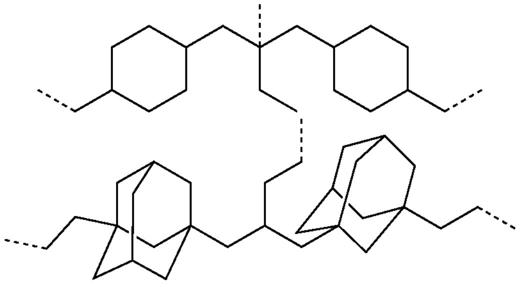
Of these, the following groups are especially preferred.
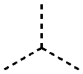
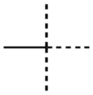
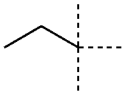
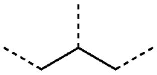

-continued

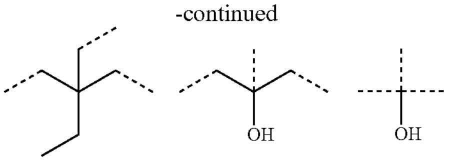

In formula (1), $R^1$, $R^2$, $R^3$, and $R^4$ are each independently hydrogen or a $C_1$-$C_{10}$ hydrocarbyl group which may contain a heteroatom. Also, $R^1$ and $R^2$ may bond together to form a ring with the carbon atom to which they are attached, and $R^3$ and $R^4$ may bond together to form a ring with the carbon atom to which they are attached.

The hydrocarbyl groups $R^1$, $R^2$, $R^3$, and $R^4$ may be saturated or unsaturated and straight, branched or cyclic. Examples thereof include $C_1$-$C_{10}$ alkyl groups such as methyl, ethyl, propyl, isopropyl, n-butyl, sec-butyl, tert-butyl, n-pentyl, n-hexyl, n-octyl, 2-ethylhexyl, n-nonyl and n-decyl; $C_3$-$C_{10}$ cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.$0^{2,6}$]decanyl, and adamantyl; $C_2$-$C_{10}$ alkenyl groups such as vinyl, allyl, propenyl, butenyl and hexenyl; $C_3$-$C_{10}$ cyclic unsaturated aliphatic hydrocarbyl groups such as cyclohexenyl; $C_6$-$C_{10}$ aryl groups such as phenyl, 4-n-butylphenyl, 4-tert-butylphenyl, 2,4-dimethylphenyl, 2,4,6-trimethylphenyl, and naphthyl; $C_7$-$C_{10}$ aralkyl groups such as benzyl, 1-phenylethyl, and 2-phenylethyl; and combinations thereof. $R^1$, $R^2$, $R^3$, and $R^4$ are preferably hydrogen.

In the hydrocarbyl group, some or all of the hydrogen atoms may be substituted by a moiety containing a heteroatom such as oxygen, sulfur, nitrogen or halogen, and some constituent —$CH_2$— may be replaced by a moiety containing a heteroatom such as oxygen, sulfur or nitrogen, so that the group may contain fluorine, chlorine, bromine, iodine, hydroxy moiety, cyano moiety, carbonyl moiety, ether bond, ester bond, sulfonic ester bond, carbonate bond, lactone ring, sultone ring, carboxylic anhydride (—C(═O)—O—C(═O)—) or haloalkyl moiety. Examples of the heteroatom-containing hydrocarbyl group include $C_3$-$C_{10}$ heteroaryl groups such as thienyl; alkoxyphenyl groups such as 2-hydroxyphenyl, 4-hydroxyphenyl, 2-methoxyphenyl, 3-methoxyphenyl and 4-methoxyphenyl; halogenated phenyl groups such as 4-fluorophenyl and 4-iodophenyl; and haloalkylphenyl groups such as 4-trifluoromethylphenyl.

In formula (1a), $R^{f1}$, $R^{f2}$, $R^{f3}$, and $R^{f4}$ are each independently hydrogen, fluorine or trifluoromethyl, at least one of $R^{f1}$ and $R^{f2}$ is fluorine or trifluoromethyl, and at least one of $R^{f3}$ and $R^{f4}$ is fluorine or trifluoromethyl. Each of $R^{f1}$, $R^{f2}$, $R^{f3}$, and $R^{f4}$ attached to the α-carbon relative to —$SO_3$— group is preferably fluorine.

The subscripts $m^1$ and $m^2$ are each independently an integer of 1 to 4, preferably 1 or 2; $n^1$ and $n^2$ are each independently an integer of 0 to 4, preferably 0, 1 or 2.

In formula (1), $L^{a1}$ and $L^{a2}$ are each independently an ether bond, ester bond, sulfonic ester bond or carbonate bond, preferably an ether bond or ester bond.

In formula (1), $L^{c1}$ and $L^{c2}$ are each independently a single bond or a $C_1$-$C_{15}$ hydrocarbylene group in which some hydrogen may be substituted by a heteroatom-containing moiety and some constituent —$CH_2$— may be replaced by —O— or —C(═O)—. Suitable heteroatom-containing moieties include hydroxy, cyano and halogen.

The hydrocarbylene groups $L^{c1}$ and $L^{c2}$ may be saturated or unsaturated and straight, branched or cyclic. Examples thereof are as will be exemplified later for the hydrocarbylene groups $L^{c1'}$ and $L^{c2'}$. $L^{c1}$ and $L^{c2}$ each are preferably a group containing a cyclic moiety.

In formula (1), $L^{b1}$, $L^{b2}$ and $L^{b3}$ are each independently a single bond, ether bond, ester bond, sulfonic ester bond, carbonate bond or carbamate bond, preferably an ether bond or ester bond.

In formula (1), Ar is a $C_3$-$C_{15}$ (p+1)-valent aromatic group in which some hydrogen may be substituted by fluorine, hydroxy or $C_1$-$C_{15}$ hydrocarbyl group. Some hydrogen in the hydrocarbyl group may be substituted by a heteroatom-containing moiety and some constituent —$CH_2$— in the hydrocarbyl group may be replaced by —O—, —C(═O)— or —N($R^N$)—. $R^N$ is hydrogen or a $C_1$-$C_{10}$ hydrocarbyl group in which some hydrogen may be substituted by a heteroatom-containing moiety and some constituent —$CH_2$— may be replaced by —O—, —C(═O)— or —S(═O)$_2$—. Suitable heteroatom-containing moieties include hydroxy, cyano and halogen. Ar is preferably an optionally substituted $C_6$-$C_{10}$ (p+1)-valent aromatic group, more preferably a (p+1)-valent group derived from an optionally substituted benzene.

In formula (1), p is an integer of 1 to 5, preferably 1 to 3.

In formula (1), $Za^+$ and $Zb^+$ are each independently a sulfonium cation or iodonium cation.

Examples of the iodonium cation include, but are not limited to, diphenyliodonium, bis(4-methylphenyl)iodonium, bis(4-ethylphenyl)iodonium, bis(4-tert-butylphenyl)iodonium, bis(4-(1,1-dimethylpropyl)phenyl)iodonium, 4-methoxyphenylphenyliodonium, 4-tert-butoxyphenylphenyliodonium, 4-acryloyloxyphenylphenyliodonium, 4-methacryloyloxyphenylphenyliodonium, 4-fluorophenylphenyliodonium, and [4-(2-methacryloyloxy-ethoxy)phenyl]phenyliodonium.

The sulfonium cation preferably has the formula (Z-1) or (Z-2).

(Z-1)

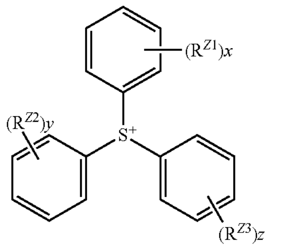

(Z-2)

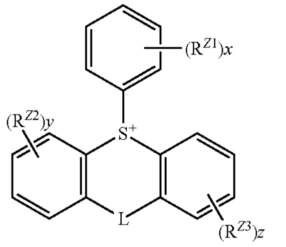

In formulae (Z-1) and (Z-2), $R^{Z1}$, $R^{Z2}$, and $R^{Z3}$ are each independently halogen, hydroxy or a $C_1$-$C_{15}$ hydrocarbyl group. The hydrocarbyl group may be saturated or unsaturated and straight, branched or cyclic. Examples thereof include $C_1$-$C_{15}$ alkyl groups such as methyl, ethyl, propyl, isopropyl, n-butyl, sec-butyl, tert-butyl, tert-pentyl, n-pentyl, n-hexyl, n-octyl, 2-ethylhexyl, n-nonyl and n-decyl;

$C_3$-$C_{15}$ cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.$0^{2,6}$]decanyl, adamantyl, and adamantylmethyl; $C_6$-$C_{15}$ aryl groups such as phenyl, naphthyl and anthracenyl; and combinations thereof. In the hydrocarbyl group, some hydrogen may be substituted by a heteroatom-containing moiety and some constituent —$CH_2$— may be replaced by —O—, —C(=O)—, —S—, —S(=O)—, —S(=O)$_2$—, or —N($R^N$)—. It is noted that the constituent —$CH_2$— in the hydrocarbyl group may be attached to the carbon atom on the aromatic ring. Suitable heteroatom-containing moieties include hydroxy, cyano and halogen.

In formula (Z-2), L is a single bond, —$CH_2$—, —O—, —C(=O)—, —S—, —S(=O)—, —S(=O)$_2$—, or —N($R^N$)—. $R^N$ is hydrogen or a $C_1$-$C_{10}$ hydrocarbyl group in which some hydrogen may be substituted by a heteroatom-containing moiety and some constituent —$CH_2$— may be replaced by —O—, —C(=O)— or —S(=O)$_2$—. Suitable heteroatom-containing moieties include hydroxy, cyano and halogen.

In formulae (Z-1) and (Z-2), x, y and z are each independently an integer of 0 to 5. When x is 2 or more, a plurality of $R^{Z1}$ may be the same or different and two $R^{Z1}$ may bond together to form a ring with the carbon atoms on the benzene ring to which they are attached. When y is 2 or more, a plurality of $R^{Z2}$ may be the same or different and two $R^{Z2}$ may bond together to form a ring with the carbon atoms on the benzene ring to which they are attached. When z is 2 or more, a plurality of $R^{Z3}$ may be the same or different and two $R^{Z3}$ may bond together to form a ring with the carbon atoms on the benzene ring to which they are attached.

Examples of the sulfonium cation having formula (Z-1) are shown below, but not limited thereto.

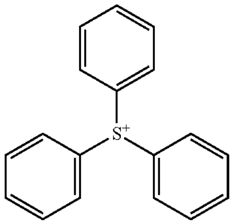

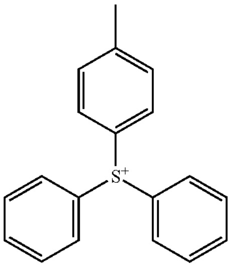

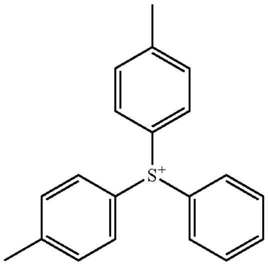

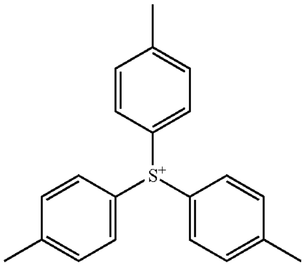

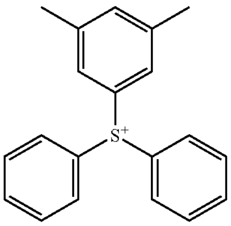

-continued

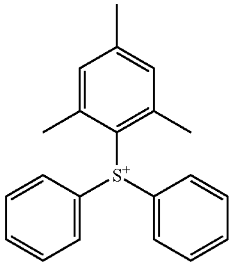

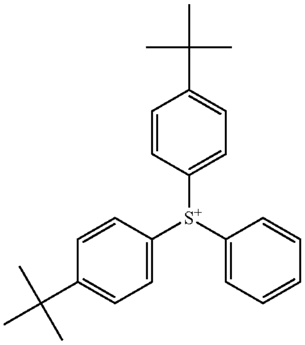

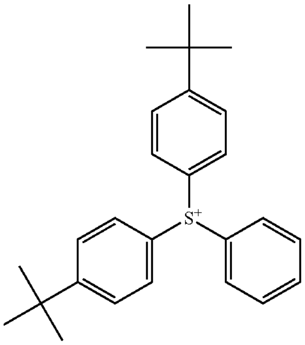

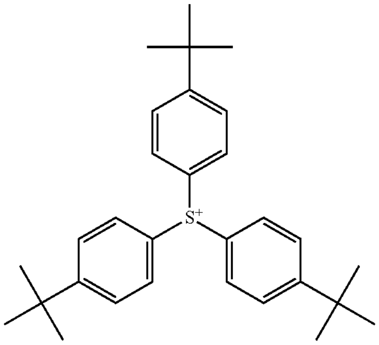

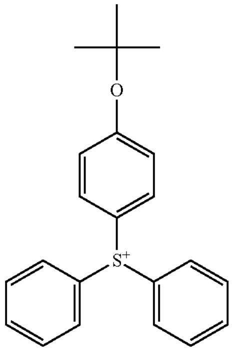

-continued
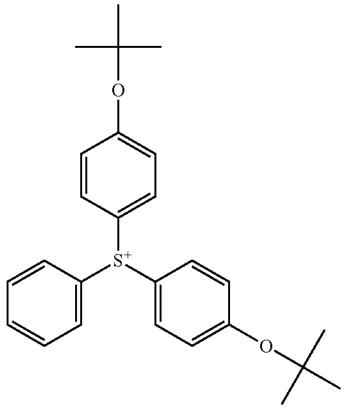
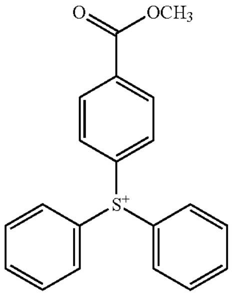
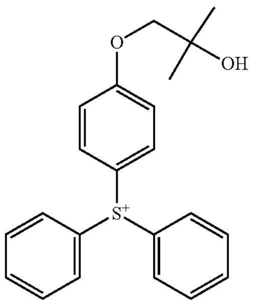
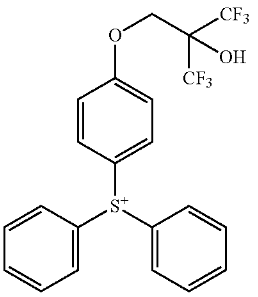
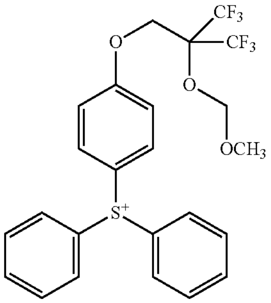
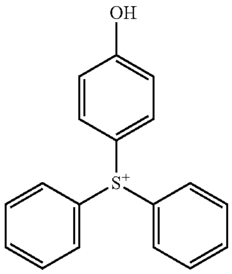
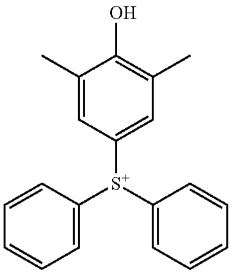
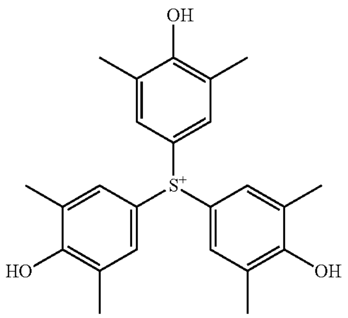
-continued
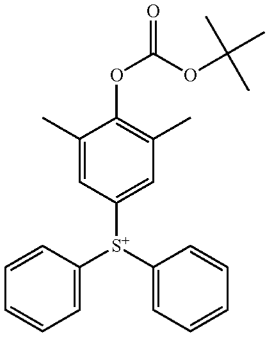
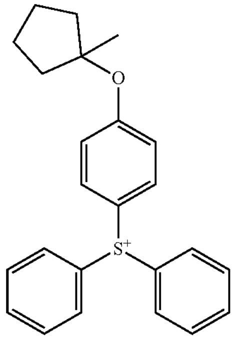
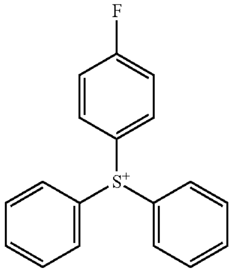
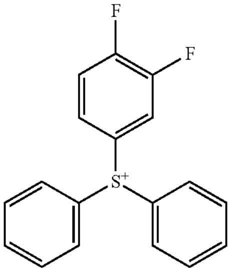
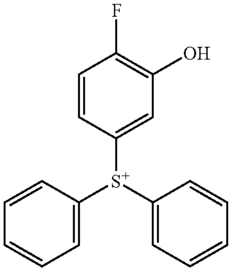
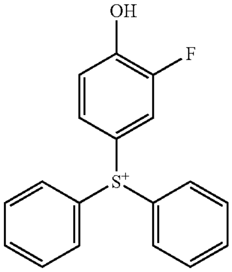
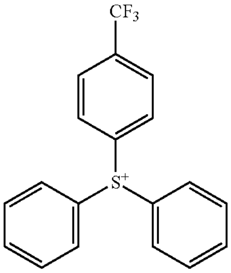
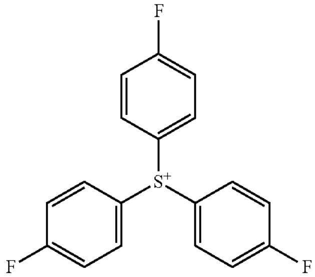
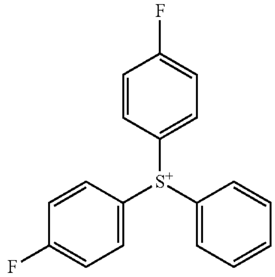

-continued
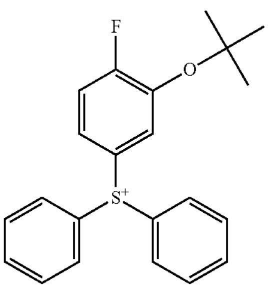
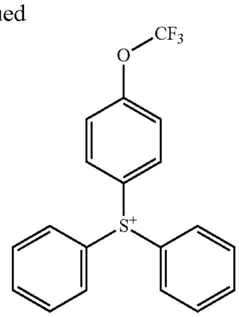
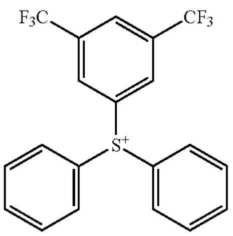
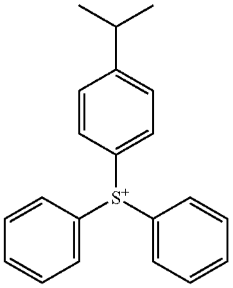
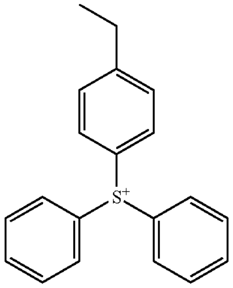
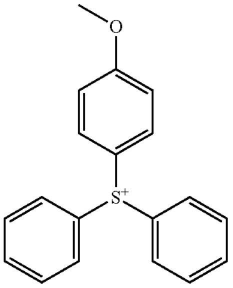
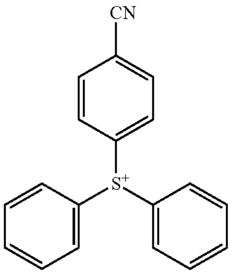
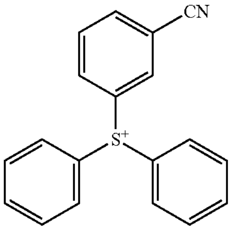
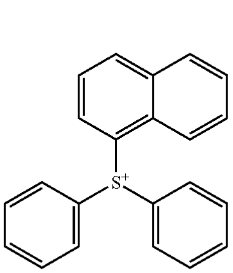
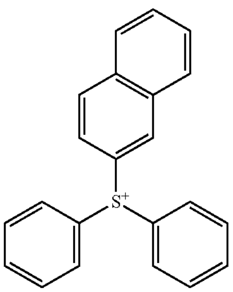
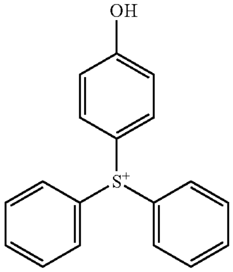
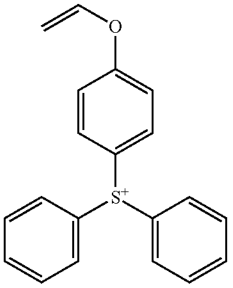
-continued
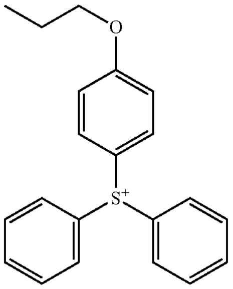
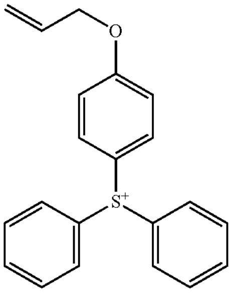
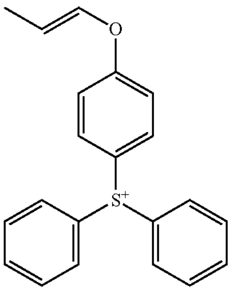
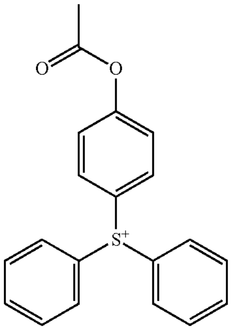
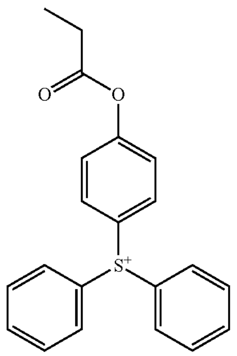
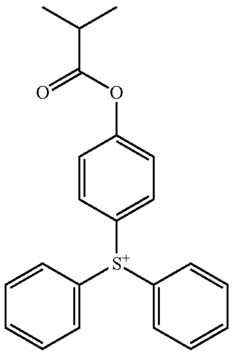
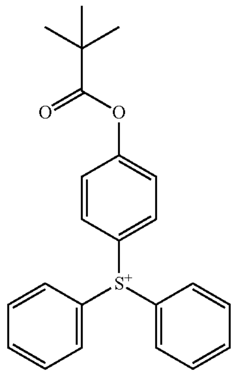
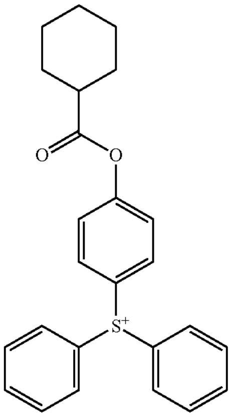

-continued
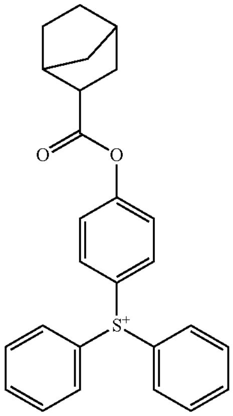
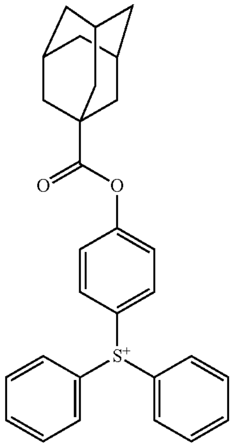
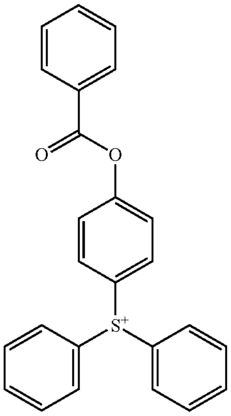
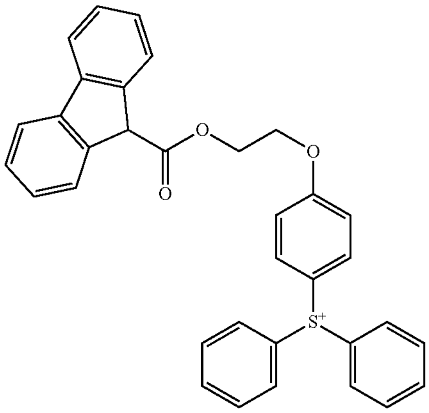
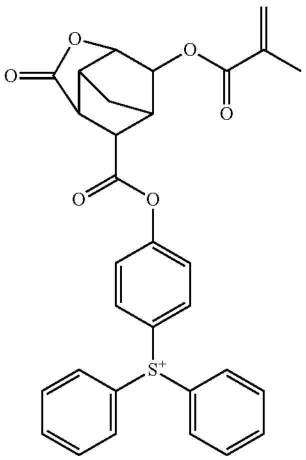
-continued
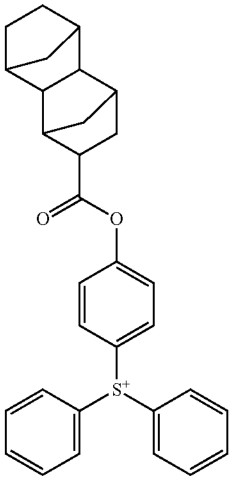
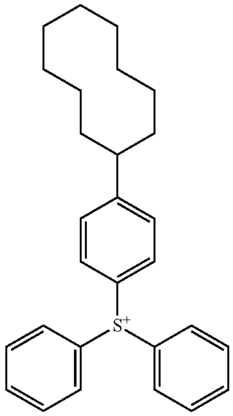
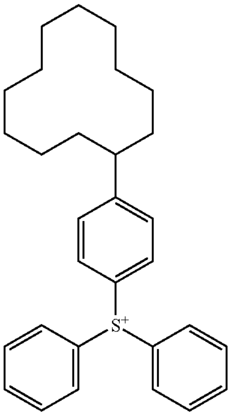
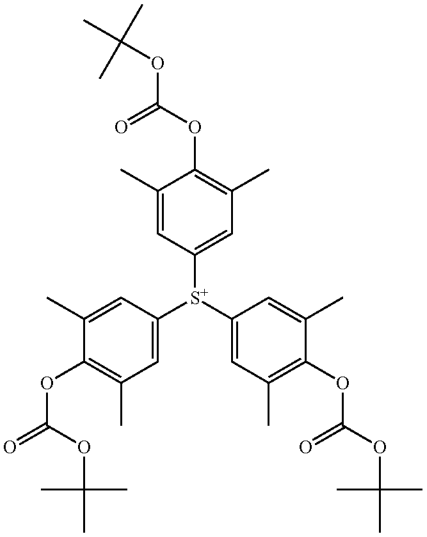

-continued
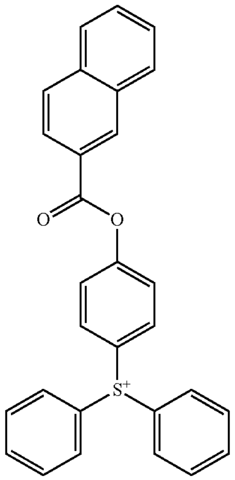
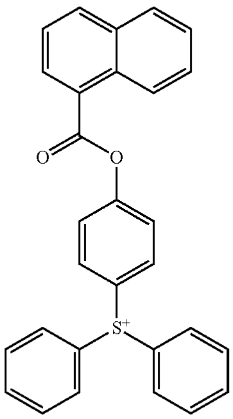
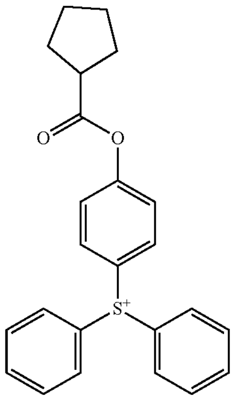
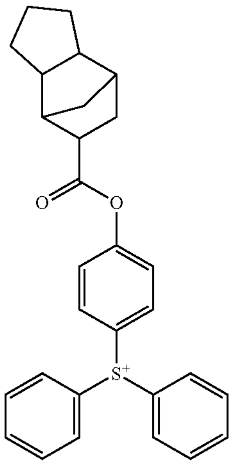
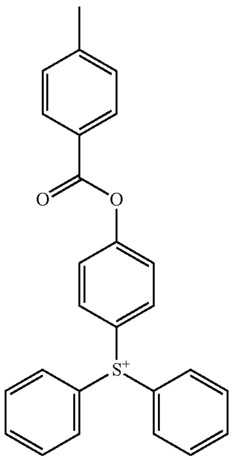
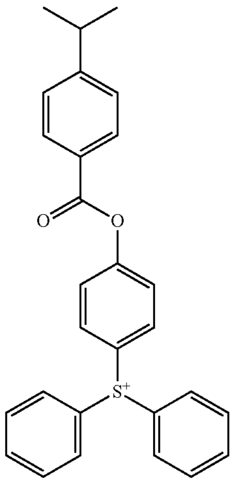
-continued
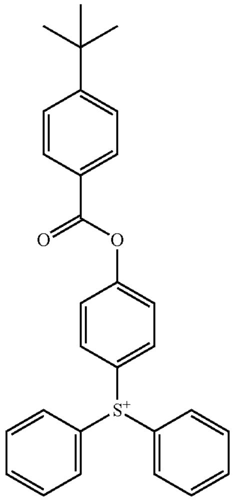
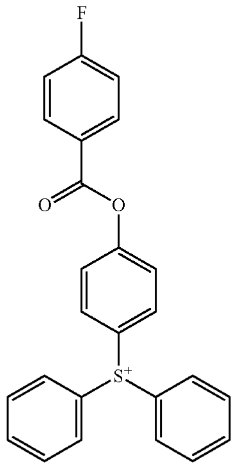
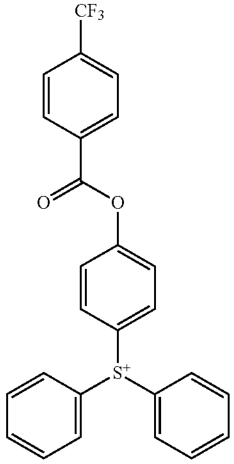
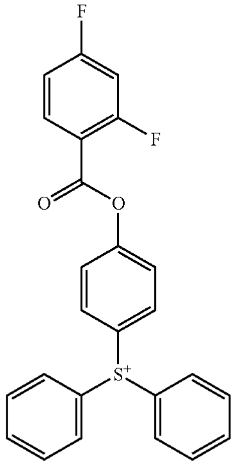
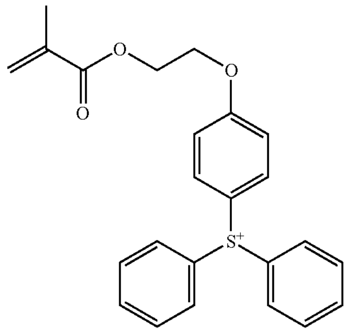
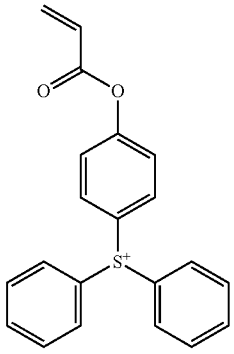
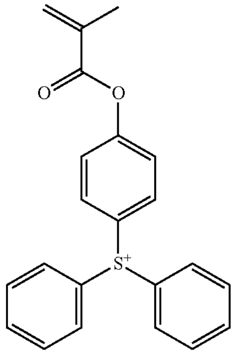

-continued
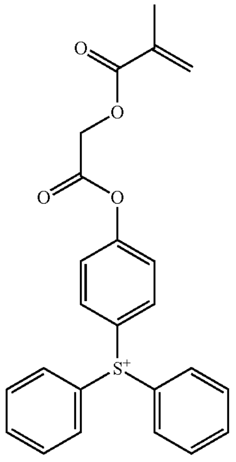
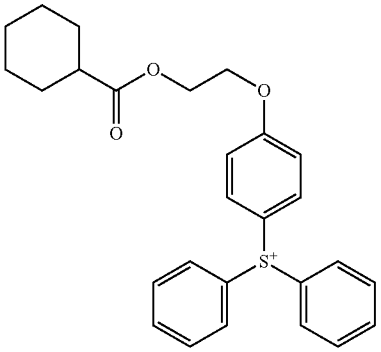
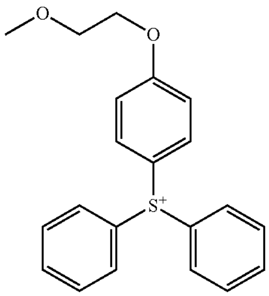
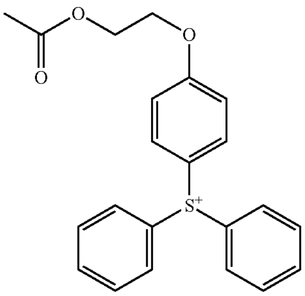
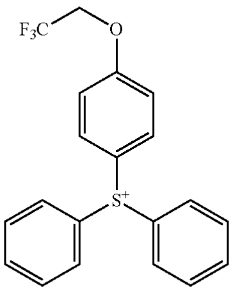
-continued
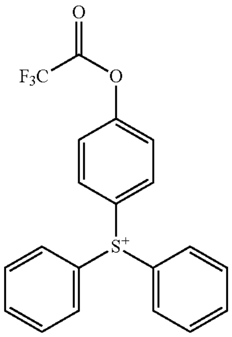
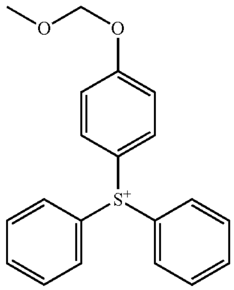
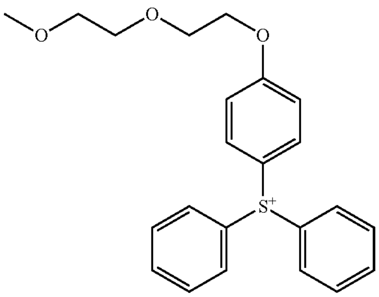
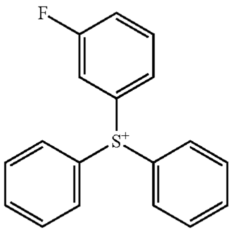
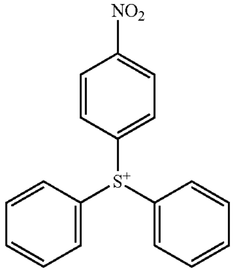
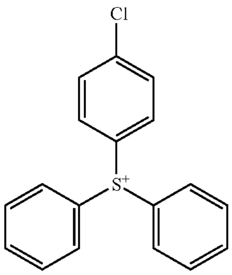
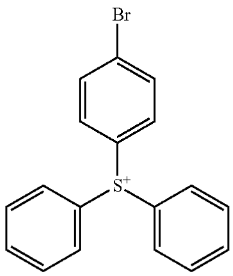
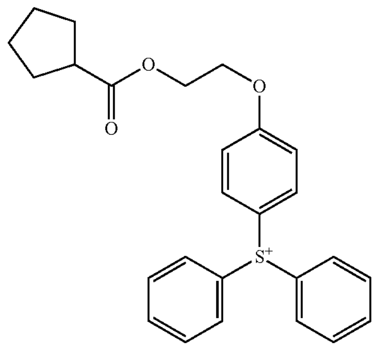

-continued
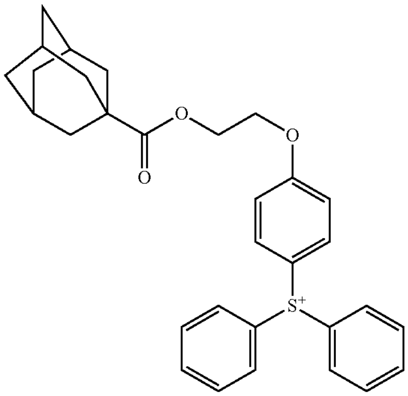
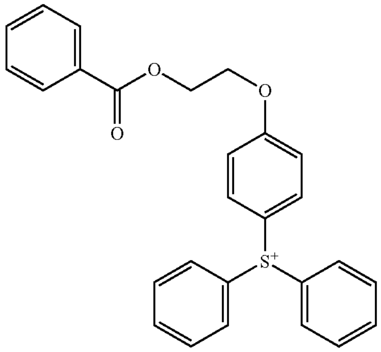
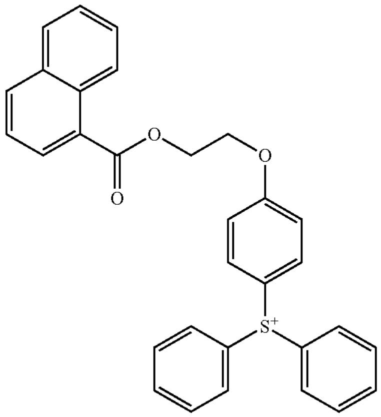
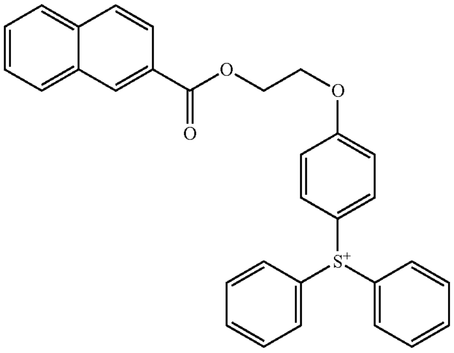
-continued
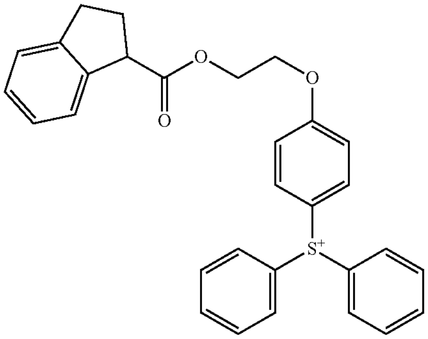
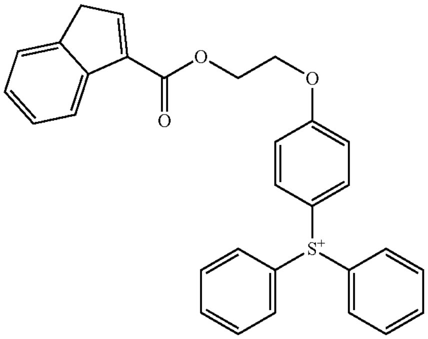
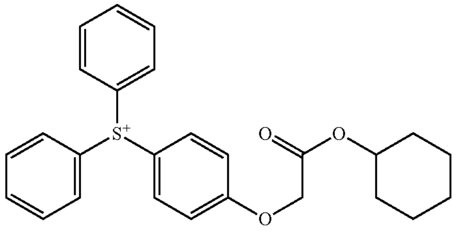
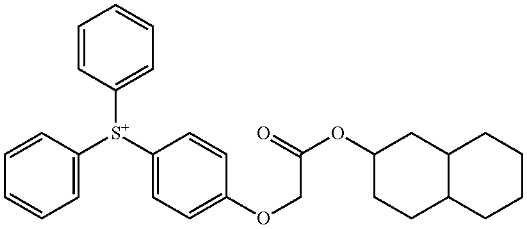
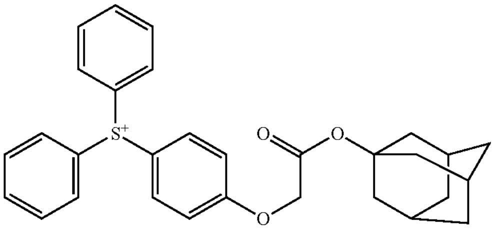
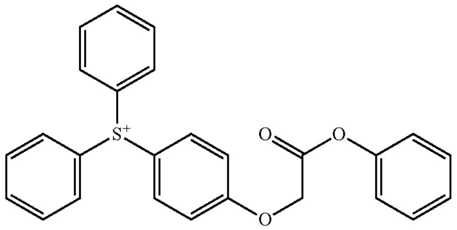

-continued
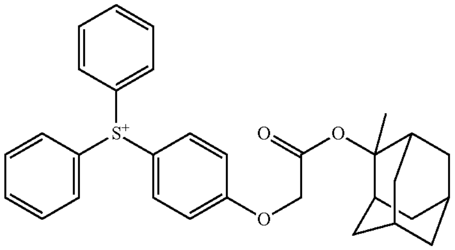
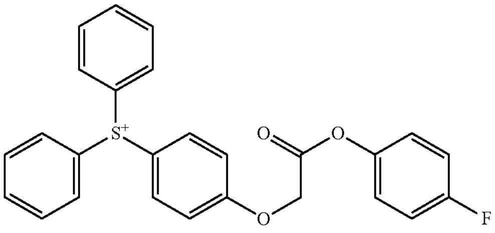
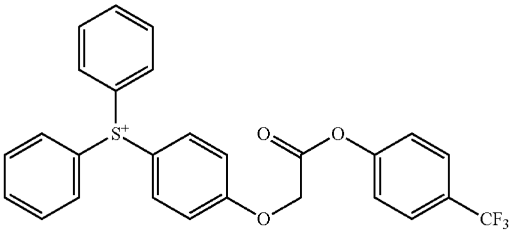
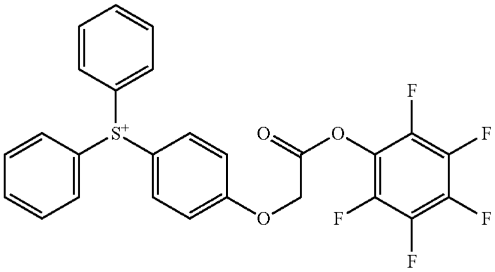
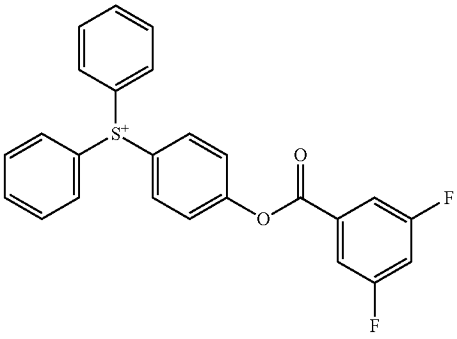
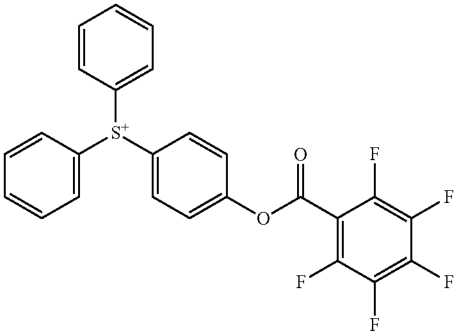
-continued
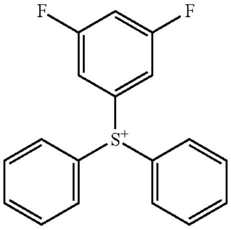
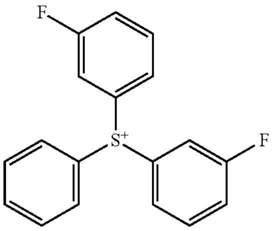
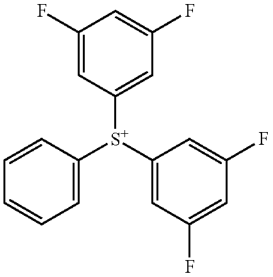
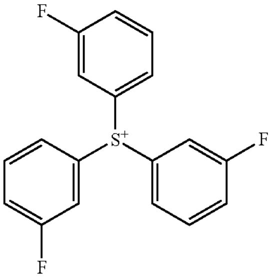
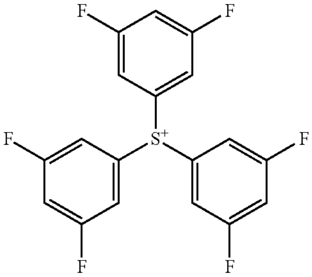
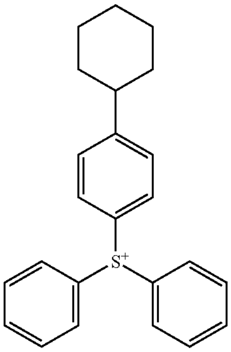

-continued
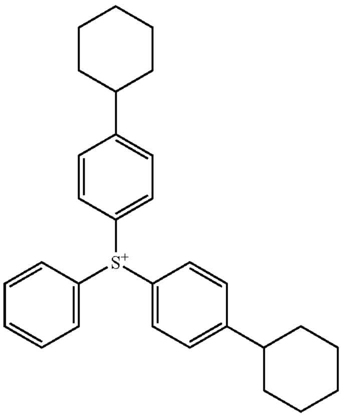
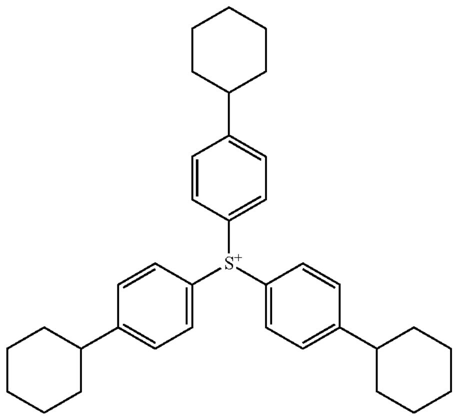
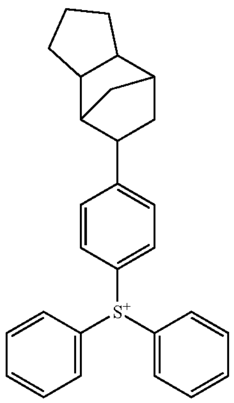
-continued
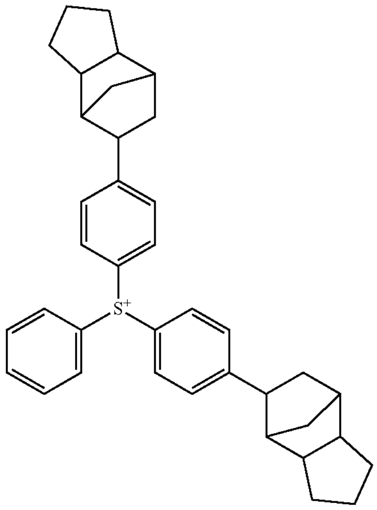
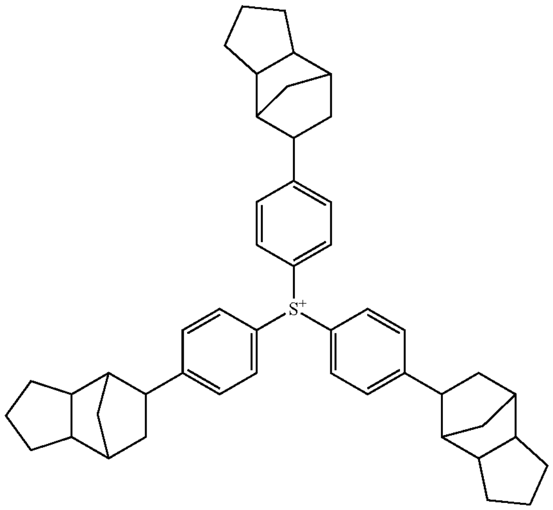
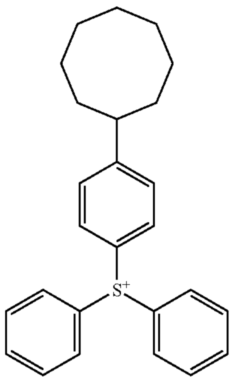

-continued
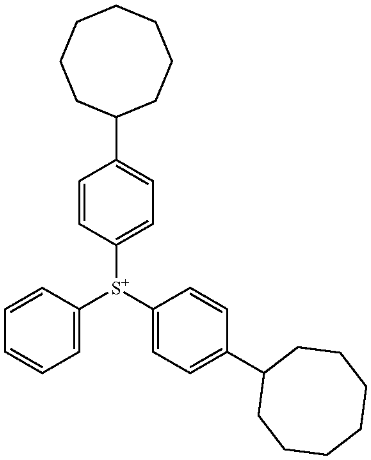
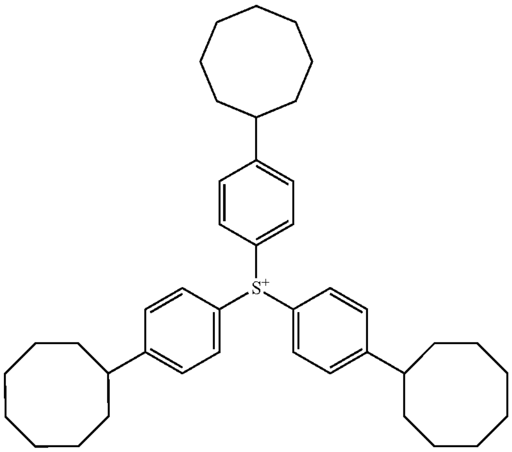
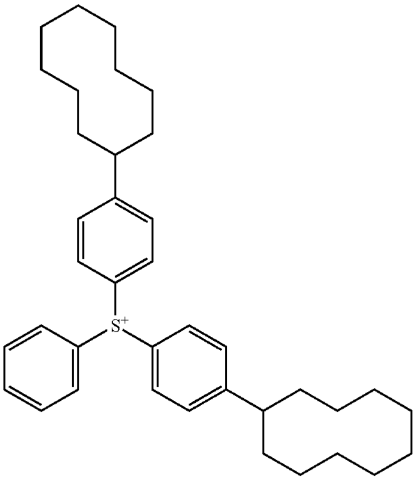
-continued
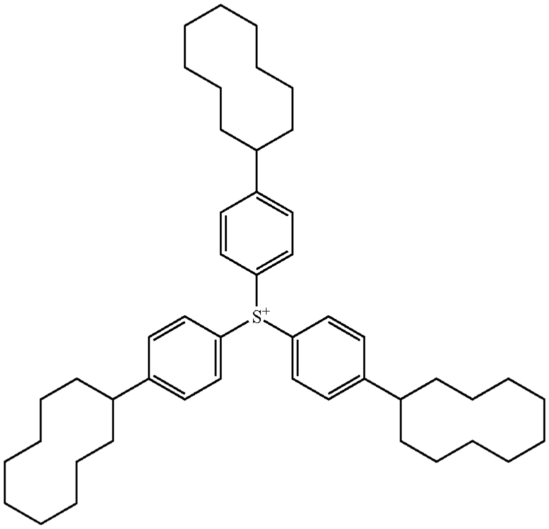
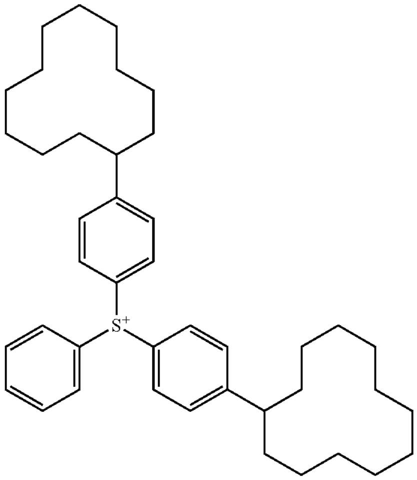
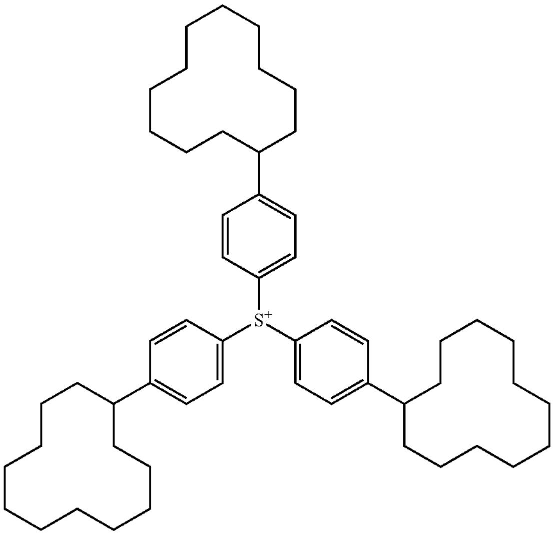
Examples of the sulfonium cation having formula (Z-2) are shown below, but not limited thereto.

-continued
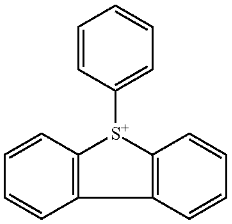
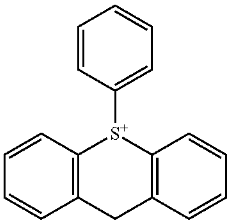
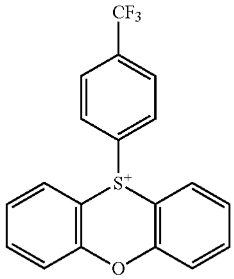
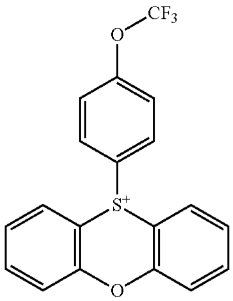
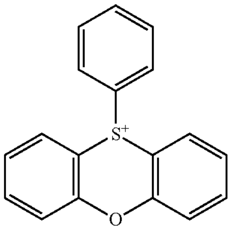
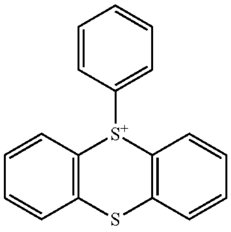
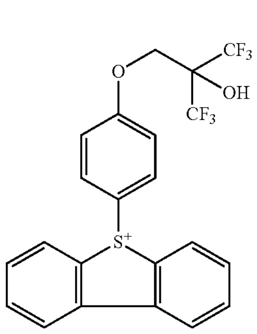
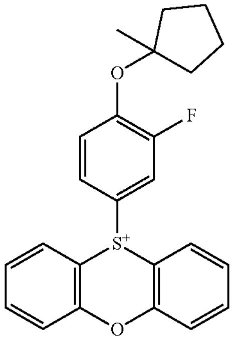
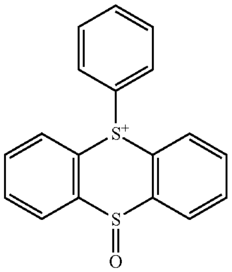
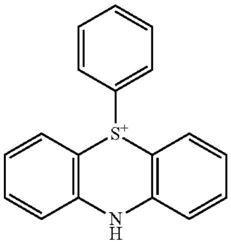
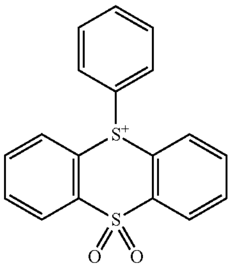
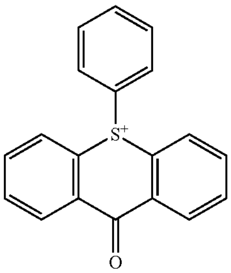
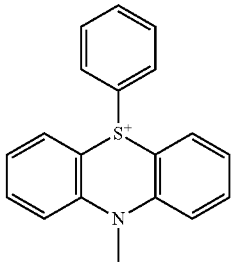
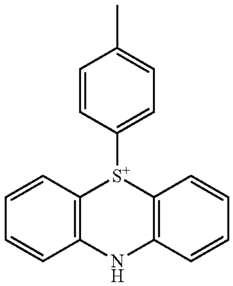
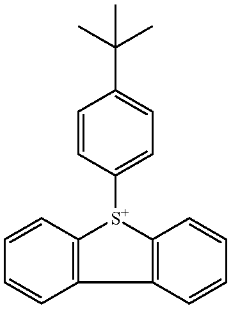
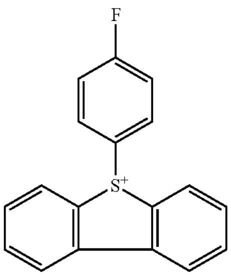
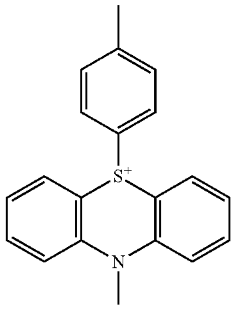
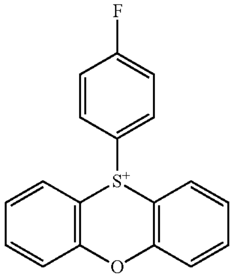
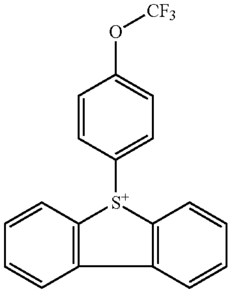
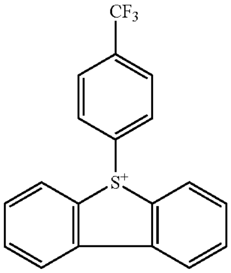
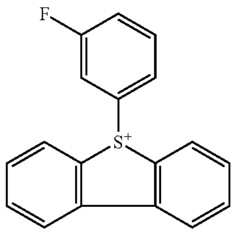
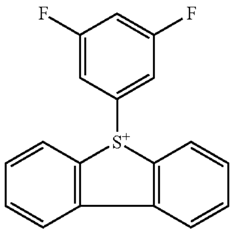

-continued

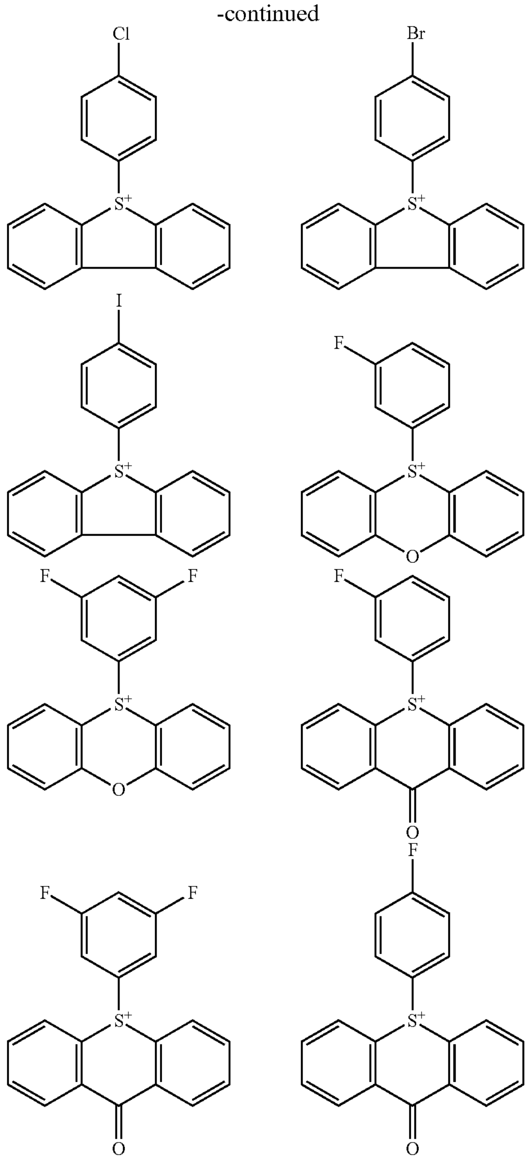

The PAG having formula (1) is preferably an onium salt having the formula (1a).

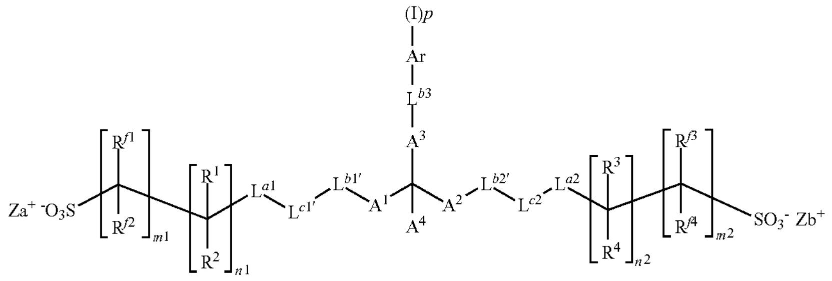

(Ia)

Herein $R^1$, $R^2$, $R^3$, $R^4$, $R^{f1}$, $R^{f2}$, $R^{f3}$, $R^{f4}$, $L^{a1}$, $L^{a2}$, $L^{b3}$, Ar, $m^1$, $m^2$, $n^1$, $n^2$, p, $Za^+$, and $Zb^+$ are as defined above.

In formula (1a), $A^1$, $A^2$, and $A^3$ are each independently a single bond or a $C_1$-$C_8$ hydrocarbylene group which may contain a heteroatom, in which some constituent —$CH_2$— may be replaced by —O— or —C(=O)—. The hydrocarbylene group may be saturated or unsaturated and straight, branched or cyclic. Examples thereof include $C_1$-$C_8$ alkanediyl groups such as methanediyl, ethane-1,2-diyl, propane-1,3-diyl, butane-1,4-diyl, pentane-1,5-diyl, hexane-1,6-diyl, heptane-1,7-diyl, and octane-1,8-diyl; $C_3$-$C_8$ cyclic saturated hydrocarbylene groups such as cyclopentanediyl, cyclohexanediyl, and norbornanediyl; $C_6$-$C_8$ arylene groups such as phenylene. Inter alia, methanediyl is preferred.

In formula (1a), $A^4$ is hydrogen, hydroxy, or a $C_1$-$C_{10}$ hydrocarbyl group which may contain a heteroatom. In the hydrocarbyl group, some constituent —$CH_2$— may be replaced by —O— or —C(=O)—. The hydrocarbyl group may be saturated or unsaturated and straight, branched or cyclic. Examples thereof include $C_1$-$C_{10}$ alkyl groups such as methyl, ethyl, propyl, butyl, sec-butyl, tert-butyl, pentyl, hexyl, heptyl, octyl, nonyl and decyl; $C_3$-$C_{10}$ cyclic saturated hydrocarbyl groups such as cyclopentyl, cyclohexyl, norbornyl and adamantyl; and $C_6$-$C_{10}$ aryl groups such as phenyl and naphthyl. $A^4$ is preferably hydrogen, methyl or ethyl.

In formula (1a), $L^{b1'}$ and $L^{b2'}$ are each independently an ether bond, ester bond, sulfonic ester bond, carbonate bond or carbamate bond. Inter alia, an ester bond is preferred.

In formula (1a), $L^{c1'}$ and $L^{c2'}$ are each independently a single bond or a $C_1$-$C_{10}$ hydrocarbylene group in which some hydrogen may be substituted by a heteroatom-containing moiety and some constituent —$CH_2$— may be replaced by —O— or —C(=O)—. Suitable heteroatom-containing moieties include hydroxy, cyano and halogen.

The hydrocarbylene groups $L^{c1'}$ and $L^{c2'}$ may be saturated or unsaturated and straight, branched or cyclic. Examples thereof include $C_1$-$C_{30}$ alkanediyl groups such as methanediyl, ethane-1,1-diyl, ethane-1,2-diyl, propane-1,2-diyl, propane-1,3-diyl, butane-1,2-diyl, butane-2,3-diyl, butane-1,4-diyl, 2,3-dimethyl-2,3-butylene, pentane-1,5-diyl, hexane-1,6-diyl, hexane-2,5-diyl, heptane-1,7-diyl, octane-1,8-diyl, nonane-1,9-diyl, decane-1,10-diyl, cyclopentane-1,3-diyl, cyclohexane-1,2-diyl, cyclohexane-1,3-diyl, cyclohexane-1,4-diyl, 4,6-dimethylcyclohexane-1,3-diyl, cyclooctane-1,4-diyl, cyclooctane-1,5-diyl, 1,2-cyclohexanedimethylene, 1,3-cyclohexanedimethylene, 1,4-cyclohexanedimethylene, 1-ethyl-1,4-cyclohexanedimethylene, 2-cyclohexyl-1,3-propylene, 1,4-cyclooctylene, 1,5-cyclooctylene, 1,2-phenylene, 4-methyl-1,2-phenylene, 1,3-phenylene, 2-methyl-1,3-phenylene, 4-methyl-1,3-phenylene, 1,4-phenylene, 2-methyl-1,4-phenylene, 2-tert-butyl-1,4-phenylene, 2,3-dimethyl-1,4-phenylene, trimethyl-1,4-phenylene, 4-(methylene)phenyl, 1,2-benzenedimethylene, 1,3-benzenedimethylene, 1,4-benzenedimethylene, 1,2-naphthylene, 1,3-naphthylene, 1,4-naphthylene, 1,5-naphthylene, 1,6-naphthylene, 1,7-naphthylene, 2,3-naphthylene, 2,6-naphthylene, 2,7-naphthylene, 3,6-naphthylene, and 1,8-naphthalenedimethylene. Of these, preference is given to cyclopentane-1,3-diyl, cyclohexane-1,2-diyl, cyclohexane-1,3-diyl, cyclohexane-1,4-diyl, and 1,2-phenylene.

Of the PAGs having formula (1a), those having the formula (1b) are more preferred.

(1b)

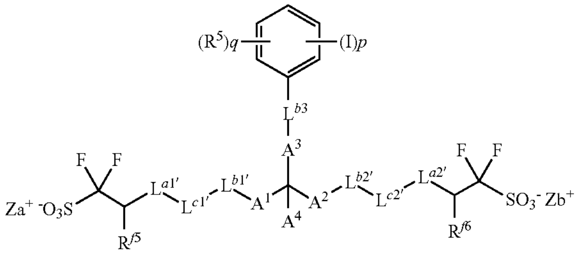

In formula (1b), $A^1$, $A^2$, $A^3$, $A^4$, $L^{b1'}$, $L^{b2'}$, $L^{b3}$, $Za^+$, and $Zb^+$ are as defined above.

In formula (1b), p is an integer of 1 to 5, q is an integer of 0 to 4, the sum of p and q is from 1 to 5. Preferably, p is an integer of 1 to 3, q is an integer of 0 to 4, the sum of p and q is from 1 to 5.

In formula (1b), $R^{f5}$ and $R^{f6}$ are each independently hydrogen or trifluoromethyl.

Preferably, $R^{f5}$ and $R^{f6}$ each are trifluoromethyl.

In formula (1b), $L^{a1'}$ and $L^{a2'}$ are each independently an ether bond or ester bond, preferably an ester bond.

In formula (1b), $R^5$ is hydroxy, fluorine, or a $C_1$-$C_{15}$ hydrocarbyl group. In the hydrocarbyl group, some hydrogen may be substituted by a heteroatom-containing moiety and some constituent —$CH_2$— may be replaced by —O—, —C(=O)— or —N($R^N$)—. $R^N$ is hydrogen or a $C_1$-$C_{10}$ hydrocarbyl group in which some hydrogen may be substituted by a heteroatom-containing moiety and some constituent —$CH_2$— may be replaced by —O—, —C(=O)— or —S(=O)$_2$—. When q is 2 or more, a plurality of $R^5$ may be the same or different and two $R^5$ may bond together to form a ring with the carbon atoms on the benzene ring to which they are attached. Suitable heteroatom-containing moieties include hydroxy, cyano, and halogen.

The hydrocarbyl group $R^5$ may be saturated or unsaturated and straight, branched or cyclic. Examples thereof include $C_1$-$C_{15}$ alkyl groups such as methyl, ethyl, propyl, isopropyl, n-butyl, sec-butyl, tert-butyl, n-pentyl, n-hexyl, n-octyl, 2-ethylhexyl, n-nonyl, and n-decyl; $C_3$-$C_{15}$ cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, and adamantyl; $C_2$-$C_{15}$ alkenyl groups such as vinyl, allyl, propenyl, butenyl, and hexenyl; $C_3$-$C_{15}$ cyclic unsaturated aliphatic hydrocarbyl groups such as cyclohexenyl; $C_6$-$C_{15}$ aryl groups such as phenyl, 2-hydroxyphenyl, 4-hydroxyphenyl, 2-methoxyphenyl, 3-methoxyphenyl, 4-methoxyphenyl, 4-fluorophenyl, 4-iodophenyl, 4-n-butylphenyl, 4-tert-butylphenyl, 4-tert-butoxyphenyl, 4-trifluoromethylphenyl, 2,4-dimethylphenyl, 2,4,6-trimethylphenyl, 2,4,6-triisopropylphenyl, and naphthyl; $C_7$-$C_{15}$ aralkyl groups such as benzyl, 1-phenylethyl, and 2-phenylethyl; and combinations thereof. Preferably, $R^5$ is hydroxy or methyl.

Of the PAGs having formula (1b), those having the formula (1c) are even more preferred.

(1c)

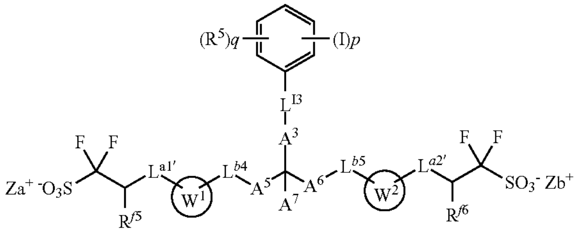

In formula (1c), $A^3$, $L^{a1'}$, $L^{a2'}$, $L^{b3}$, $R^5$, $R^f$, $R^{f6}$, p, q, $Za^+$, and $Zb^+$ are as defined above.

In formula (1c), $L^{b4}$ and $L^{b5}$ are each independently an ether bond or ester bond, preferably an ester bond.

In formula (1c), $A^5$ and $A^6$ are each independently a $C_1$-$C_4$ straight hydrocarbylene group, preferably methylene or ethylene.

In formula (1c), $A^7$ is hydrogen, hydroxy, or a $C_1$-$C_8$ alkyl group. Preferably, $A^7$ is hydrogen or hydroxy.

In formula (1c), the rings $W^1$ and $W^2$ are each independently a $C_3$-$C_{10}$ alicyclic hydrocarbon group which may contain a heteroatom. Suitable alicyclic hydrocarbon groups include $C_6$-$C_{10}$ alicyclic saturated hydrocarbon groups such as cyclohexanediyl, cycloheptanediyl, and cyclooctanediyl and $C_6$-$C_{10}$ aromatic hydrocarbon groups such as phenylene, xylylene, and naphthylene. Preferably, the rings $W^1$ and $W^2$ are $C_6$-$C_{10}$ alicyclic saturated hydrocarbon groups.

Of the PAGs, those compounds having formula (1c) wherein $Za^+$ and $Zb^+$ each are a sulfonium cation having formula (Z-1) or (Z-2) are preferred.

Examples of the anion in the onium salt having formula (1) are shown below, but not limited thereto. Herein, p is an integer of 1 to 5, q is an integer of 0 to 4, 1≤p+q≤5, s is an integer of 1 to 4, and t is an integer of 1 to 4.

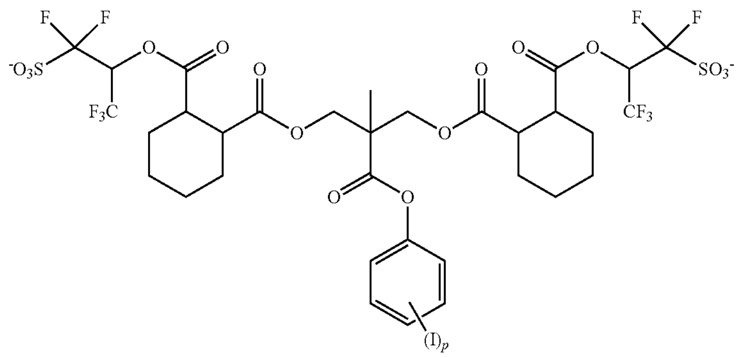
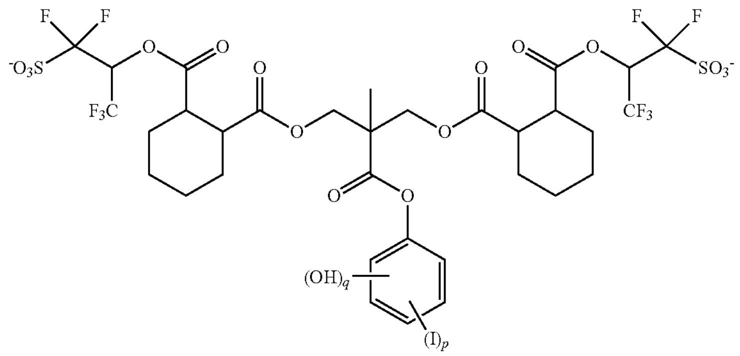
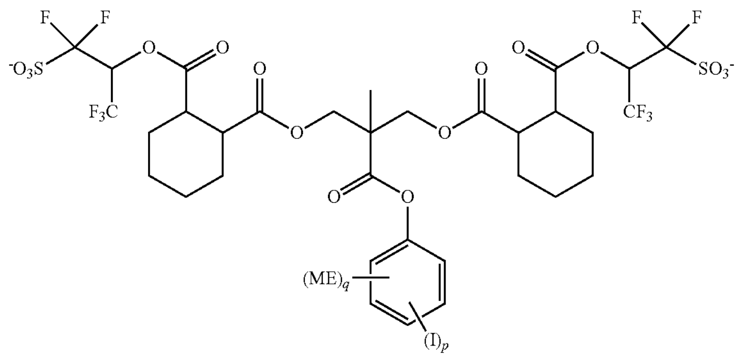
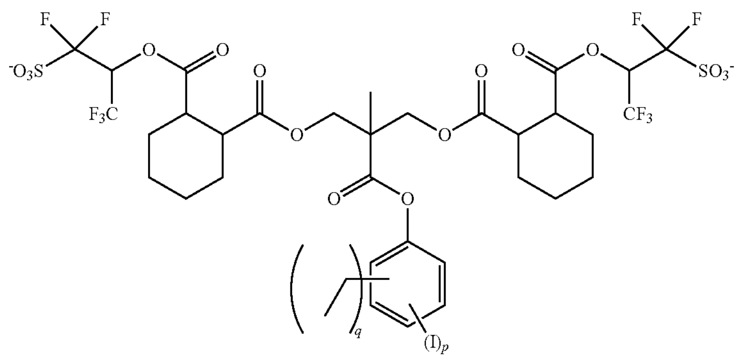

-continued
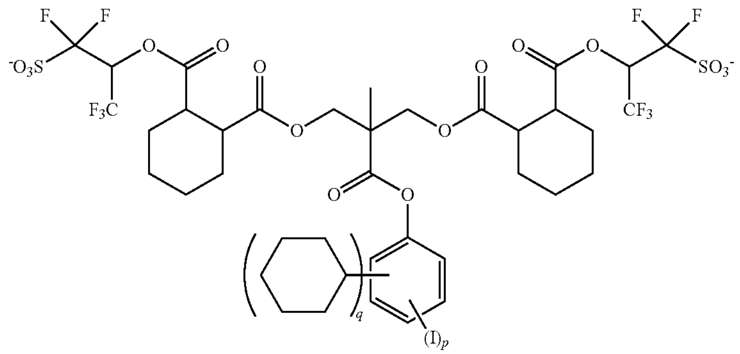
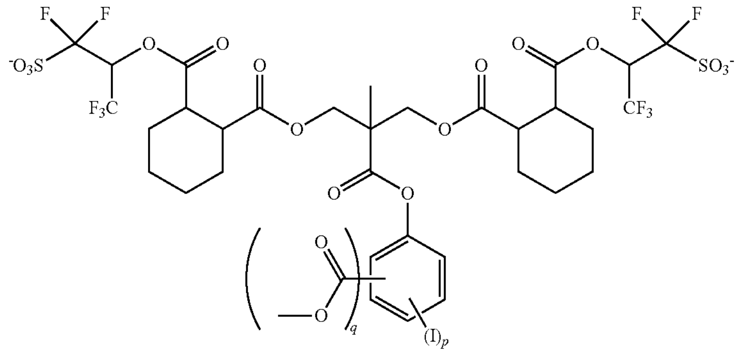
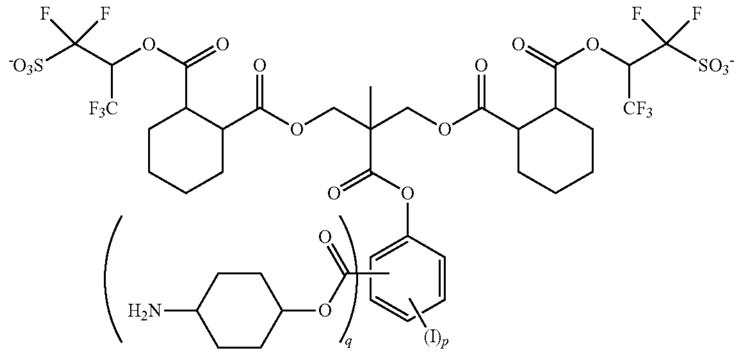
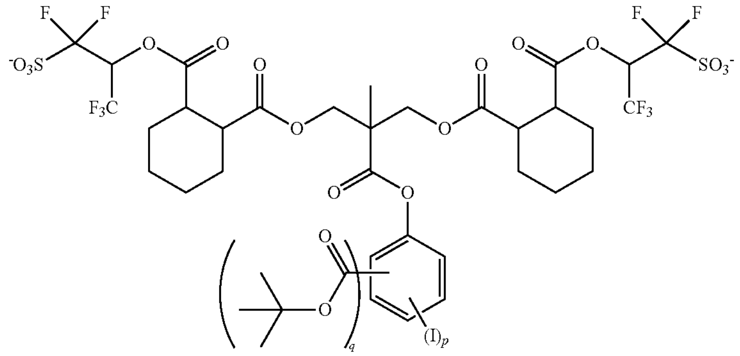

-continued
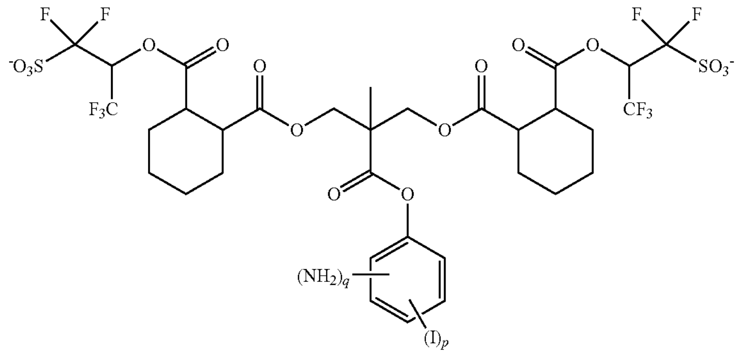
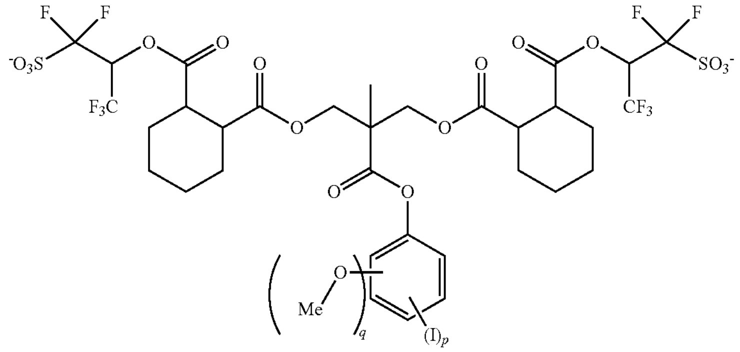
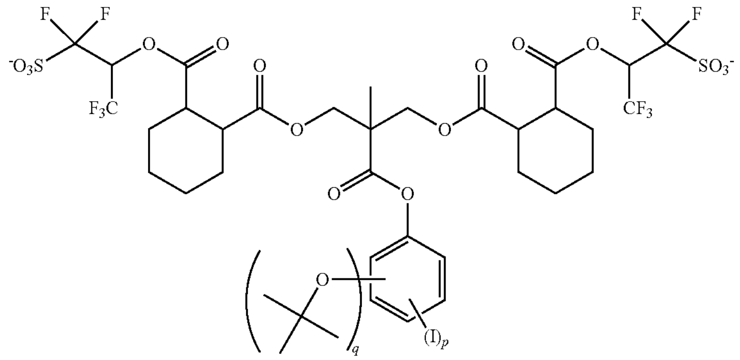
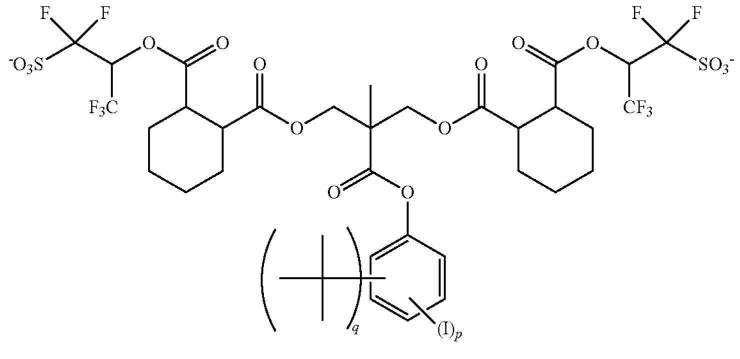

-continued
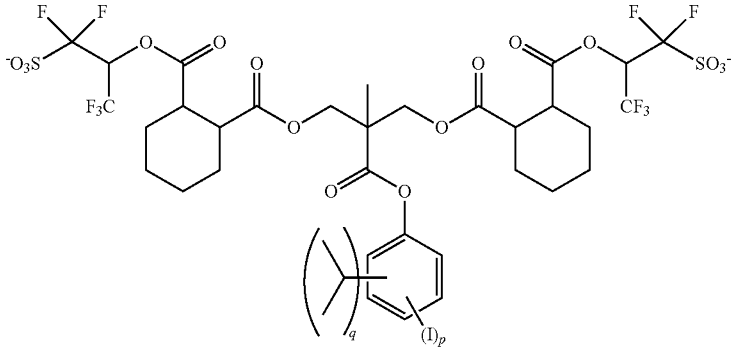
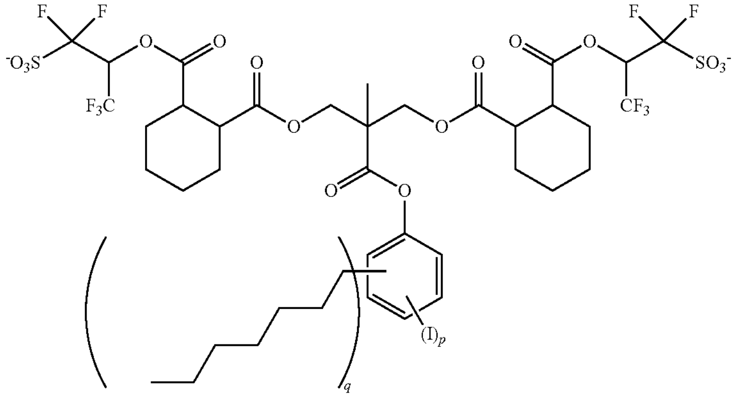
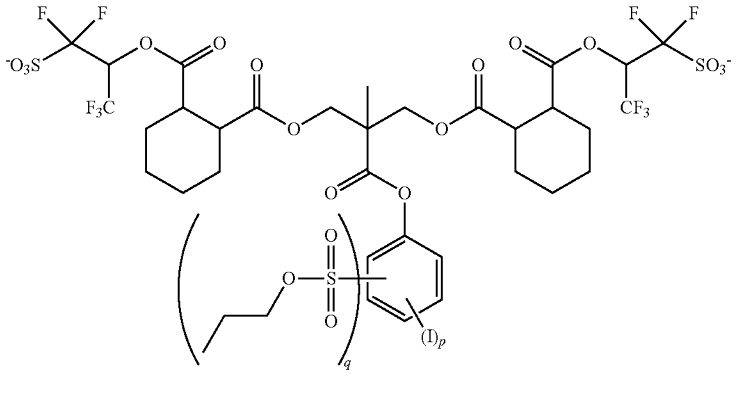
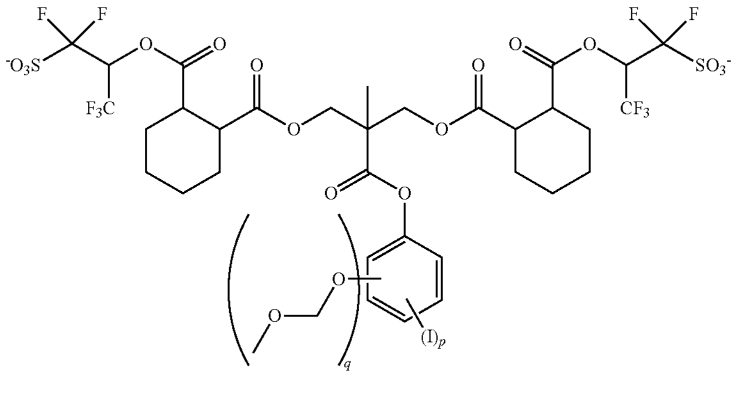

-continued
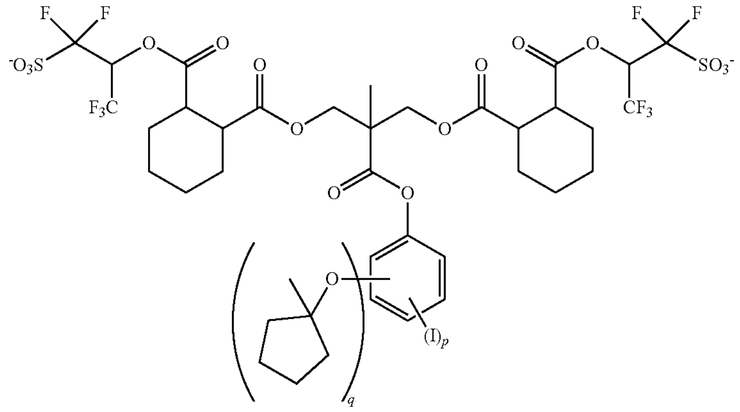
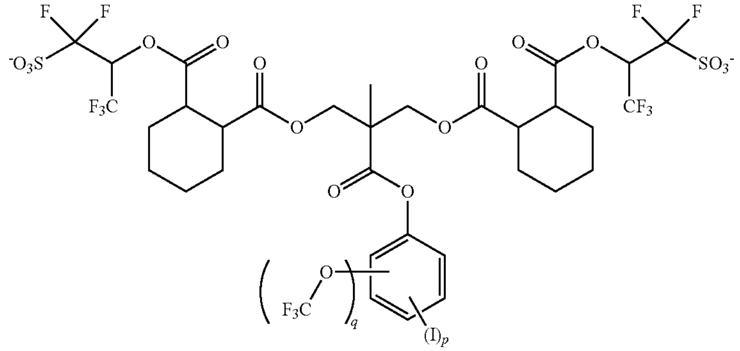
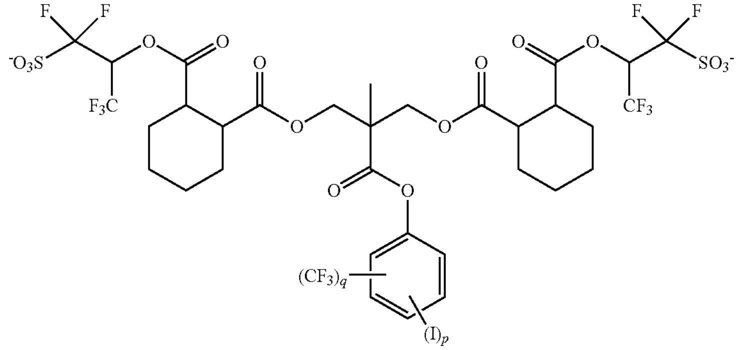
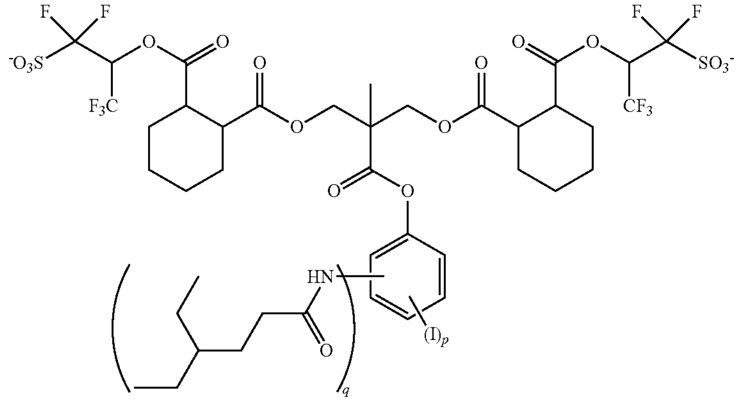

-continued
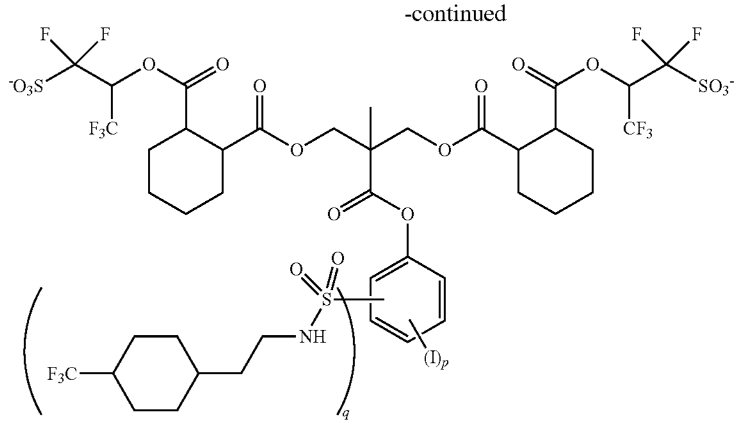
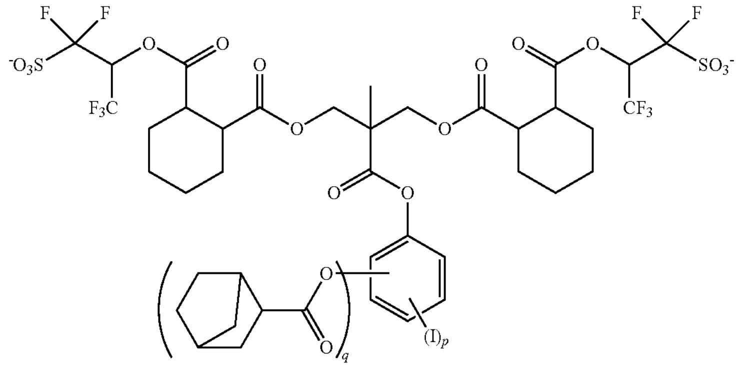
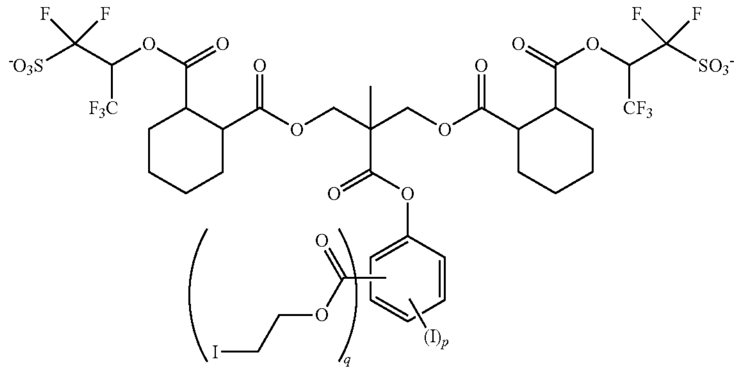
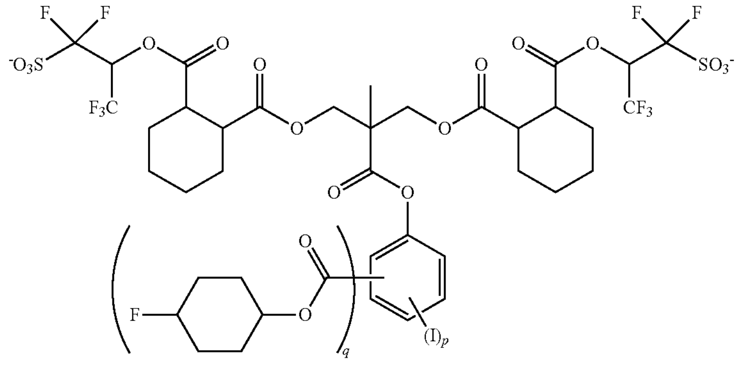

-continued
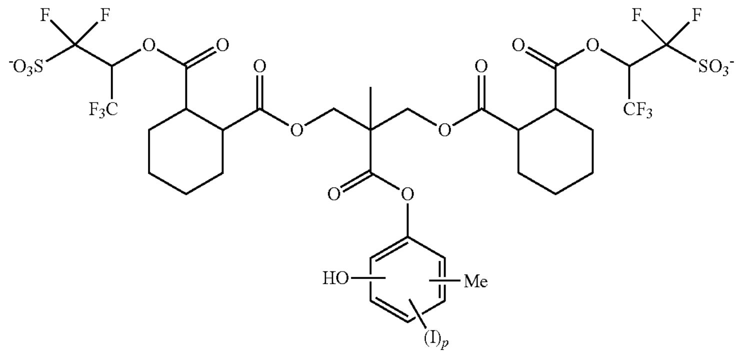
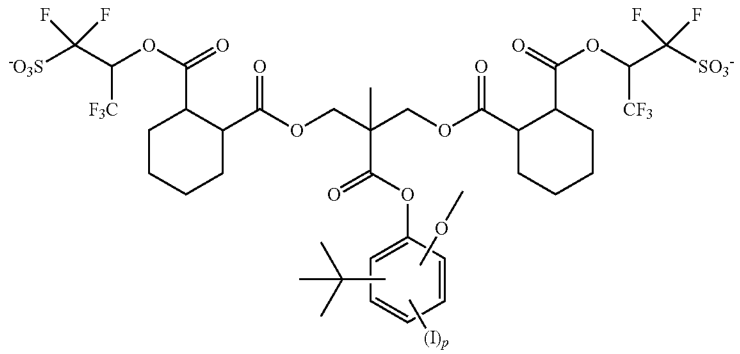
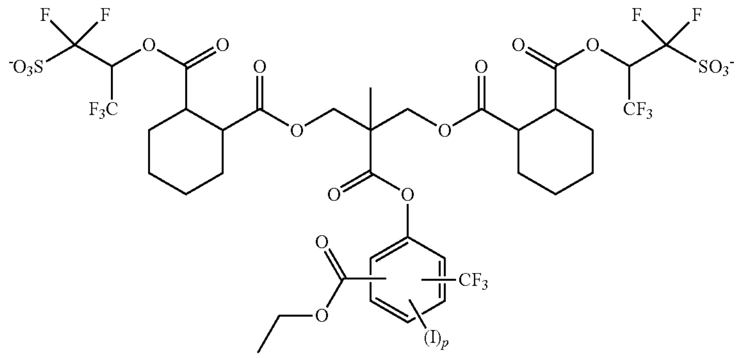
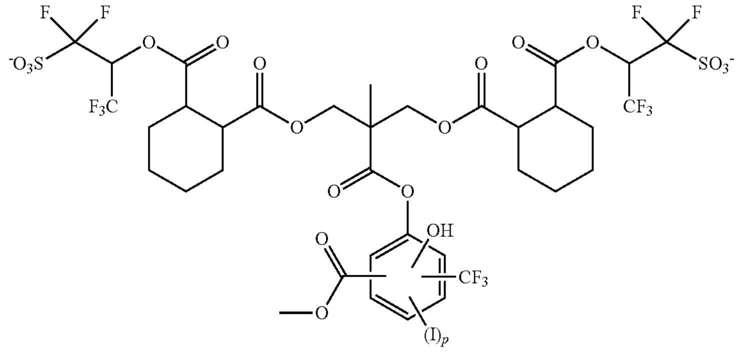

-continued
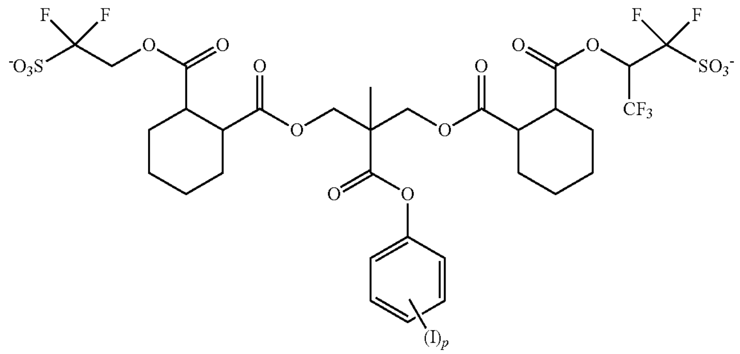
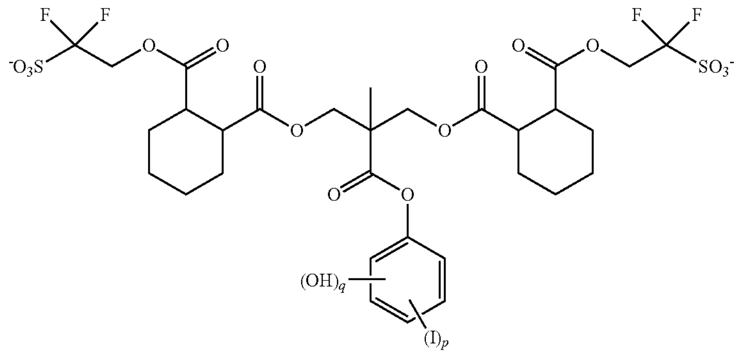
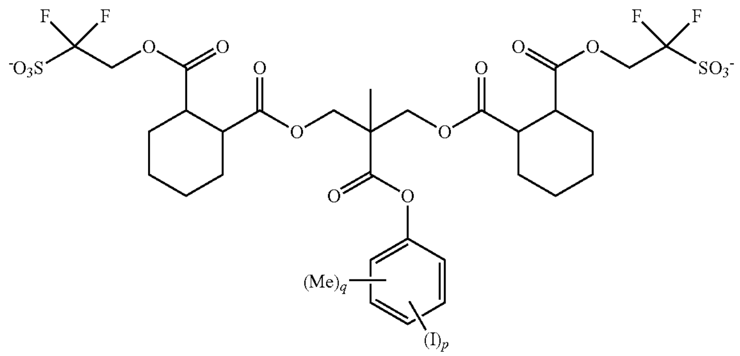
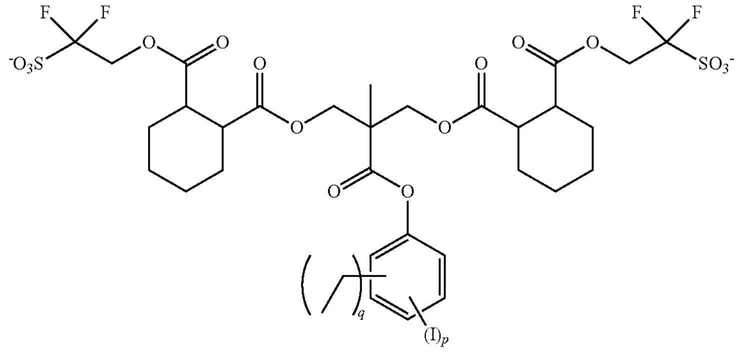

-continued
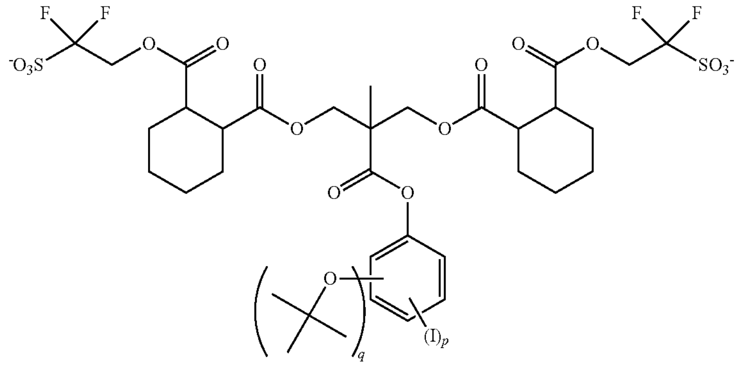
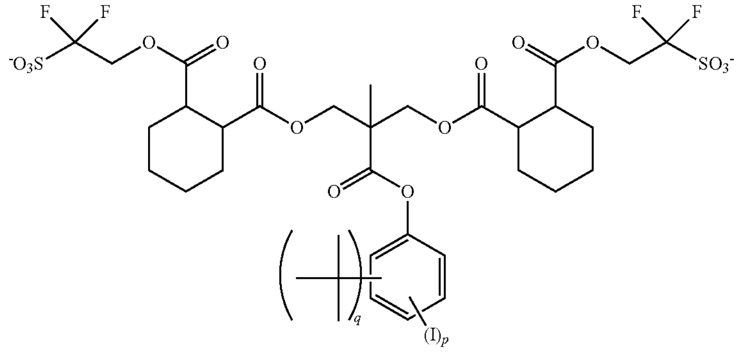
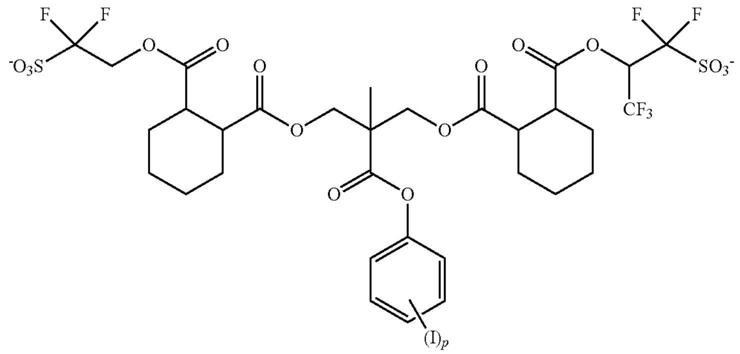
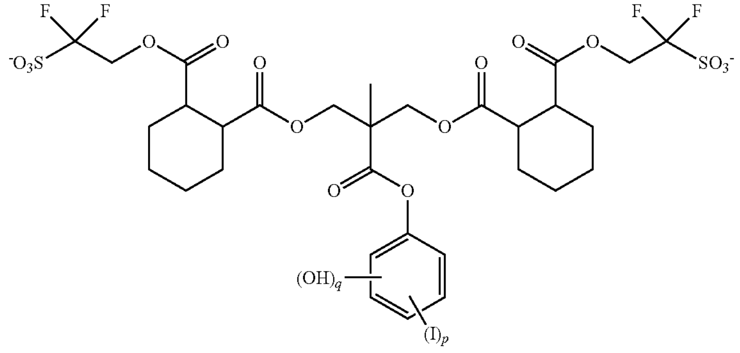

-continued
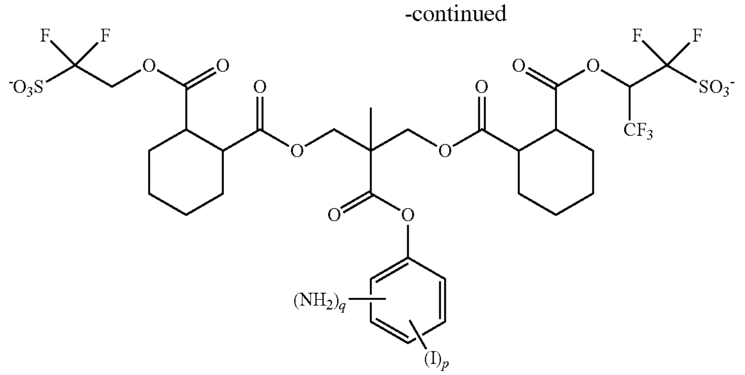
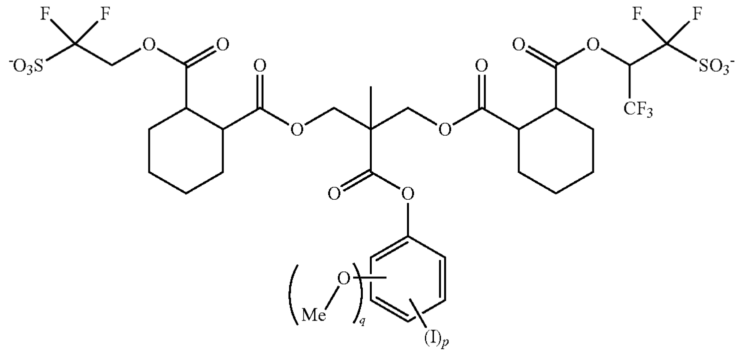
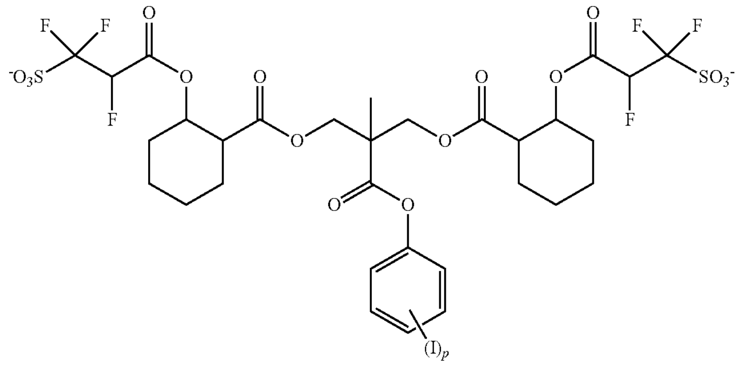
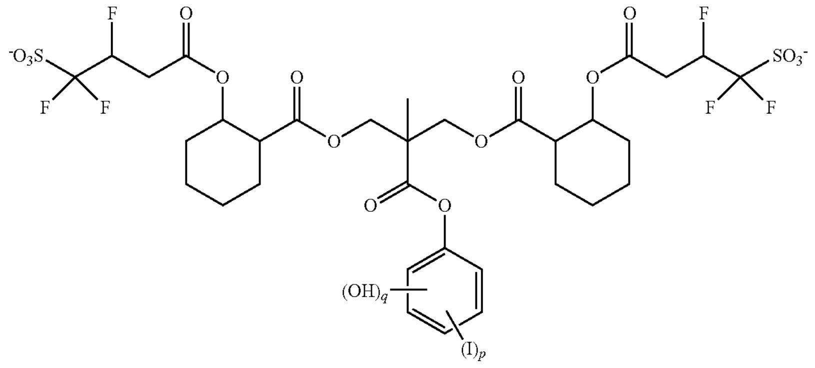

-continued
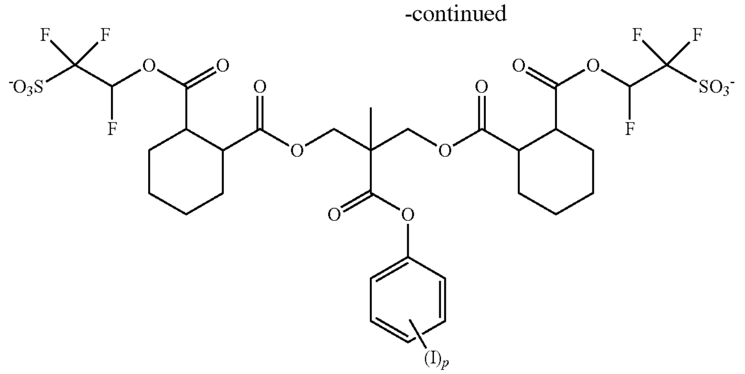
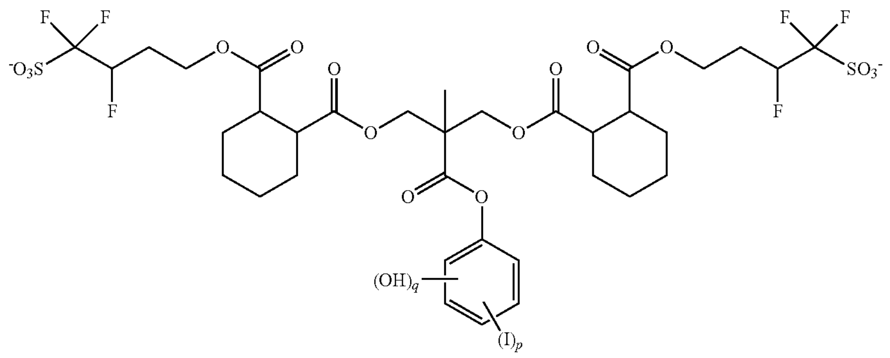
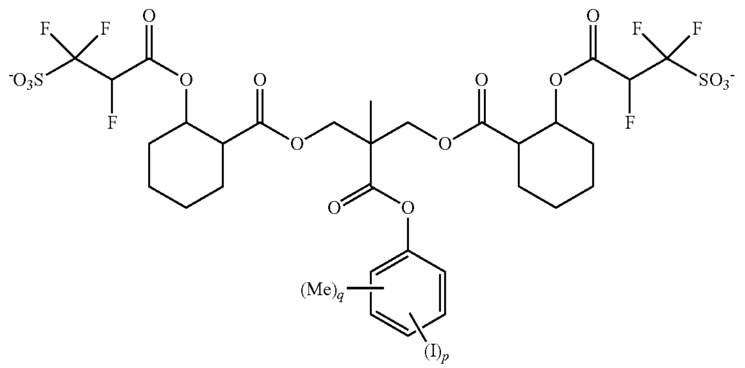
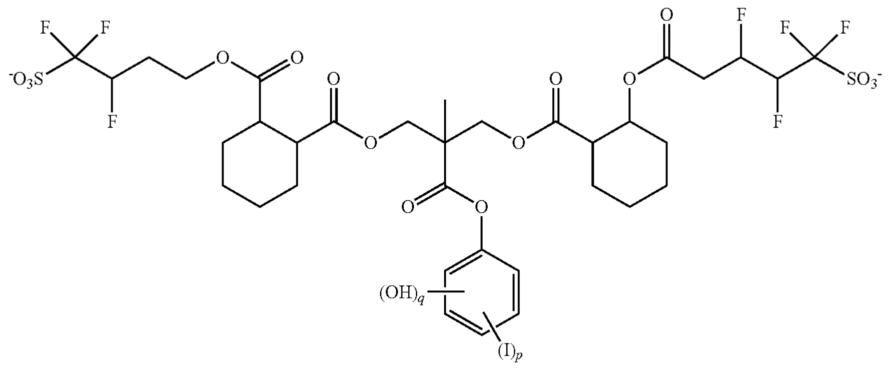

-continued
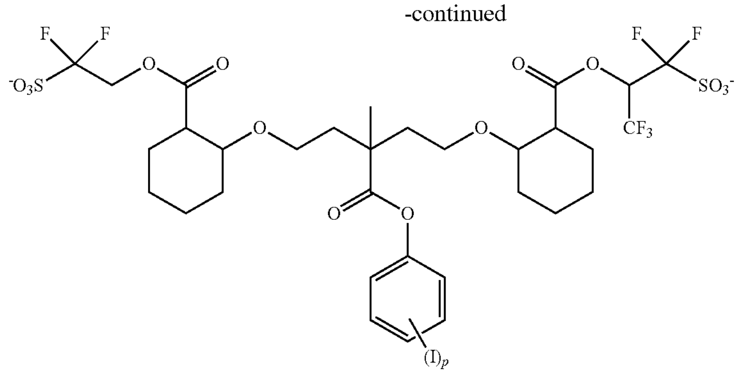
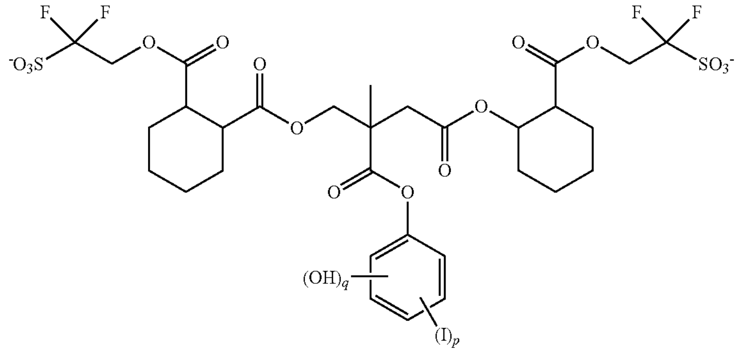
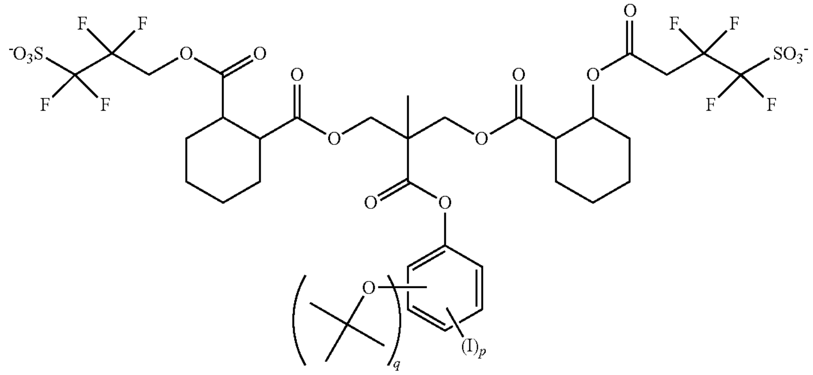
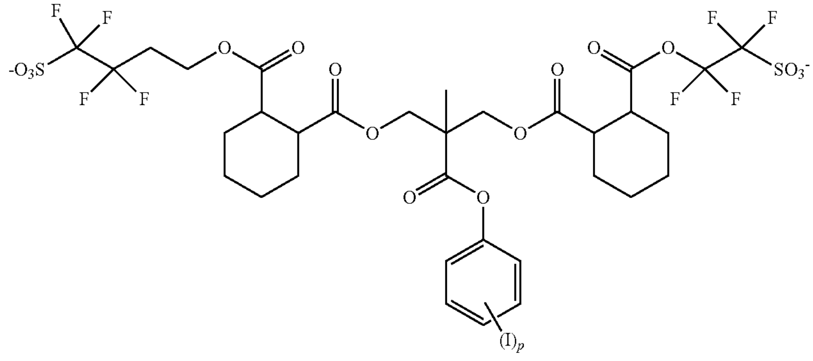

-continued
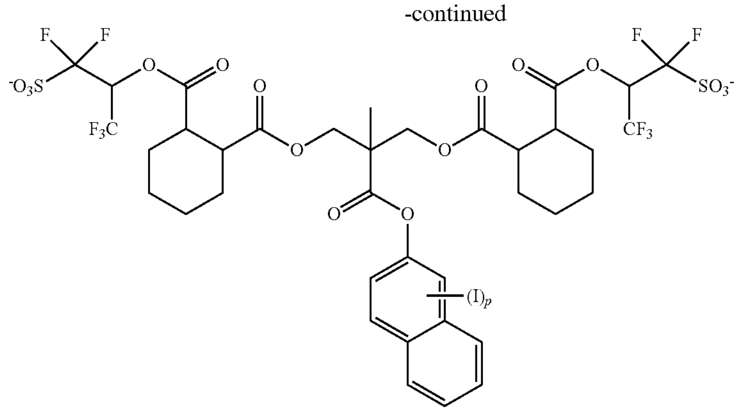
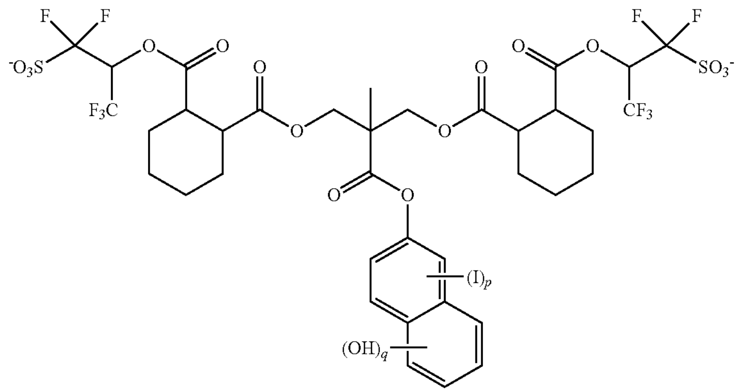
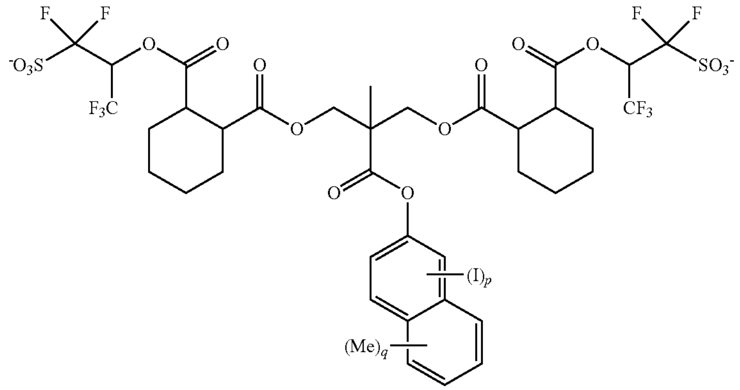
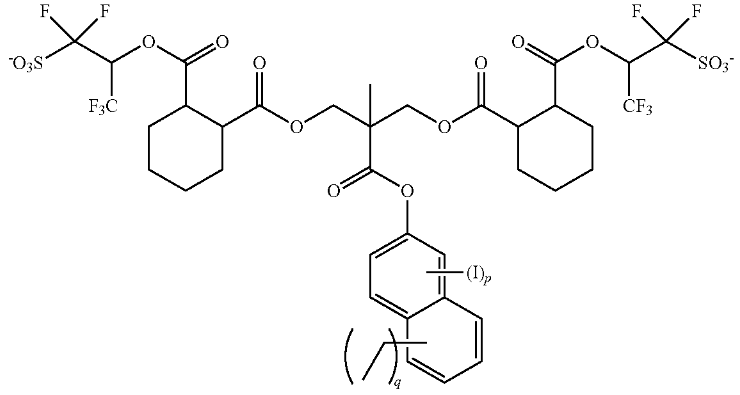

-continued
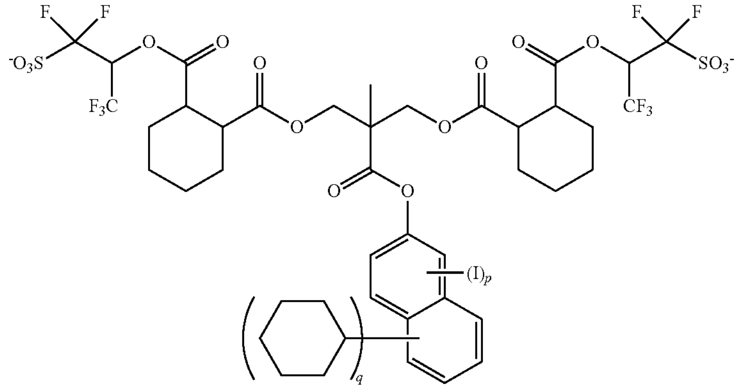
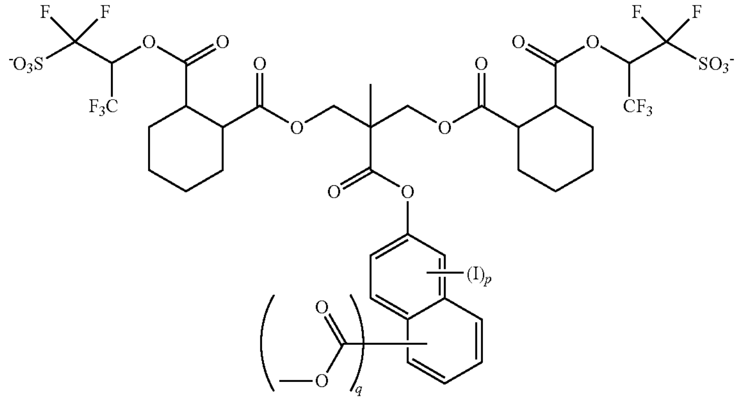
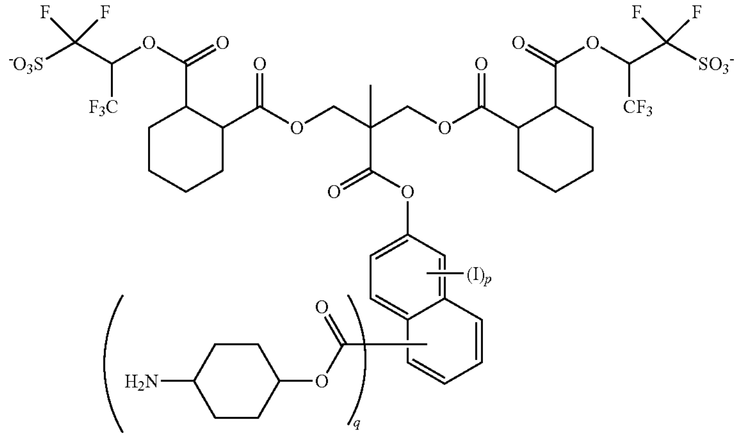
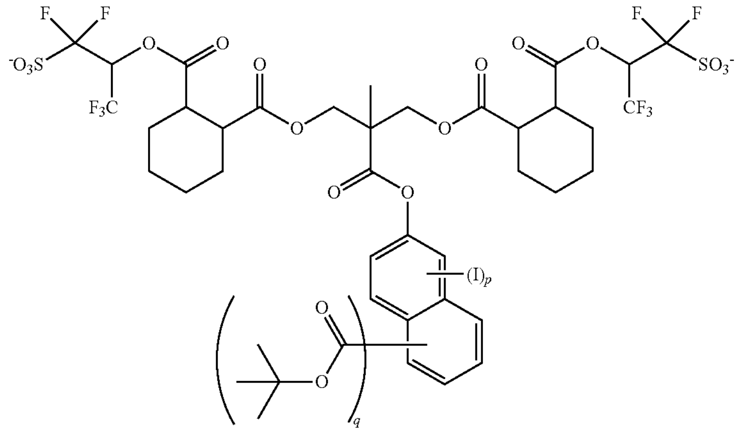

-continued
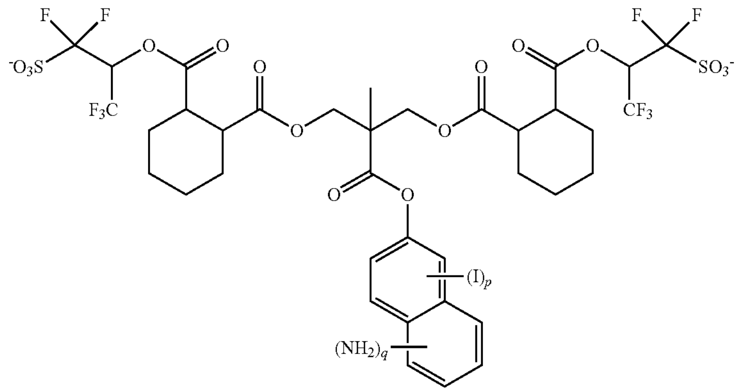
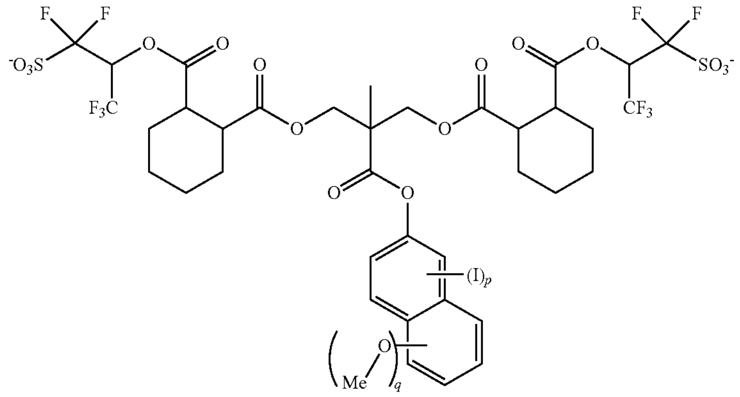
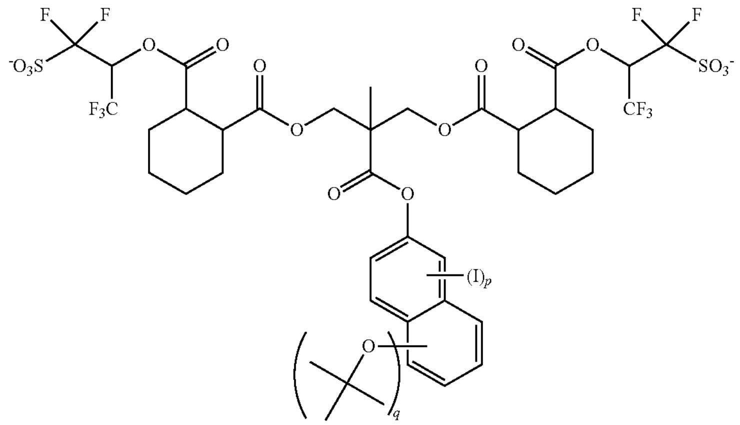
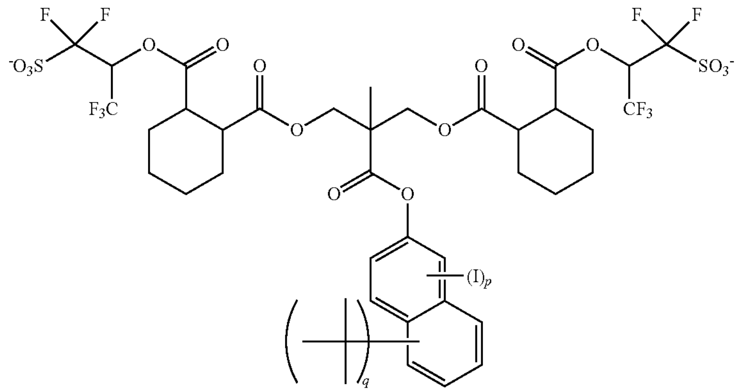

-continued
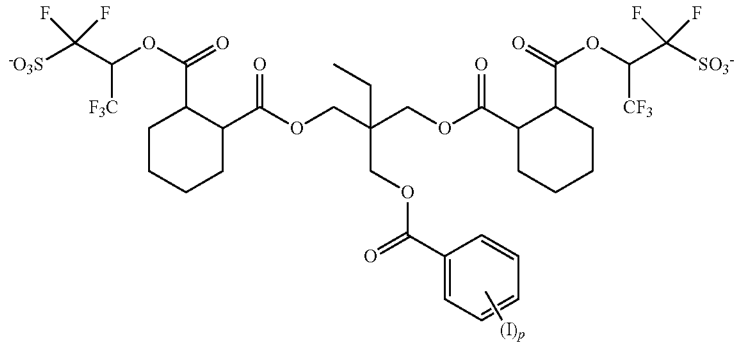
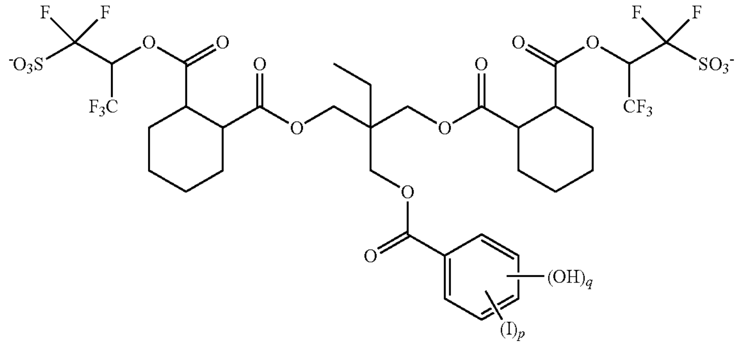
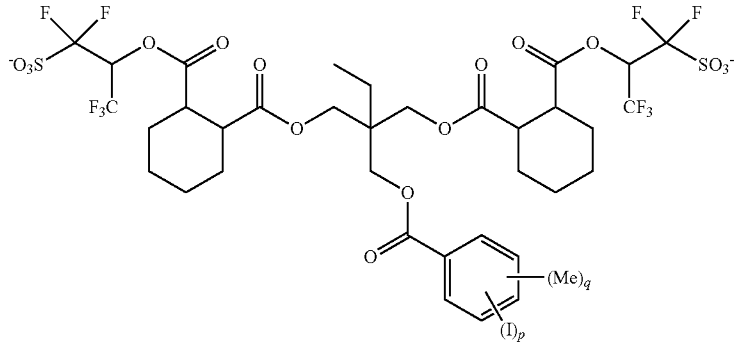
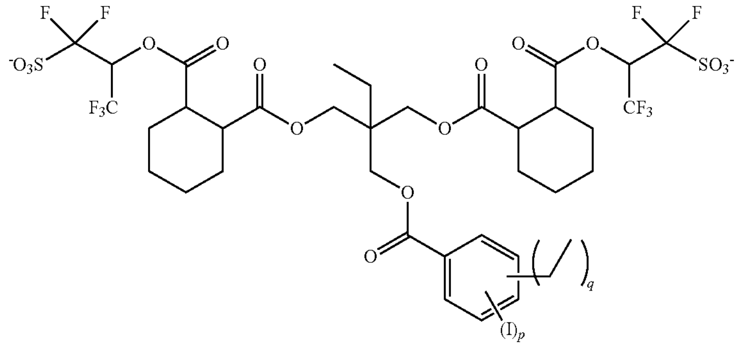
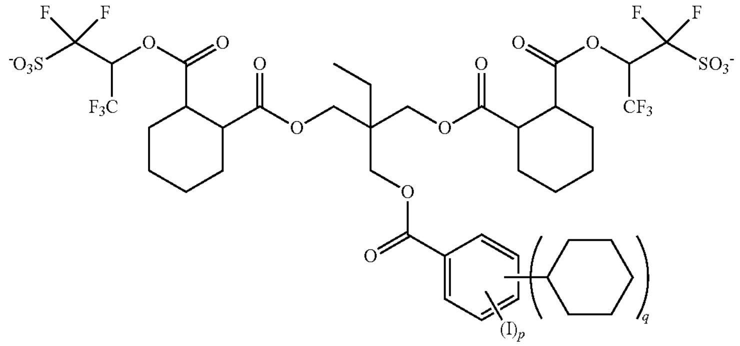

-continued
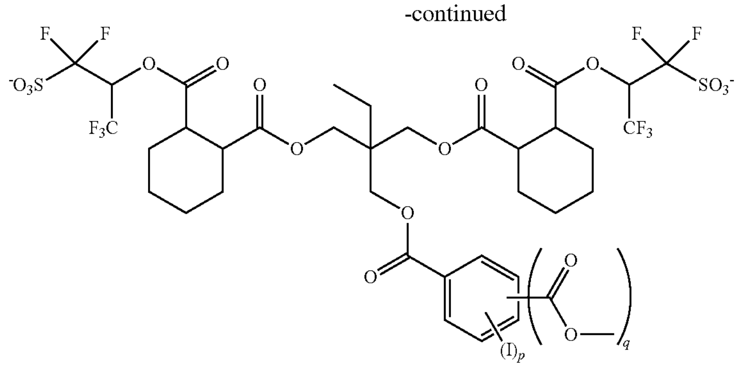
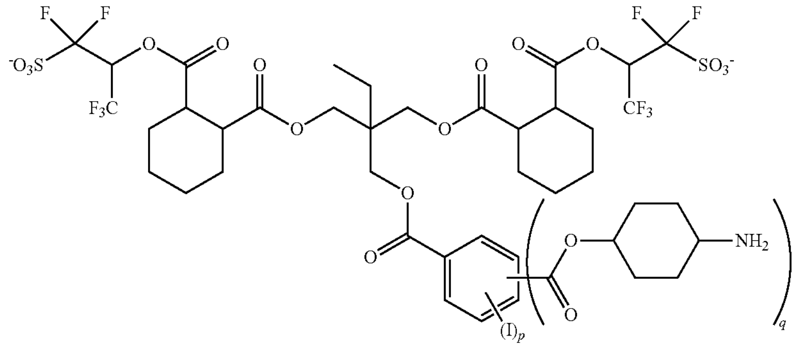
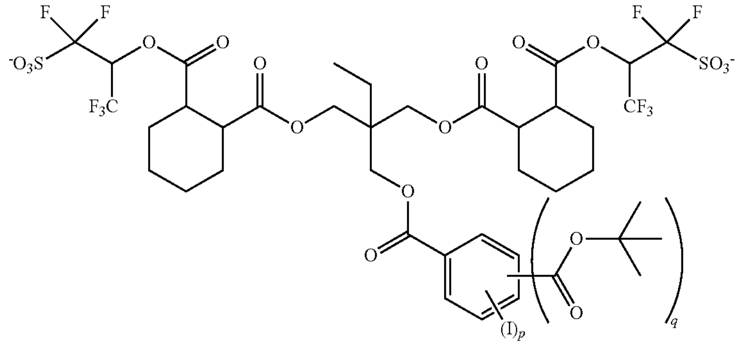
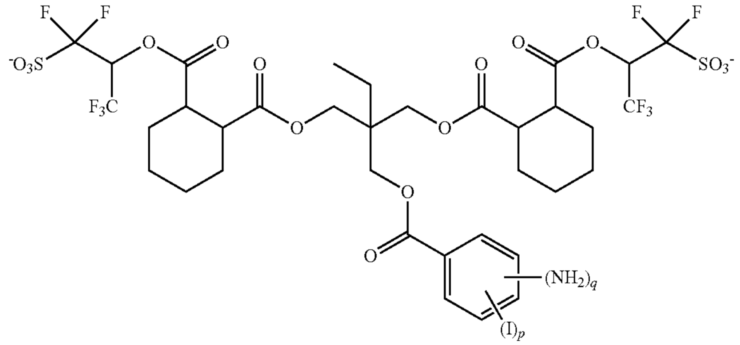
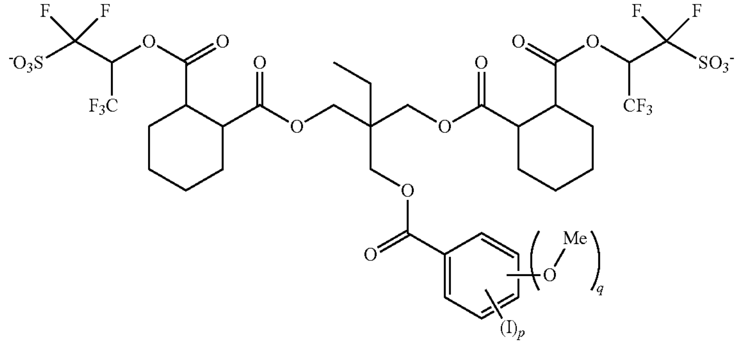

-continued
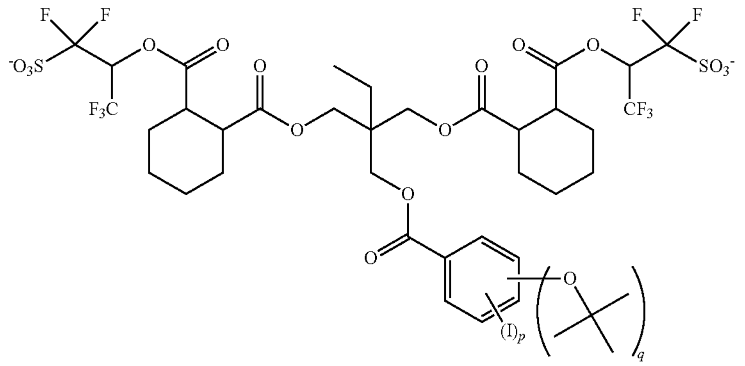
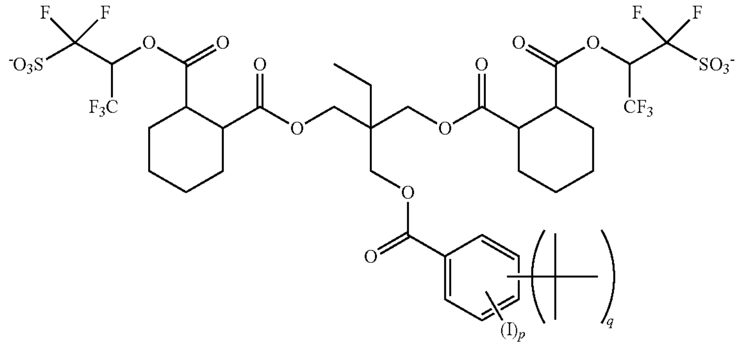
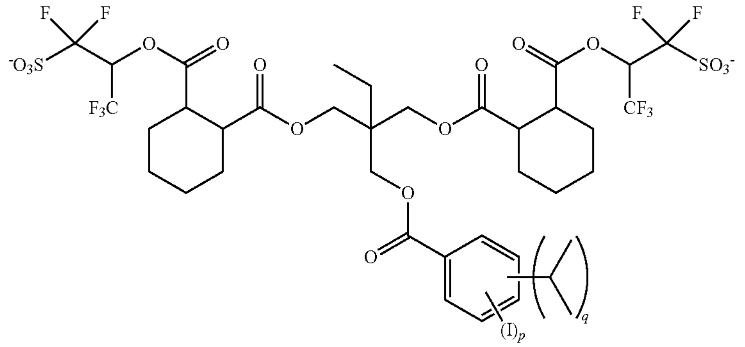
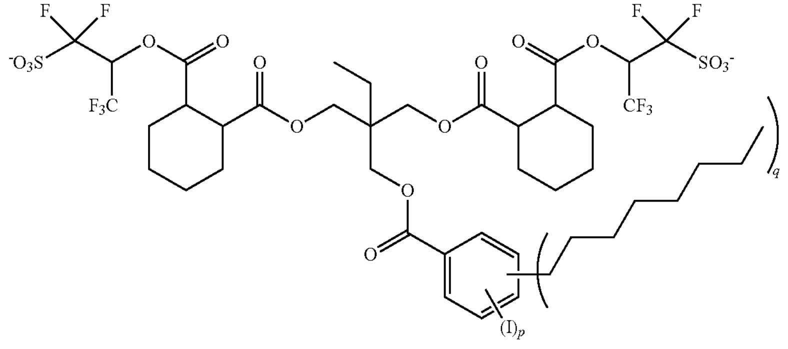

-continued
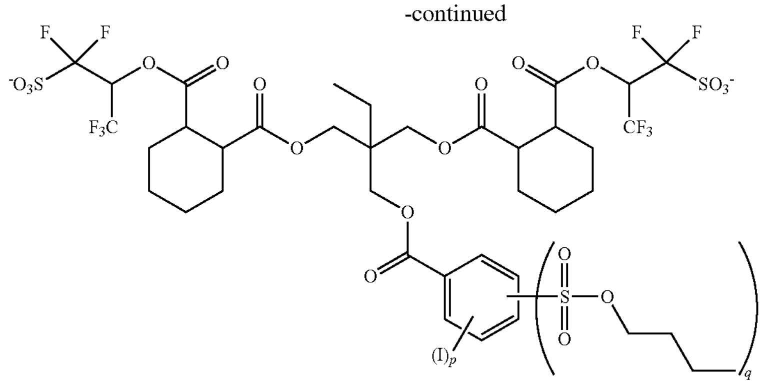
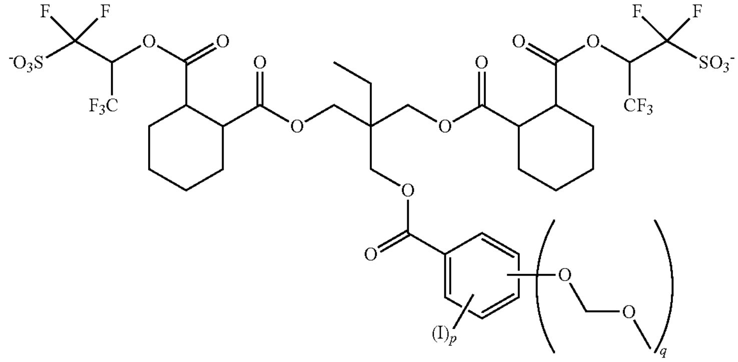
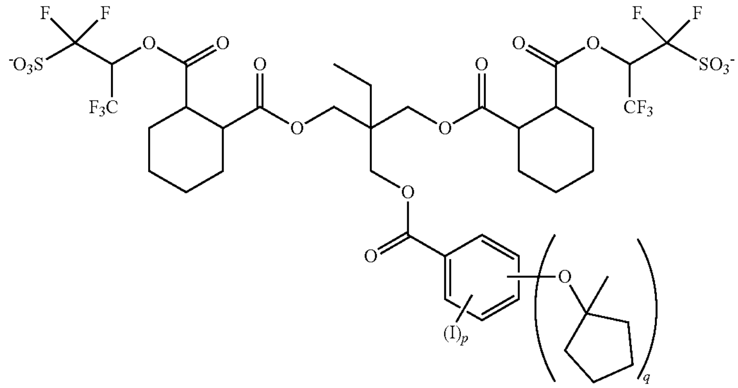
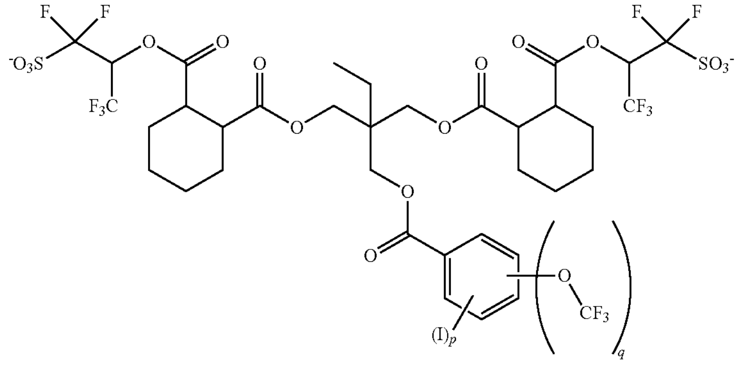

-continued
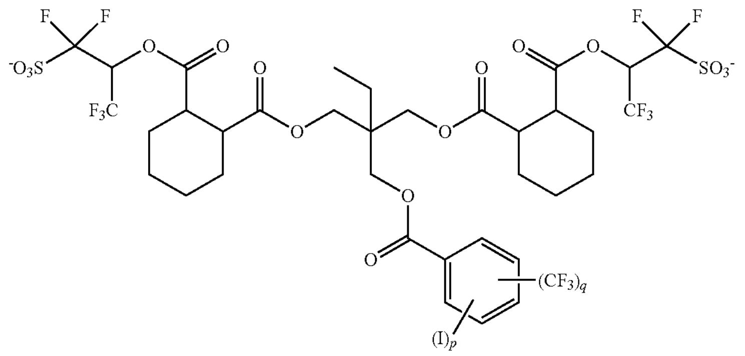
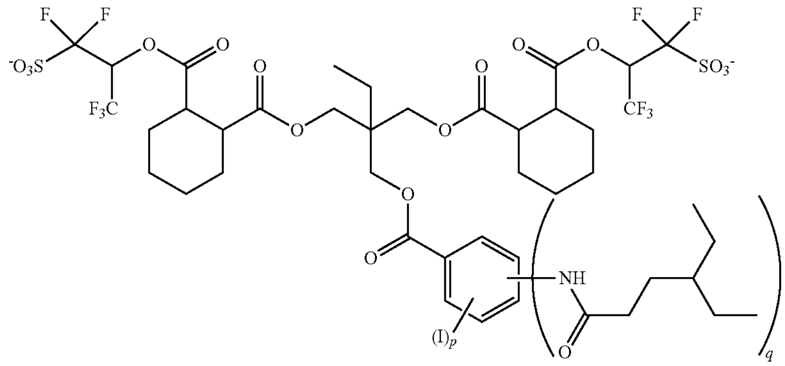
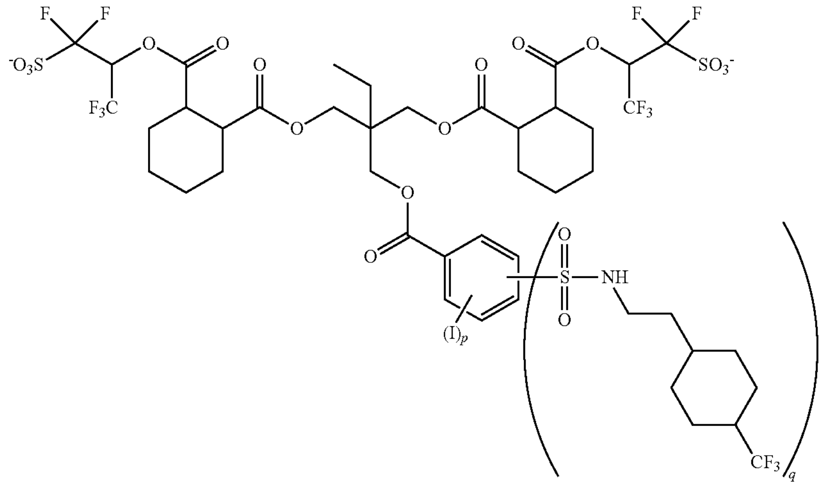
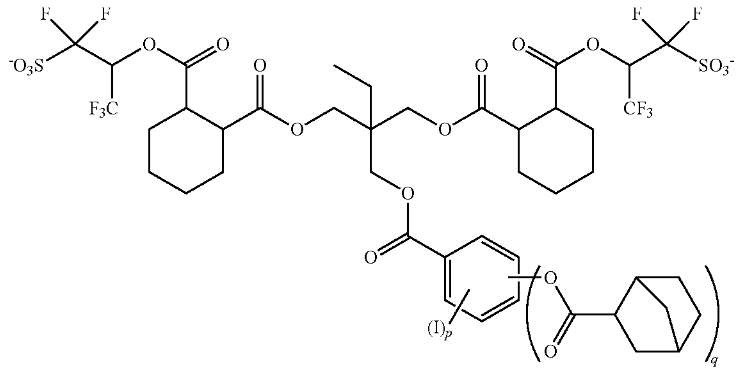

-continued
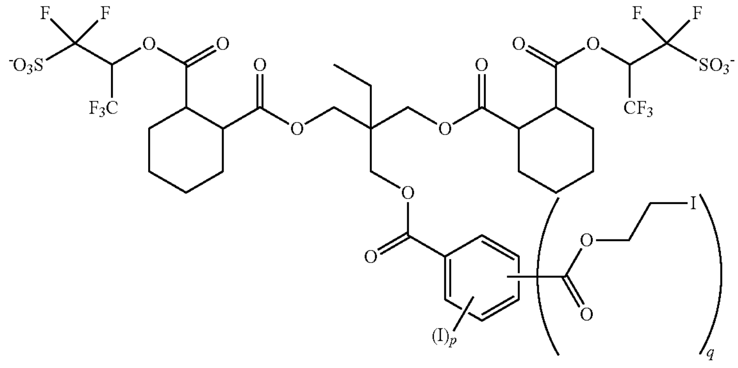
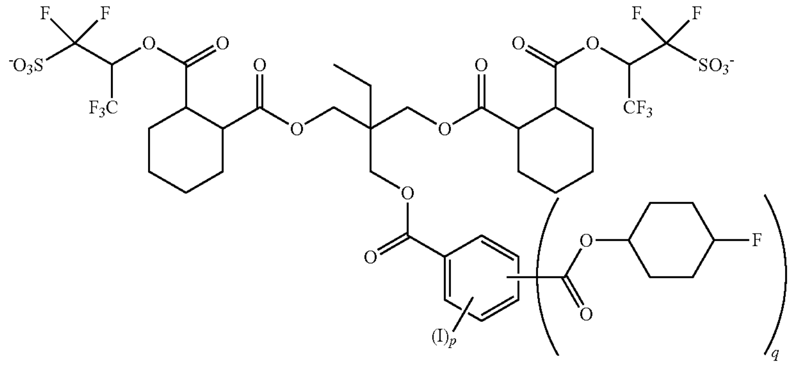
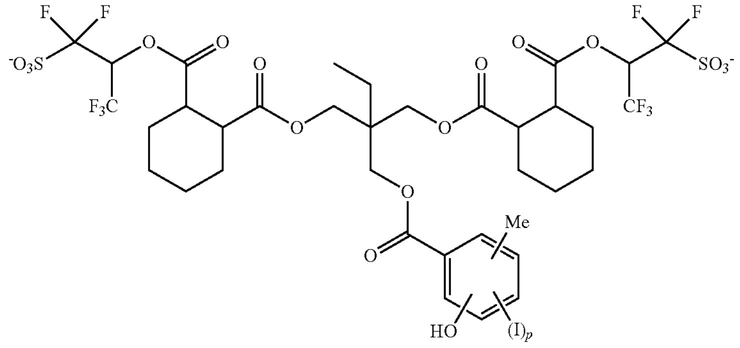
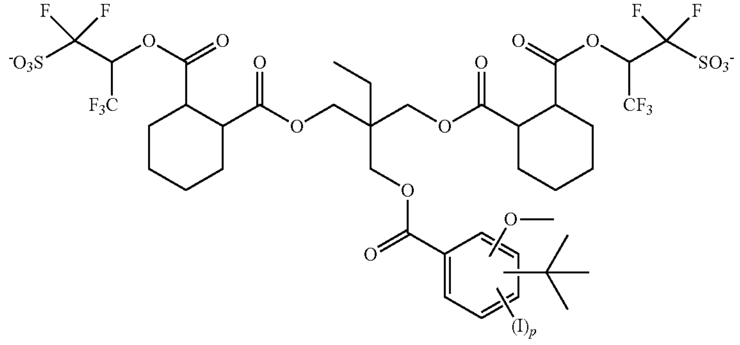

-continued
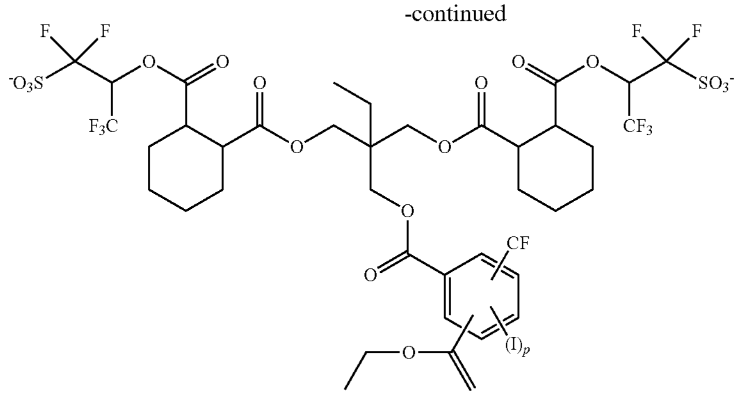
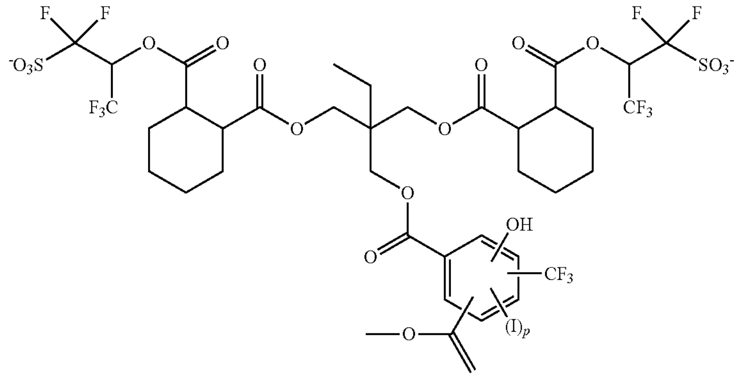
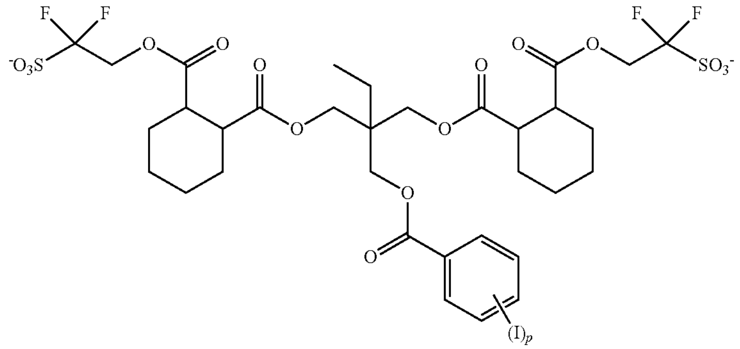
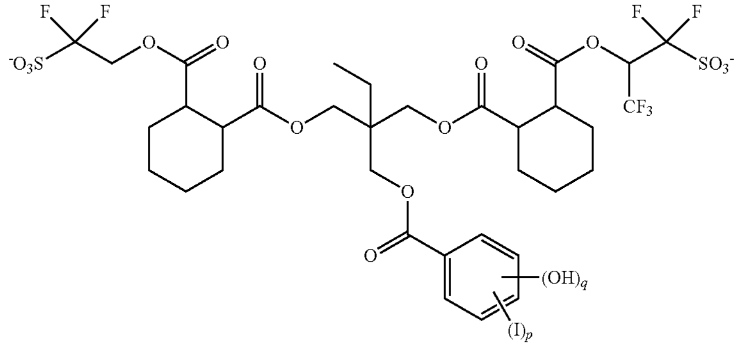

-continued
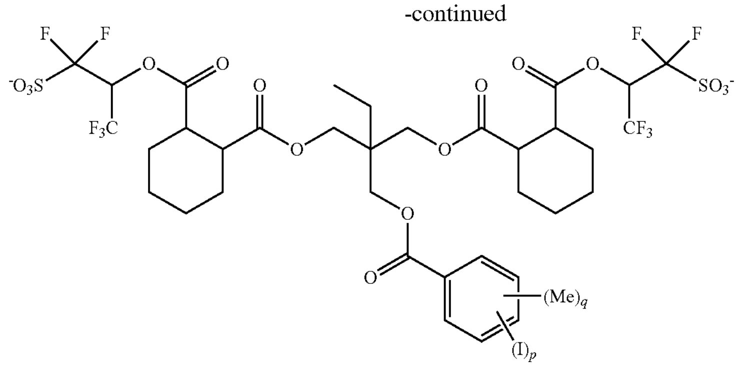
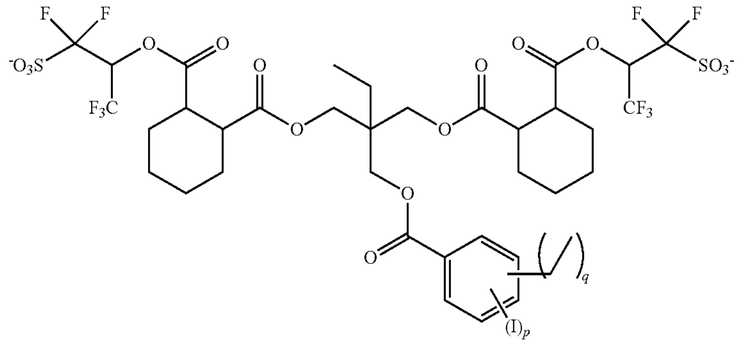
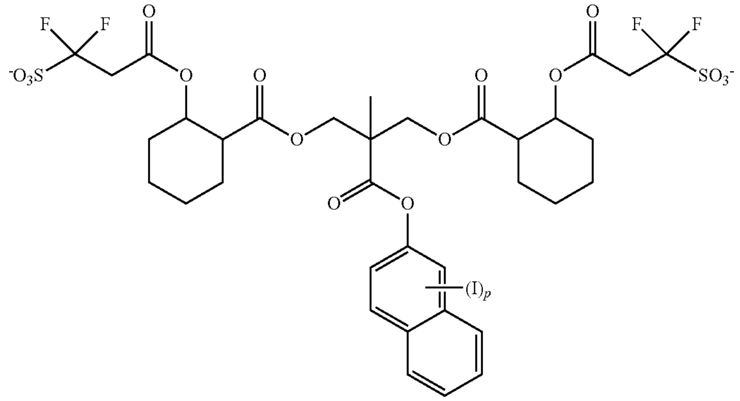
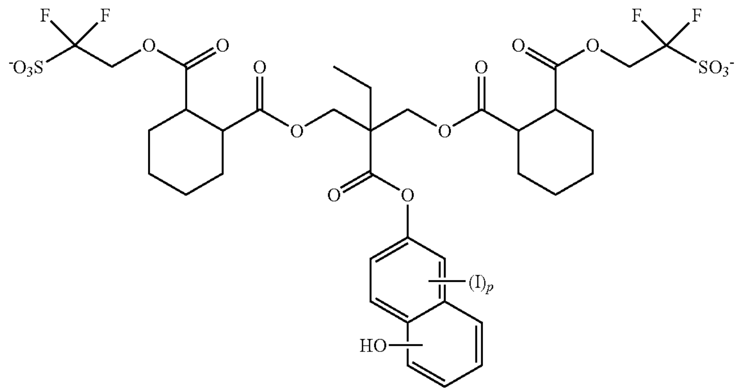

-continued
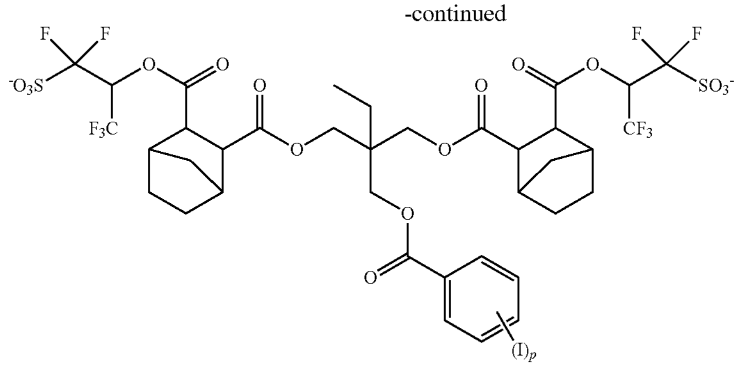
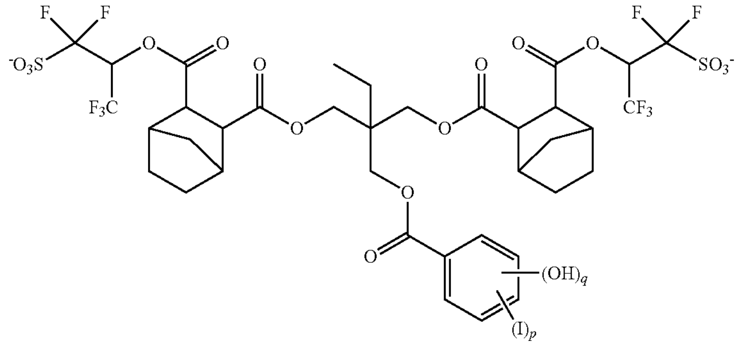
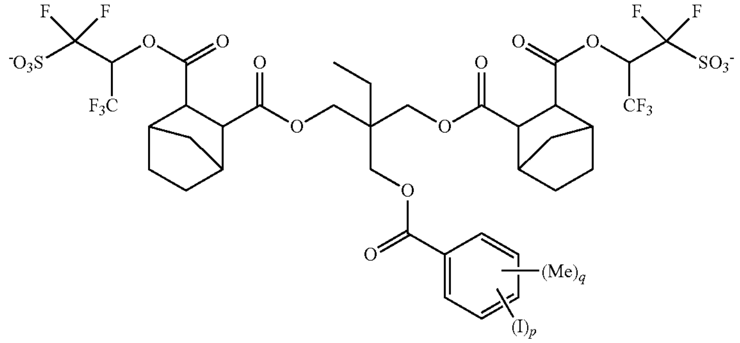
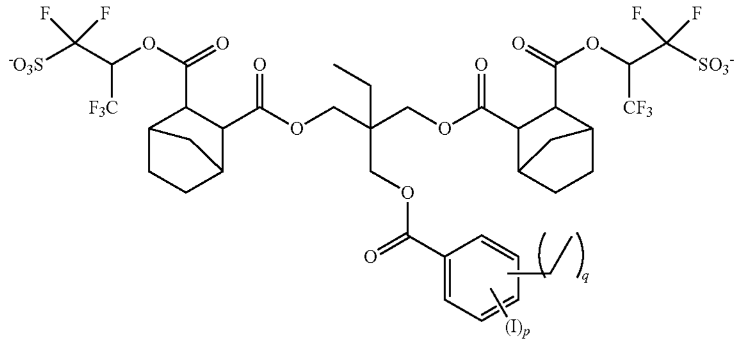
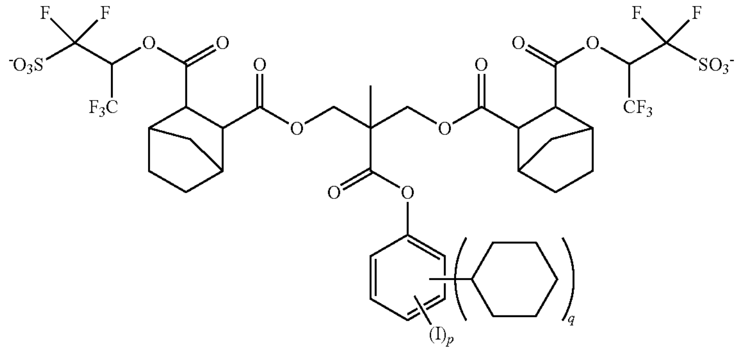

-continued
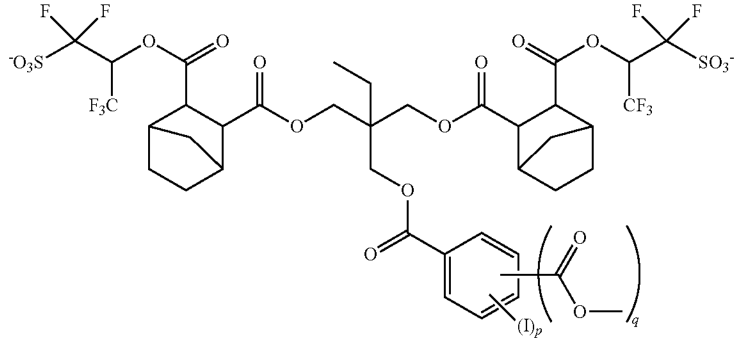
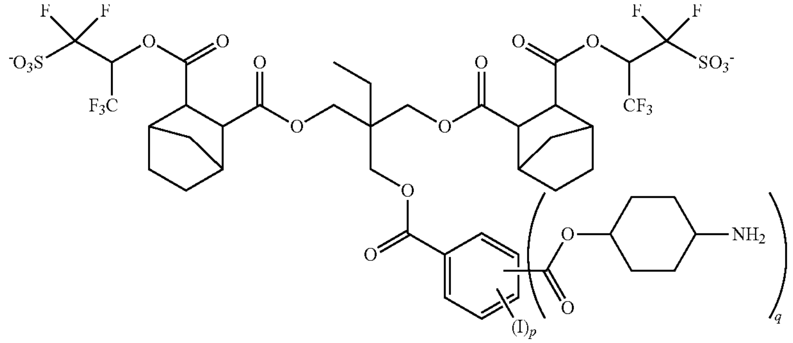
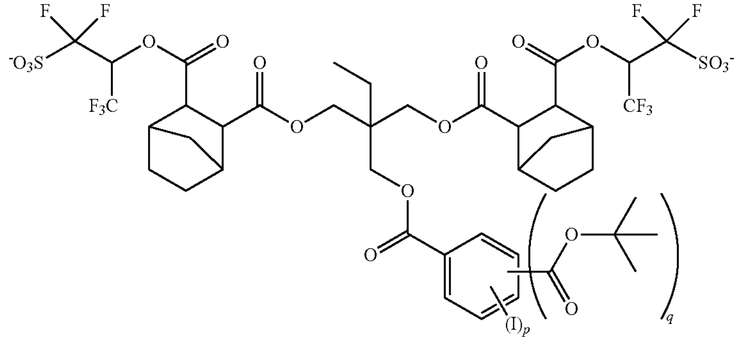
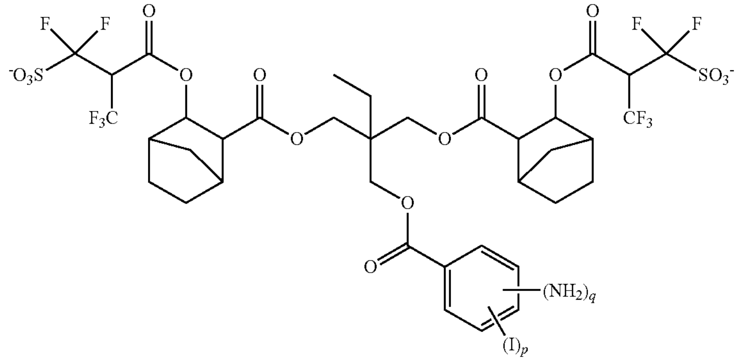
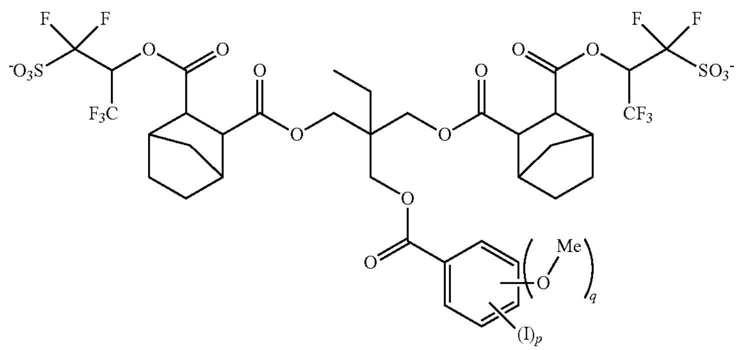

-continued
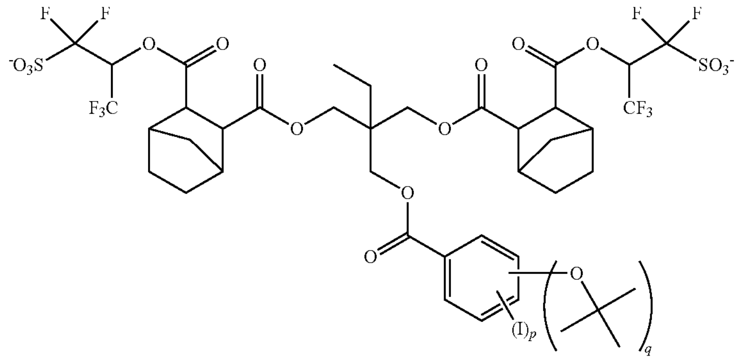
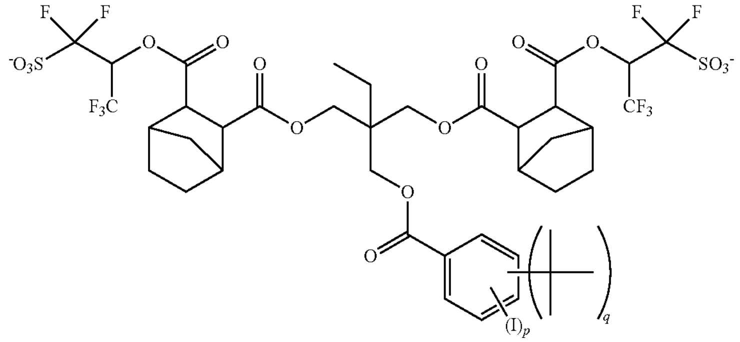
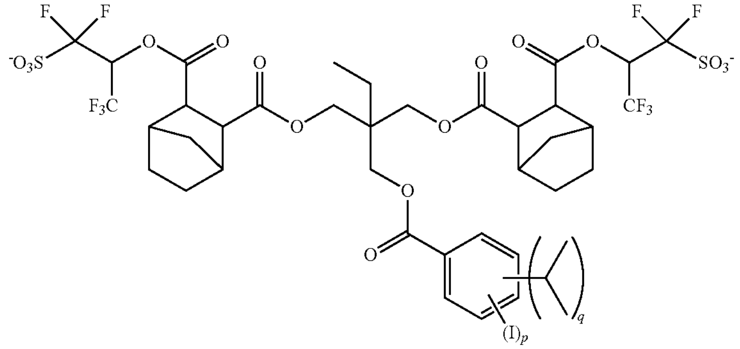
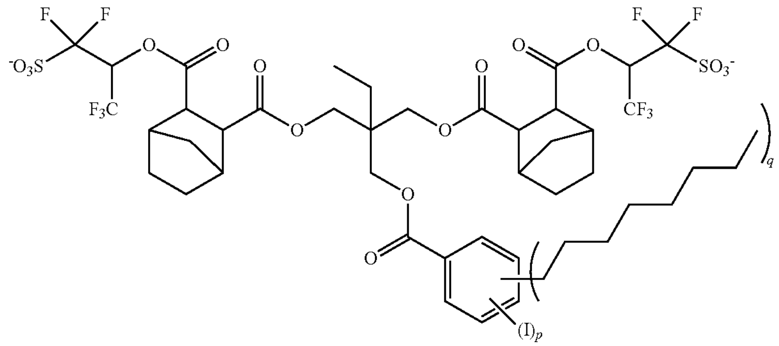

-continued
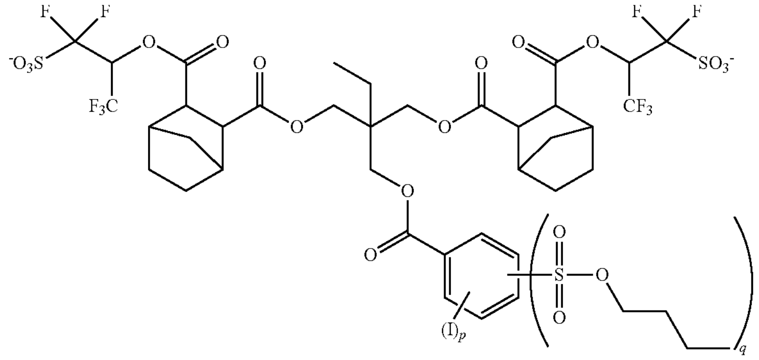
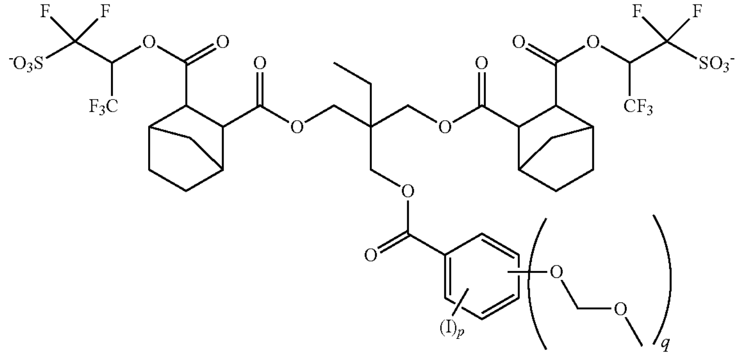
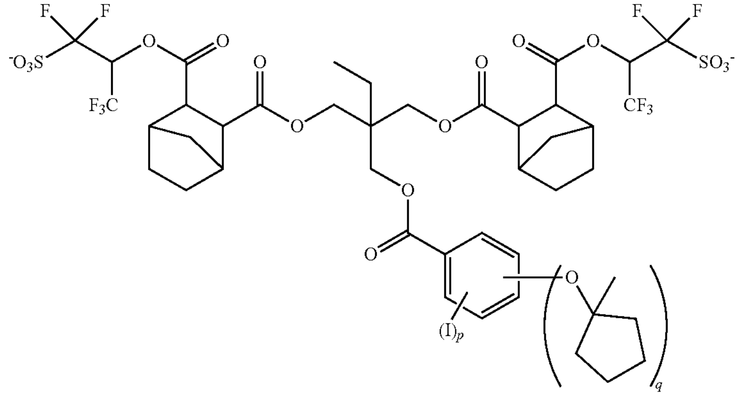
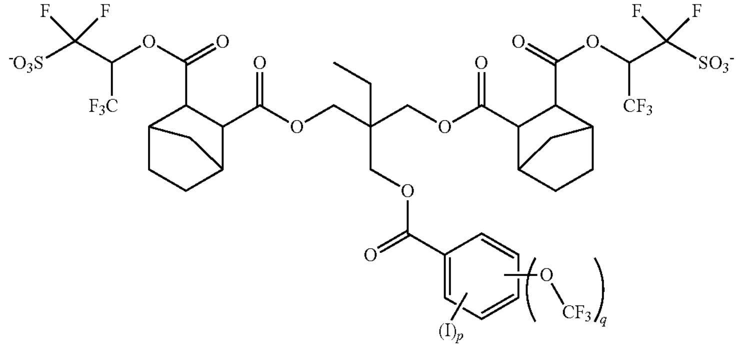

-continued
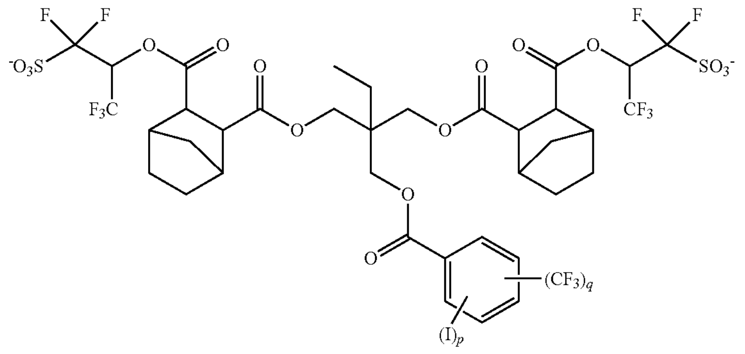
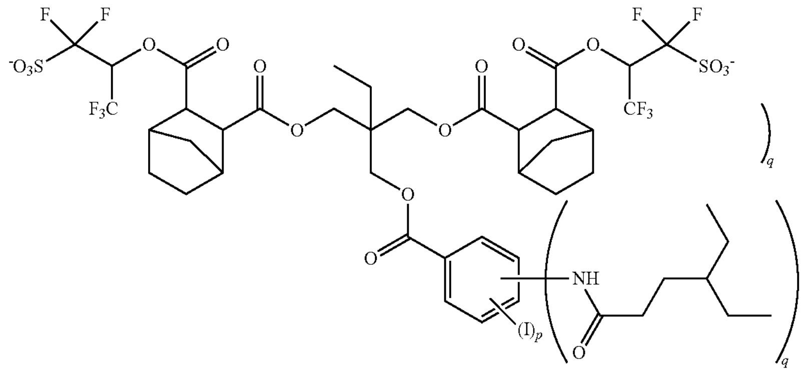
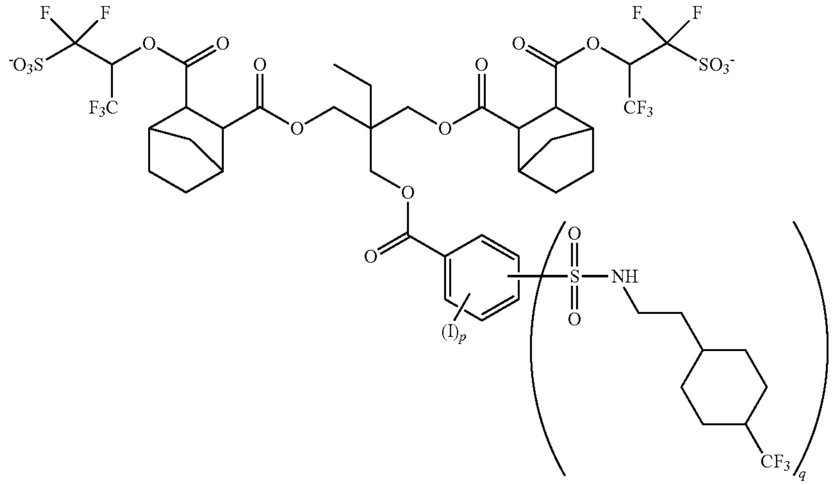
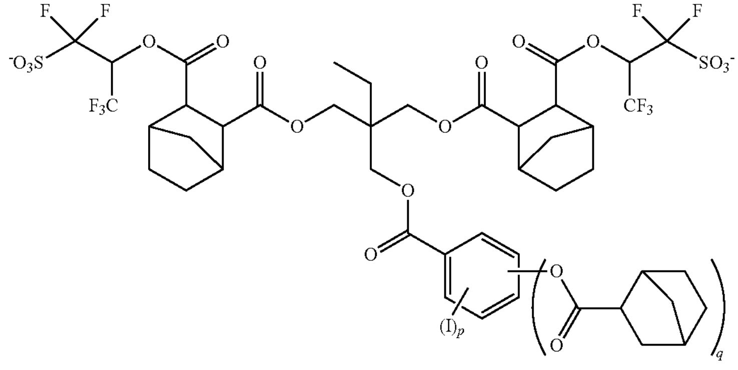

-continued
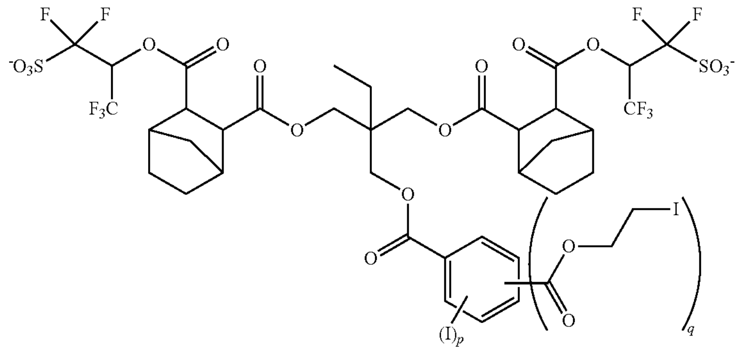
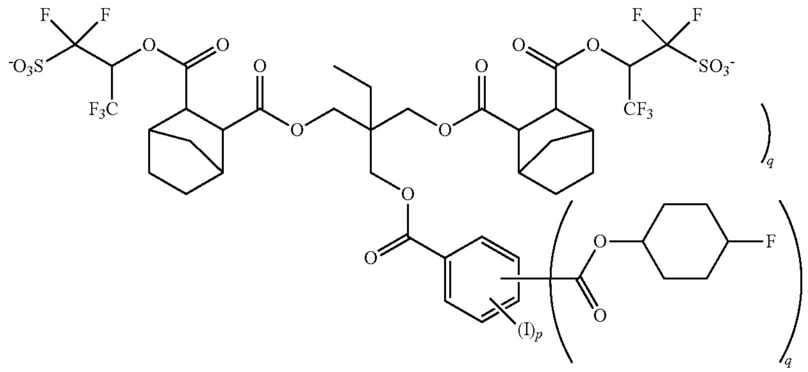
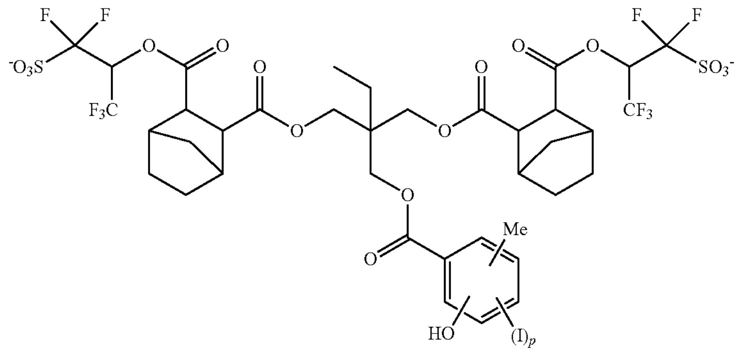
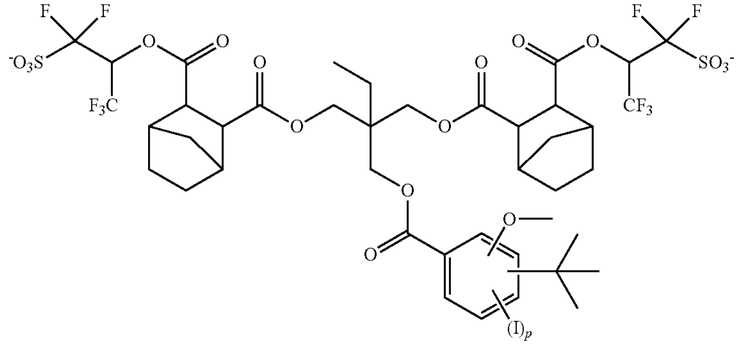

-continued
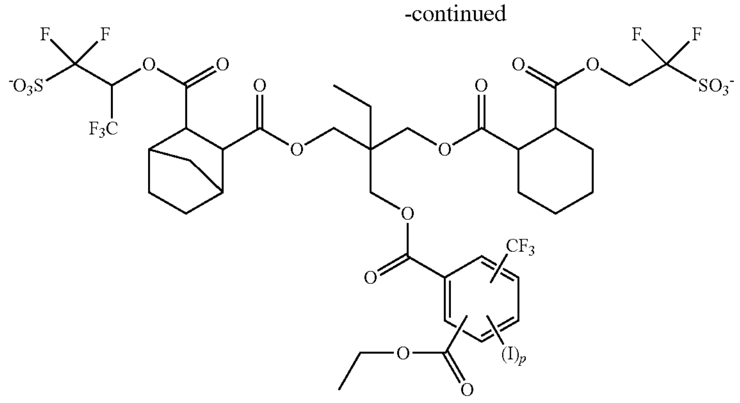
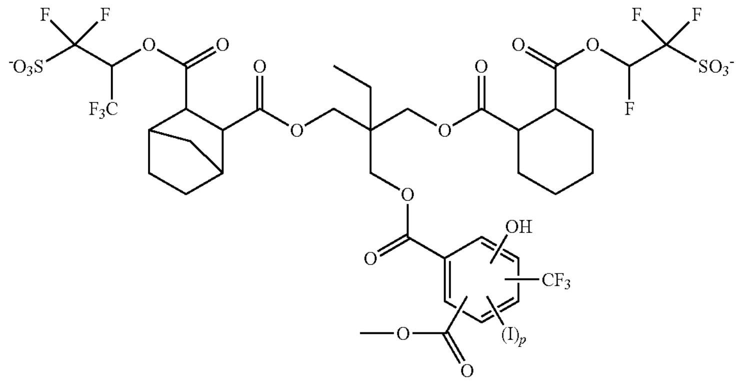
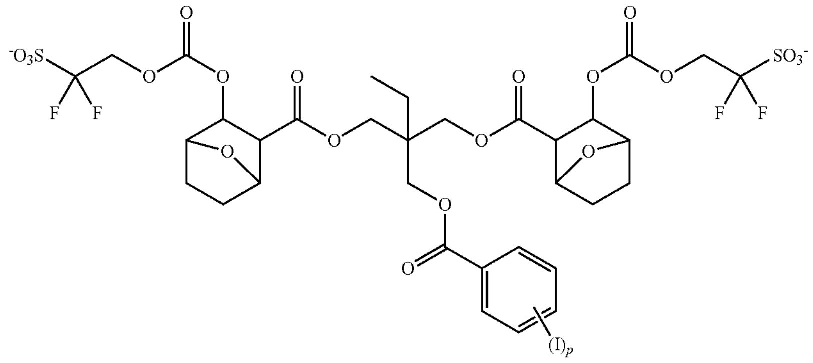
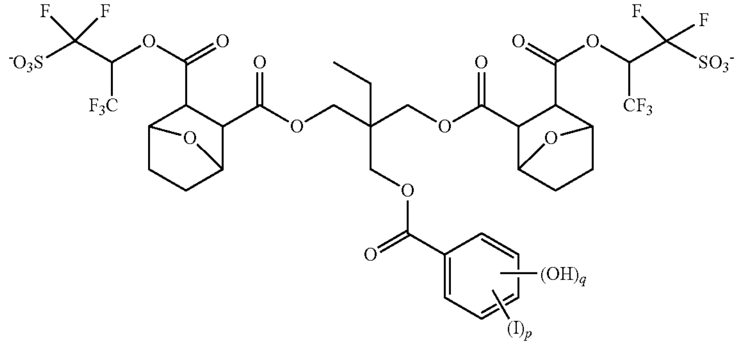

-continued
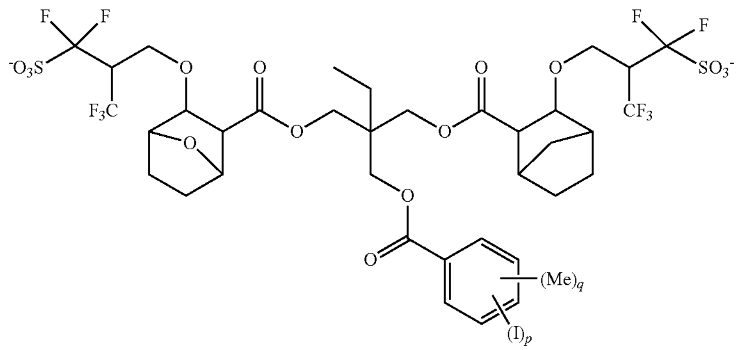
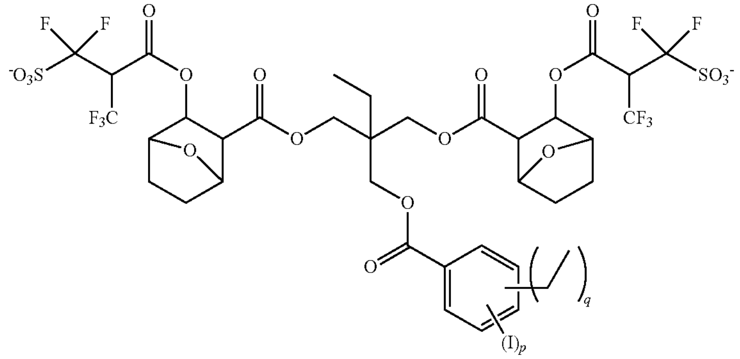
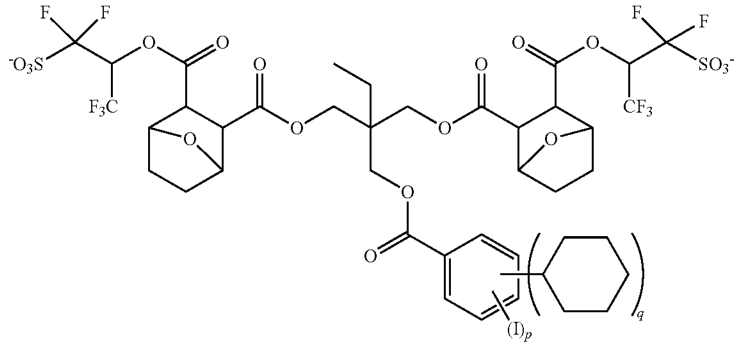
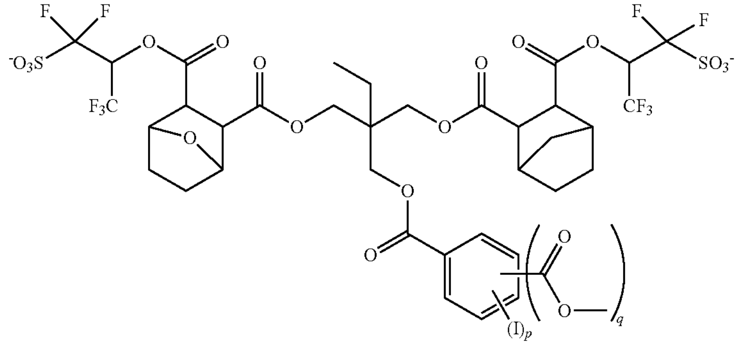

-continued
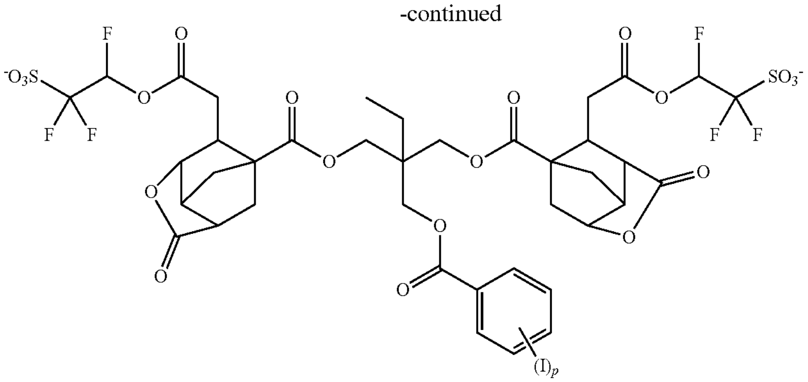
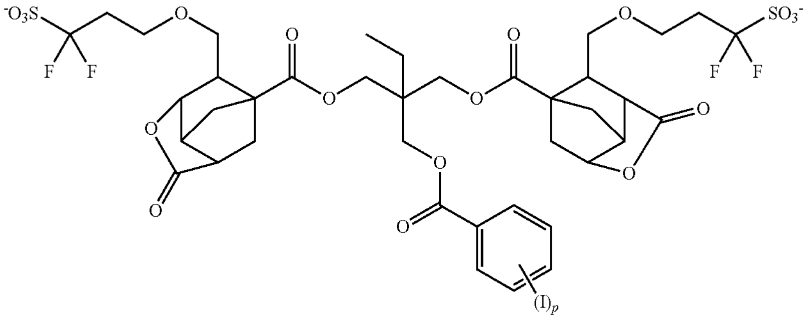
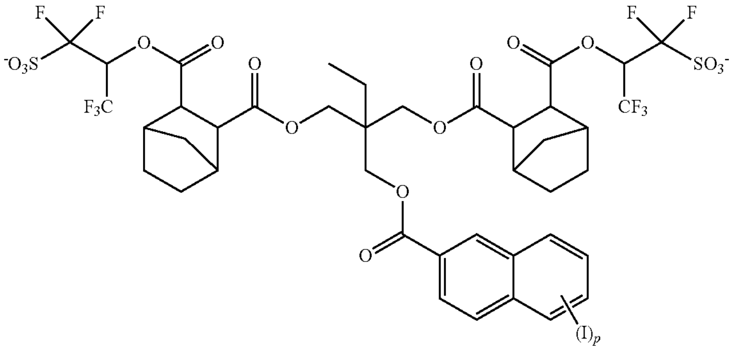
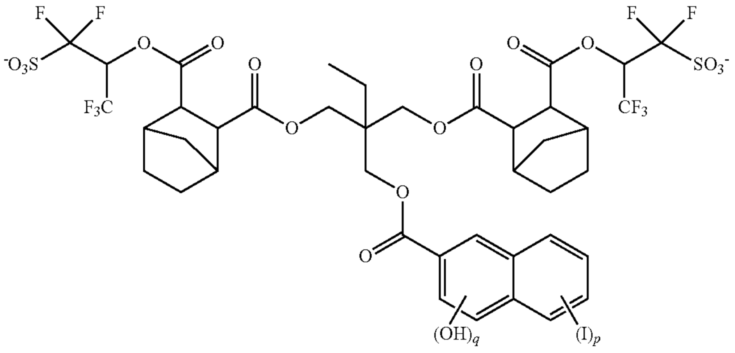

-continued
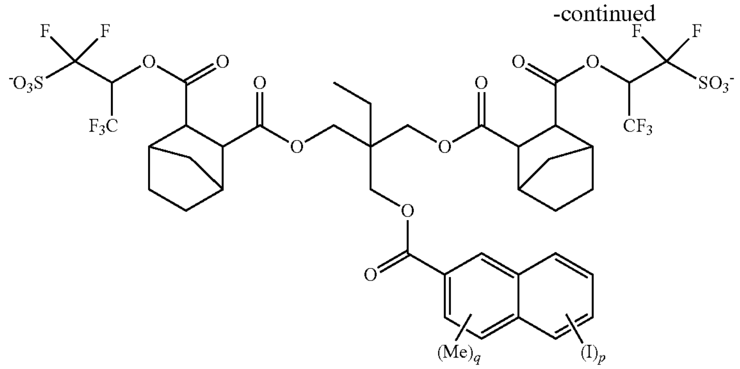
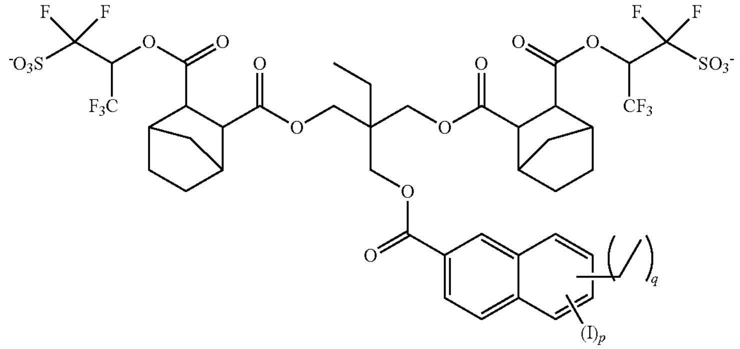
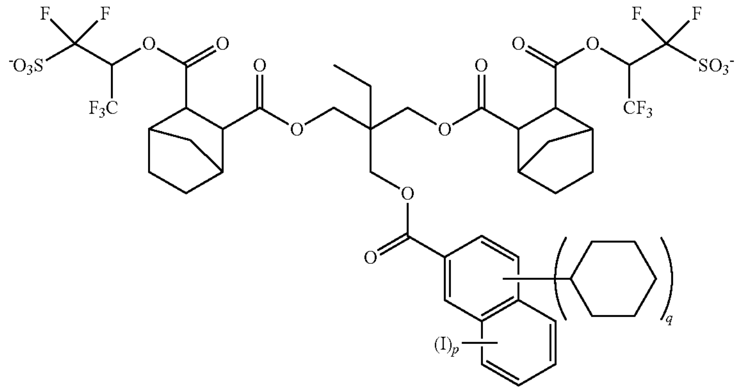
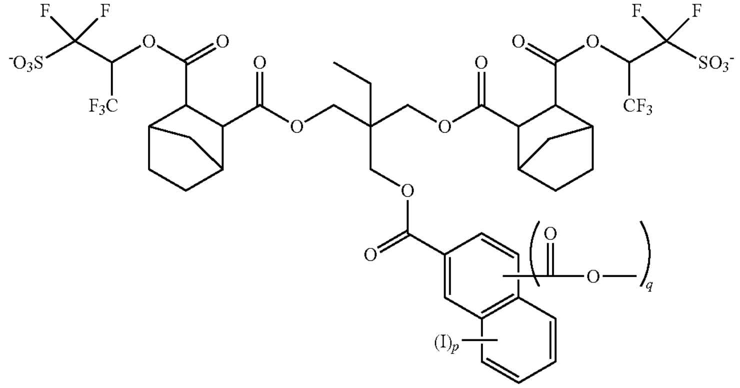

-continued
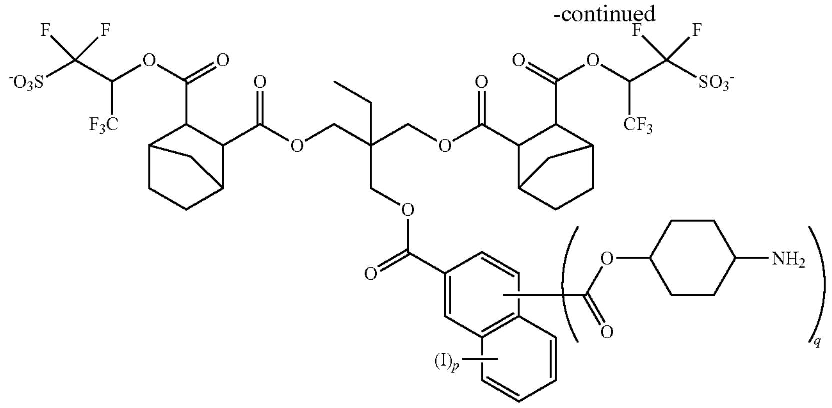
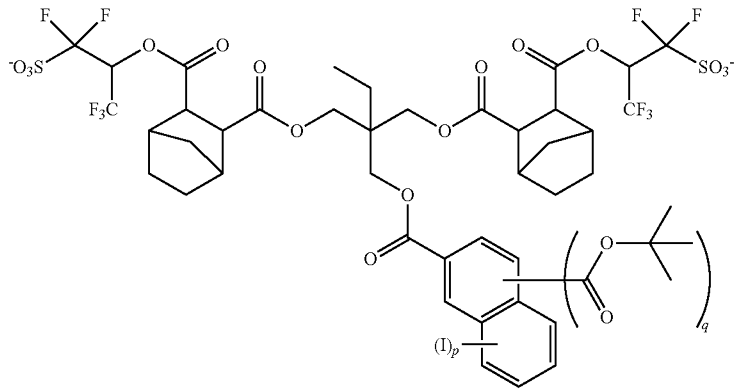
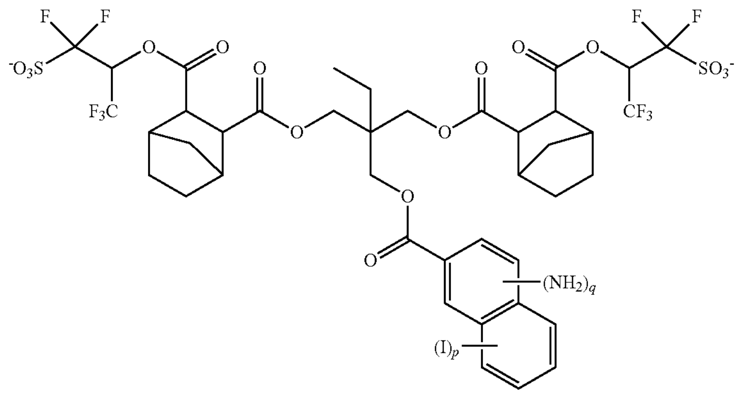
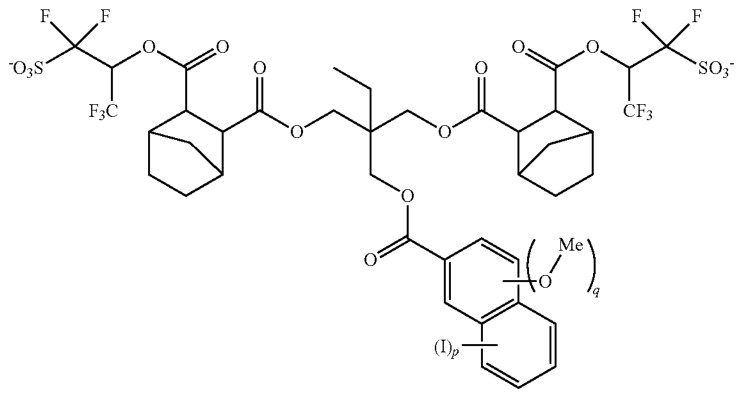

-continued
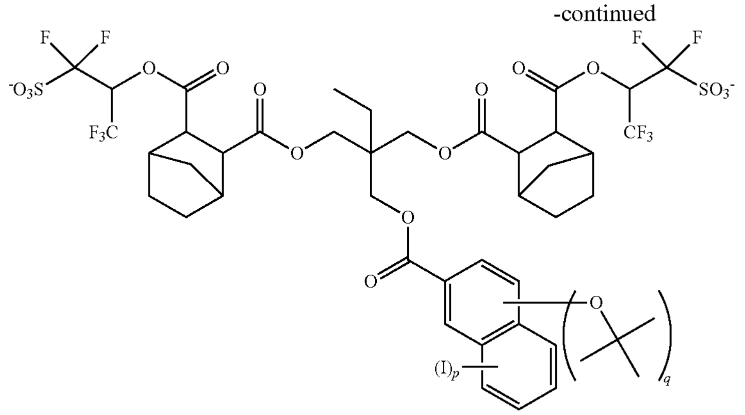
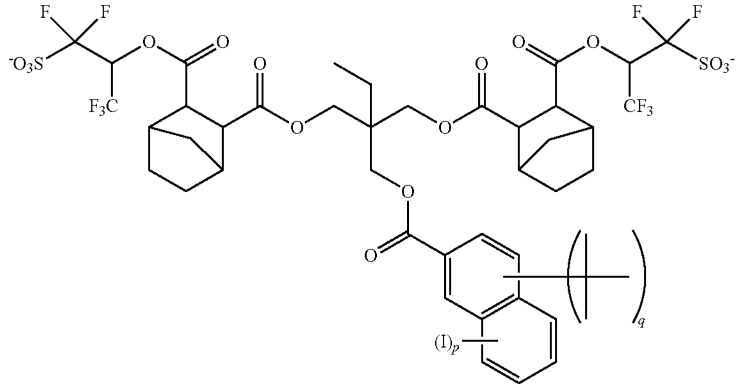
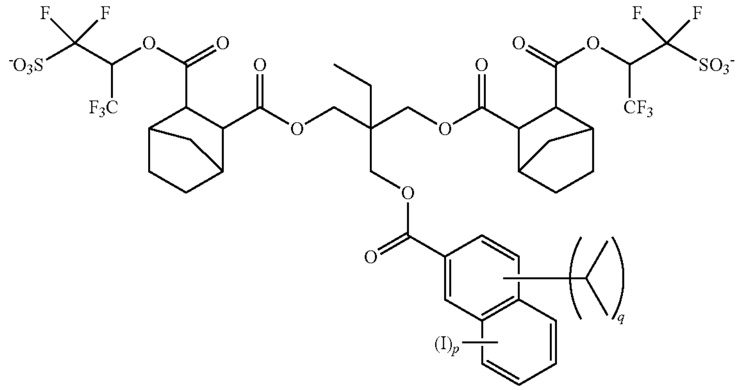
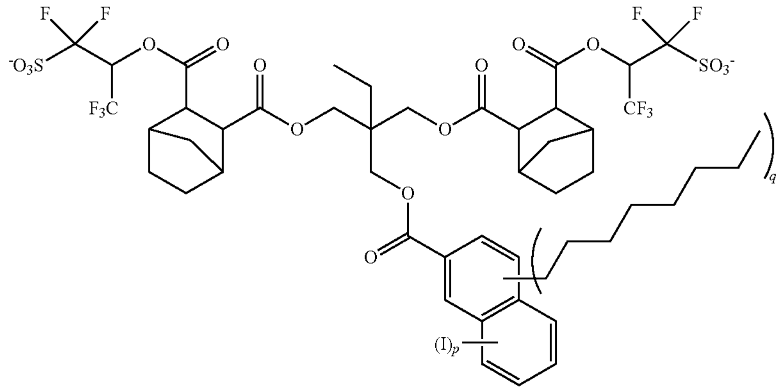

-continued
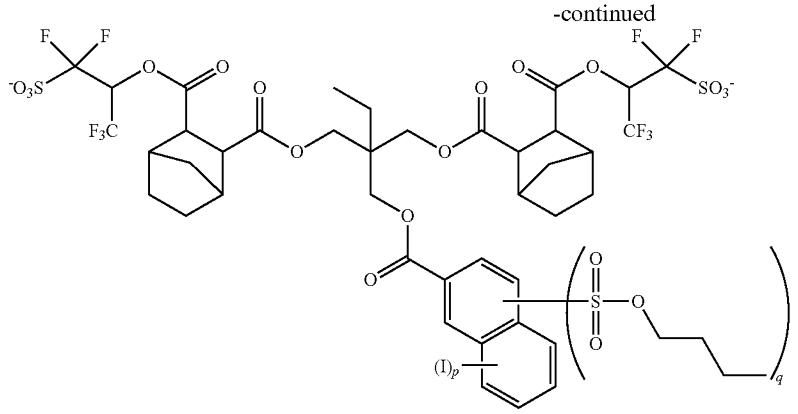
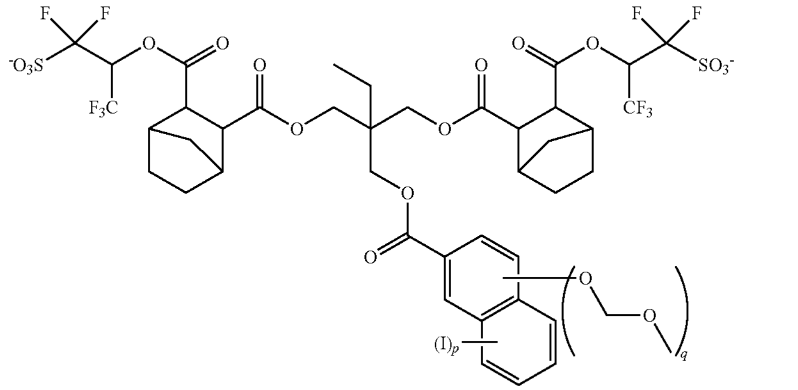
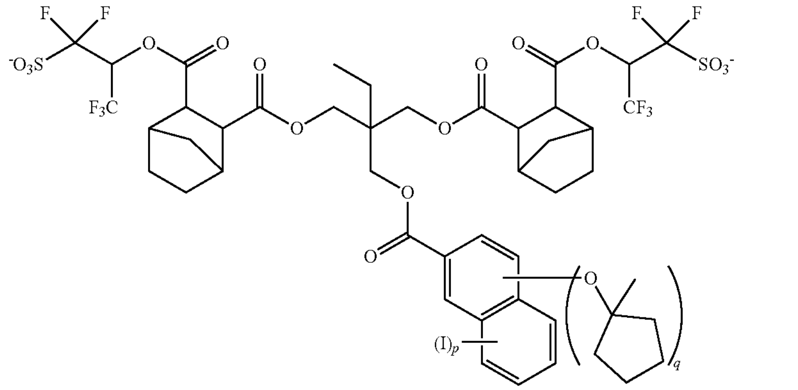
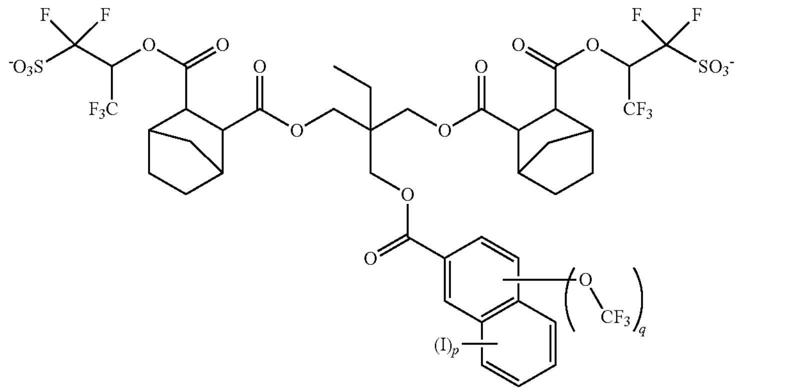

-continued
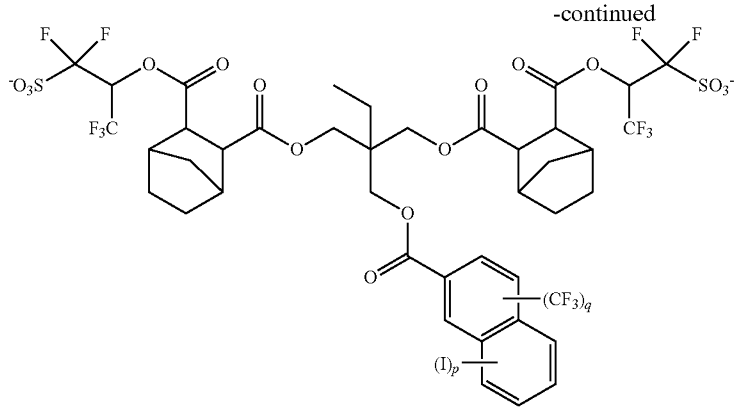
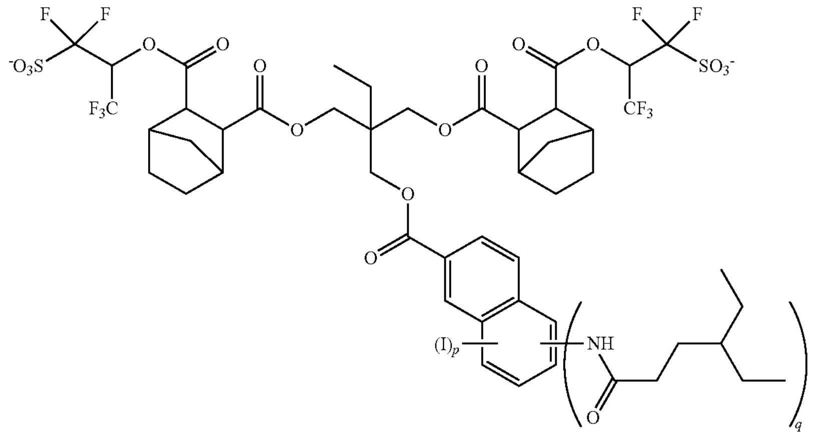
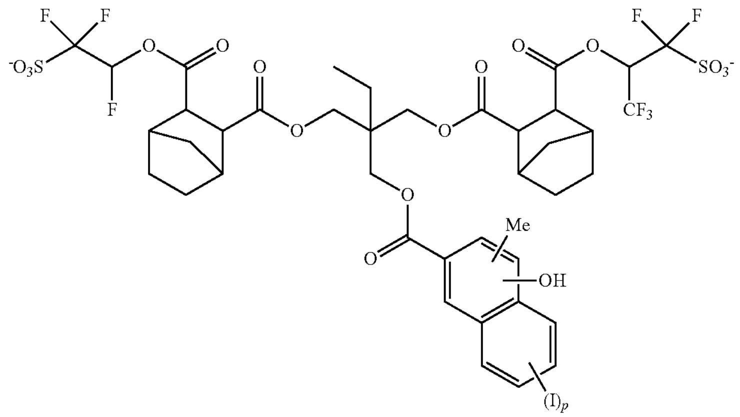
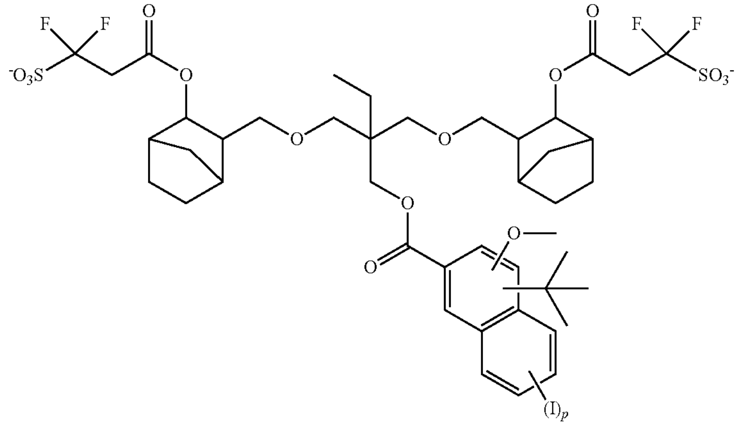

-continued
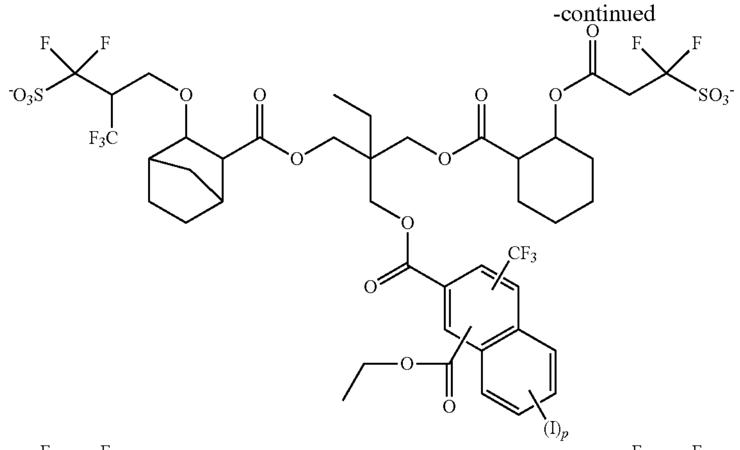
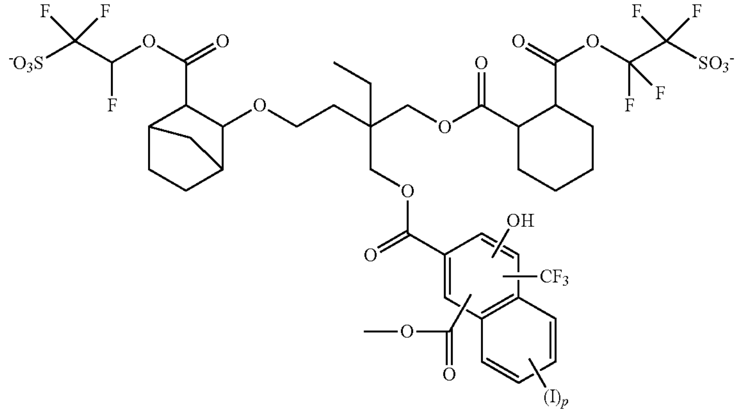
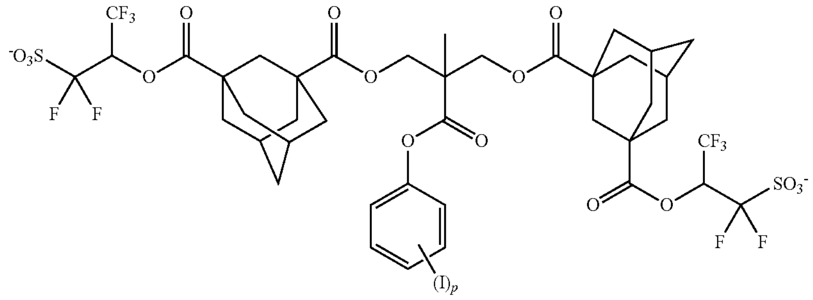
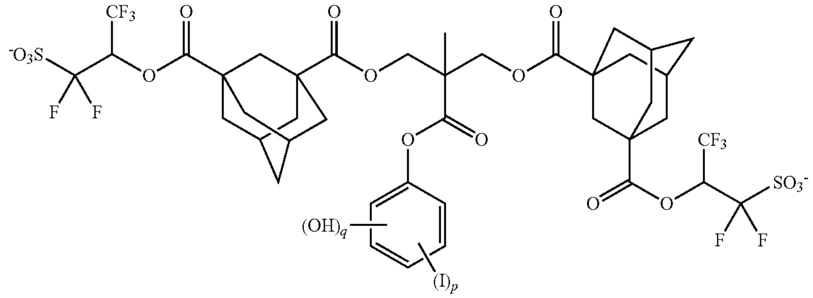
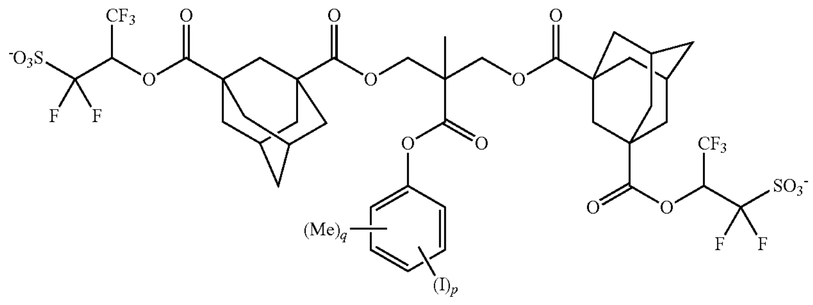

-continued
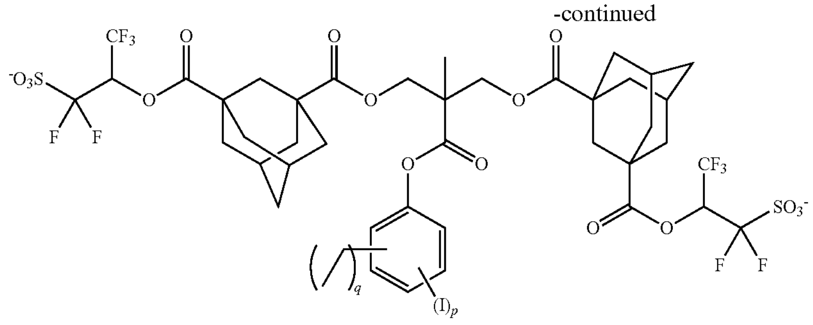
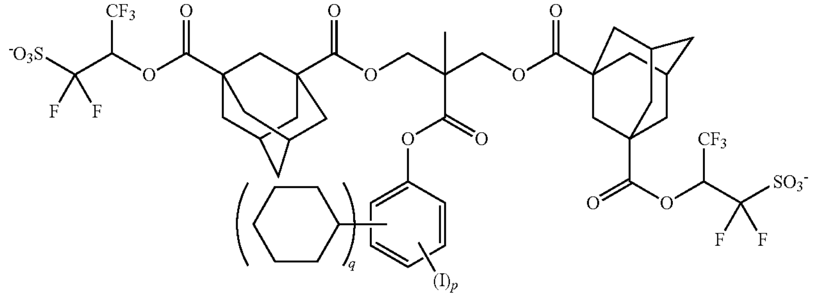
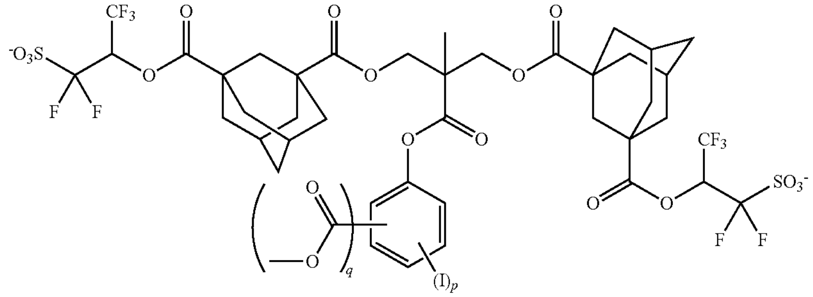
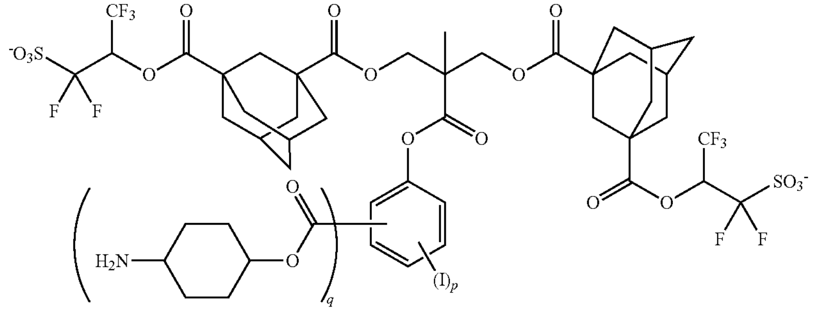
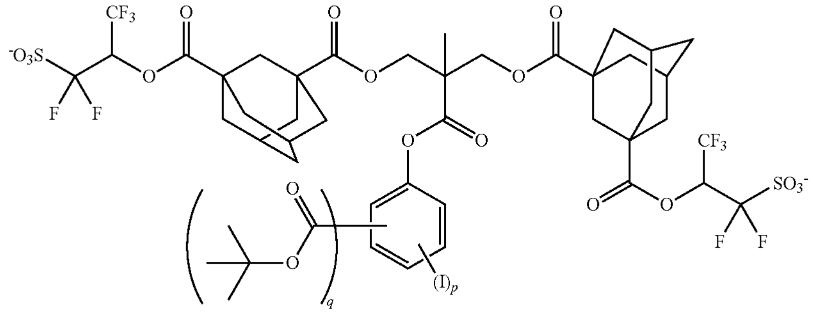

-continued
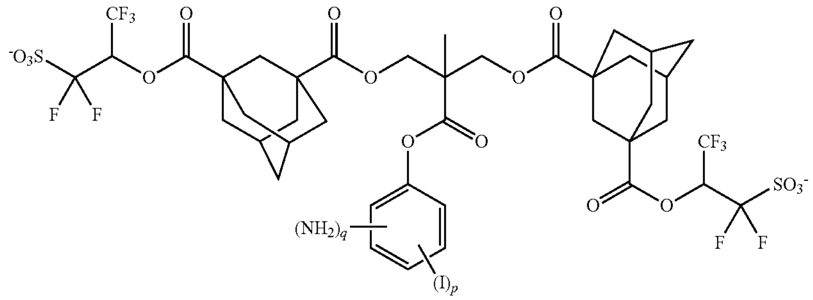
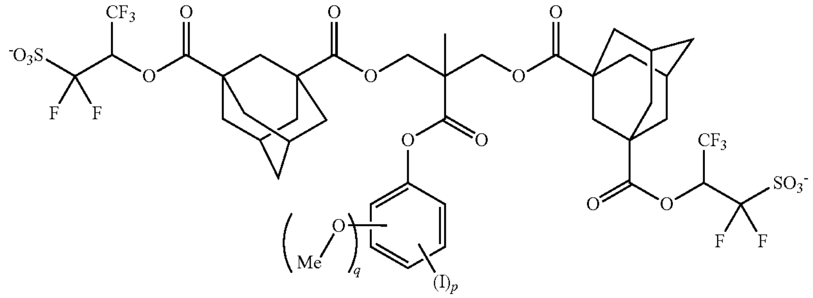
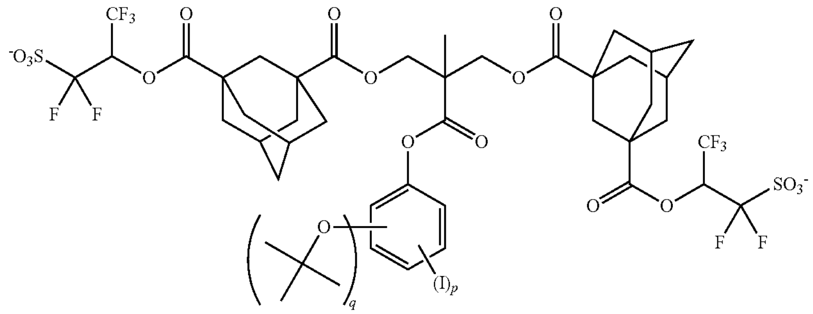
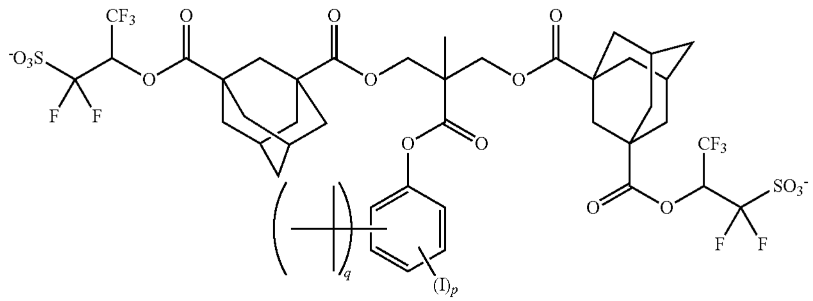
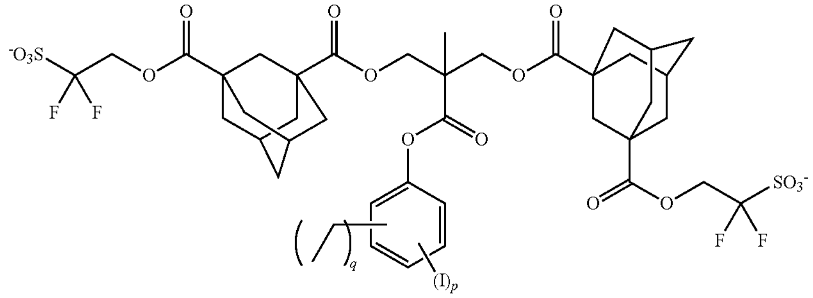

-continued
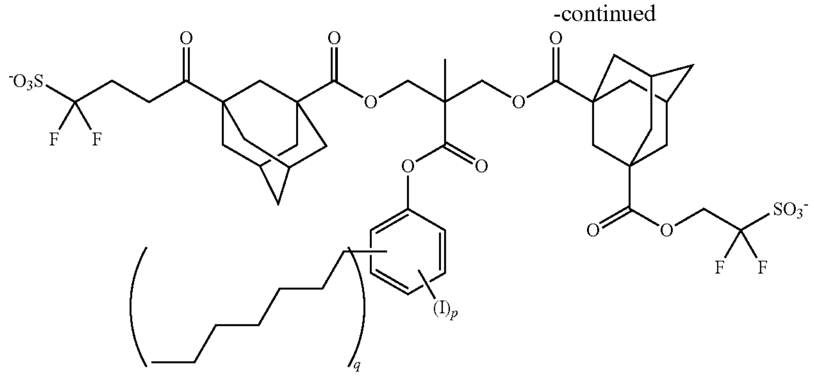
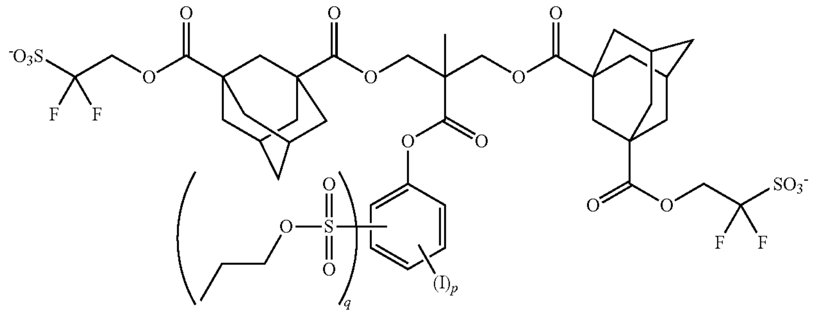
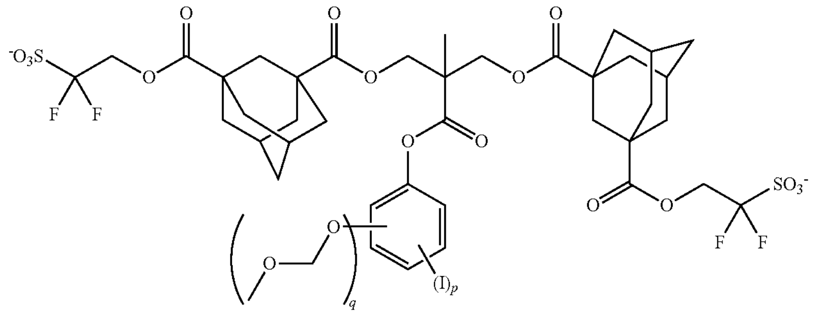
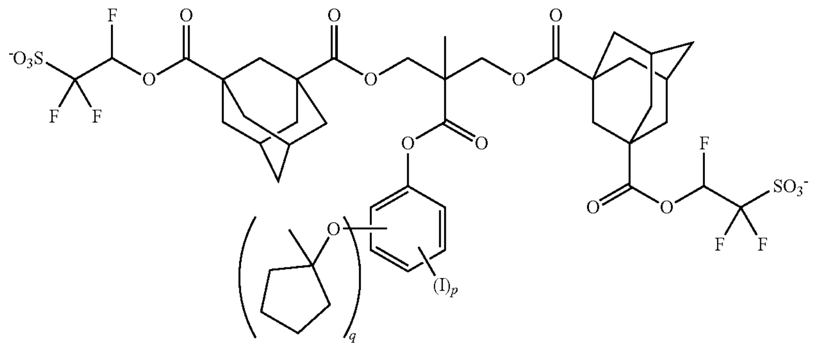
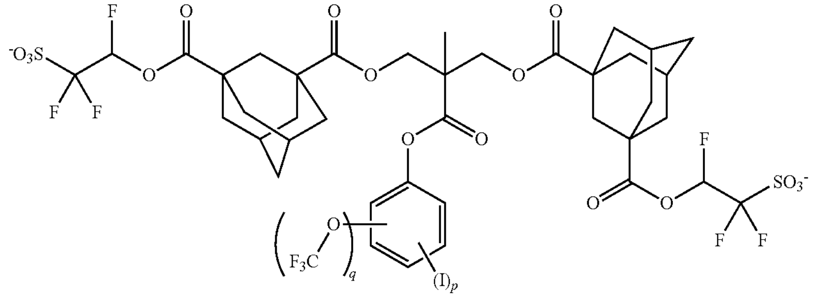

-continued
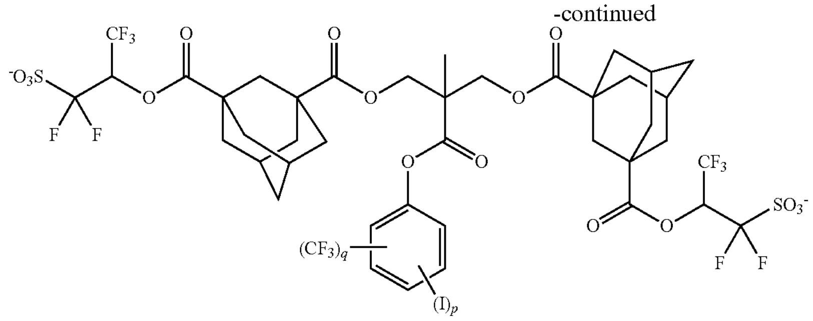
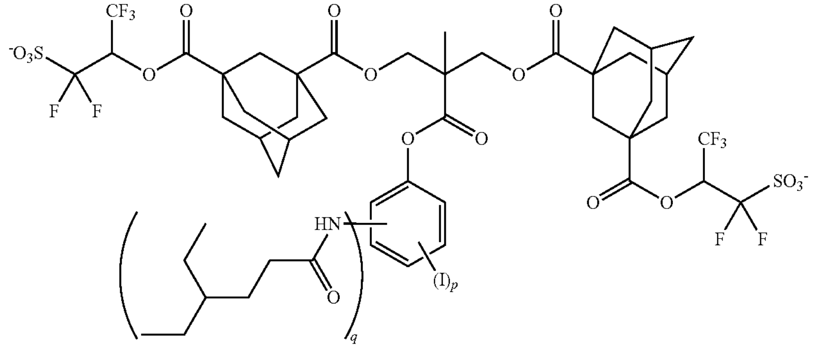
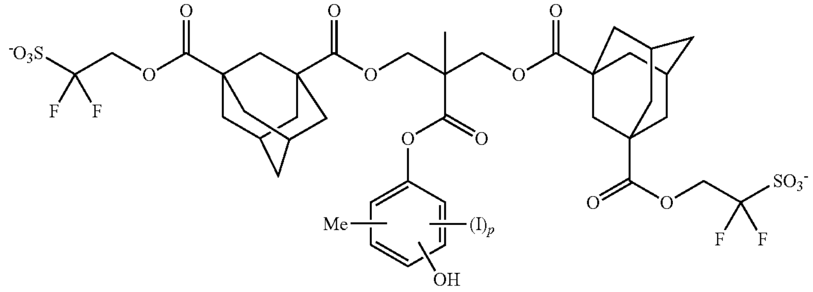
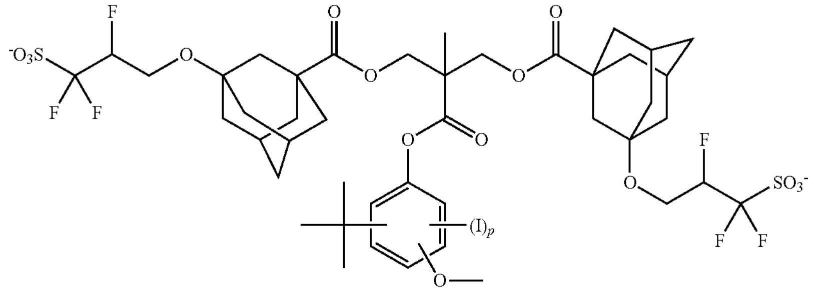
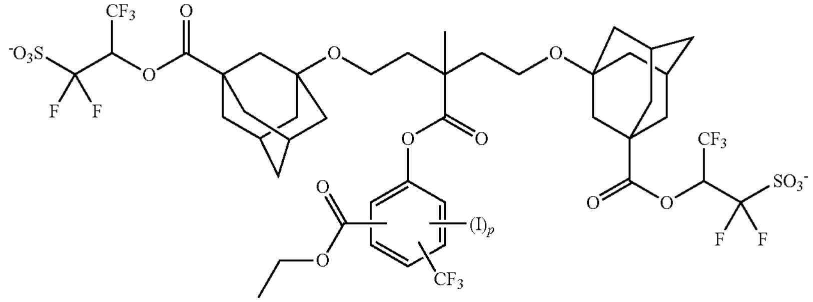

-continued
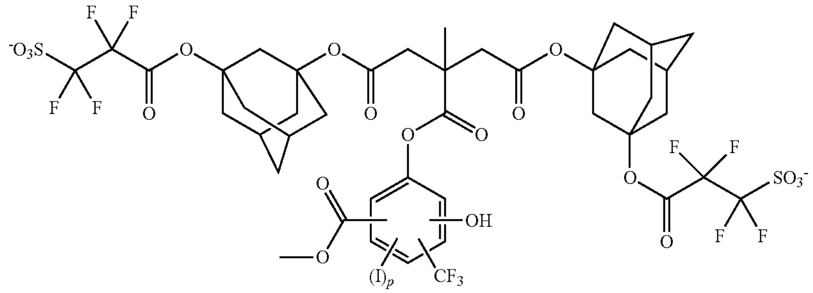
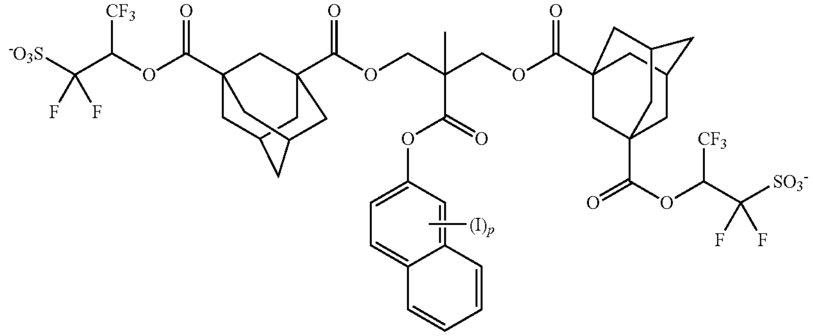
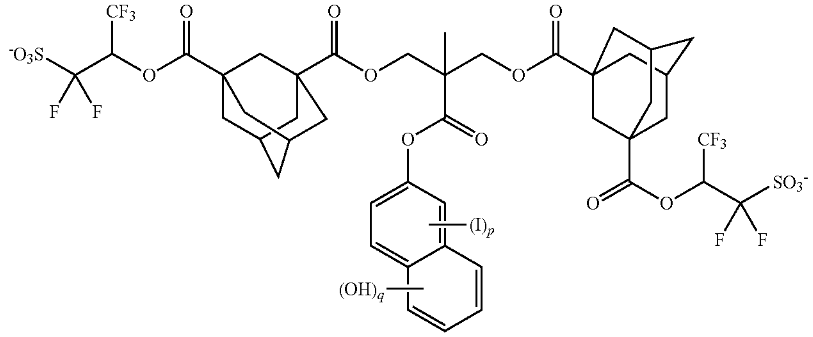
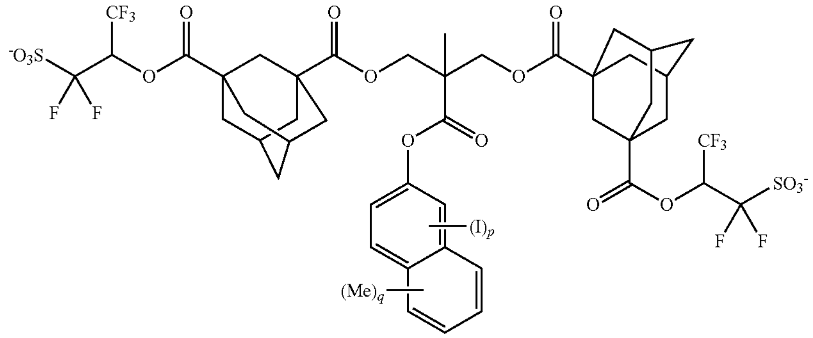
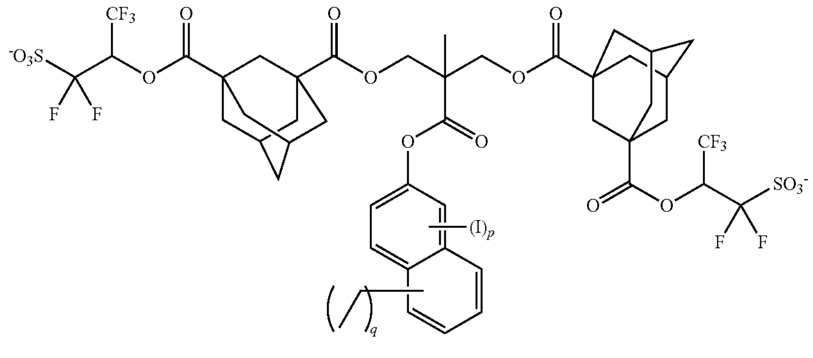

-continued
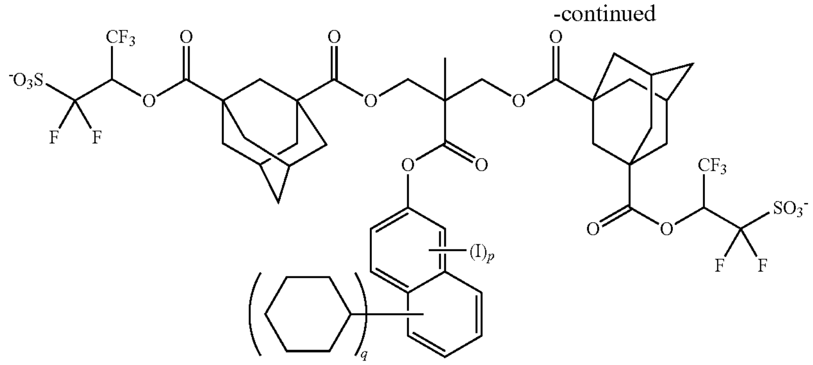
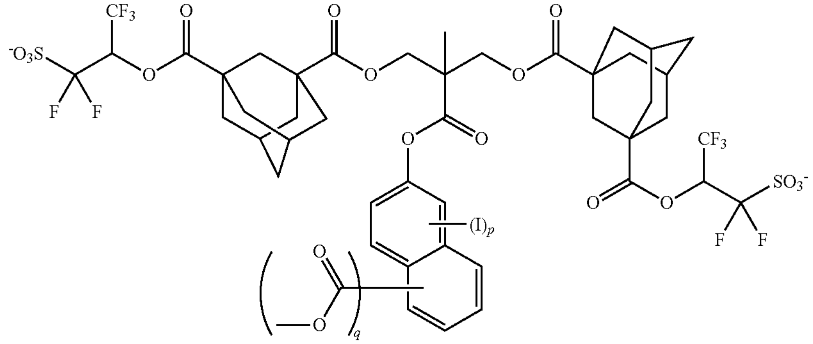
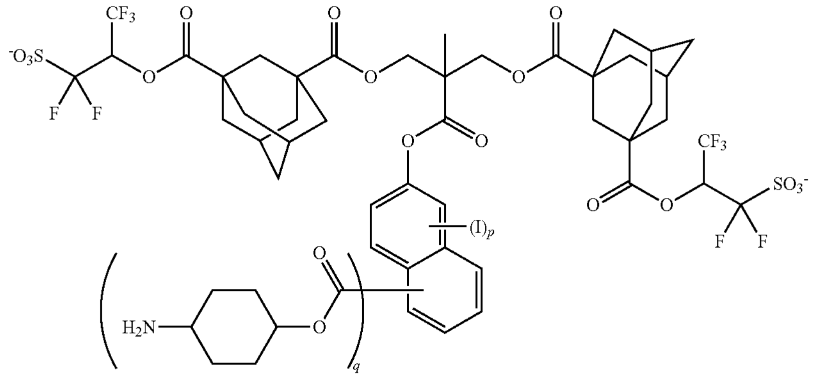
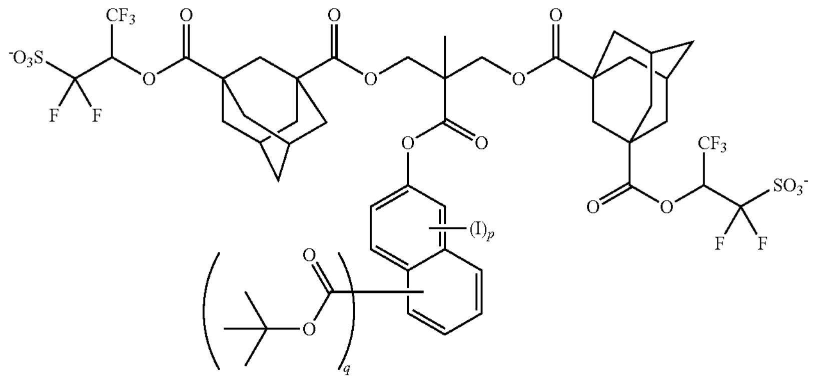

-continued
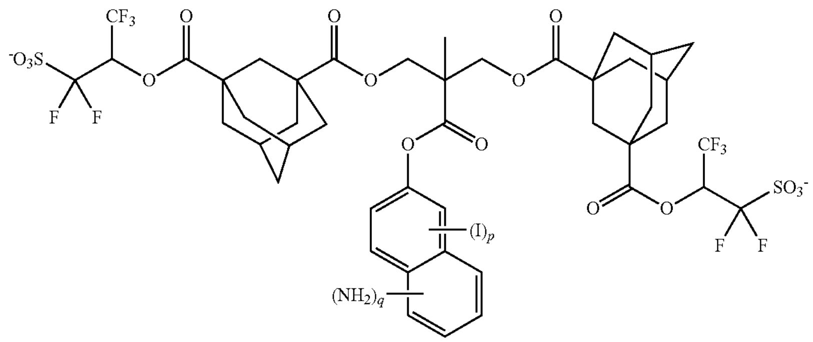
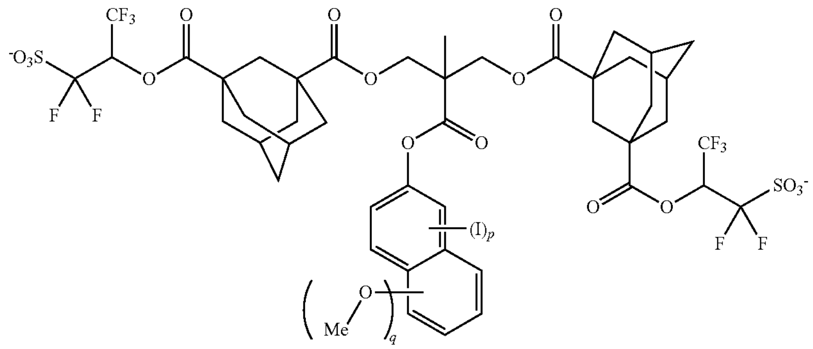
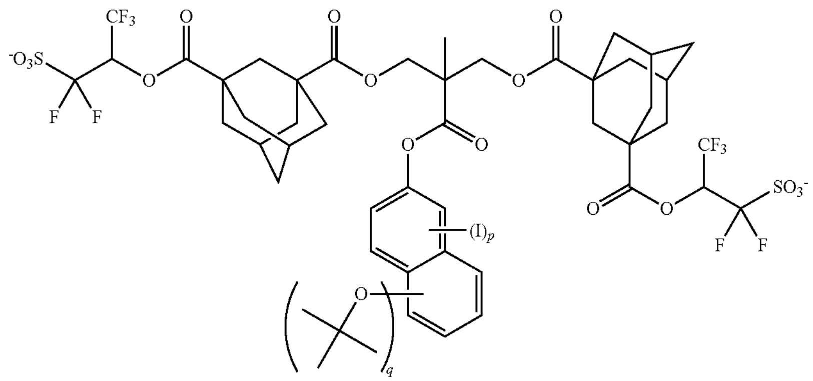
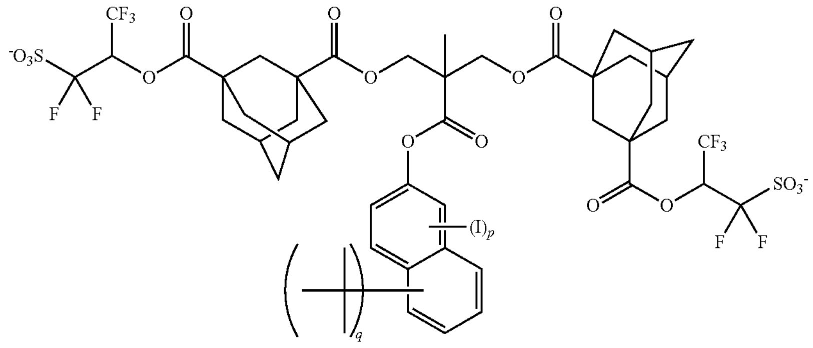

-continued
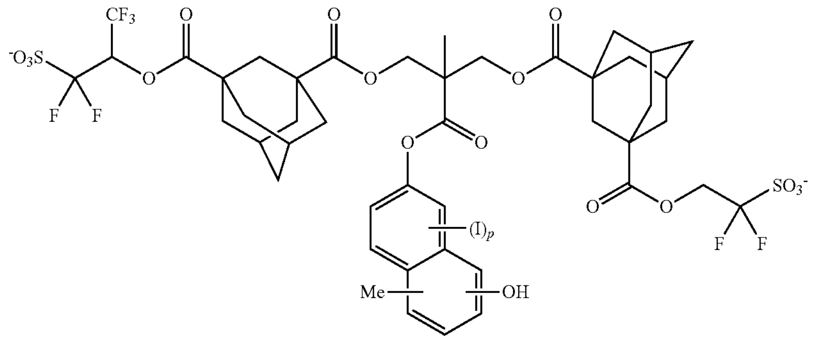
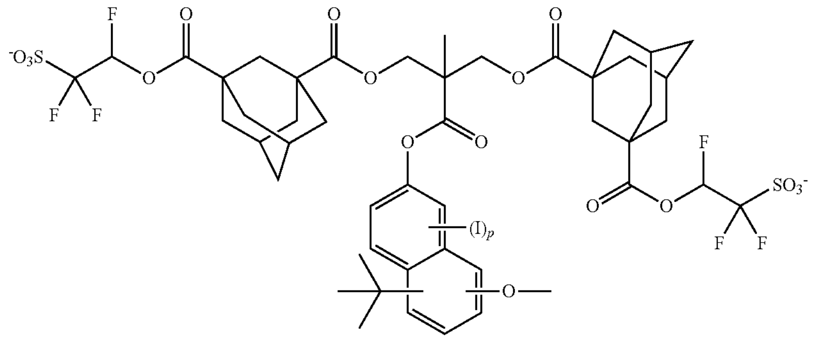
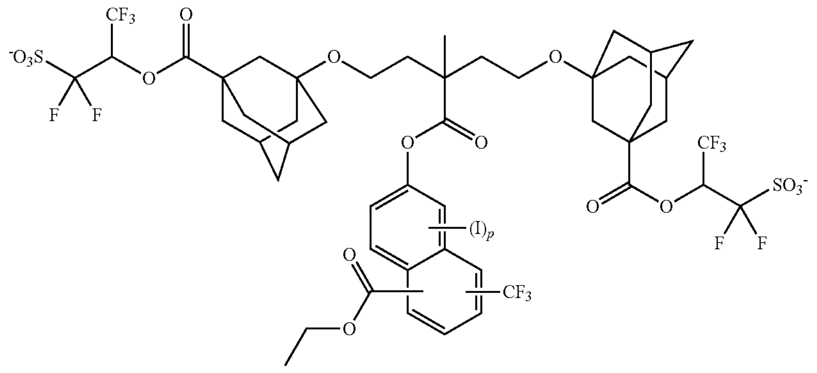
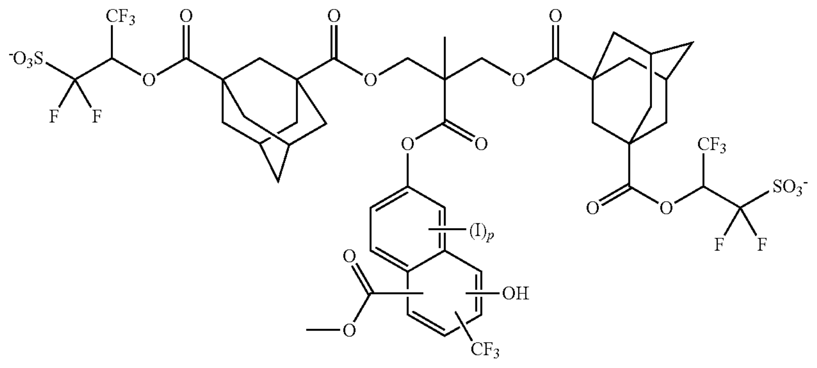

-continued
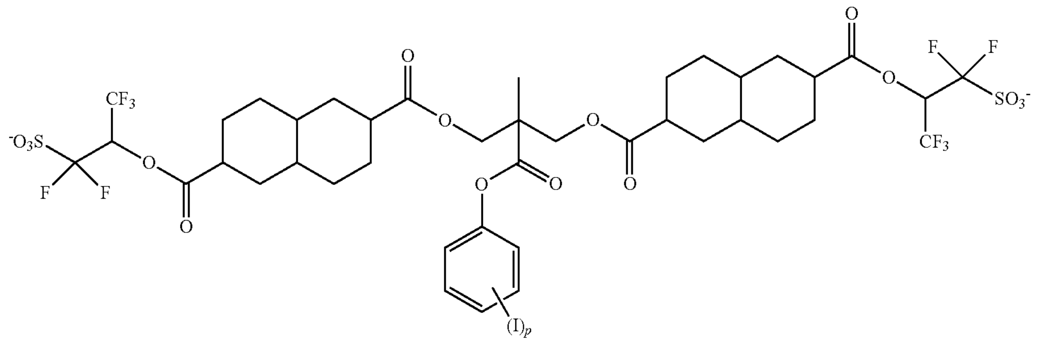
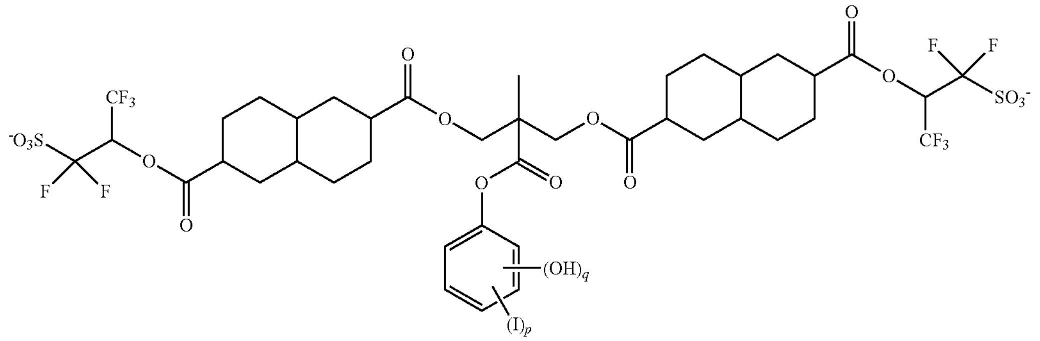
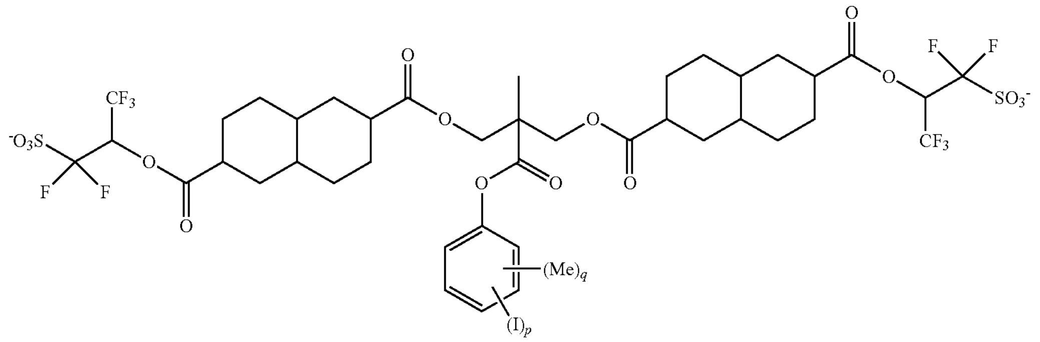
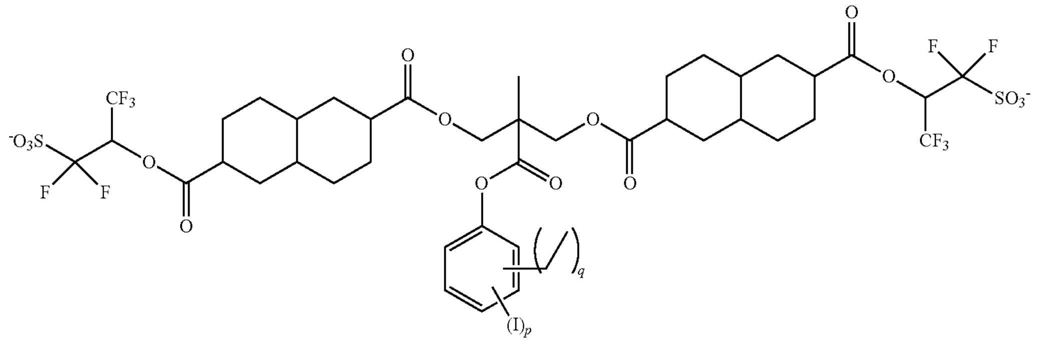
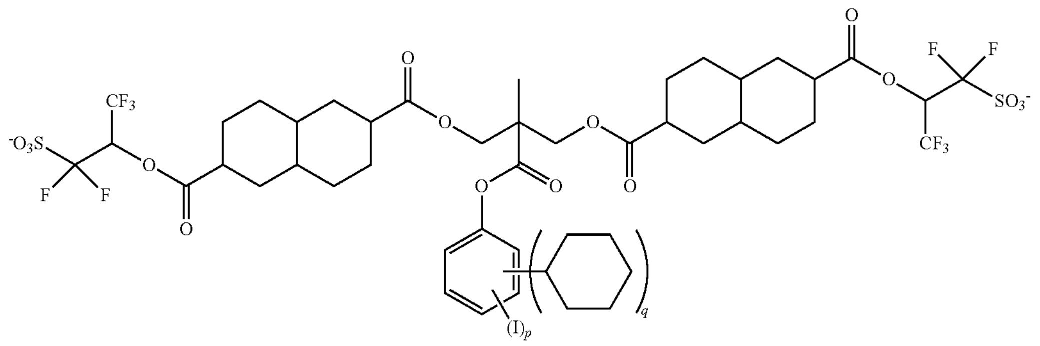

-continued
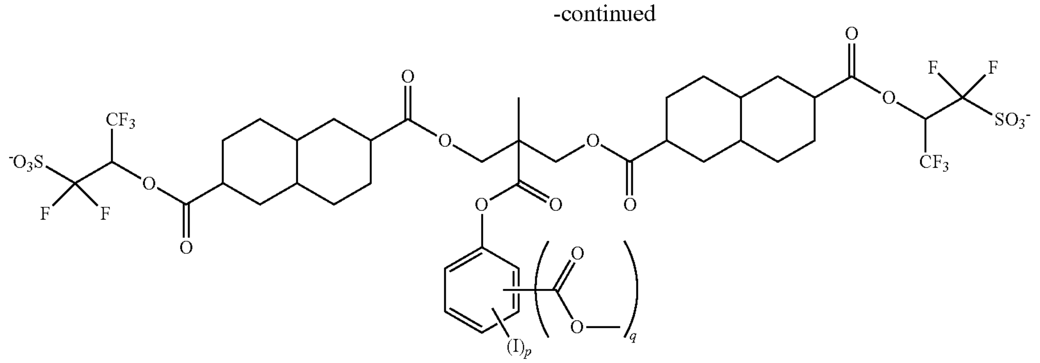
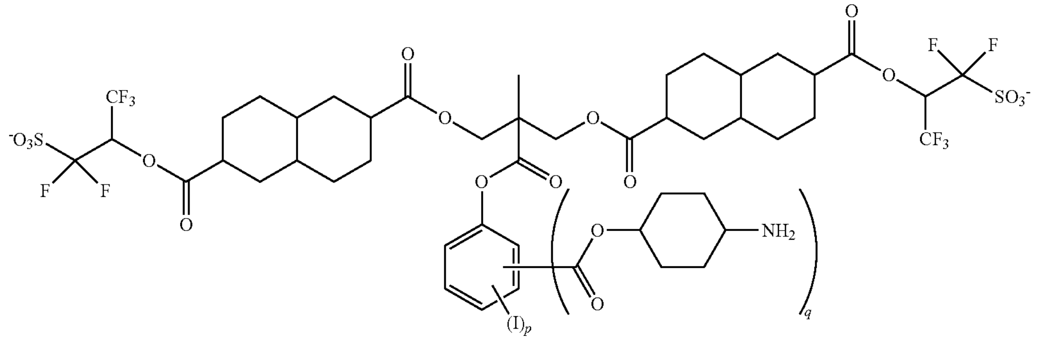
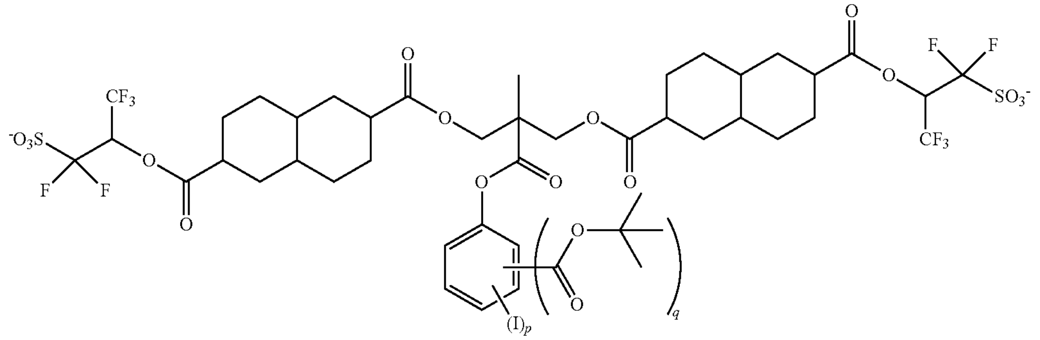
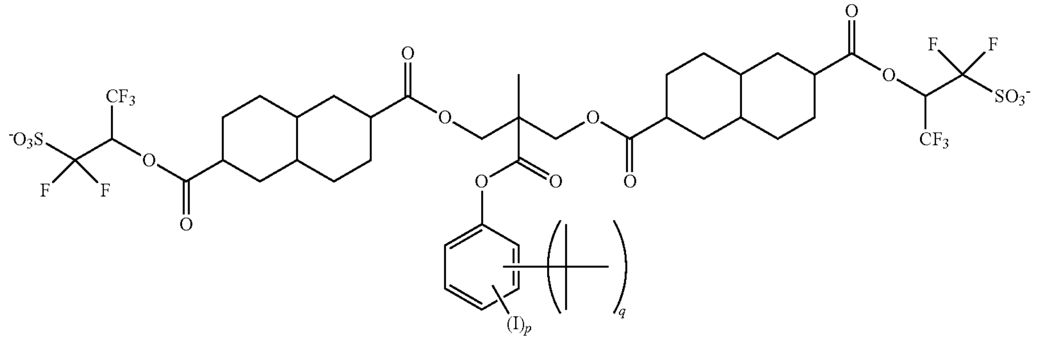
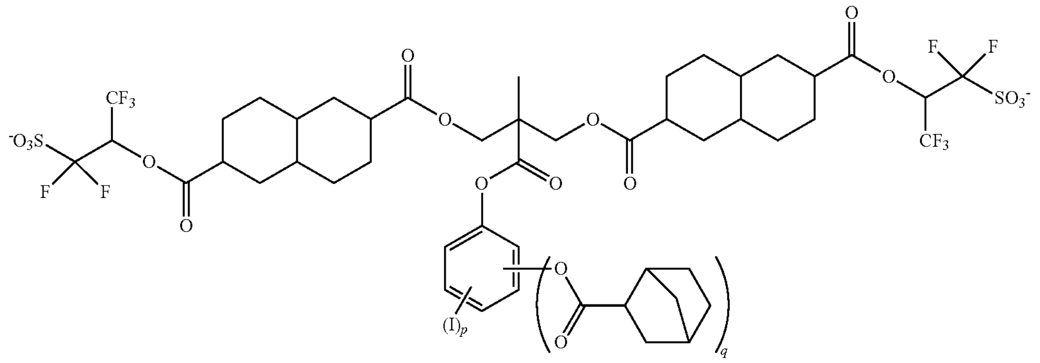

-continued
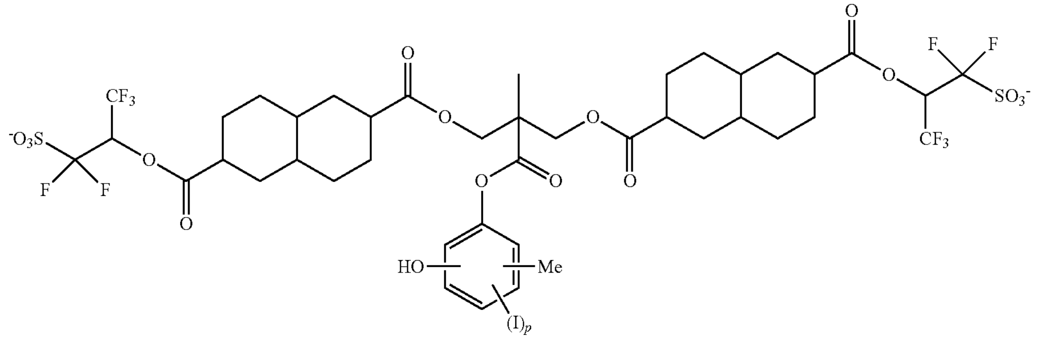
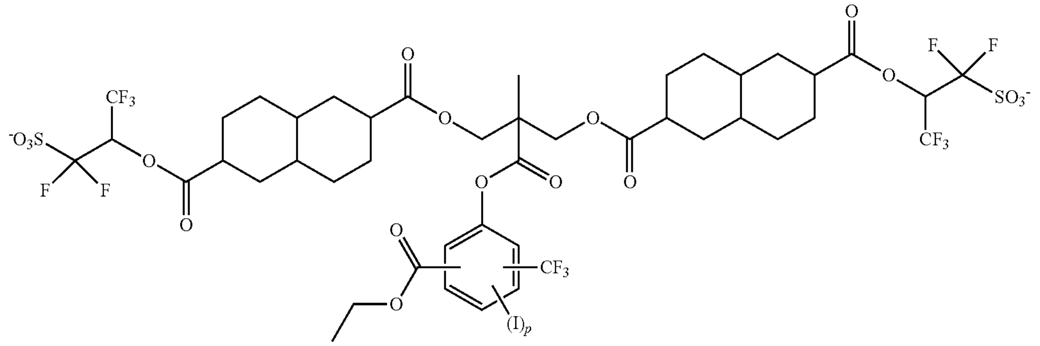
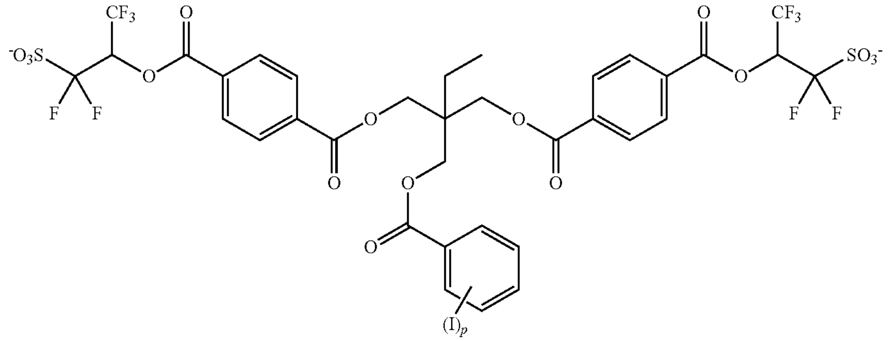
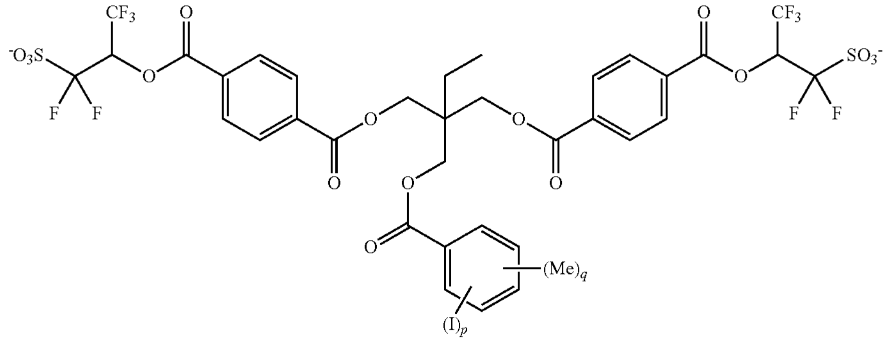
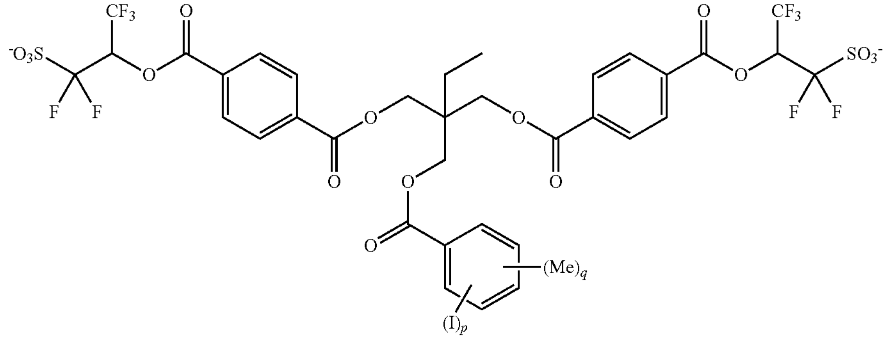

-continued
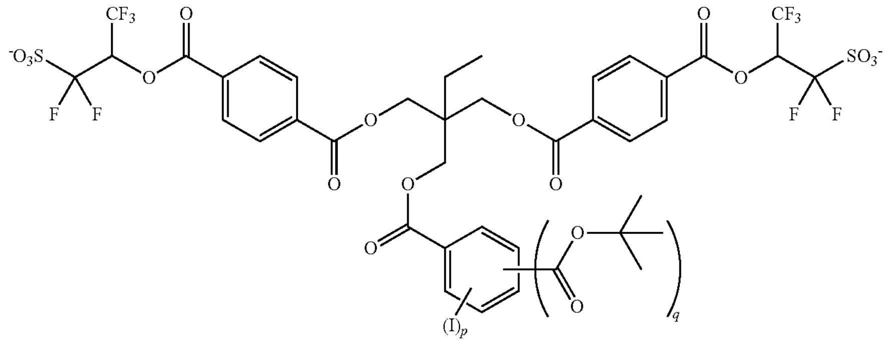
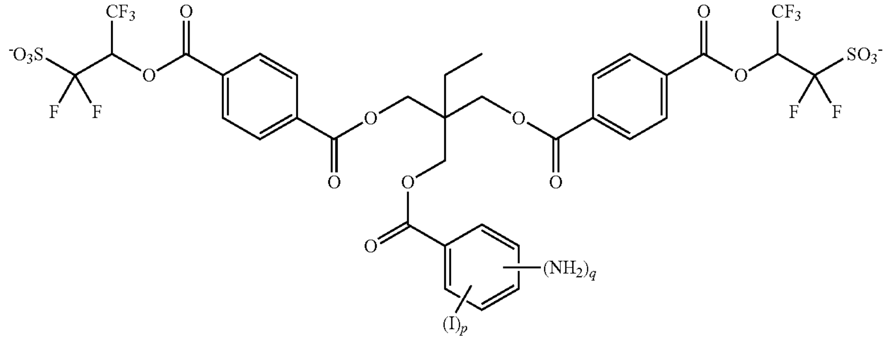
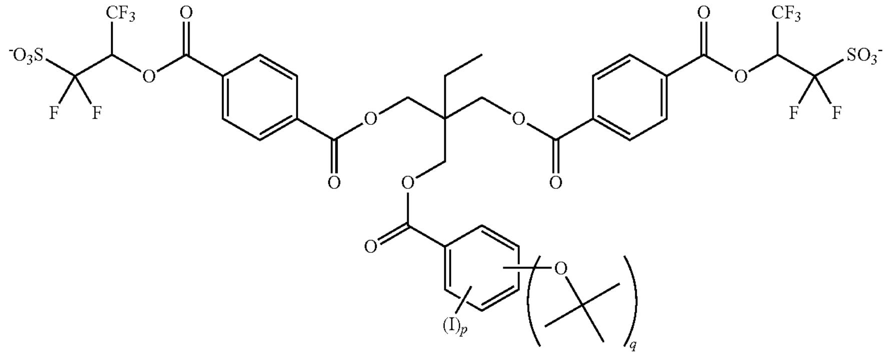
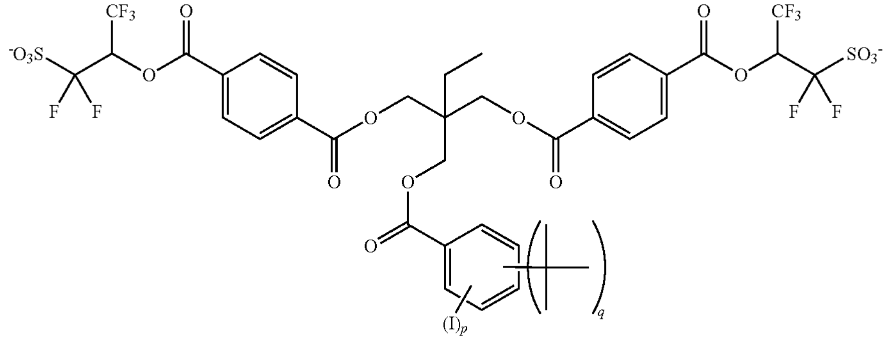

-continued
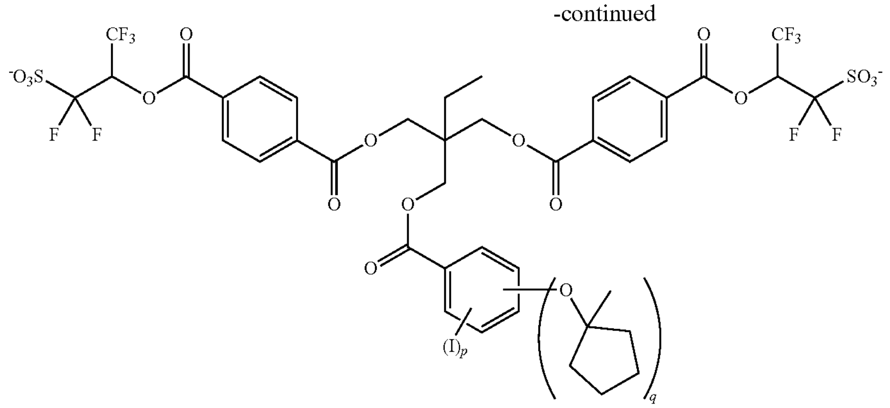
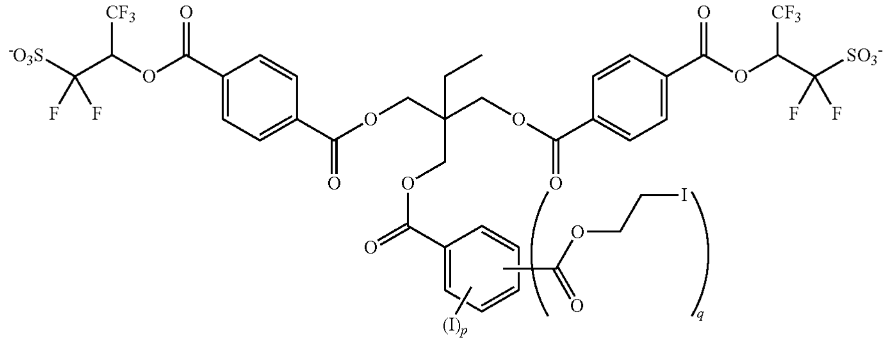
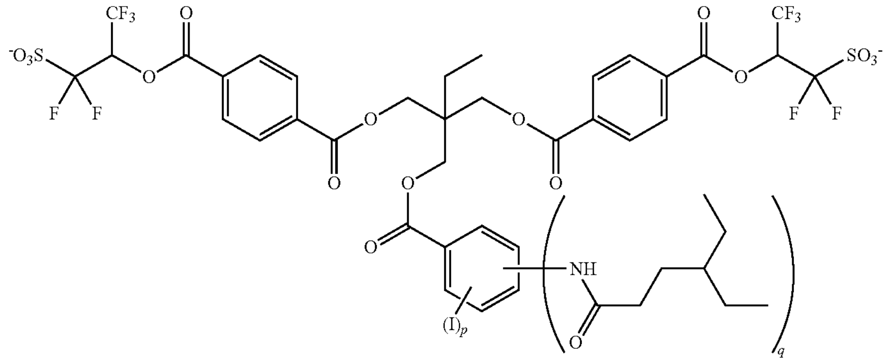
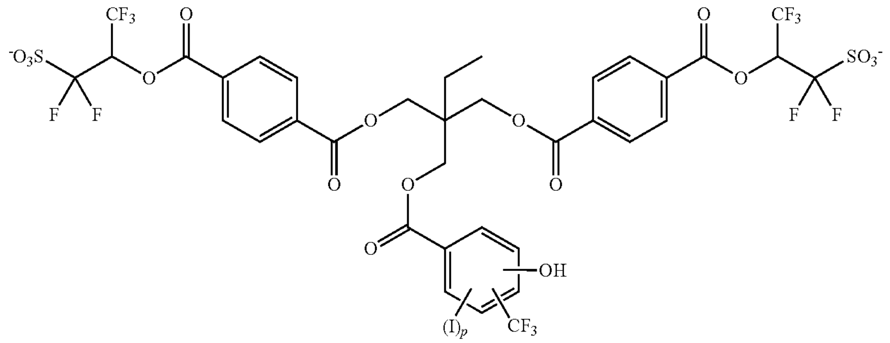

-continued
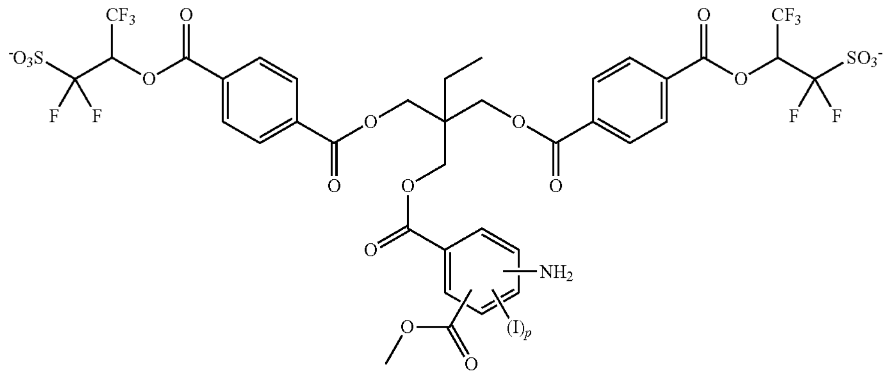
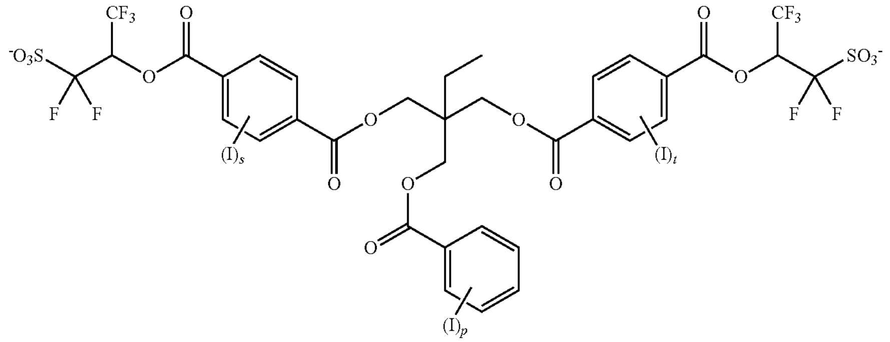
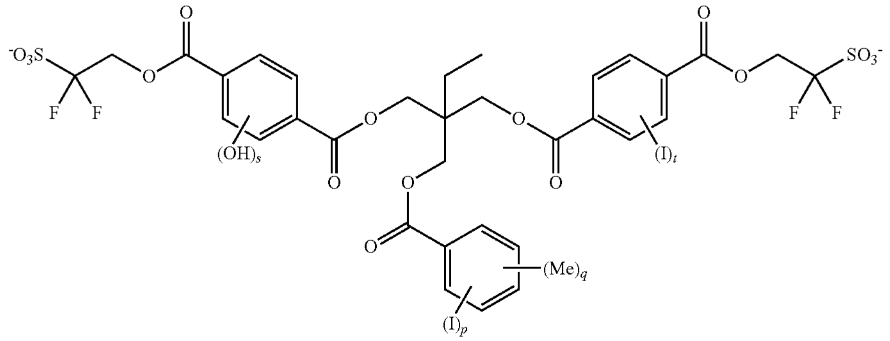
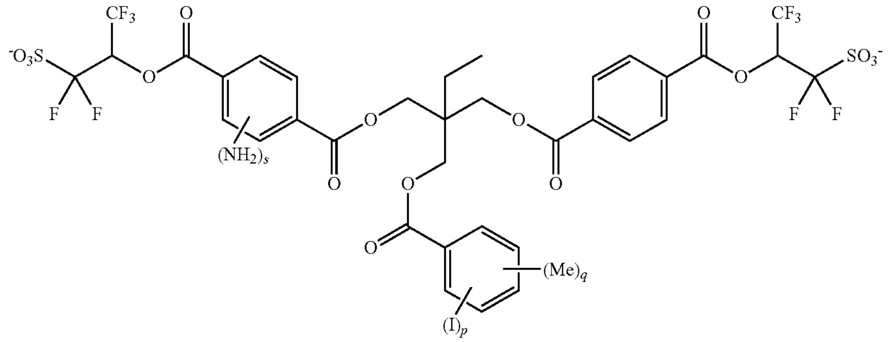

-continued
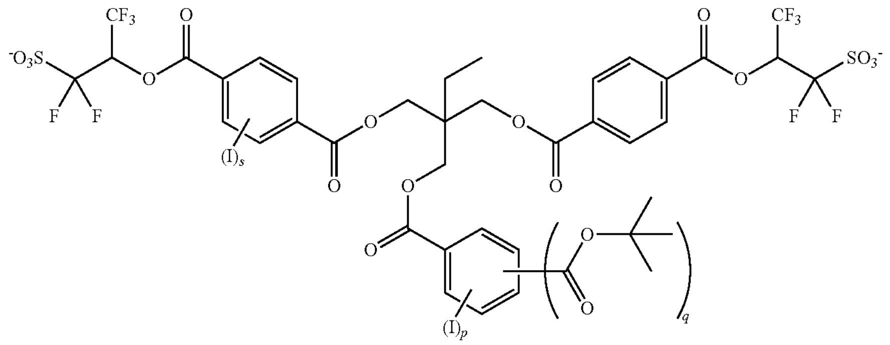
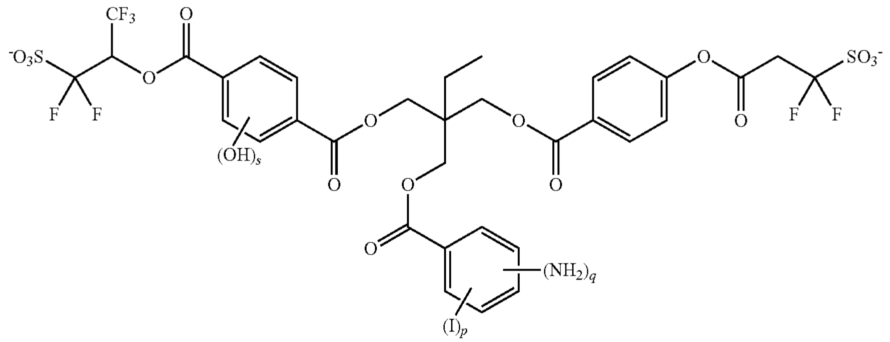
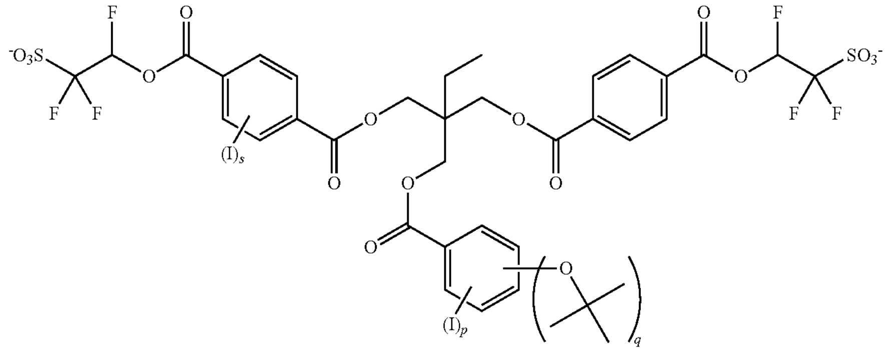
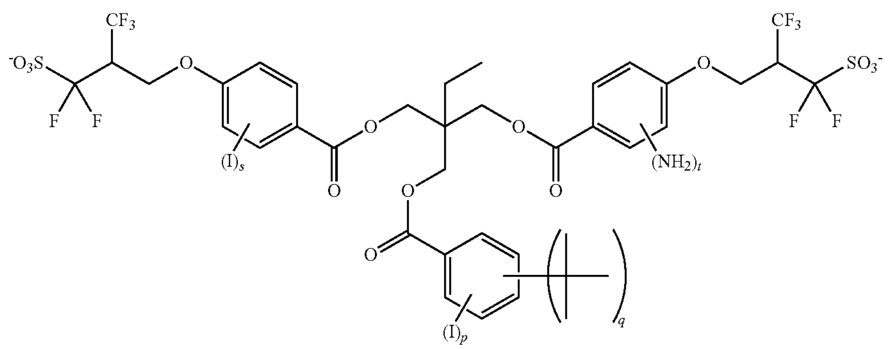

-continued
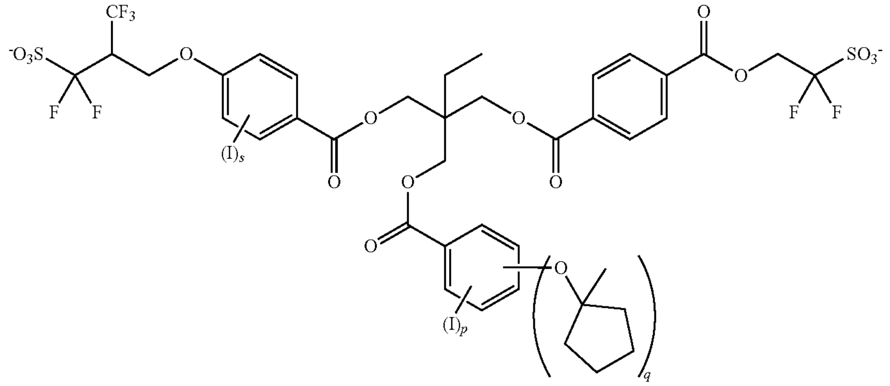
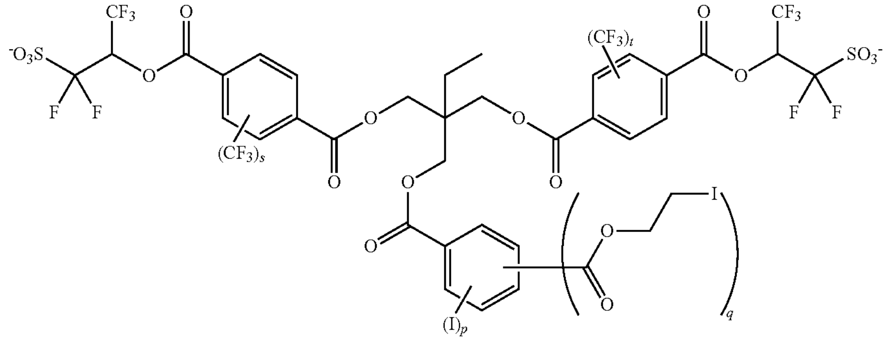
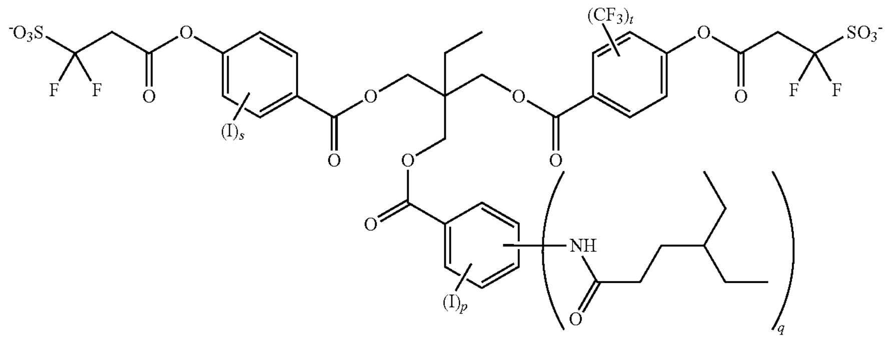
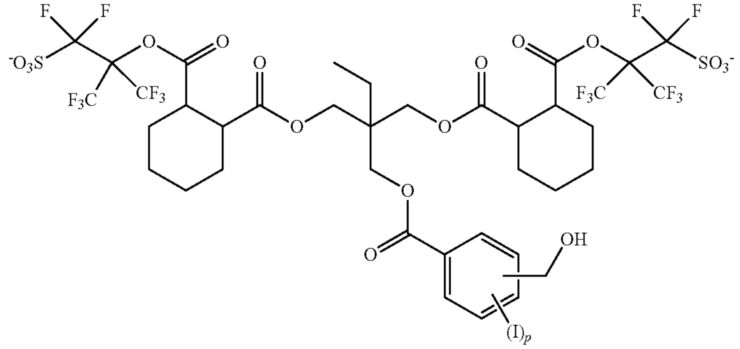

-continued
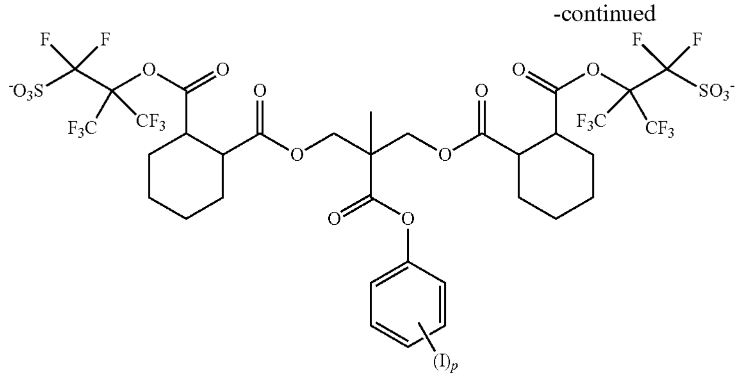
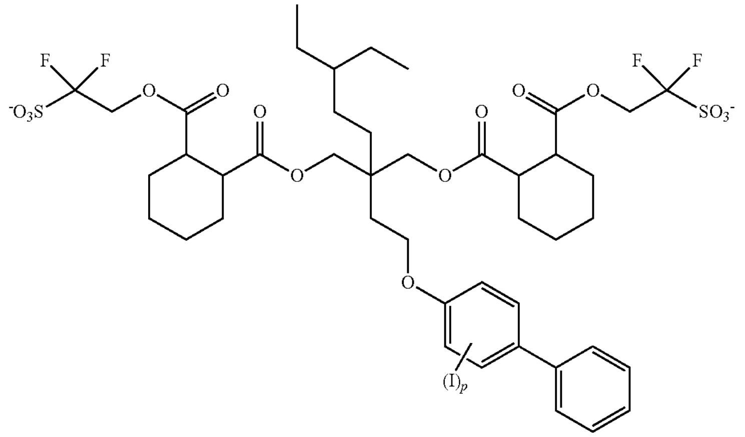
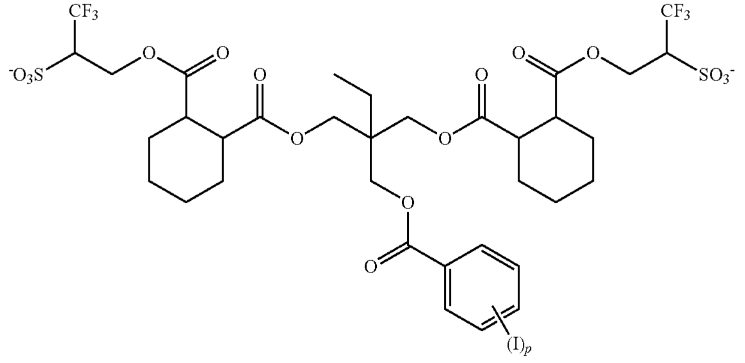
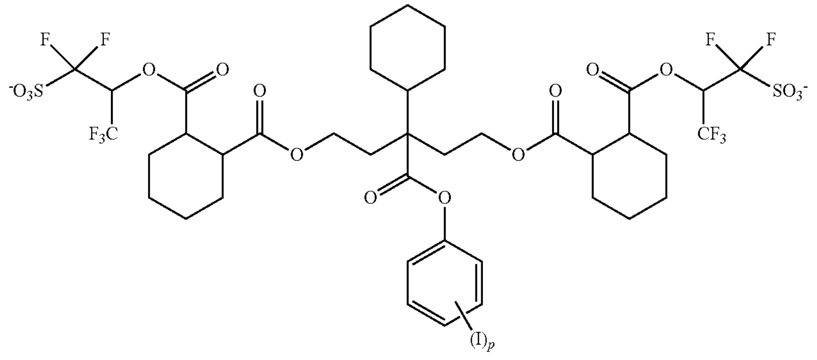

-continued
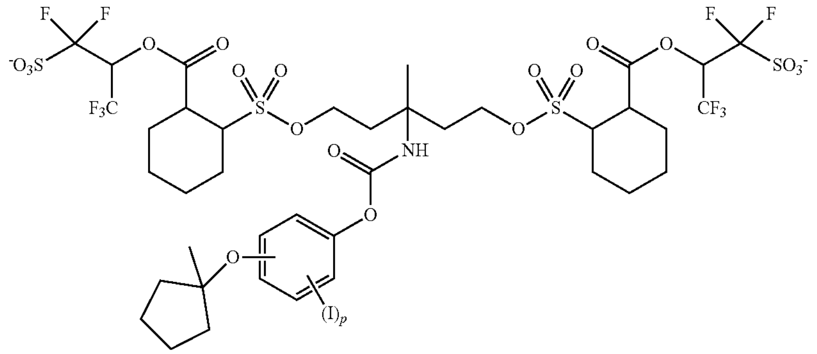
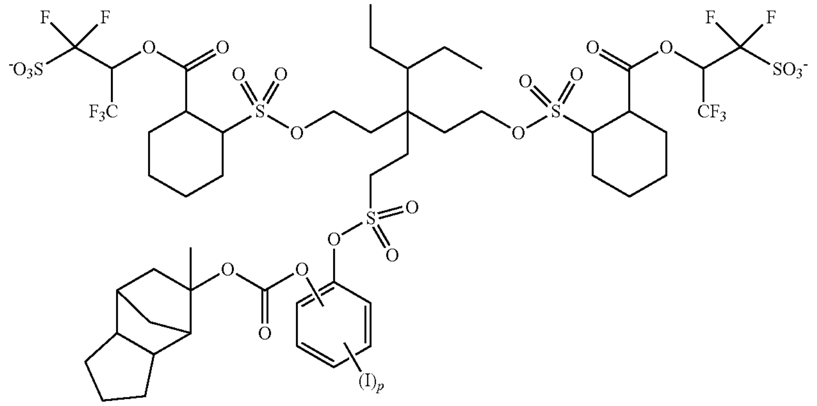
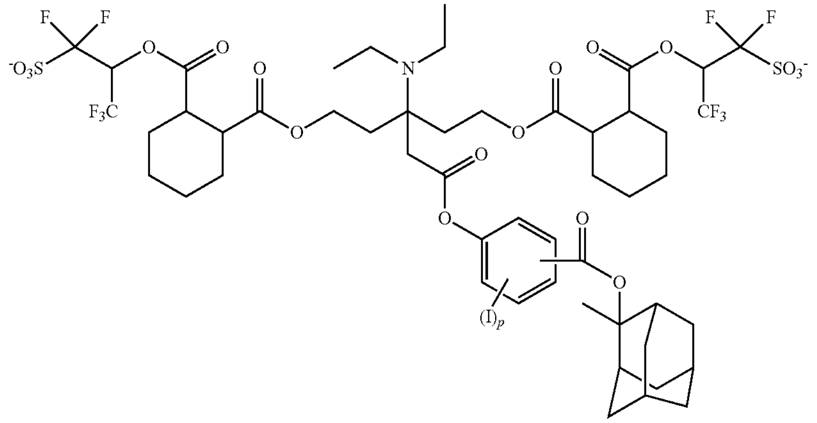
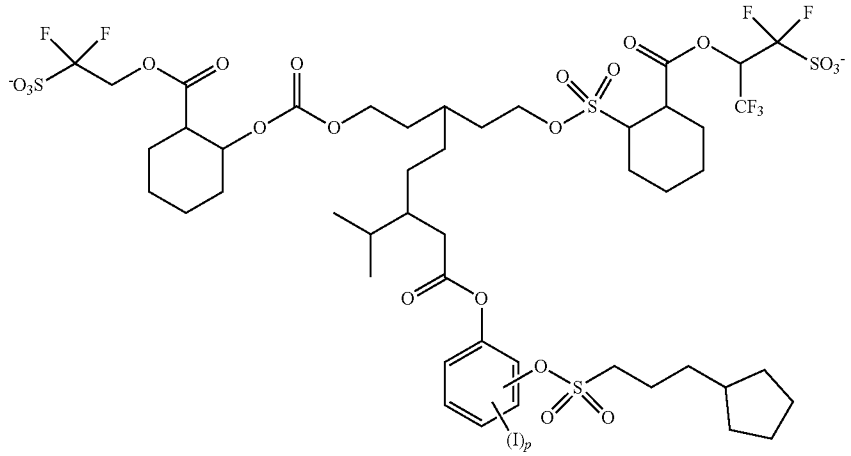

-continued
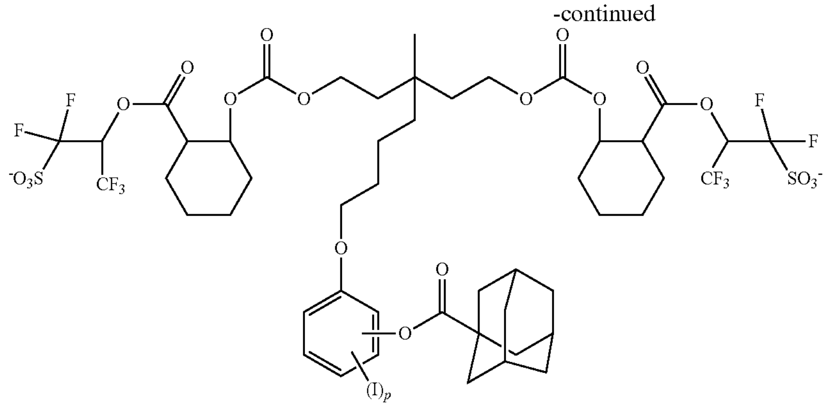
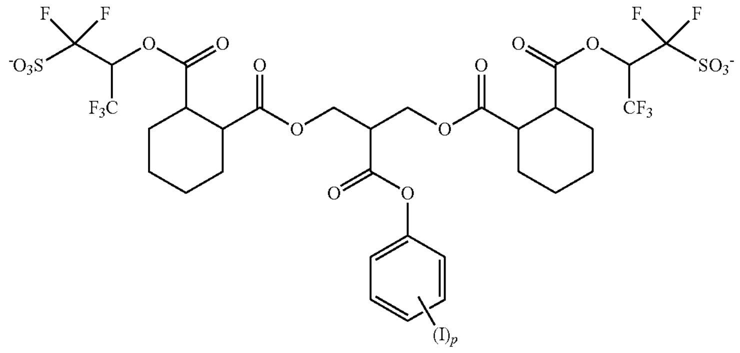
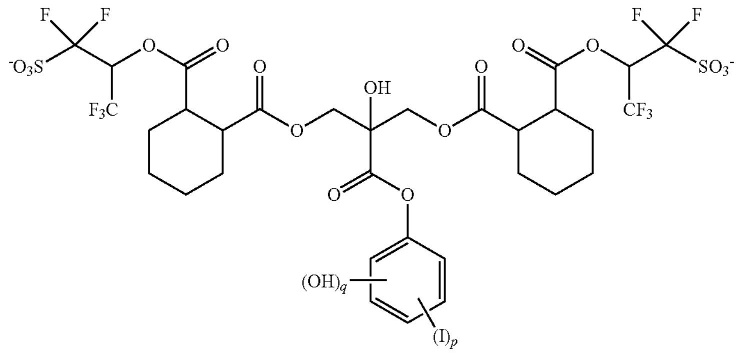
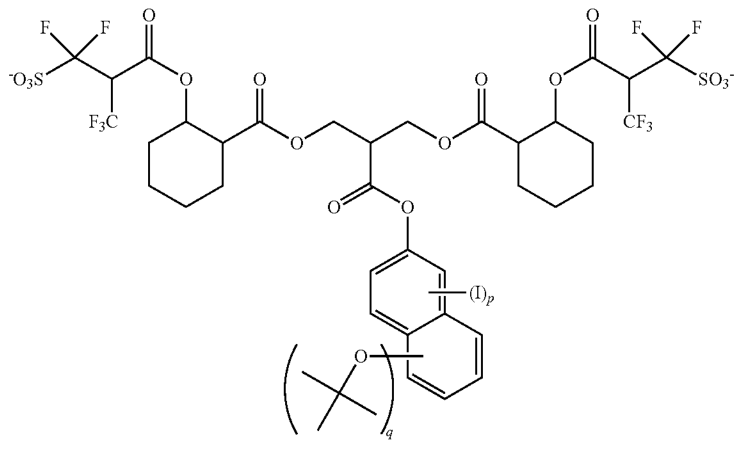

-continued
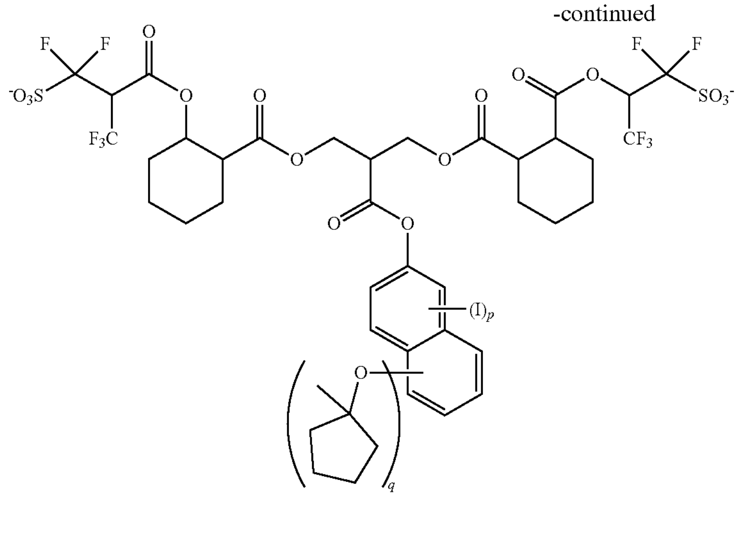
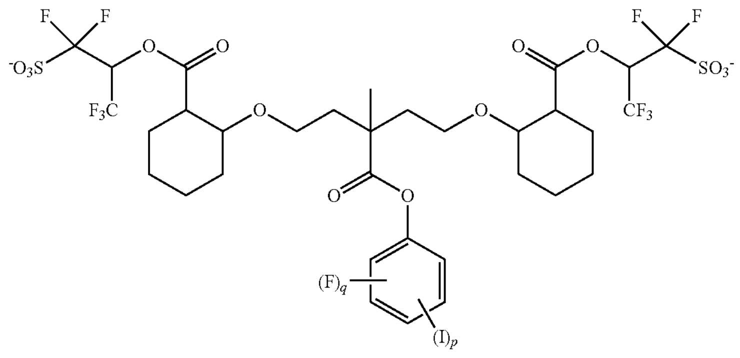
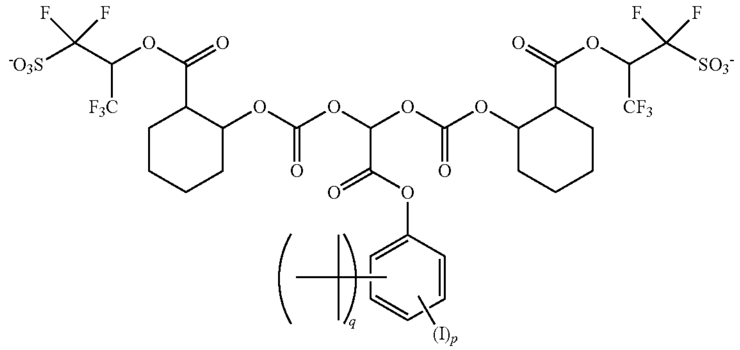
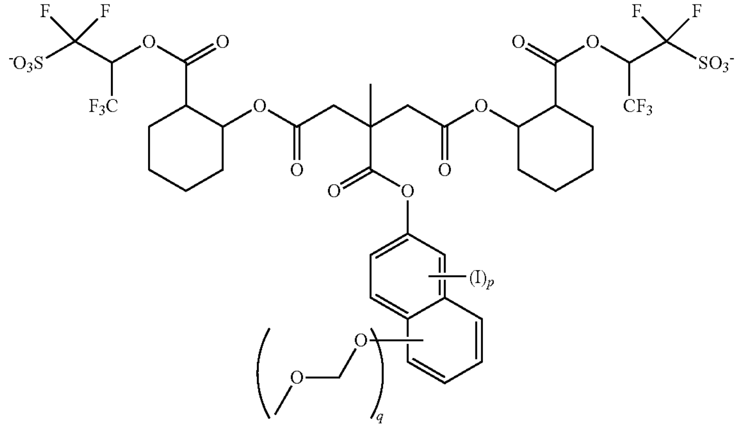

-continued
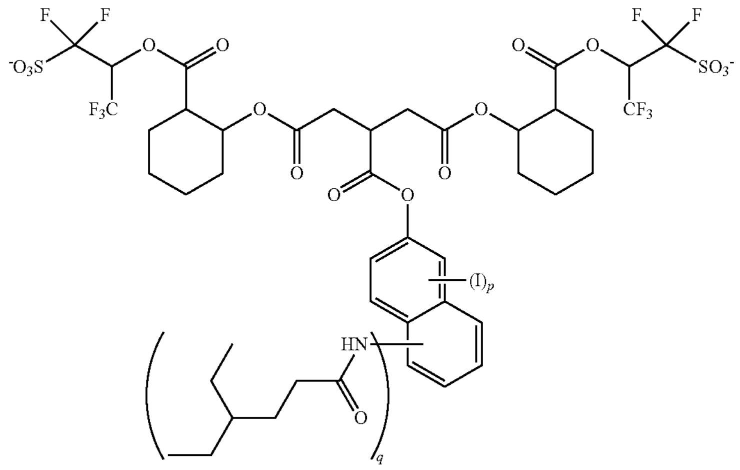
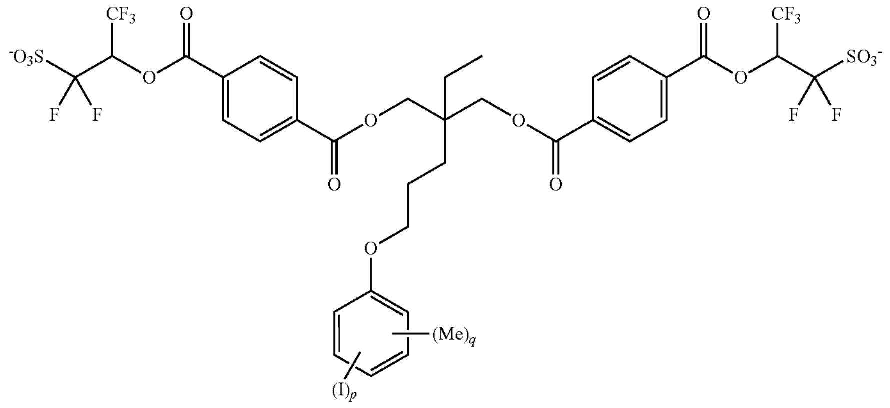
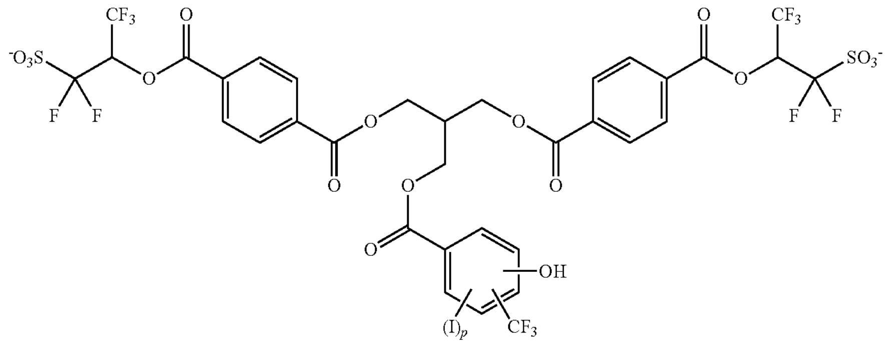
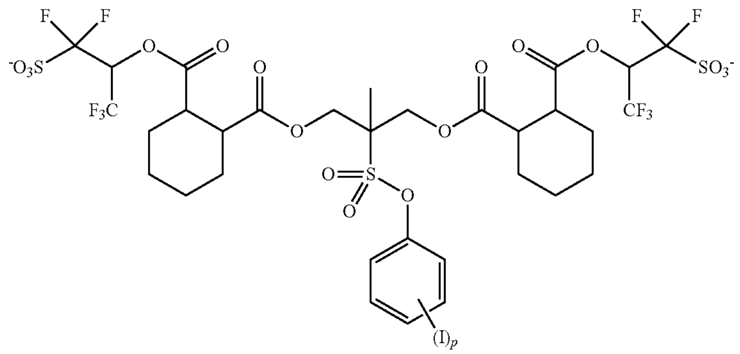

-continued
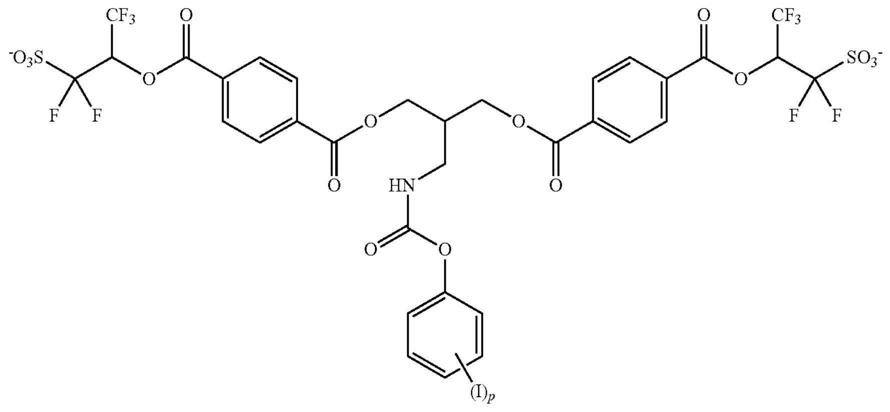
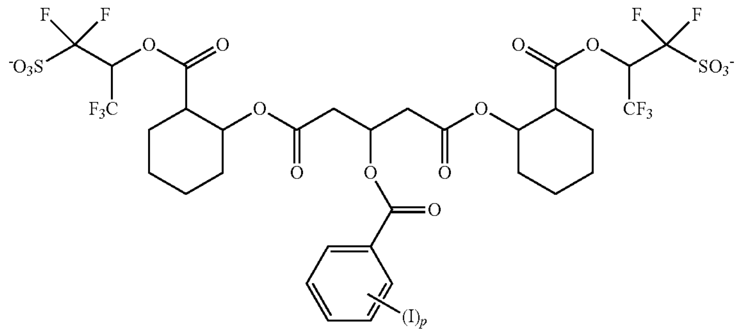
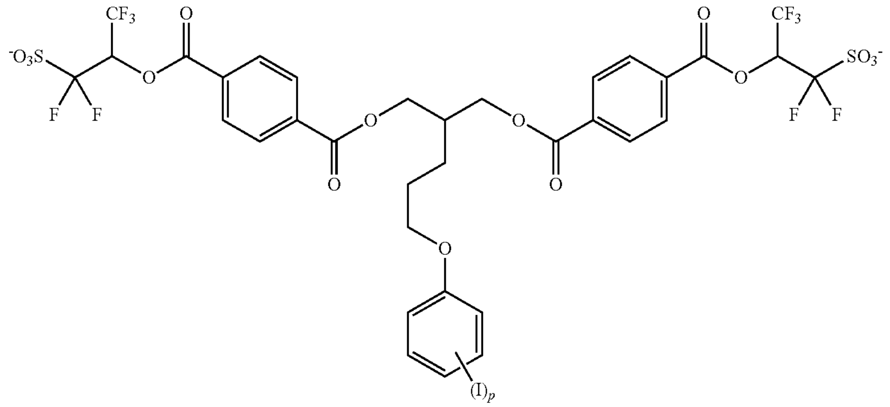
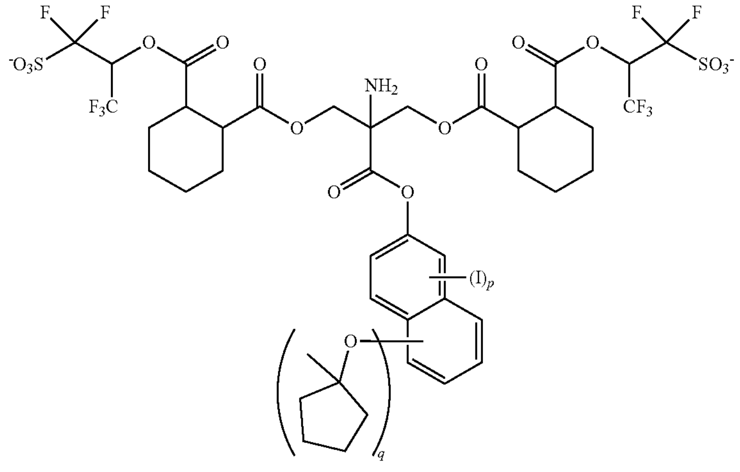

-continued
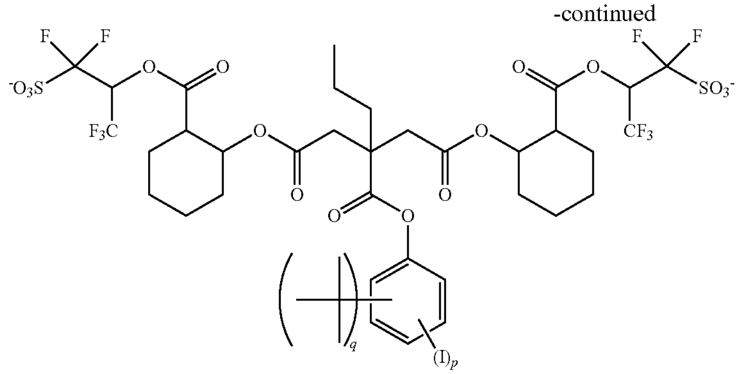
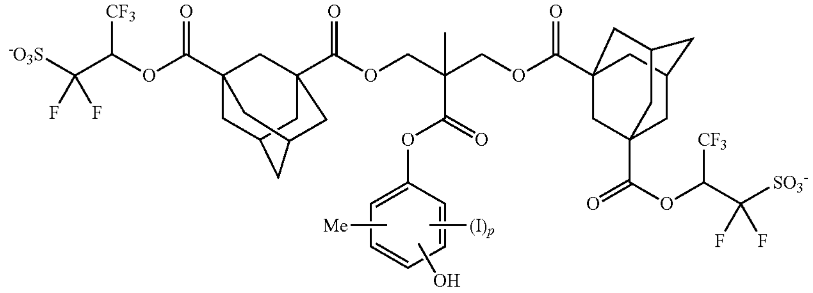
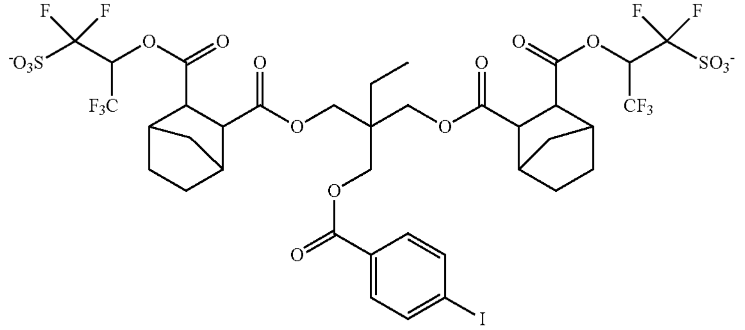
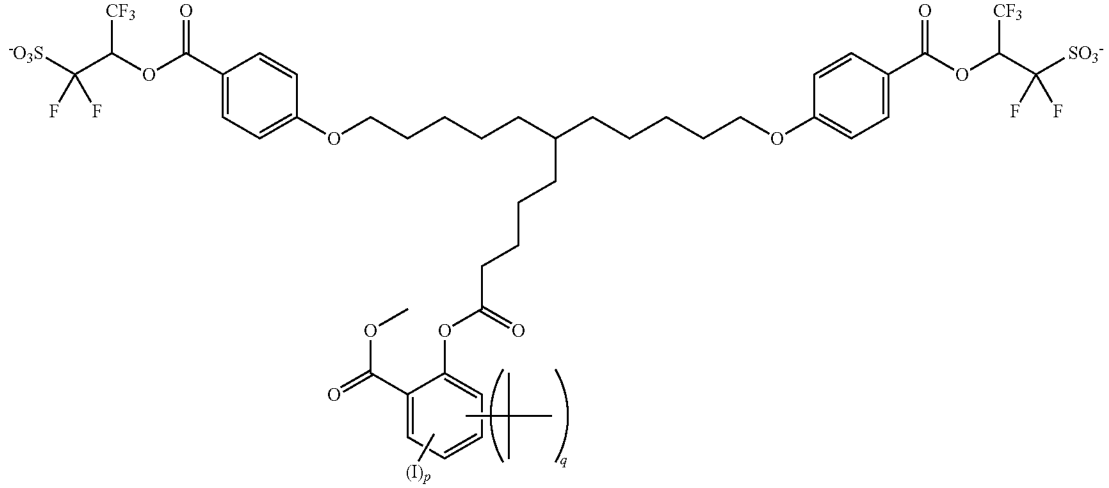

-continued
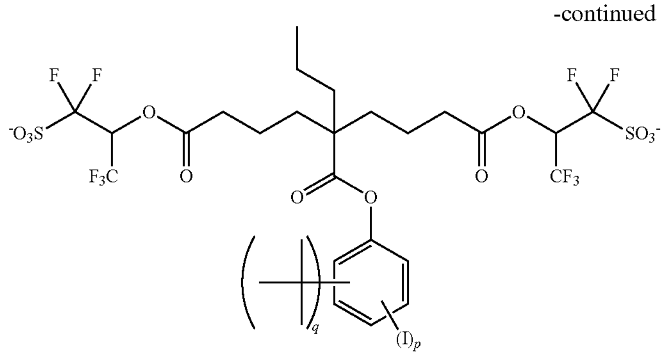
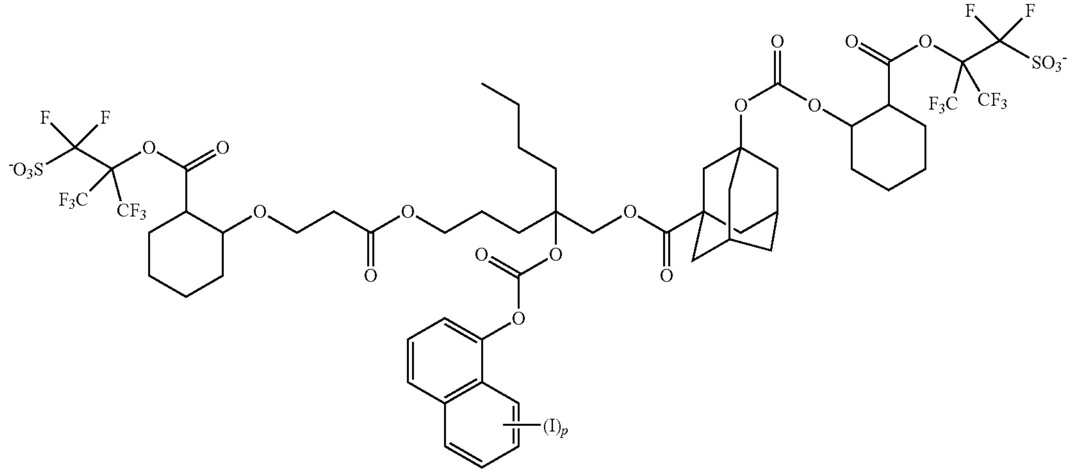
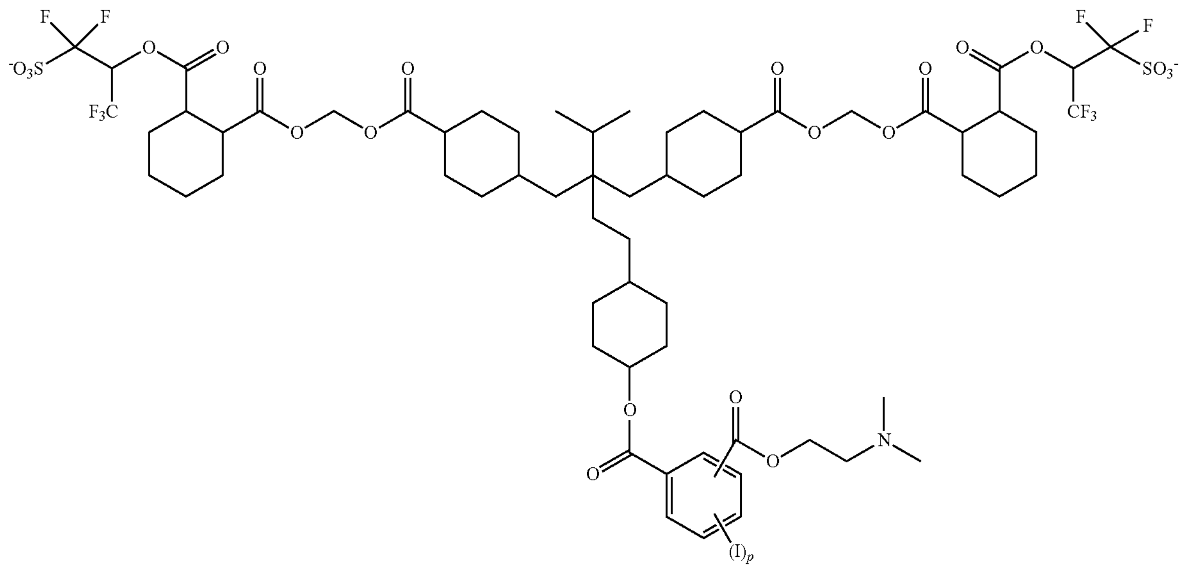

-continued
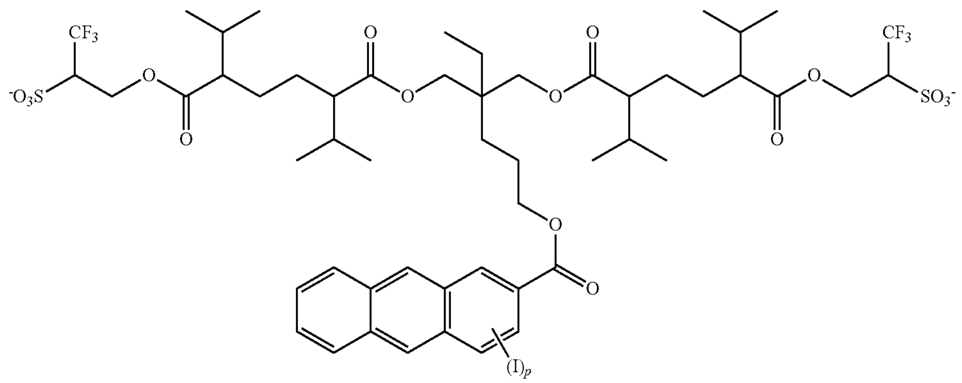
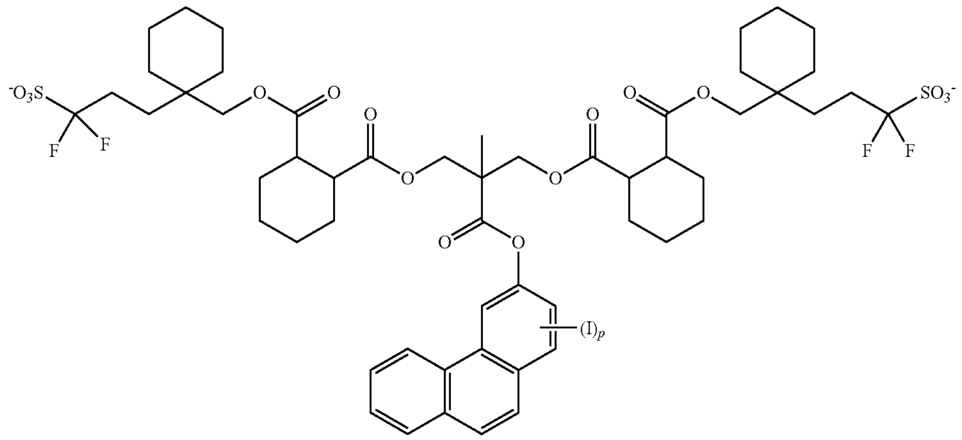
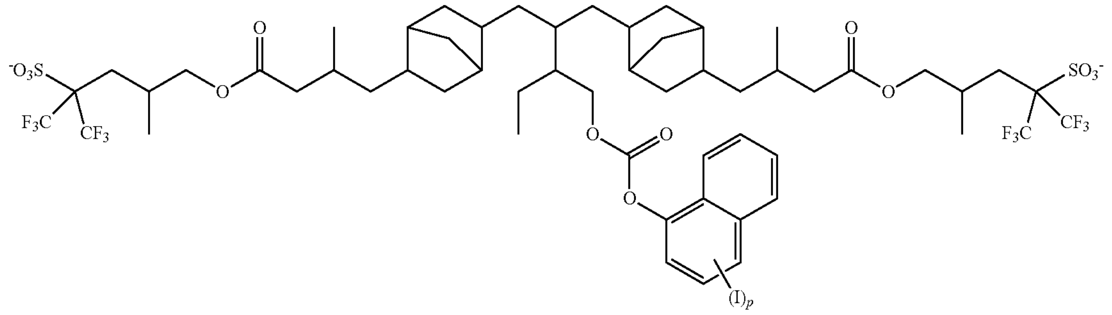

Illustrative structures of the PAG include combinations of anions with cations, both as exemplified above, although the PAG is not limited thereto.

Among others, the following compounds are most preferred.

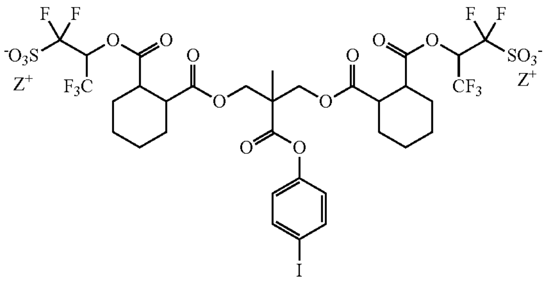

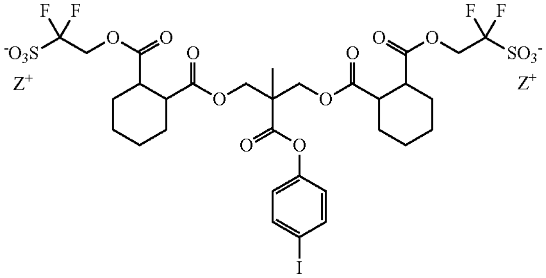

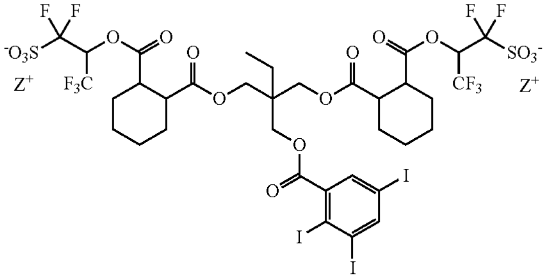

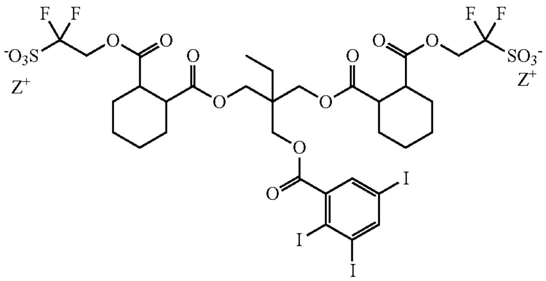

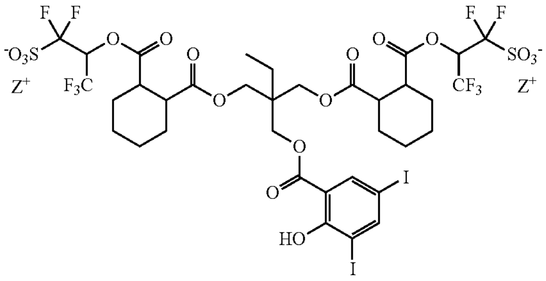

-continued

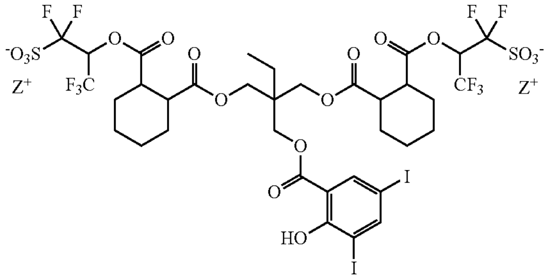

Herein, $Z^+$ is a sulfonium cation having any of the following formulae.

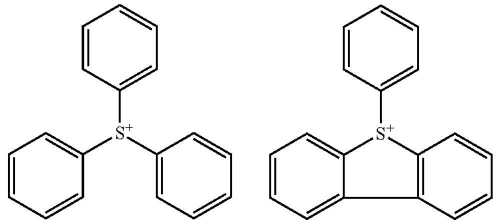

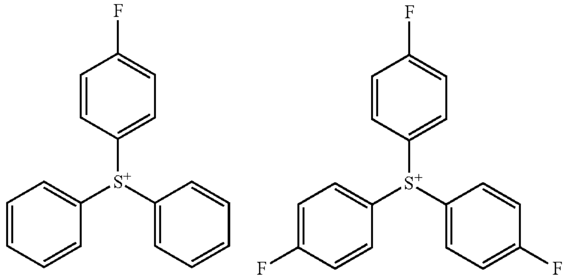

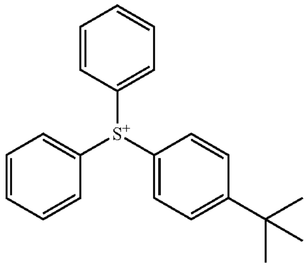

With respect to the synthesis of the onium salt having formula (1), for example, the onium salt having formula (1) wherein $L^{b1}$ and $L^{b2}$ are ester bonds and $Za^+$ and $Zb^+$ are the same can be synthesized according to the following scheme.

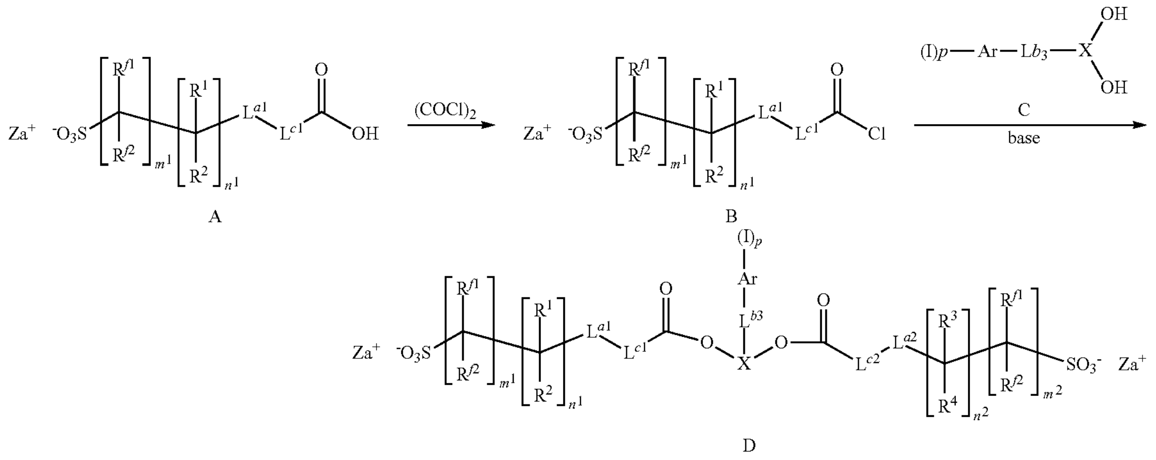

Herein, X, $R^1$, $R^2$, $R^3$, $R^4$, $R^{f1}$, $R^{f2}$, $R^{f3}$, $R^{f4}$, $m^1$, $m^2$, $n^1$, $n^2$, $L^{a1}$, $L^{a2}$, $L^{c1}$, $L^{c2}$, $L^{b3}$, Ar, p, and $Za^+$ are as defined above.

In the first step, carboxylic acid sulfonium salt A is reacted with oxalyl chloride to synthesize acid chloride B.

In the second step, acid chloride B is reacted with diol C in the presence of a base for esterification to synthesize the desired compound D. Pyridine is typical of the base.

Alternatively, the desired compound can be synthesized by synthesizing the cation of the starting compound as an alkali metal (e.g., sodium or potassium) salt or ammonium salt according to the above scheme, and converting the cation to the desired cation species through ion exchange reaction. It is noted that the ion exchange reaction may be performed by any well-known methods, for example, with reference to JP-A 2007-145797.

The synthesis method mentioned above is merely exemplary and the invention is not limited thereto.

The inventive PAG is characterized by the anion of specific bis-sulfonate structure containing at least one iodine atom. A resist composition comprising the PAG has a considerably high acid diffusion-suppressing ability and is accordingly effective for improving resist performance factors, especially LWR, CDU and MEF. It is believed that such improvements are attributable to a highly polar structure possessing two salt structures within a single molecule. When a cyclic group is contained, the bulky structure of the cyclic group collaborates with the high atomic weight of iodine atom to reduce the acid diffusion length, achieving improvements in CDU and LWR. Notably, Patent Document 1 describes a resist composition comprising a PAG having a bis-sulfonium cation. Herein the polarity of the anion is unchanged from that of conventional mono-sulfonium salts. It is thus believed that the PAG of Patent Document 1 does not possess a high acid diffusion-suppressing ability as does the inventive PAG, failing to exert satisfactory lithography performance.

Patent Documents 3 and 4 describe a resist composition comprising a PAG having a bis-sulfonate anion. In general, bis-onium salts have a low organic solvent solubility because of their high polarity. This nature suggests risks of causing coating defects, leach-out in water during immersion exposure and concomitant defects. In contrast, the inventive PAG causes few defects because the cyclic group within its molecule contributes to an improvement in lipophilicity prior to acid elimination reaction. The inventive PAG is quite useful as an ingredient for resist compositions.

Also, Patent Document 5 describes a resist composition comprising a similar PAG. This resist composition has a low sensitivity, leaving concern about film residues after development. In contrast, the inventive PAG is quite absorptive to EUV of wavelength 13.5 nm due to iodine atom within the molecule. The iodine atom generates secondary electrons upon exposure. Then, a high sensitivity is achievable as compared with conventional mono-onium salts and prior art bis-sulfonium salts. Accordingly, the inventive PAG is successful in overcoming the outstanding tradeoff relationship of sensitivity to roughness in a good balance. The inventive PAG is quite useful in forming resist patterns by the EUV lithography.

Resist Composition

Another embodiment of the invention is a chemically amplified resist composition comprising (A) the photoacid generator having formula (1), (B) a base polymer adapted to change its solubility in a developer under the action of acid, and (C) an organic solvent as essential components.

In the resist composition, the PAG (A) is preferably used in an amount of 0.1 to 40 parts by weight, more preferably 1 to 20 parts by weight per 80 parts by weight of the base polymer (B). The range of the PAG ensures a photoacid generating function without the risks of losing sensitivity and forming foreign particles due to shortage of solubility. The PAG may be used alone or in admixture of two or more.

(B) Base Polymer

The base polymer as component (B) is preferably a polymer comprising repeat units having the formula (a) or repeat units having the formula (b). These units are also referred to as repeat units (a) and (b).

(a)

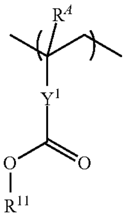

-continued (b)

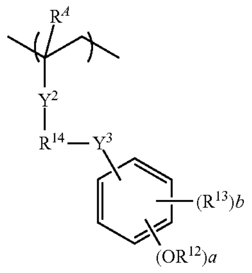

In formulae (a) and (b), $R^A$ is each independently hydrogen or methyl. $Y^1$ is a single bond, phenylene, naphthylene, or a $C_1$-$C_{12}$ linking group containing an ester bond and/or lactone ring. $Y^2$ is a single bond or ester bond. $Y^3$ is a single bond, ether bond or ester bond. $R^{11}$ and $R^{12}$ each are an acid labile group. When the base polymer contains both repeat units (a) and (b), $R^{11}$ and $R^{12}$ may be the same or different. $R^{13}$ is halogen, hydroxy, cyano, or a $C_1$-$C_6$ hydrocarbyl group in which some constituent —$CH_2$— may be replaced by —O— or —C(=O)—. $R^{14}$ is a single bond or a $C_1$-$C_6$ alkanediyl group in which some constituent —$CH_2$— may be replaced by an ether bond or ester bond. The subscript "a" is 1 or 2, "b" is an integer of 0 to 4, and 1≤a+b≤5.

Examples of the monomer from which repeat units (a) are derived are shown below, but not limited thereto. Herein $R^A$ and $R^{11}$ are as defined above.

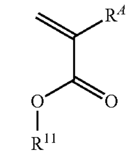
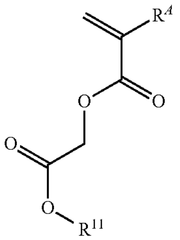
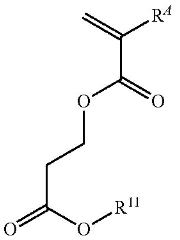
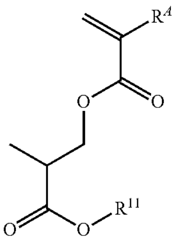
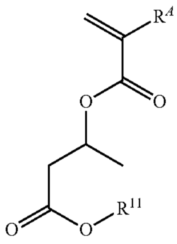
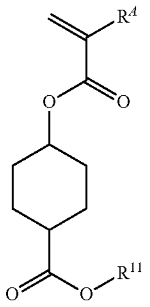
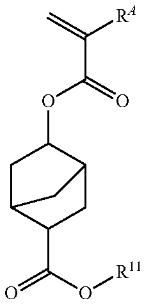
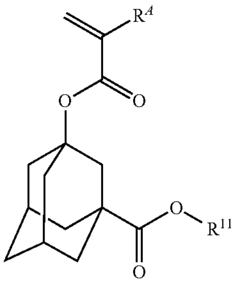

-continued

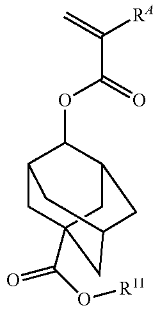
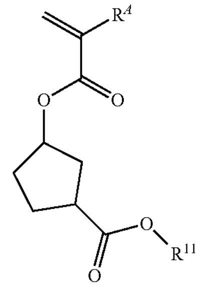
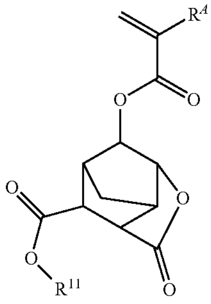
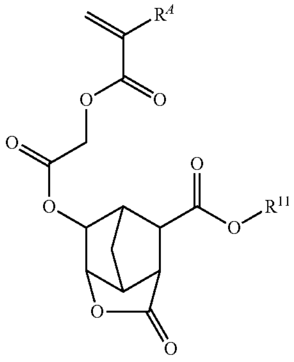
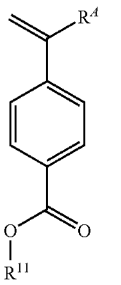
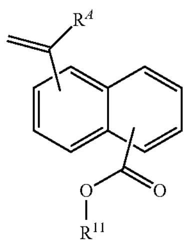

Examples of the monomer from which repeat units (b) are derived are shown below, but not limited thereto. Herein $R^A$ and $R^{12}$ are as defined above.

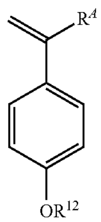
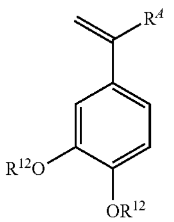
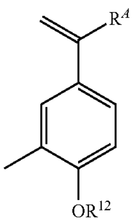
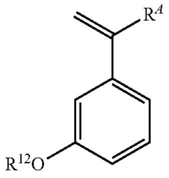
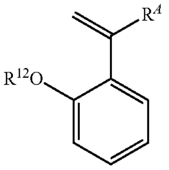
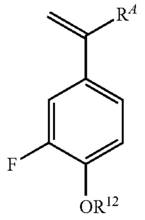

-continued

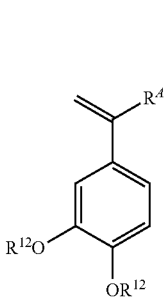
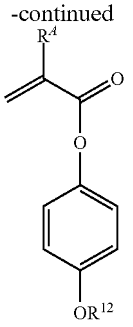
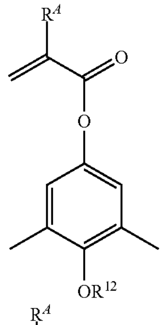
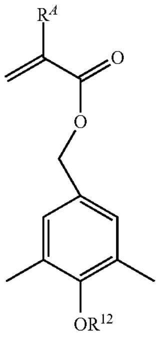
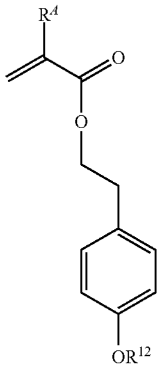
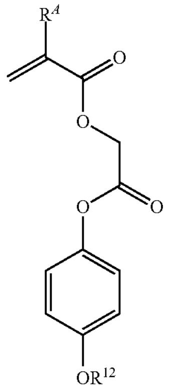
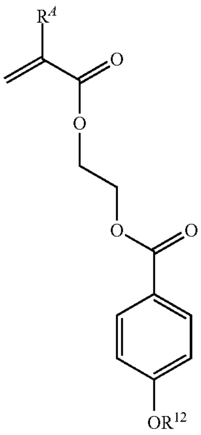
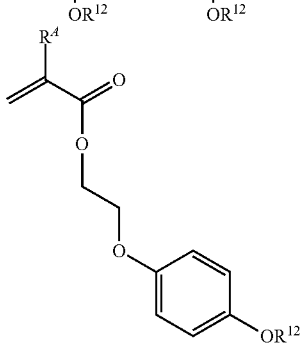

The acid labile groups represented by $R^{11}$ and $R^{12}$ may be selected from a variety of such groups, as described in JP-A 2013-080033 and JP-A 2013-083821, for example.

Typical are acid labile groups having the following formulae (AL-1) to (AL-3).

(AL-1)

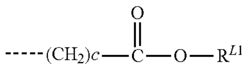

(AL-2)

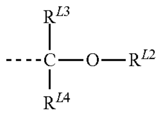

(AL-3)

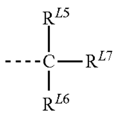

In formulae (AL-1) and (AL-2), $R^{L1}$ and $R^{L2}$ are each independently a $C_1$-$C_{40}$ hydrocarbyl group which may contain a heteroatom such as oxygen, sulfur, nitrogen or fluorine. The hydrocarbyl group may be saturated or unsaturated and straight, branched or cyclic. Of the hydrocarbyl groups, saturated hydrocarbyl groups of 1 to 40 carbon atoms, especially 1 to 20 carbon atoms are preferred.

In formula (AL-1), c is an integer of 0 to 10, preferably 1 to 5.

In formula (AL-2), $R^{L3}$ and $R^{L4}$ are each independently hydrogen or a $C_1$-$C_{20}$ hydrocarbyl group which may contain a heteroatom such as oxygen, sulfur, nitrogen or fluorine. The hydrocarbyl group may be saturated or unsaturated and straight, branched or cyclic. Of the hydrocarbyl groups, saturated hydrocarbyl groups of 1 to 20 carbon atoms are preferred.

Any two of $R^{L2}$, $R^{L3}$, and $R^{L4}$ may bond together to form a ring with the carbon atom or carbon and oxygen atoms to which they are attached. The ring thus formed is of 3 to 20 carbon atoms, preferably 4 to 16 carbon atoms, and especially alicyclic.

In formula (AL-3), $R^{L5}$, $R^{L6}$ and $R^{L7}$ are each independently a $C_1$-$C_{20}$ hydrocarbyl group which may contain a heteroatom such as oxygen, sulfur, nitrogen or fluorine. The hydrocarbyl group may be saturated or unsaturated and straight, branched or cyclic. Inter alia, saturated hydrocarbyl groups of 1 to 20 carbon atoms are preferred. Any two of $R^{L5}$, $R^{L6}$, and $R^{L7}$ may bond together to form a ring with the carbon atom to which they are attached. The ring thus formed is of 3 to 20 carbon atoms, preferably of 4 to 16 carbon atoms and especially alicyclic.

The base polymer may further comprise repeat units (c) having a phenolic hydroxy group as an adhesive group. Examples of the monomer from which repeat units (c) are derived are given below, but not limited thereto. Herein $R^A$ is as defined above.

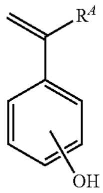
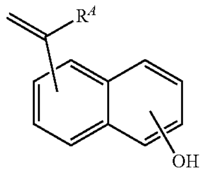
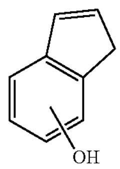
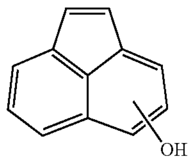
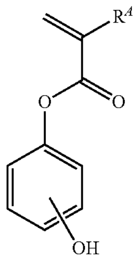
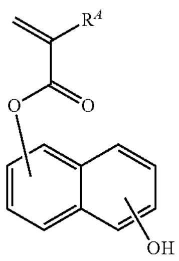
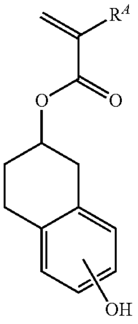
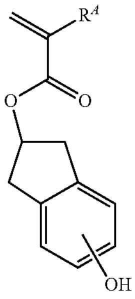
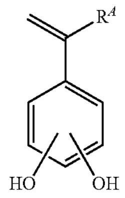

-continued

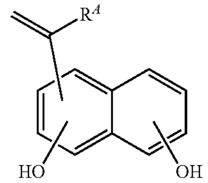
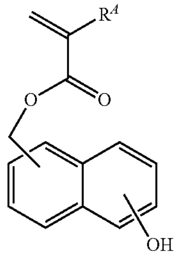
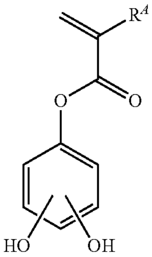
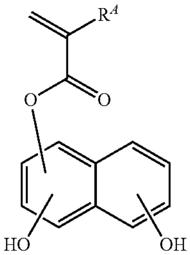
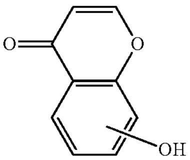
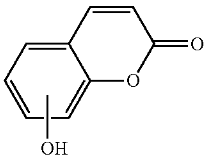
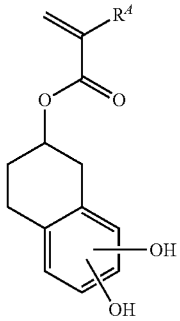
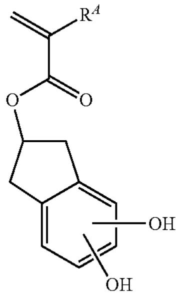
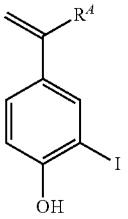
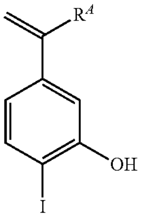
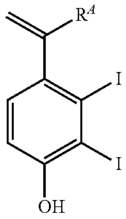
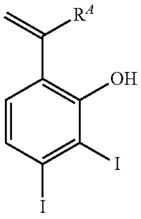
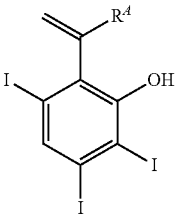
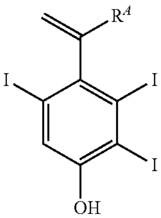
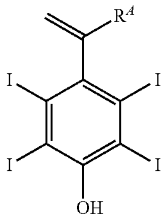
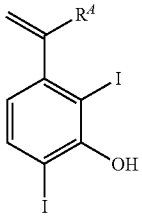
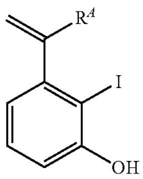
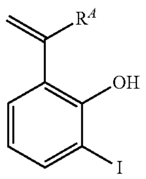
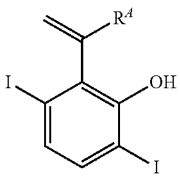
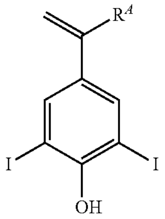
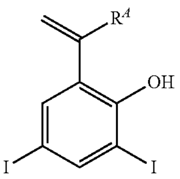

-continued

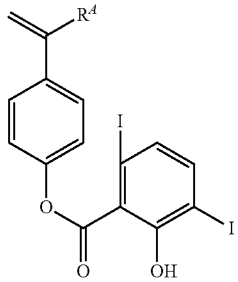
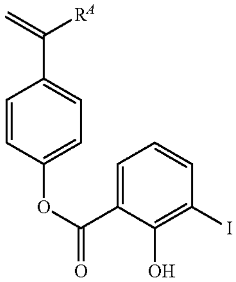
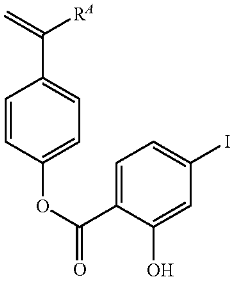
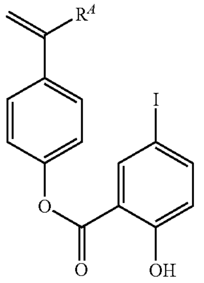
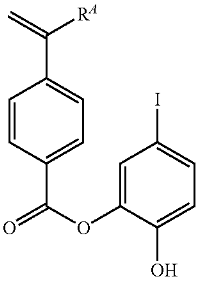
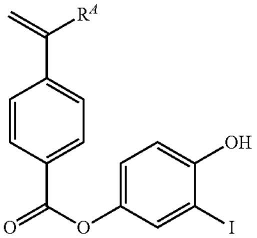
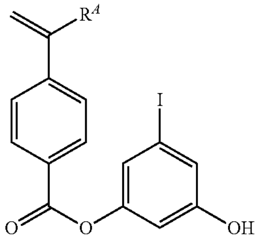

The base polymer may further comprise repeat units (d) having another adhesive group, which is selected from hydroxy (other than phenolic hydroxy), lactone ring, sultone ring, ether bond, ester bond, sulfonic ester bond, carbonyl, sulfonyl, cyano and carboxy groups. Examples of the monomer from which repeat units (d) are derived are given below, but not limited thereto. Herein $R^A$ is as defined above.

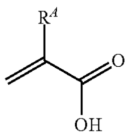
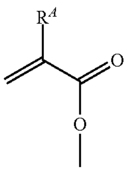
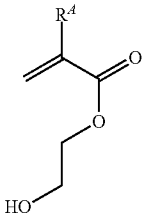

-continued
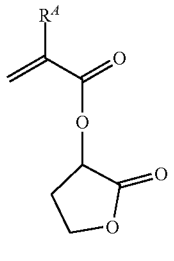
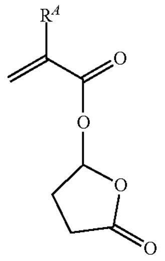
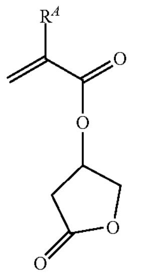
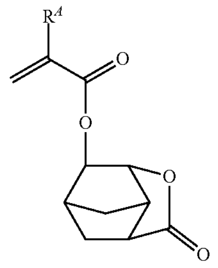
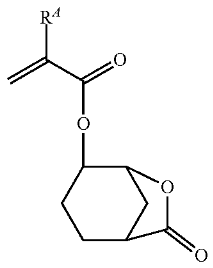
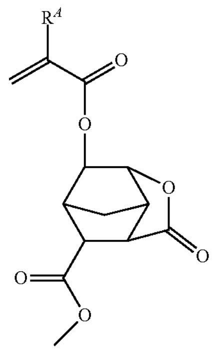
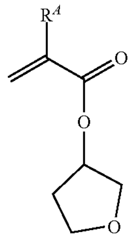
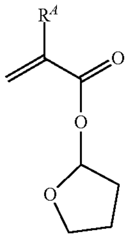
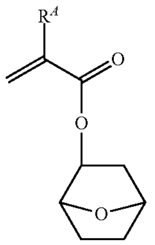
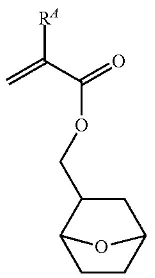
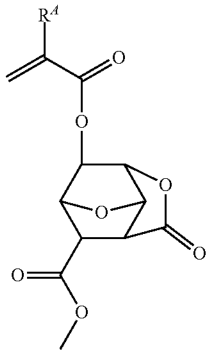
-continued
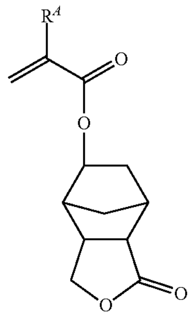
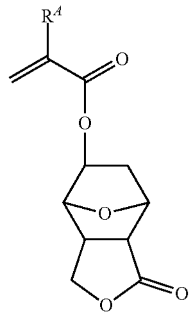
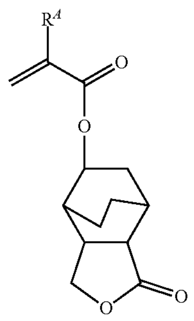
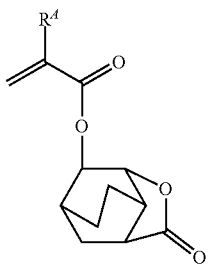
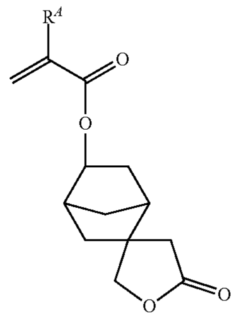
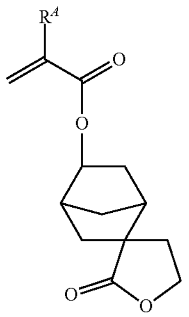
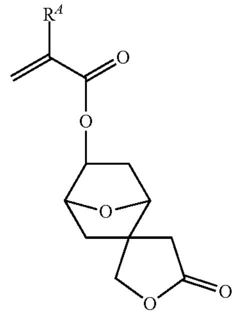
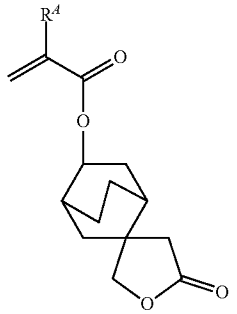
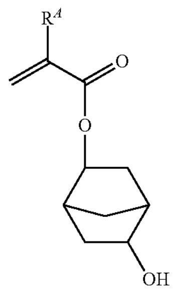
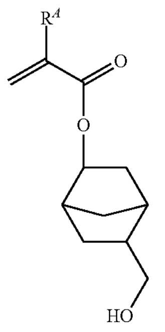

-continued
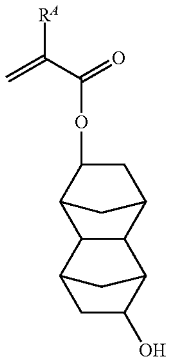
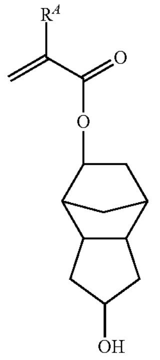
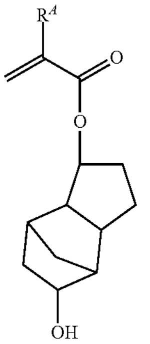
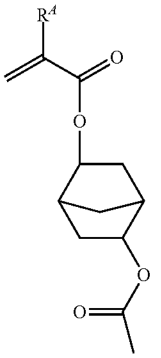
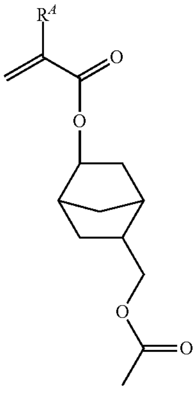
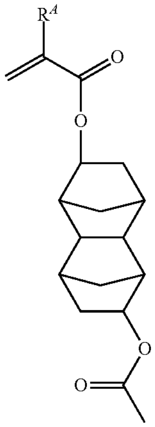
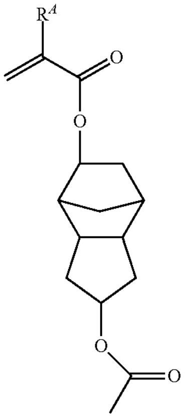
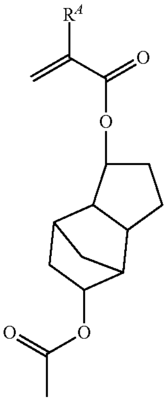
-continued
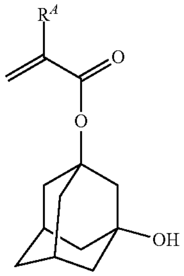
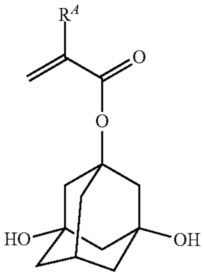
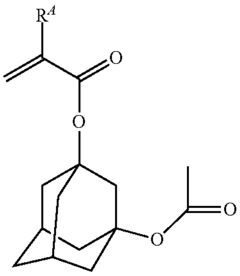
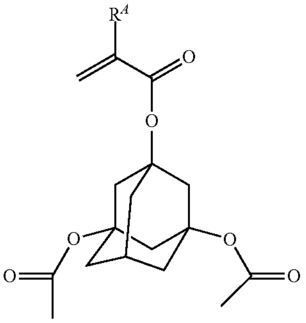
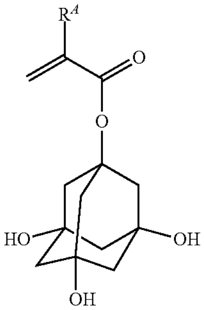
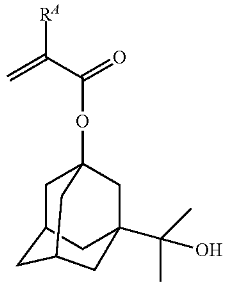
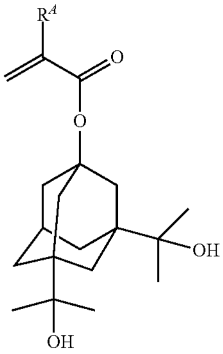
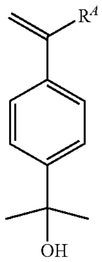
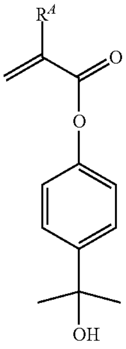
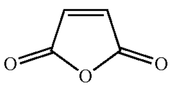
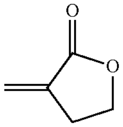

-continued
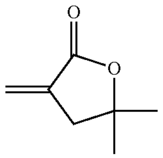
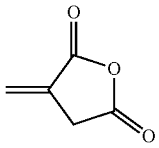
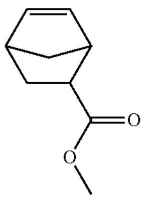
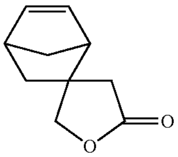
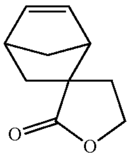
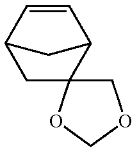
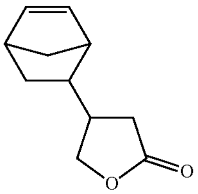
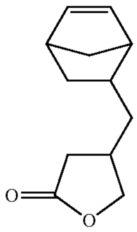
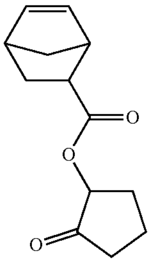
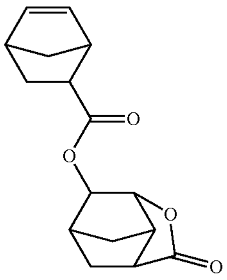
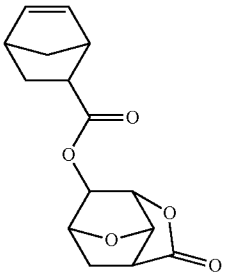
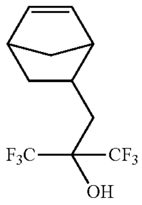
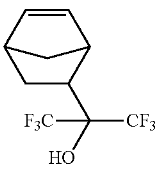
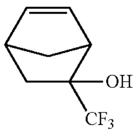
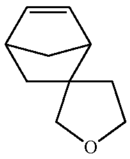
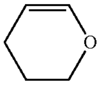
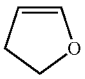
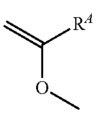
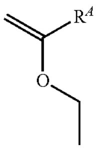
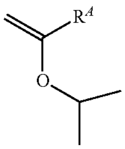
-continued
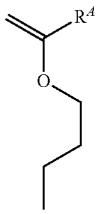
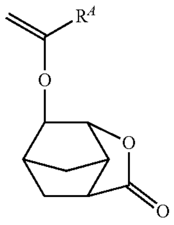
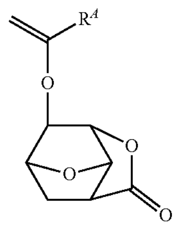
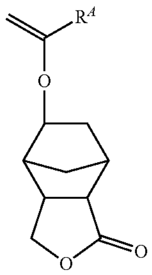
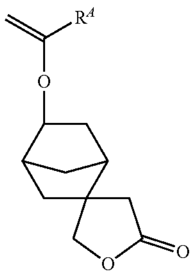
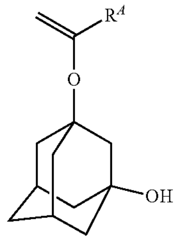
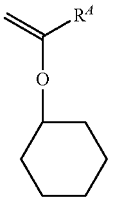
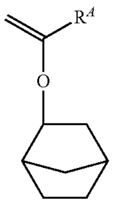
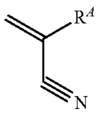
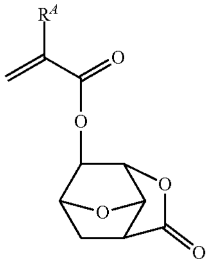
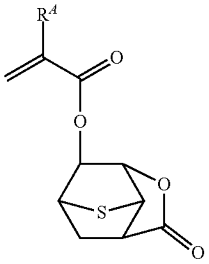
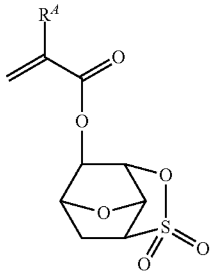
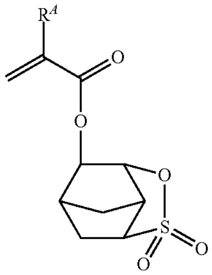

-continued
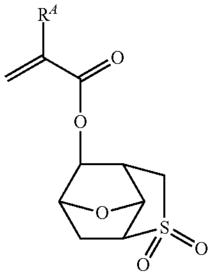
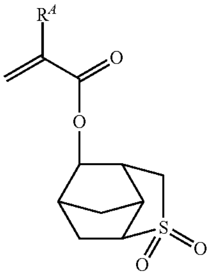
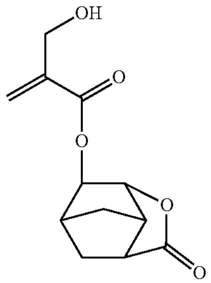
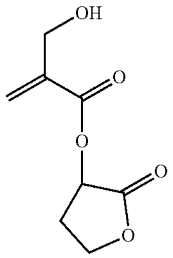
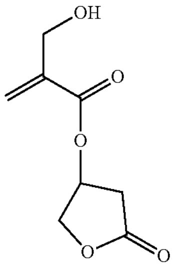
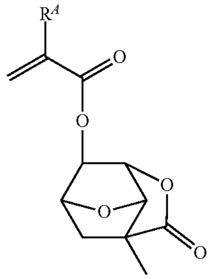
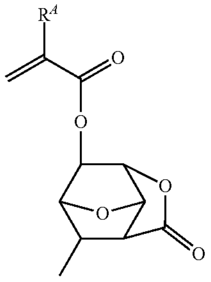
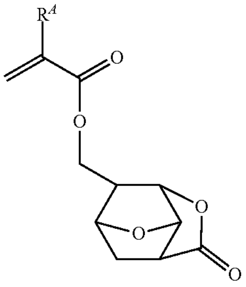
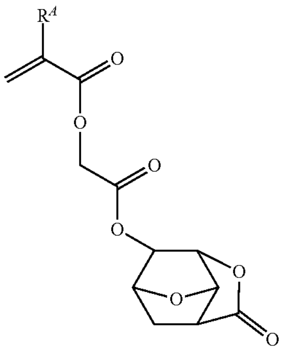
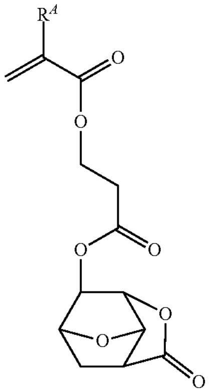
-continued
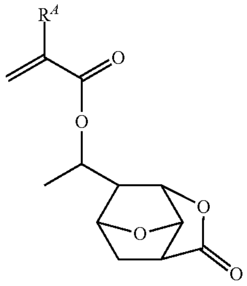
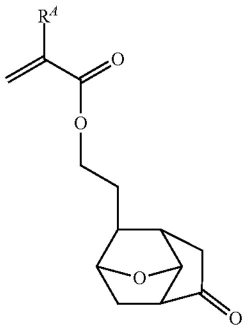
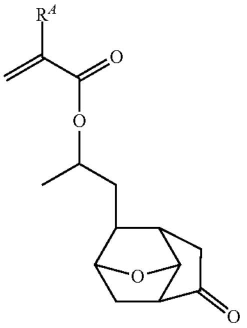
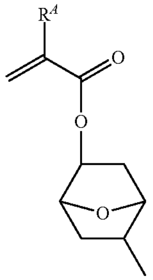
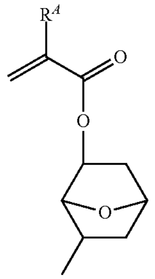
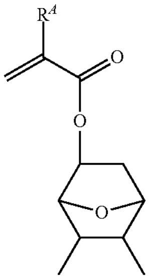
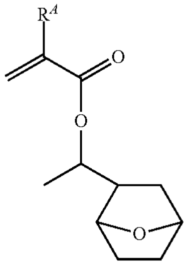
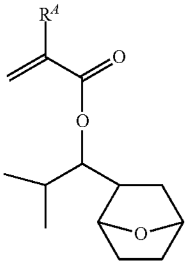
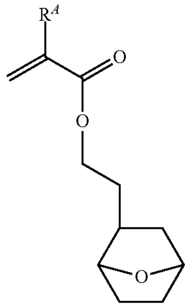
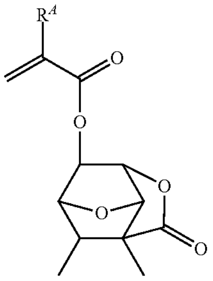

-continued
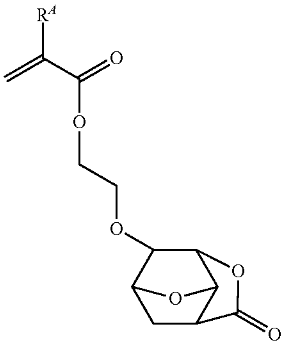
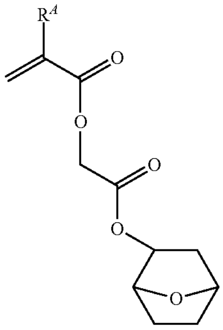
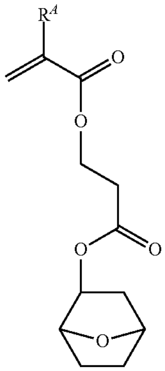
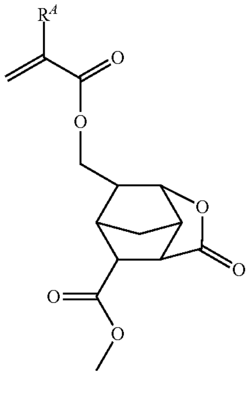
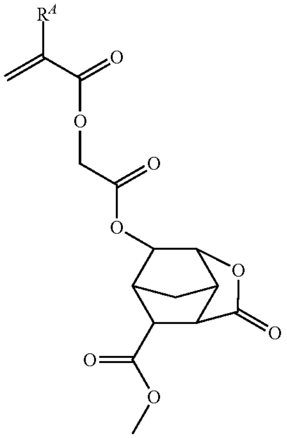
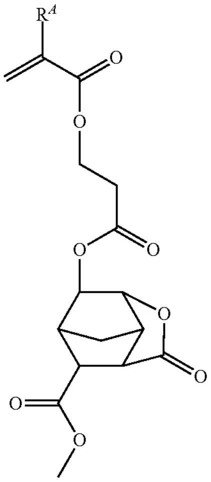
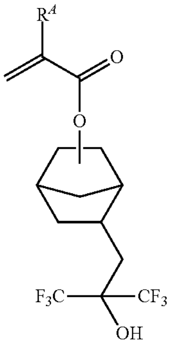
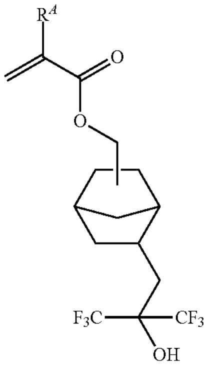
-continued
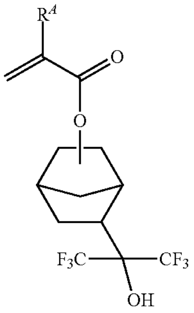
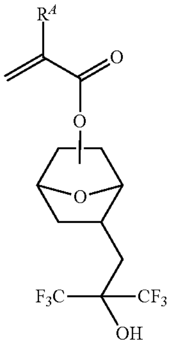
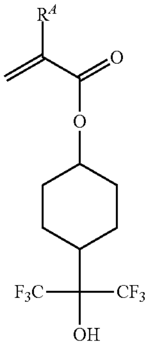
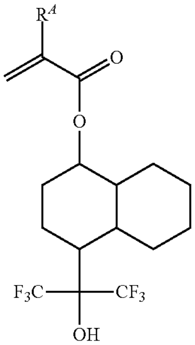
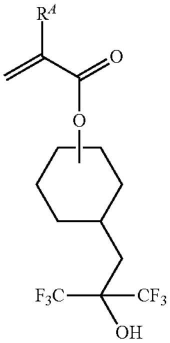
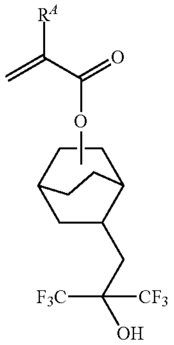
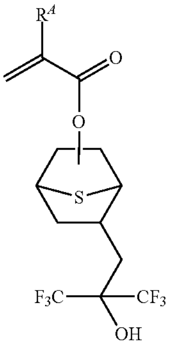
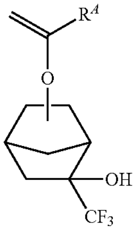
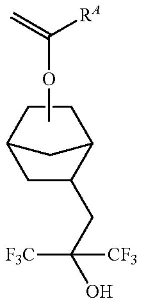
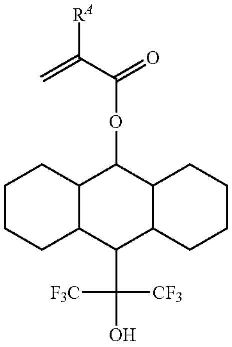

-continued
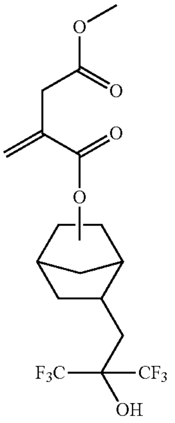
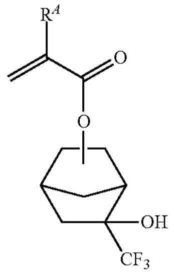
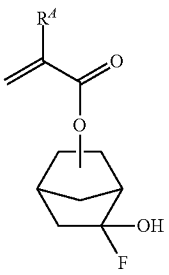
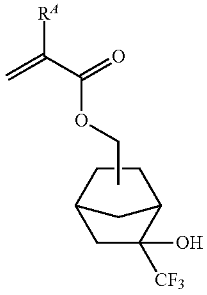
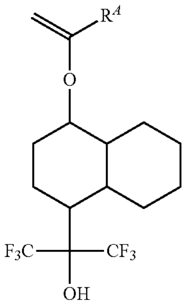
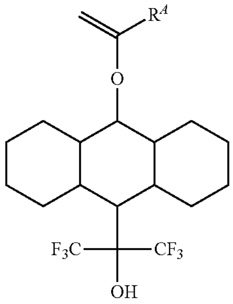
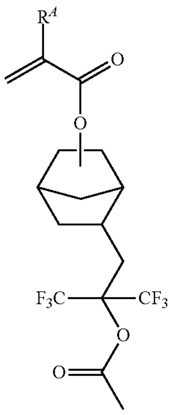
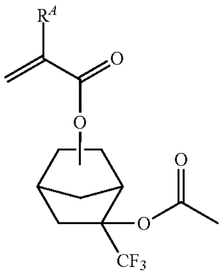
-continued
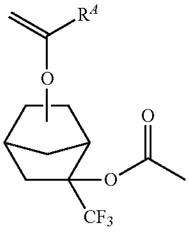
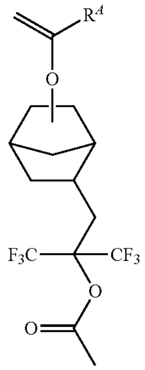
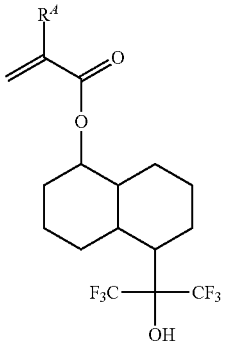
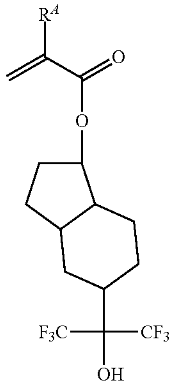
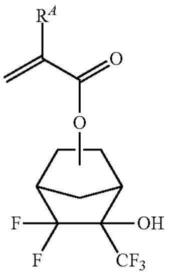
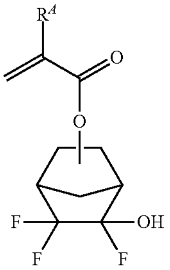
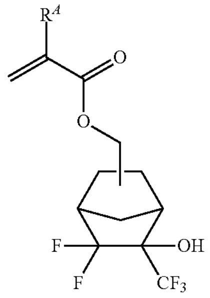
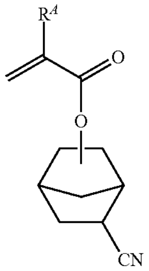
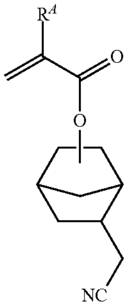
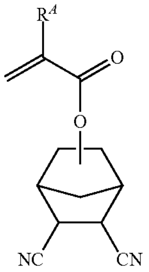

-continued
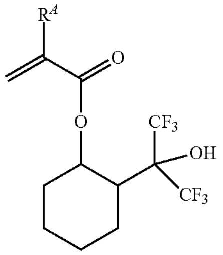
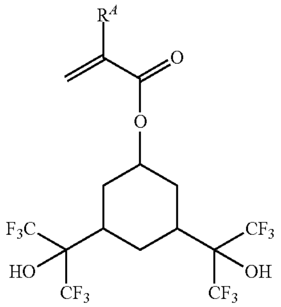
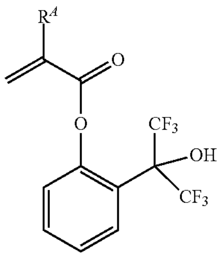
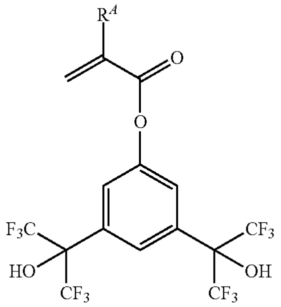
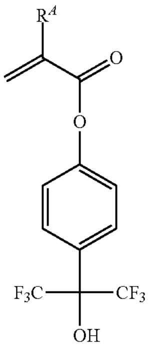
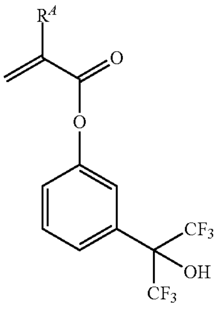
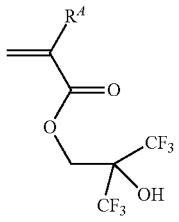
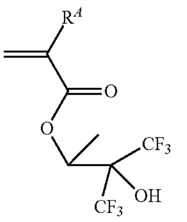
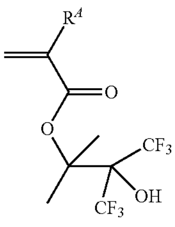
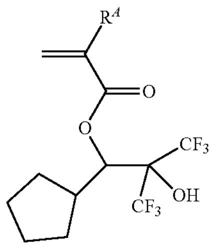
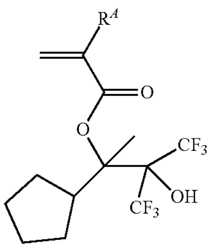
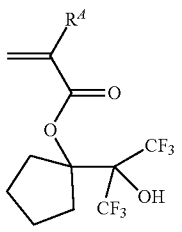
-continued
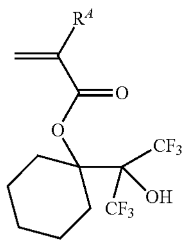
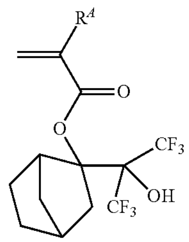
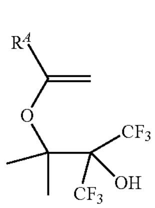
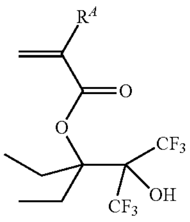
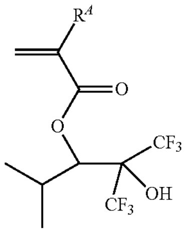
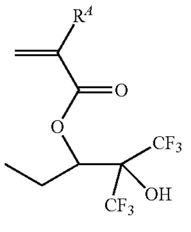
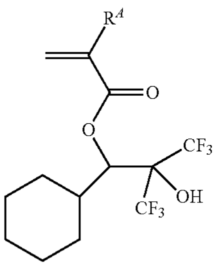
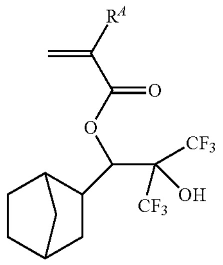
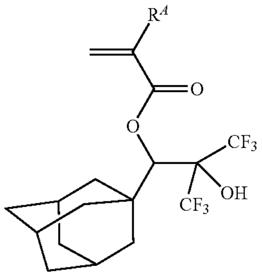
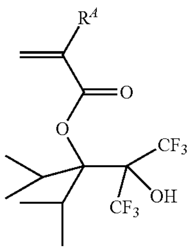
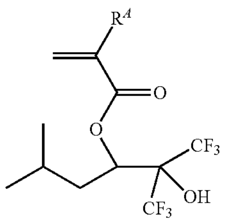
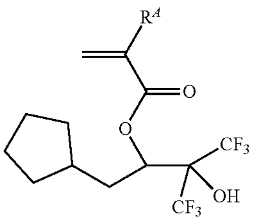
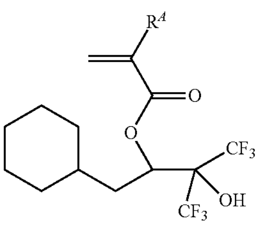
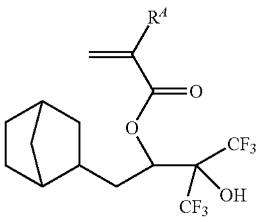

-continued
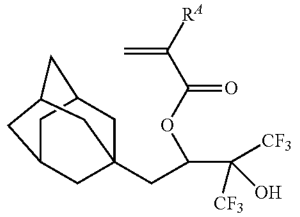
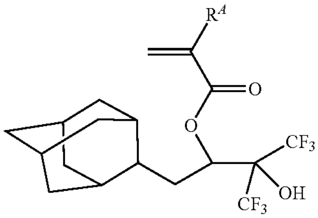
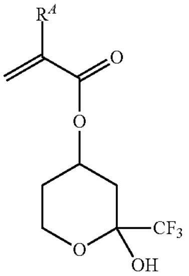
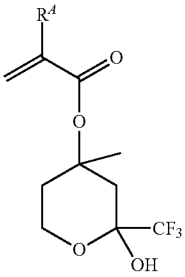
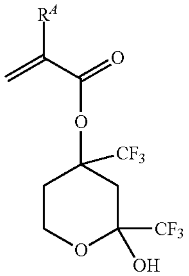
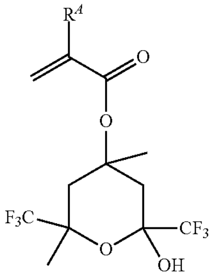
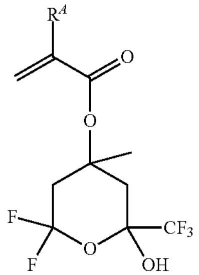
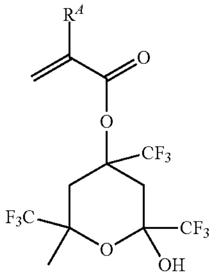
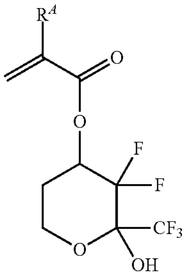
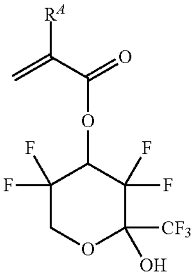
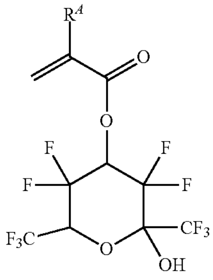
-continued
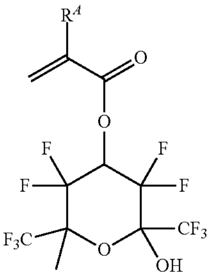
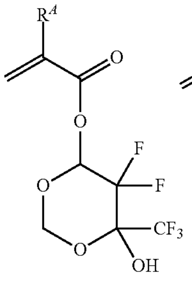
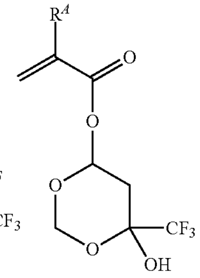
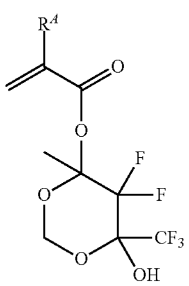
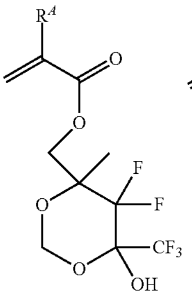
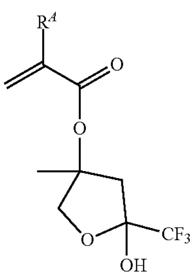
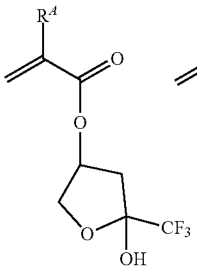
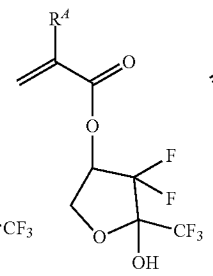
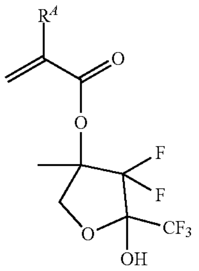
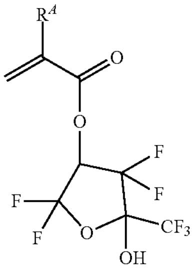
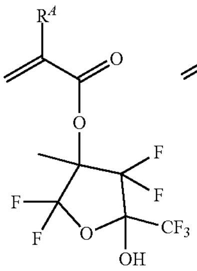
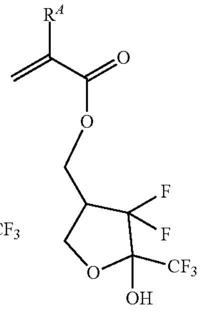
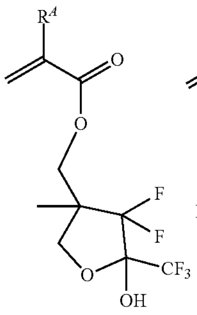
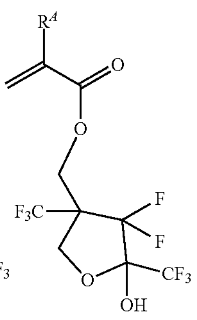
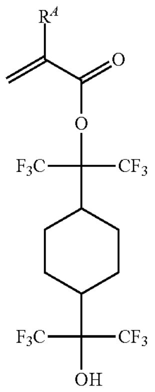

-continued
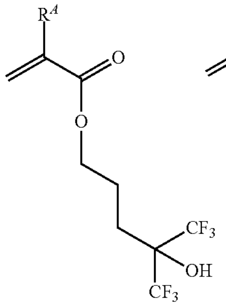
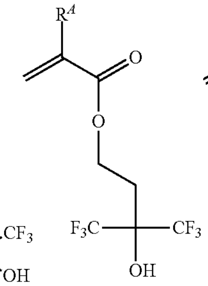
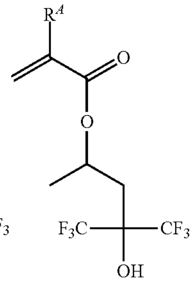
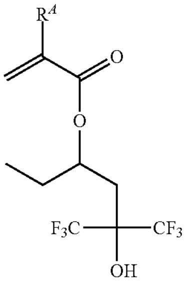
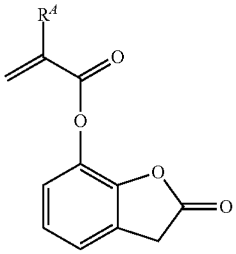
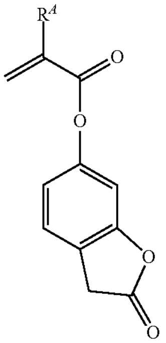
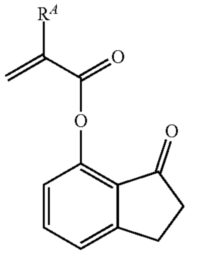
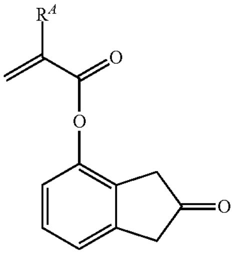
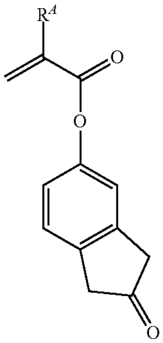
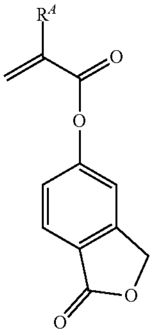
-continued
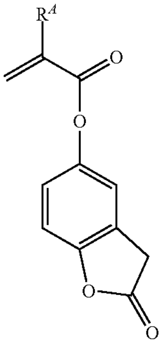
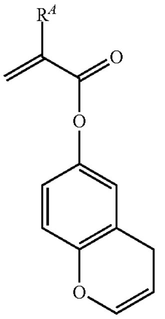
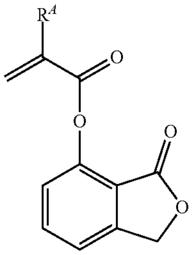
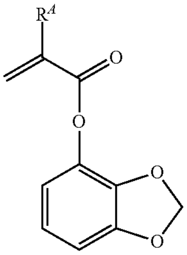
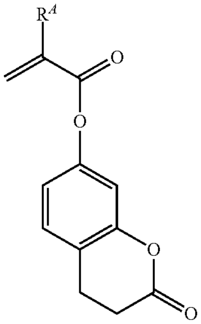
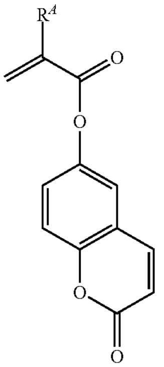
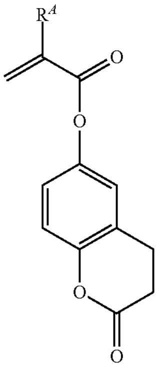
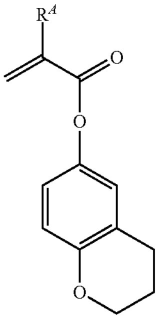
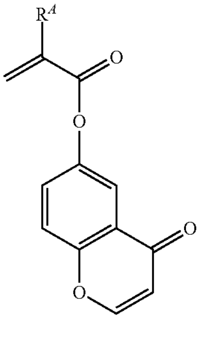
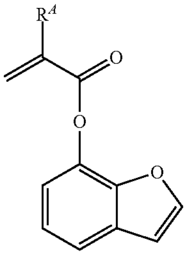

-continued
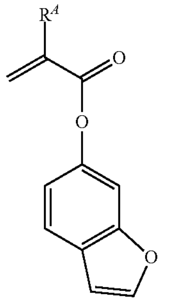
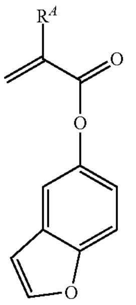
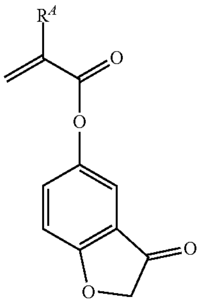
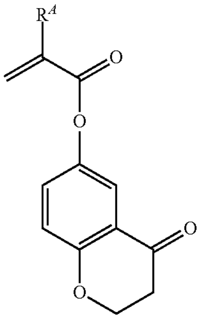
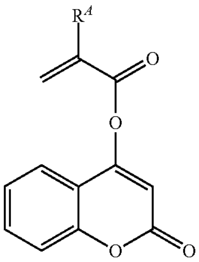
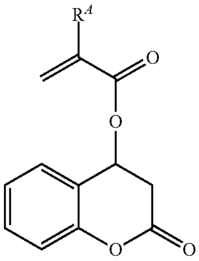
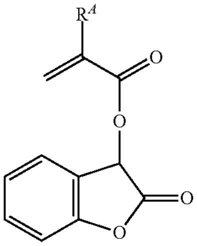
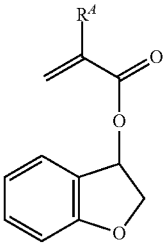
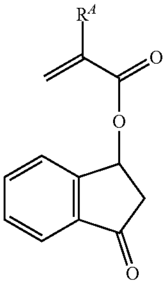
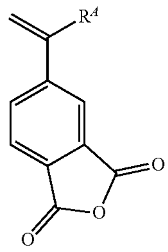
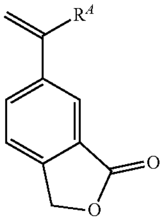
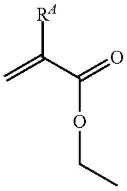
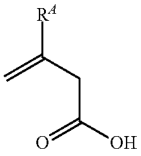
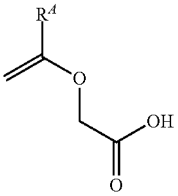
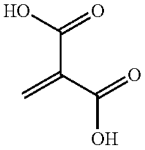
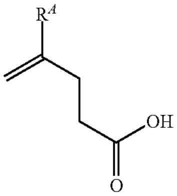
-continued
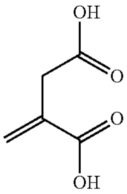
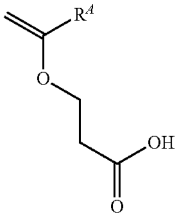
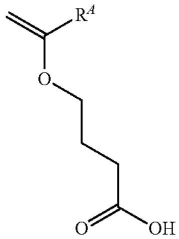
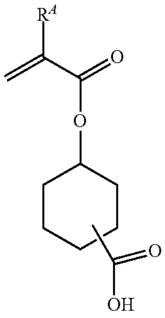
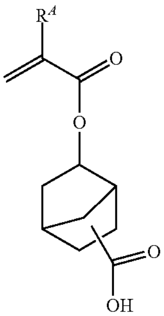
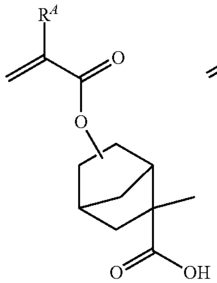
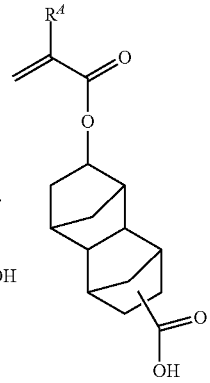
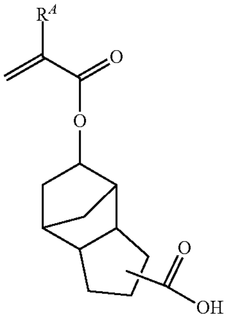
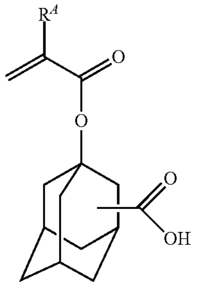
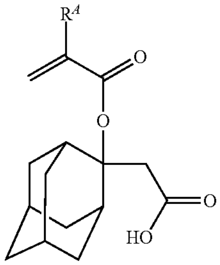
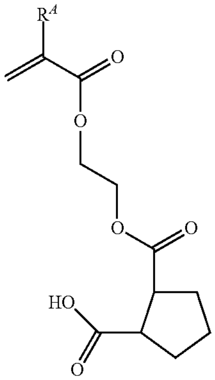

-continued
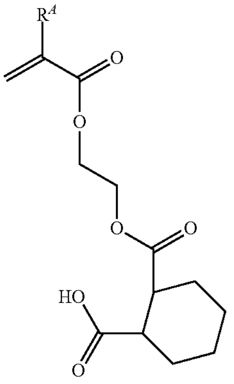
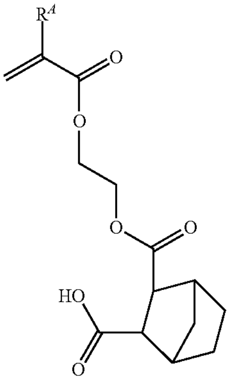
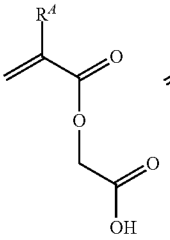
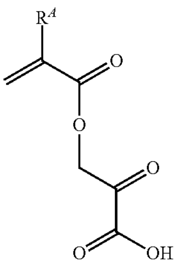
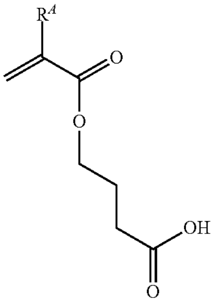
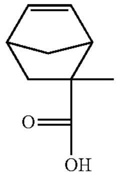
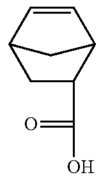
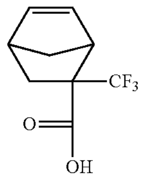
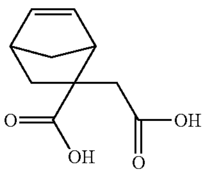
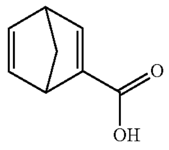
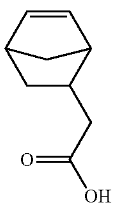
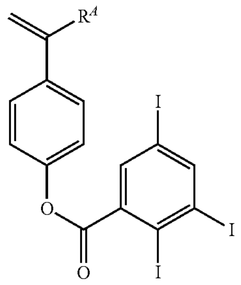
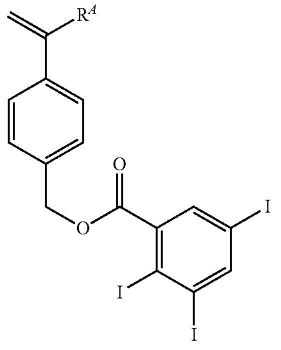
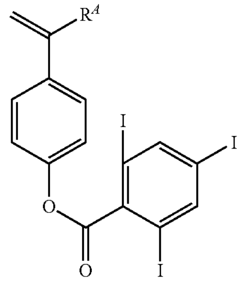
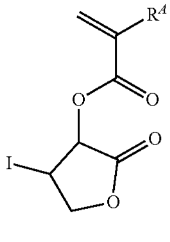
-continued
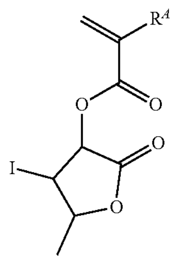
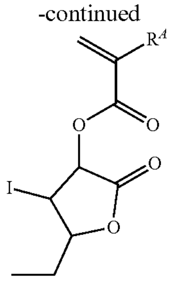
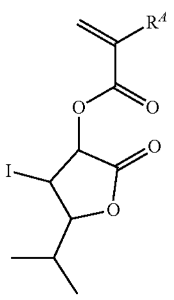
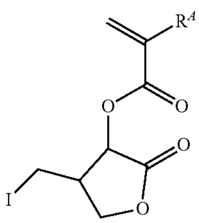
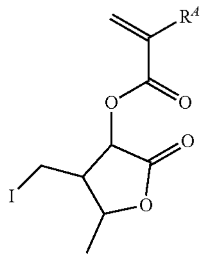
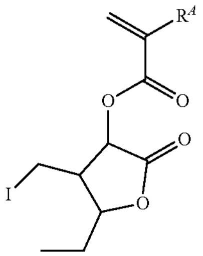
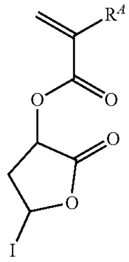
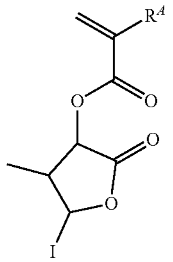
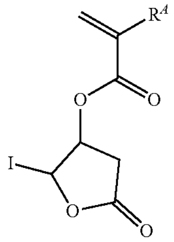
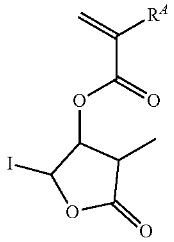
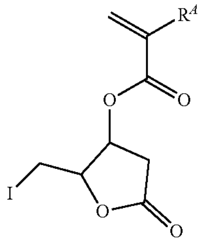
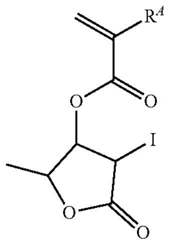
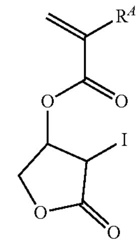
The base polymer may further comprise repeat units (e) which are derived from indene, benzofuran, benzothiophene, acenaphthylene, chromone, coumarin, norbornadiene, and derivatives thereof. Examples of the monomer from which repeat units (e) are derived are given below, but not limited thereto.

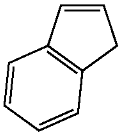
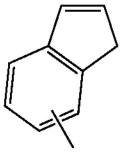
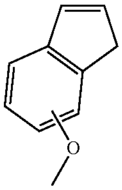
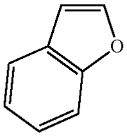
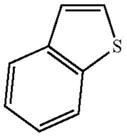
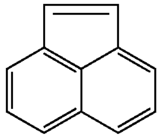
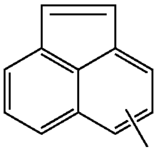
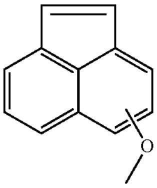
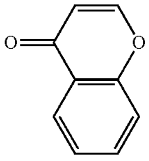
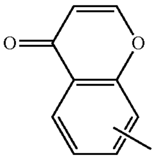
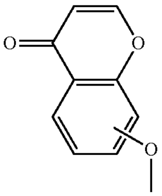
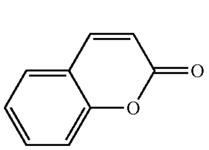
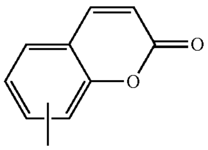
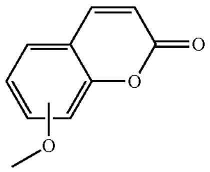
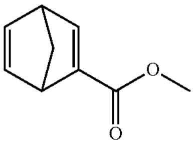

The base polymer may further comprise repeat units (f) which are derived from styrene, vinylnaphthalene, vinylanthracene, vinylpyrene, methyleneindene, vinylpyridine, vinylcarbazole and derivatives thereof.

The base polymer may further comprise repeat units (g) which are derived from onium salts having a polymerizable unsaturated bond. The preferred repeat units (g) include repeat units having the formula (g1), repeat units having the formula (g2), and repeat units having the formula (g3). These units are simply referred to as repeat units (g1), (g2), and (g3), which may be used alone or in admixture of two or more types.

(g1)

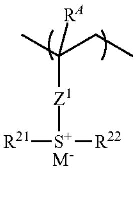

-continued (g2)

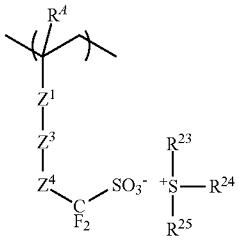

(g3)

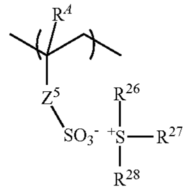

In formulae (g1) to (g3), $R^A$ is each independently hydrogen or methyl. $Z^1$ is a single bond, or a $C_1$-$C_6$ aliphatic hydrocarbylene group, phenylene group, naphthylene group, or a $C_7$-$C_{18}$ group obtained by combining the foregoing, or —O—$Z^{11}$—, —C(═O)—O—$Z^{11}$— or —C(═O)—NH—$Z^{11}$—, wherein $Z^{11}$ is a $C_1$-$C_6$ aliphatic hydrocarbylene group, phenylene group, naphthylene group, or a $C_7$-$C_{18}$ group obtained by combining the foregoing, which may contain a carbonyl moiety, ester bond, ether bond or hydroxy moiety. $Z^2$ is a single bond or ester bond. $Z^3$ is a single bond, —$Z^{31}$—C(═O)—O—, —$Z^{31}$—O—, or —$Z^{31}$—O—C(═O)—, wherein $Z^{31}$ is a $C_1$-$C_{12}$ aliphatic hydrocarbylene group, phenylene group or a $C_7$-$C_{18}$ group obtained by combining the foregoing, which may contain a carbonyl moiety, ester bond, ether bond, bromine or iodine. $Z^4$ is methylene, 2,2,2-trifluoro-1,1-ethanediyl or carbonyl. $Z^5$ is a single bond, methylene, ethylene, phenylene, fluorinated phenylene, trifluoromethyl-substituted phenylene group, —O—$Z^{51}$—, —C(═O)—O—$Z^{51}$— or —C(═O)—NH—$Z^{51}$—, wherein $Z^{51}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond, or halogen or hydroxy moiety.

In formulae (g1) to (g3), $R^{21}$ to $R^{28}$ are each independently halogen or a $C_1$-$C_{20}$ hydrocarbyl group which may contain a heteroatom. The hydrocarbyl group may be saturated or unsaturated and straight, branched or cyclic and examples thereof are as will be exemplified later for the hydrocarbyl group represented by $R^{101}$ to $R^{103}$ in formula (2). In the hydrocarbyl group, some or all of the hydrogen atoms may be substituted by a moiety containing a heteroatom such as oxygen, sulfur, nitrogen or halogen, or some constituent —$CH_2$— may be replaced by a moiety containing a heteroatom such as oxygen, sulfur or nitrogen, so that the group may contain a hydroxy moiety, fluorine, chlorine, bromine, iodine, cyano moiety, nitro moiety, carbonyl moiety, ether bond, ester bond, sulfonic ester bond, carbonate bond, lactone ring, sultone ring, carboxylic anhydride (—C(═O)—O—C(═O)—) or haloalkyl moiety. Also, a pair of $R^{23}$ and $R^{24}$, or $R^{26}$ and $R^{27}$ may bond together to form a ring with the sulfur atom to which they are attached. Examples of the ring are as will be exemplified later for the ring that $R^{101}$ and $R^{102}$ in formula (2), taken together, form with the sulfur atom to which they are attached.

In formula (g1), $M^-$ is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl)imide and bis(perfluorobutylsulfonyl)imide; methide ions such as tris(trifluoromethylsulfonyl)methide and tris(perfluoroethylsulfonyl)methide.

Also included are sulfonate ions having fluorine substituted at α-position as represented by the formula (g1-1) and sulfonate ions having fluorine substituted at α-position and trifluoromethyl at β-position as represented by the formula (g1-2).

(g1-1)

$R^{31}—CF_2—SO_3^-$ (g1-2)

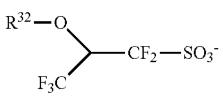

In formula (g1-1), $R^{31}$ is hydrogen, or a $C_1$-$C_{20}$ hydrocarbyl group which may contain an ether bond, ester bond, carbonyl moiety, lactone ring, or fluorine atom. The hydrocarbyl group may be saturated or unsaturated and straight, branched or cyclic and examples thereof are as will be exemplified later for the hydrocarbyl group $R^{111}$ in formula (1A').

In formula (g1-2), $R^{32}$ is hydrogen, or a $C_1$-$C_{30}$ hydrocarbyl group or $C_2$-$C_{30}$ hydrocarbylcarbonyl group which may contain an ether bond, ester bond, carbonyl moiety or lactone ring. The hydrocarbyl group and hydrocarbyl moiety in the hydrocarbylcarbonyl group may be saturated or unsaturated and straight, branched or cyclic and examples thereof are as will be exemplified later for the hydrocarbyl group $R^{111}$ in formula (1A').

Examples of the cation in the monomer from which repeat unit (g1) is derived are shown below, but not limited thereto. $R^A$ is as defined above.

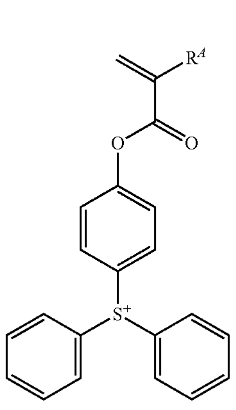

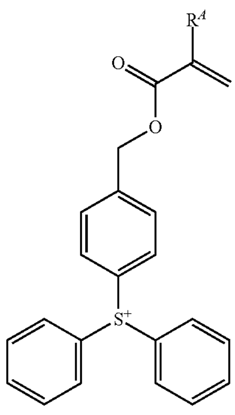

-continued

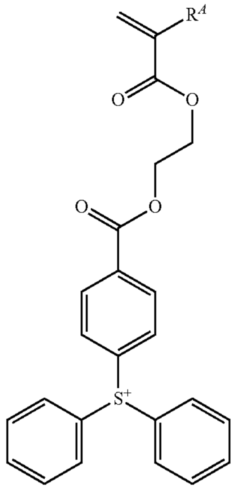

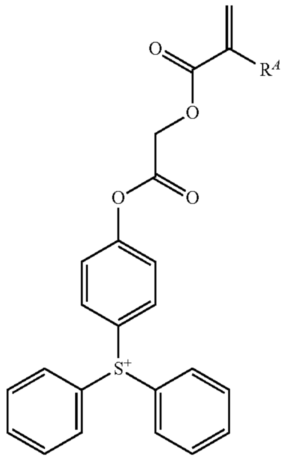

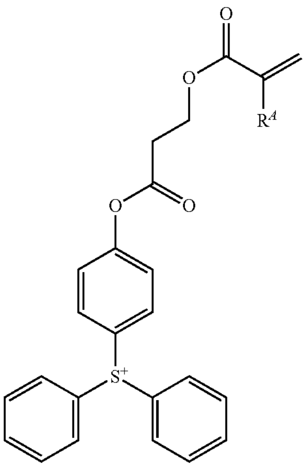

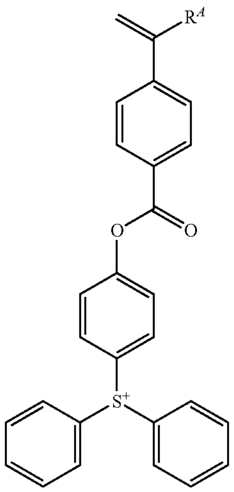

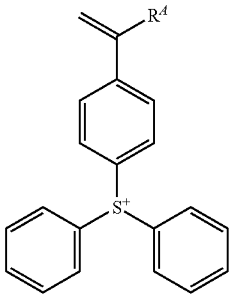

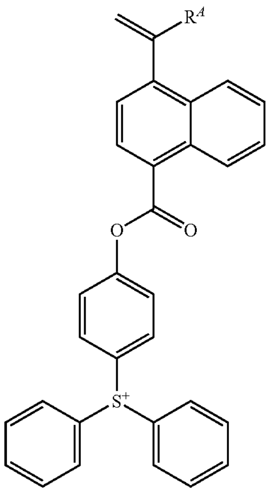

-continued
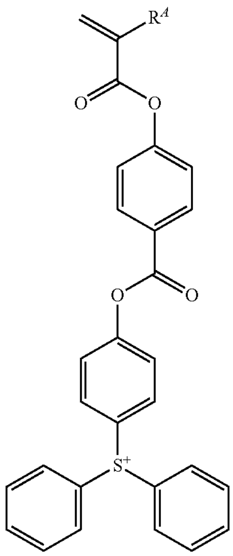
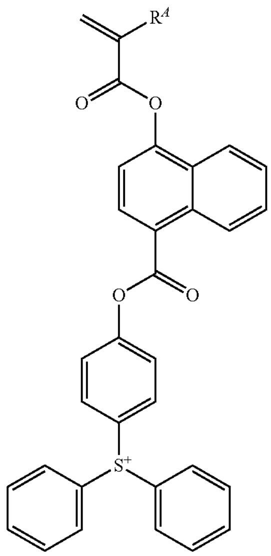
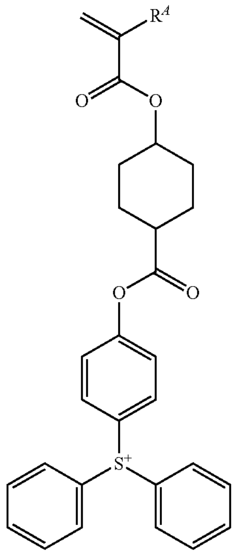
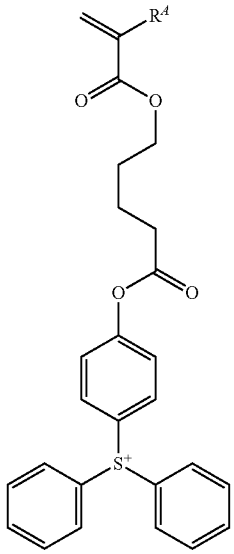
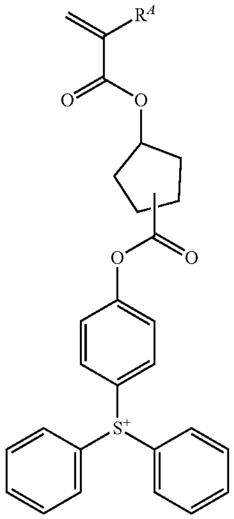
-continued
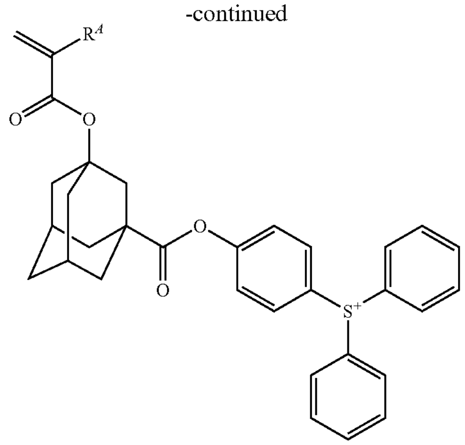
Examples of the cation in the monomer from which repeat unit (g2) or (g3) is derived are as will be exemplified later for the cation in the sulfonium salt having formula (2).
Examples of the anion in the monomer from which repeat unit (g2) is derived are shown below, but not limited thereto. $R^A$ is as defined above.
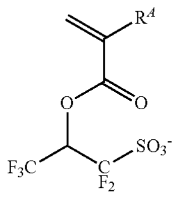
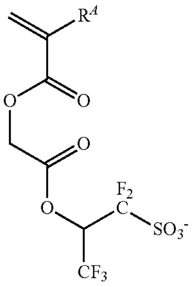
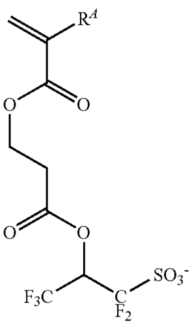
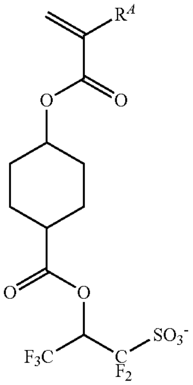
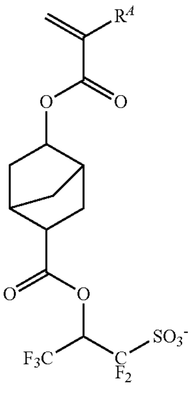
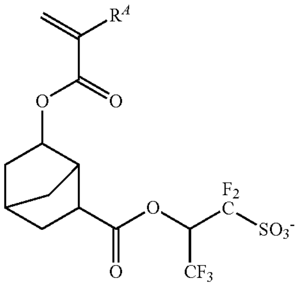

-continued
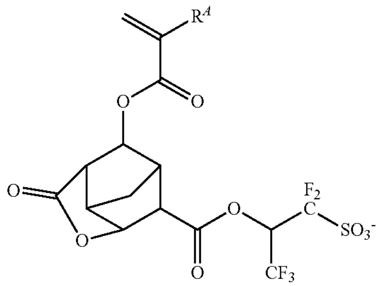
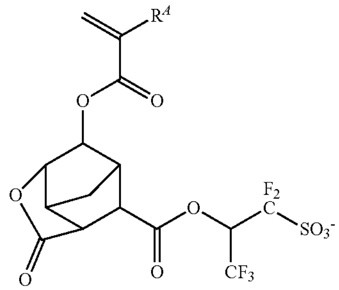
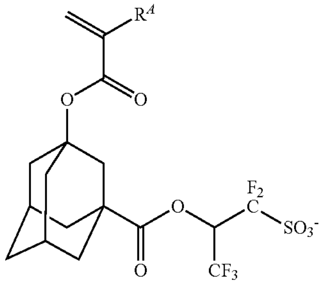
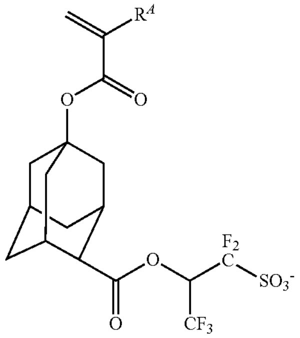
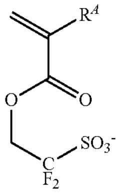
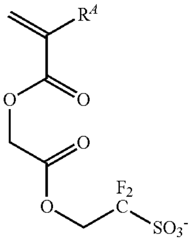
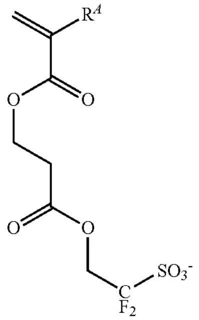
-continued
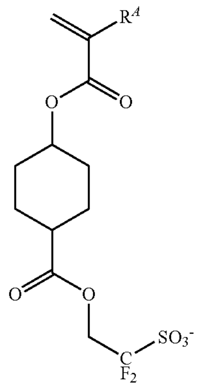
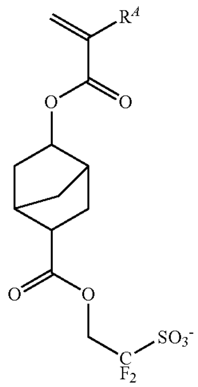
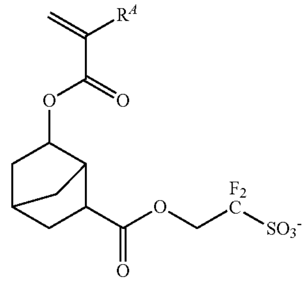
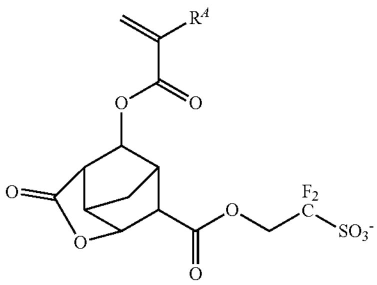
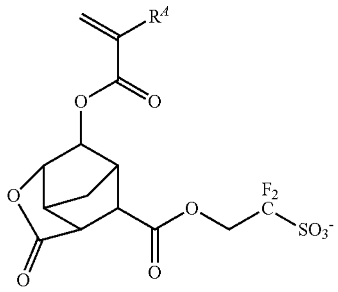
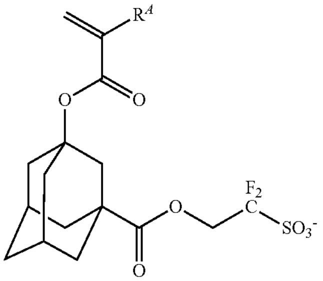

-continued
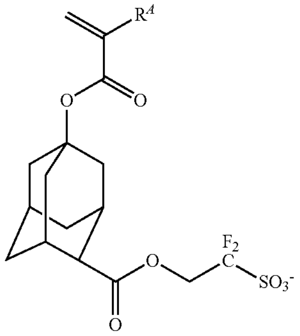
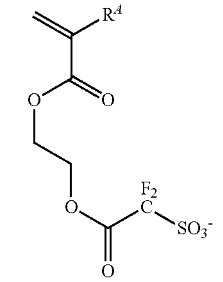
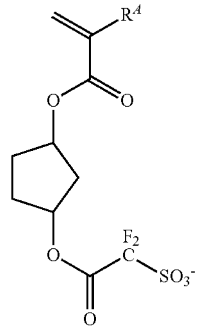
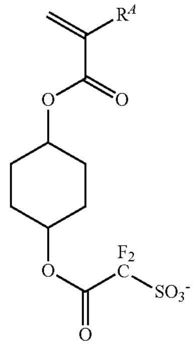
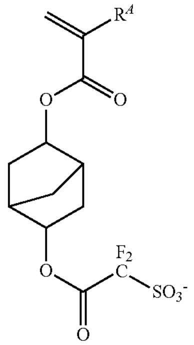
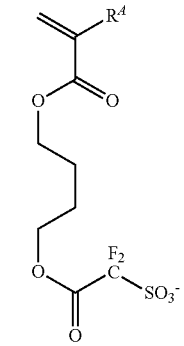
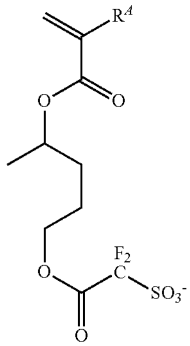
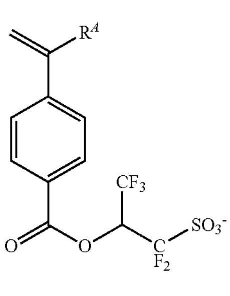
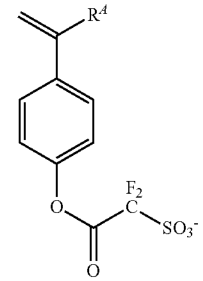
-continued
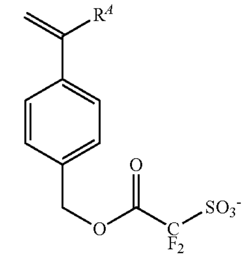
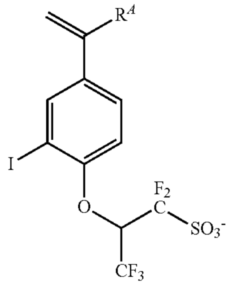
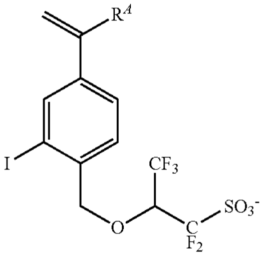
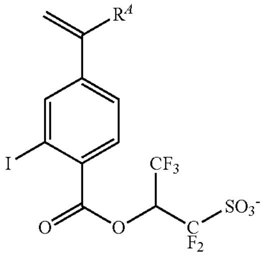
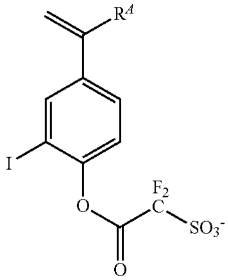
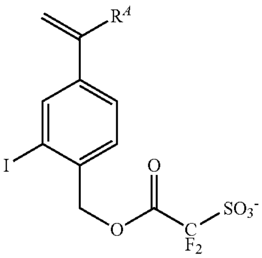
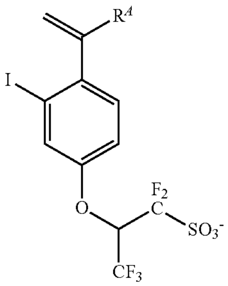
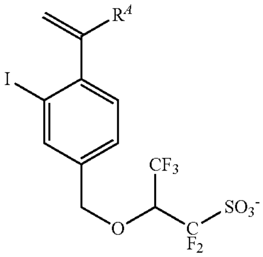
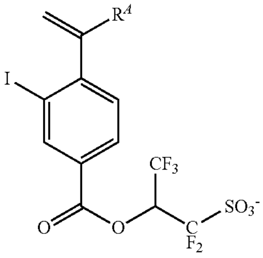
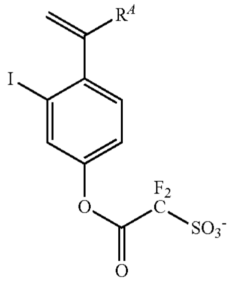
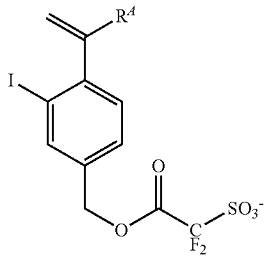
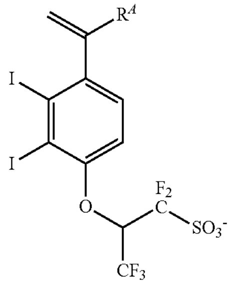

-continued
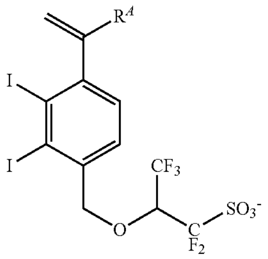
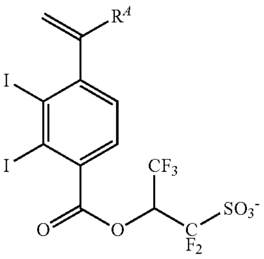
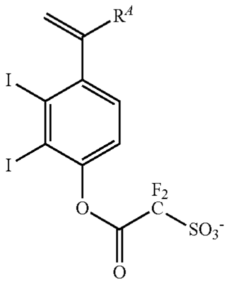
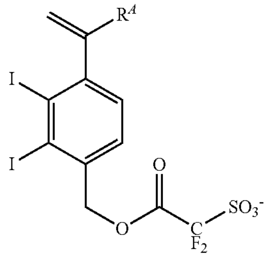
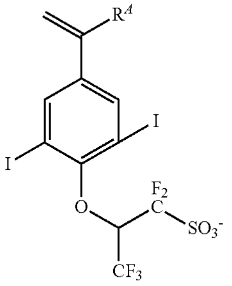
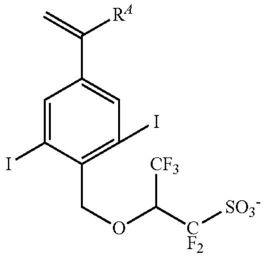
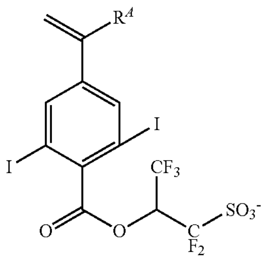
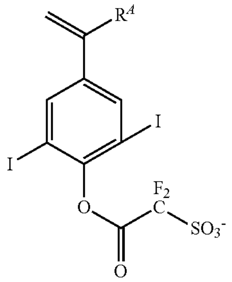
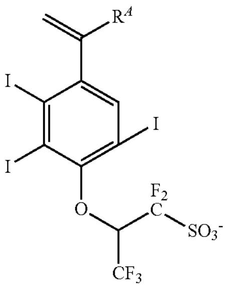
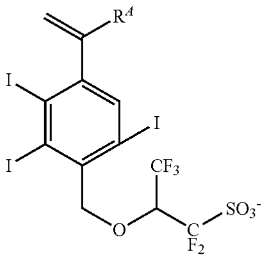
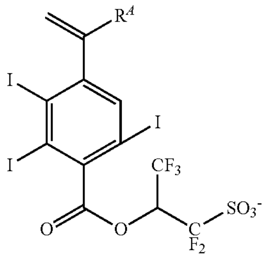
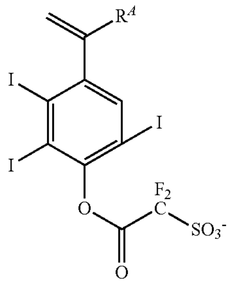
-continued
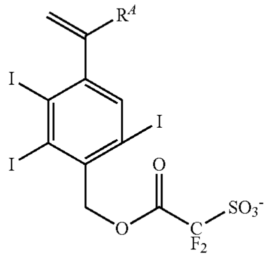
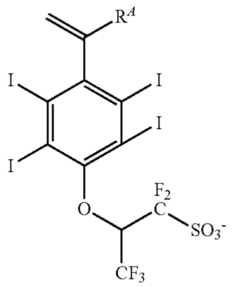
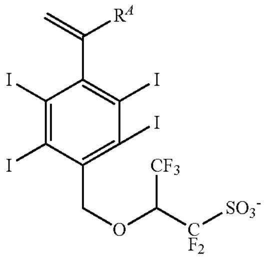
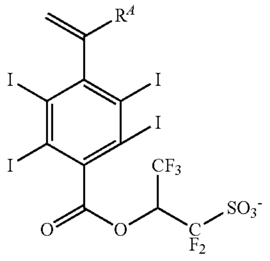
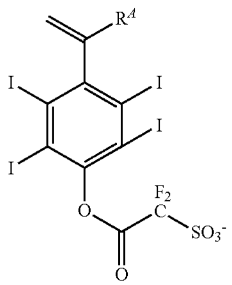
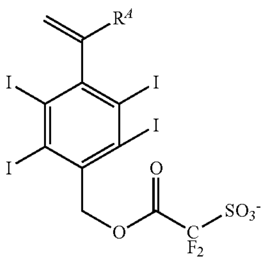
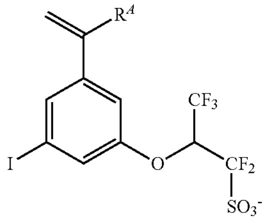
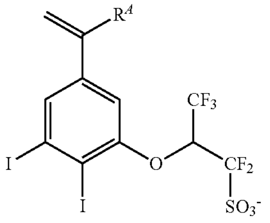
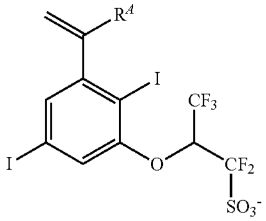
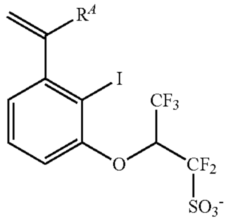
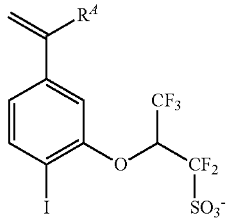
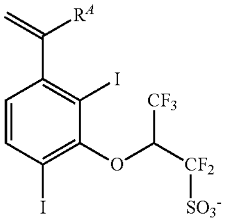

-continued
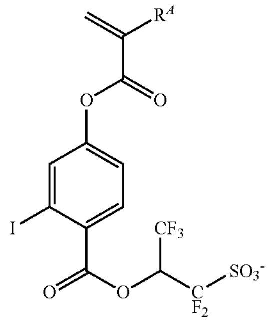
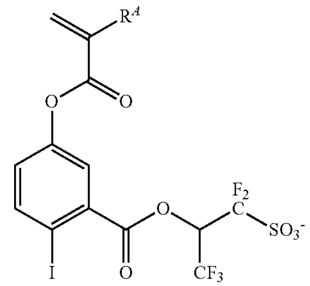
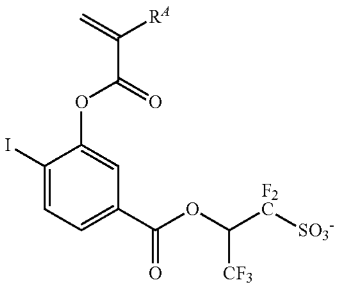
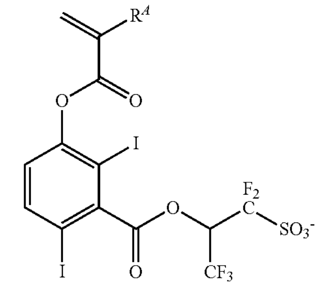
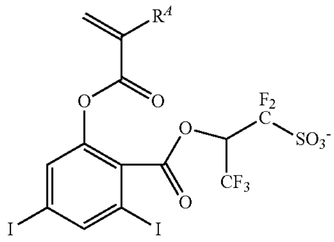
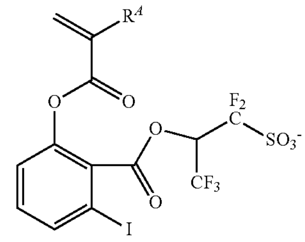
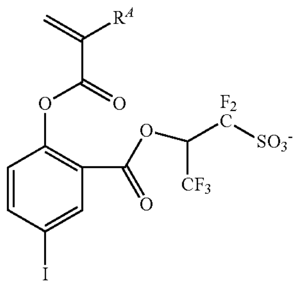
-continued
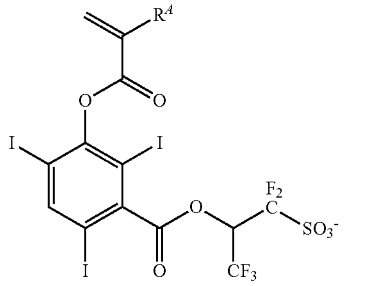
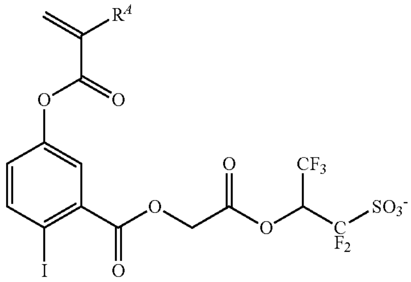
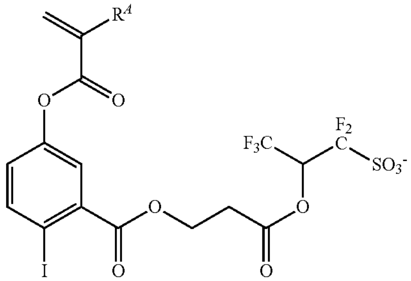
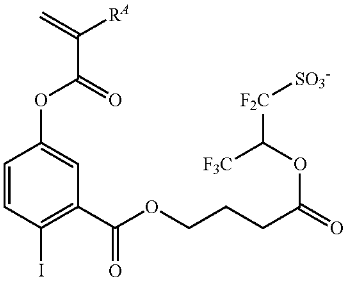
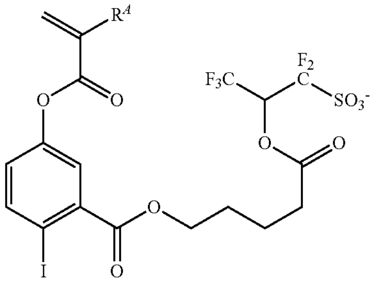

-continued
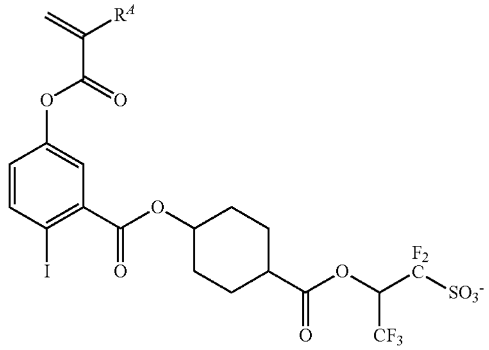
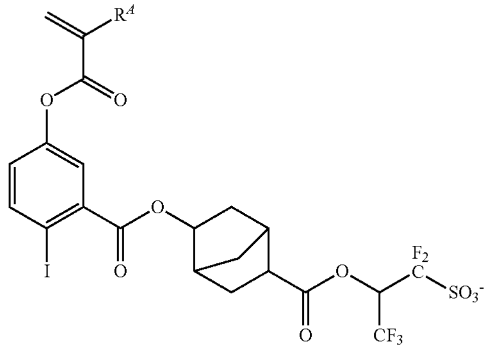
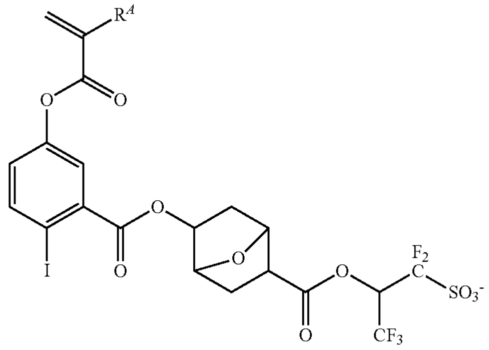
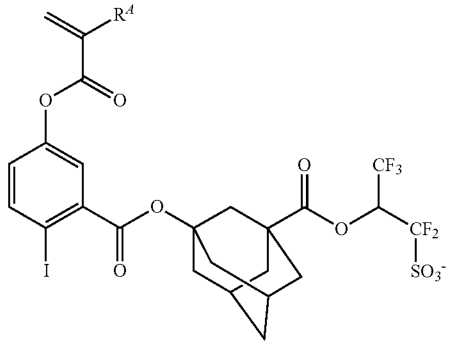
-continued
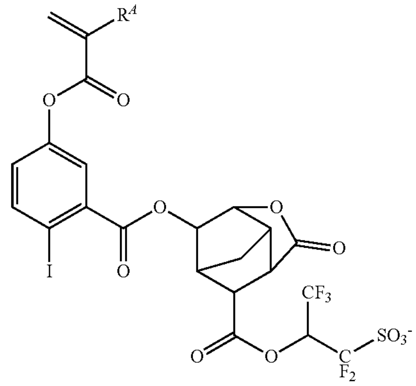
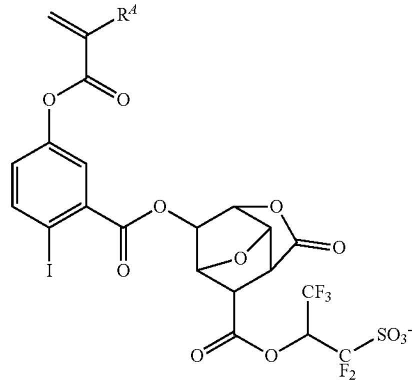
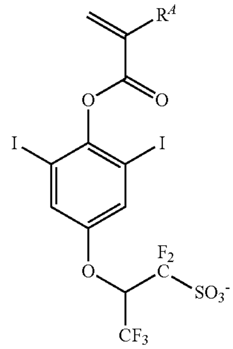
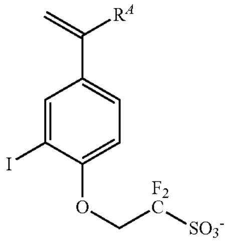
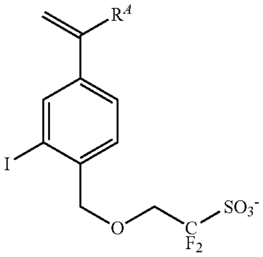
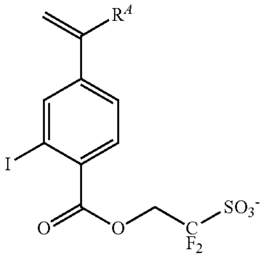
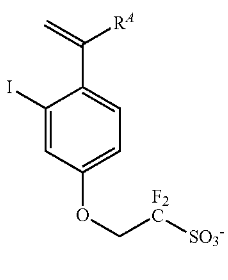
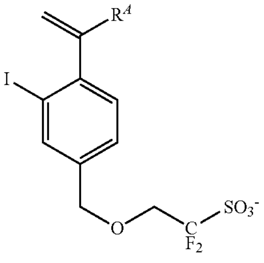

-continued
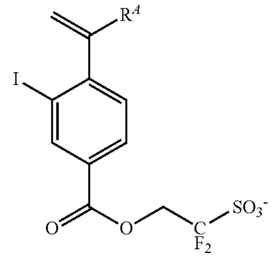
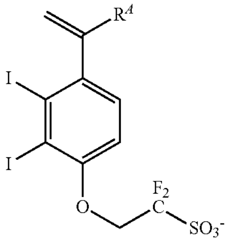
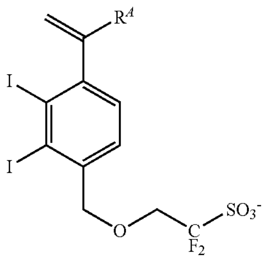
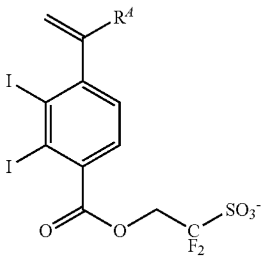
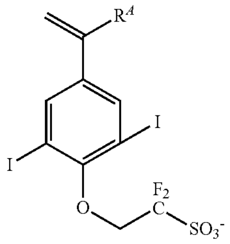
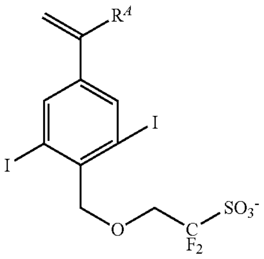
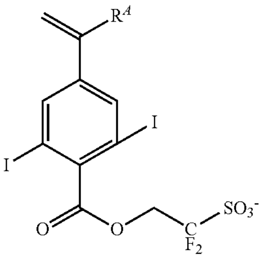
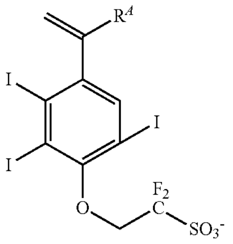
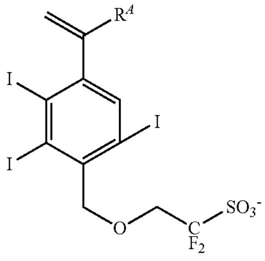
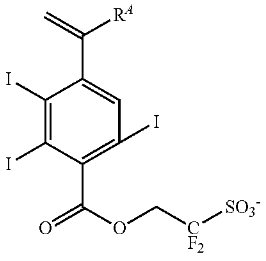
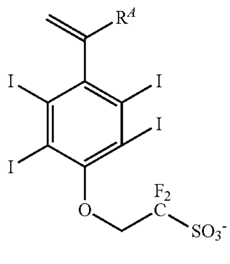
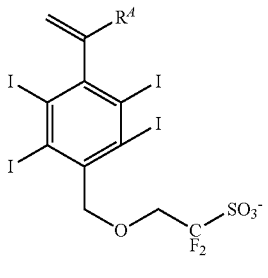
-continued
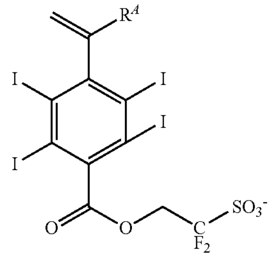
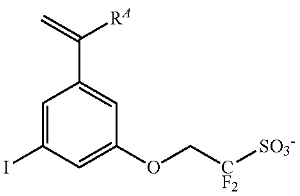
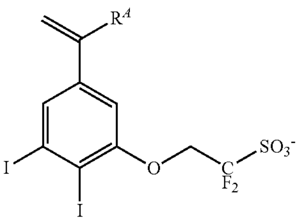
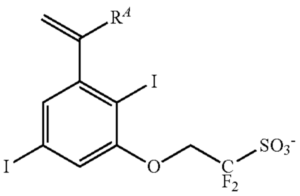
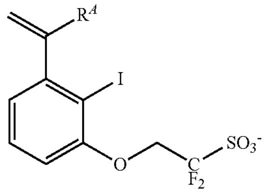
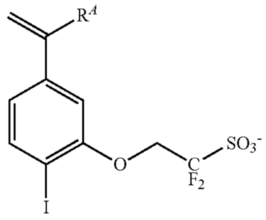
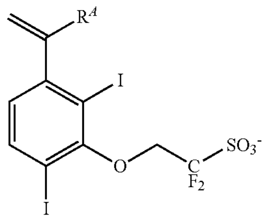

-continued
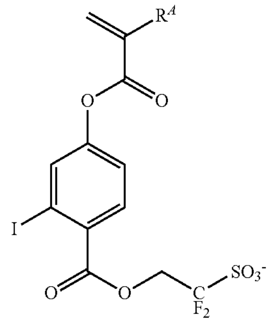
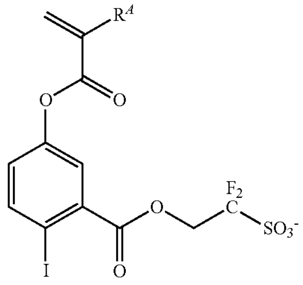
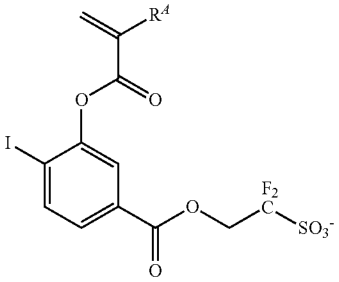
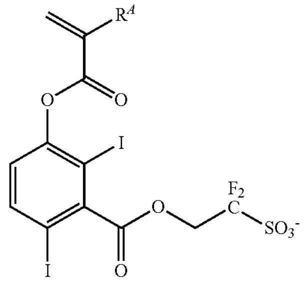
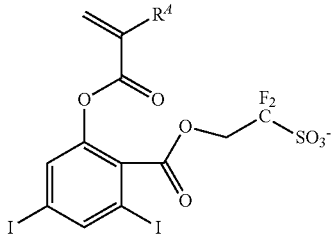
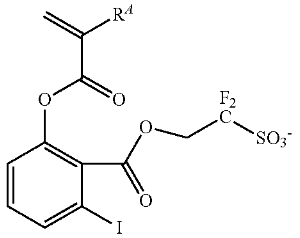
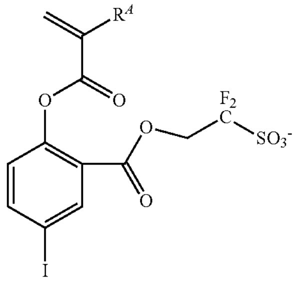
-continued
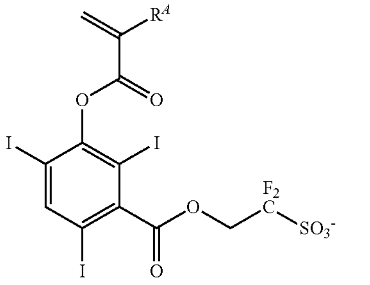
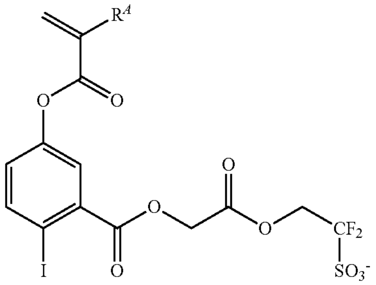
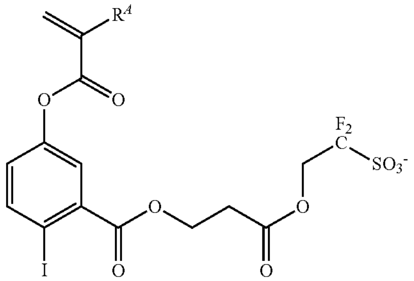
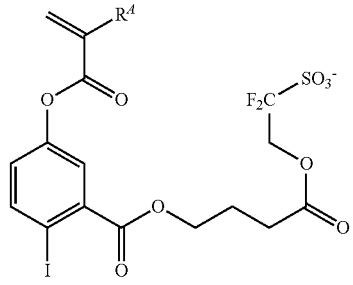
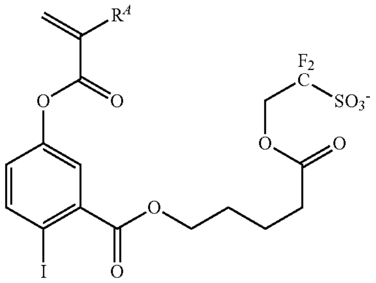

-continued
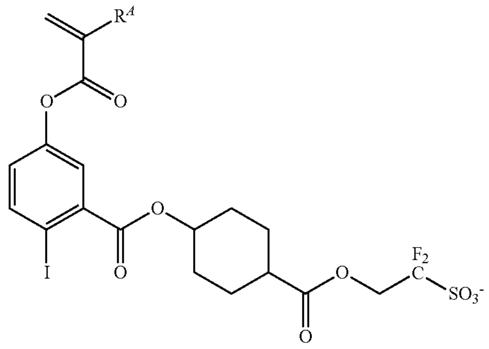
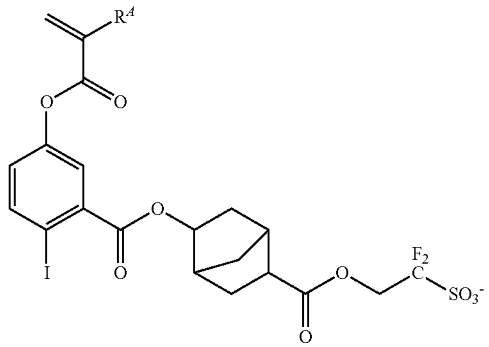
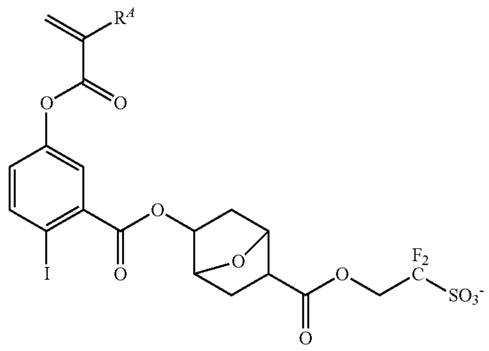
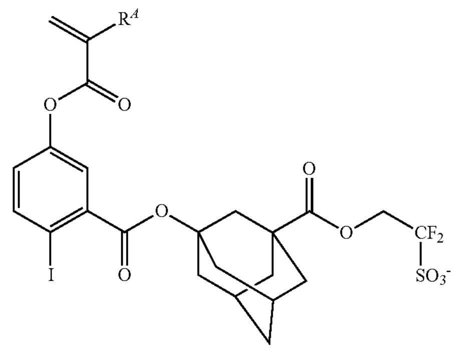
-continued
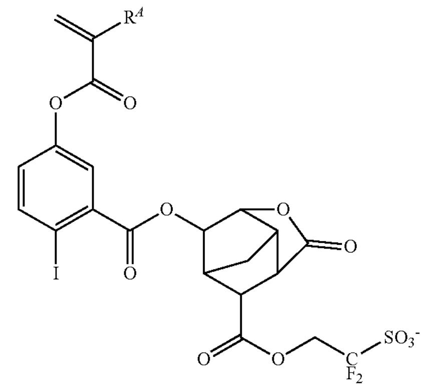
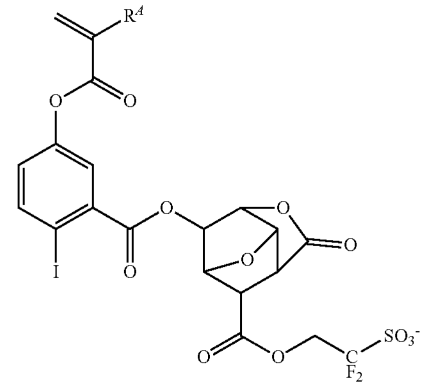
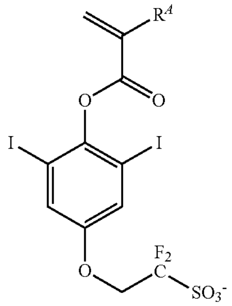
Examples of the anion in the monomer from which repeat unit (g3) is derived are shown below, but not limited thereto. $R^A$ is as defined above.
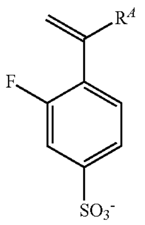
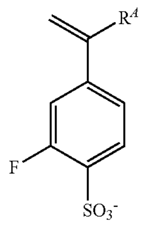
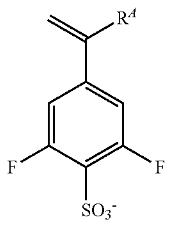
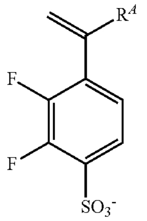
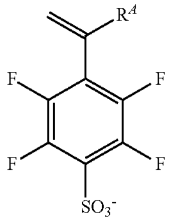
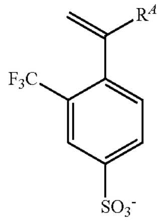

-continued

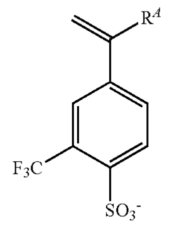
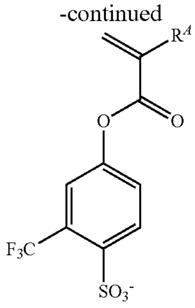
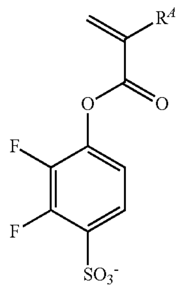
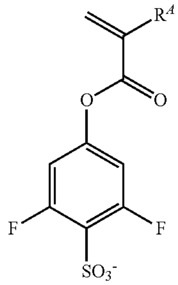
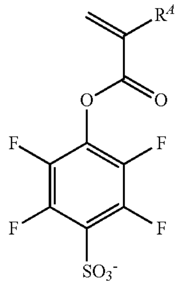
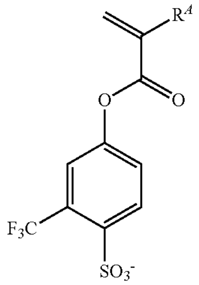
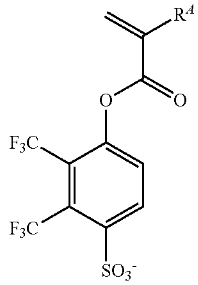
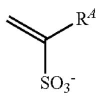
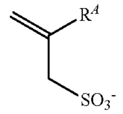

The attachment of an acid generator to the polymer main chain is effective in restraining acid diffusion, thereby preventing a reduction of resolution due to blur by acid diffusion. Also LWR and CDU are improved since the acid generator is uniformly distributed. When a base polymer comprising repeat units (g), i.e., polymer-bound acid generator is used, an acid generator of addition type (to be described later) may be omitted.

The base polymer for formulating the positive resist composition comprises repeat units (a) or (b) having an acid labile group as essential component and additional repeat units (c), (d), (e), (f), and (g) as optional components. A fraction of units (a), (b), (c), (d), (e), (f), and (g) is: preferably $0 \le a < 1.0$, $0 \le b < 1.0$, $0 < a+b < 1.0$, $0 \le c \le 0.9$, $0 \le d \le 0.9$, $0 \le e \le 0.8$, $0 \le f \le 0.8$, and $0 \le g \le 0.5$; more preferably $0 \le a \le 0.9$, $0 \le b \le 0.9$, $0.1 \le a+b \le 0.9$, $0 \le c \le 0.8$, $0 \le d \le 0.8$, $0 \le e \le 0.7$, $0 \le f \le 0.7$, and $0 \le g \le 0.4$; and even more preferably $0 \le a \le 0.8$, $0 \le b \le 0.8$, $0.1 \le a+b \le 0.8$, $0 \le c \le 0.75$, $0 \le d \le 0.75$, $0 \le e \le 0.6$, $0 \le f \le 0.6$, and $0 \le g \le 0.3$. Notably, $g=g1+g2+g3$, meaning that unit (g) is at least one of units (g1) to (g3), and $a+b+c+d+e+f+g=1.0$.

For the base polymer for formulating the negative resist composition, an acid labile group is not necessarily essential. The base polymer comprises repeat units (c), and optionally repeat units (d), (e), (f), and/or (g). A fraction of these units is: preferably $0 < c \le 1.0$, $0 \le d \le 0.9$, $0 \le e \le 0.8$, $0 \le f \le 0.8$, and $0 \le g \le 0.5$; more preferably $0.2 \le c \le 1.0$, $0 \le d \le 0.8$, $0 \le e \le 0.7$, $0 \le f \le 0.7$, and $0 \le g \le 0.4$; and even more preferably $0.3 \le c \le 1.0$, $0 \le d \le 0.75$, $0 \le e \le 0.6$, $0 \le f \le 0.6$, and $0 \le g \le 0.3$. Notably, $g=g1+g2+g3$, meaning that unit (g) is at least one of units (g1) to (g3), and $c+d+e+f+g=1.0$.

The base polymer may be synthesized by any desired methods, for example, by dissolving one or more monomers selected from the monomers corresponding to the foregoing repeat units in an organic solvent, adding a radical polymerization initiator thereto, and heating for polymerization. Examples of the organic solvent which can be used for polymerization include toluene, benzene, tetrahydrofuran (THF), diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably, the reaction temperature is 50 to 80° C. and the reaction time is 2 to 100 hours, more preferably 5 to 20 hours.

Where a monomer having a hydroxy group is copolymerized, the hydroxy group may be replaced by an acetal group susceptible to deprotection with acid, typically ethoxyethoxy, prior to polymerization, and the polymerization be followed by deprotection with weak acid and water. Alternatively, the hydroxy group may be replaced by an acetyl, formyl, pivaloyl or similar group prior to polymerization, and the polymerization be followed by alkaline hydrolysis.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to hydroxystyrene or hydroxyvinylnaphthalene. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

The base polymer should preferably have a weight average molecular weight (Mw) in the range of 1,000 to 500,000, and more preferably 2,000 to 30,000, as measured by GPC versus polystyrene standards using tetrahydrofuran (THF) solvent. The range of Mw ensures that a resist film has heat resistance and satisfactory solubility in alkaline developer.

If a base polymer has a wide molecular weight distribution or dispersity (Mw/Mn), which indicates the presence of lower and higher molecular weight polymer fractions, there is a possibility that foreign matter is left on the pattern or the pattern profile is degraded. The influences of Mw and Mw/Mn become stronger as the pattern rule becomes finer. Therefore, the base polymer should preferably have a narrow dispersity (Mw/Mn) of 1.0 to 2.0, especially 1.0 to 1.5, in order to provide a resist composition suitable for micropatterning to a small feature size.

It is understood that a blend of two or more polymers which differ in compositional ratio, Mw or Mw/Mn is acceptable.

(C) Organic Solvent

The organic solvent used herein as component (C) is not particularly limited as long as the base polymer, PAG, quencher and other additives are soluble therein. Examples of the organic solvent are described in JP-A 2008-111103, paragraphs [0144]-[0145](U.S. Pat. No. 7,537,880). Exemplary solvents include ketones such as cyclohexanone and methyl-2-n-pentyl ketone; alcohols such as 3-methoxybutanol, 3-methyl-3-methoxybutanol, 1-methoxy-2-propanol, and 1-ethoxy-2-propanol; ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone (GBL). Where an acid labile group of acetal form is used, a high-boiling alcohol solvent such as diethylene glycol, propylene glycol, glycerol, 1,4-butanediol or 1,3-butanediol may be added for accelerating deprotection reaction of acetal. Of the foregoing organic solvents, it is recommended to use 1-ethoxy-2-propanol, PGMEA, cyclohexanone, GBL, and mixtures thereof because the PAG is most soluble therein.

The organic solvent (C) is preferably added in an amount of 200 to 7,000 parts, and more preferably 400 to 5,000 parts by weight per 80 parts by weight of the base polymer (B). The organic solvent may be used alone or in admixture.

(D) Other Photoacid Generator

The chemically amplified resist composition may comprise (D) a photoacid generator other than the photoacid generator having formula (1) as component (A).

The other PAG is preferably a salt having the formula (2).

(2)

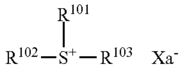

In formula (2), $R^{101}$, $R^{102}$ and $R^{103}$ are each independently a $C_1$-$C_{10}$ straight, branched or cyclic alkyl or alkenyl group which may be substituted with a heteroatom or separated by a heteroatom, or a $C_6$-$C_{18}$ aryl or aralkyl group which may be substituted with a heteroatom or separated by a heteroatom. Any two of $R^{101}$, $R^{102}$ and $R^{103}$ may bond together to form a ring with the sulfur atom to which they are attached.

Examples of the cation in the sulfonium salt having formula (2) are as exemplified above for the sulfonium cation having formula (Z-1) and the sulfonium cation having formula (Z-2).

In formula (2), $Xa^-$ is an anion selected from the formulae (2A) to (2D).

(2A)

$R^{fa}$—$CF_2$—$SO_3^-$ (2B)

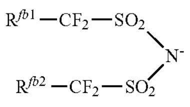

(2C)

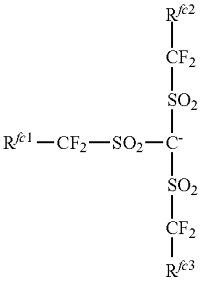

-continued (2D)

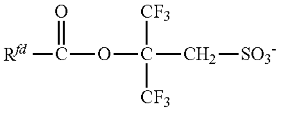

In formula (2A), $R^{fa}$ is fluorine or a $C_1$-$C_{40}$ hydrocarbyl group which may contain a heteroatom. The hydrocarbyl group may be saturated or unsaturated and straight, branched or cyclic. Examples thereof are as will be exemplified later for $R^{111}$ in formula (2A').

Of the anions having formula (2A), anions having the formula (2A') are preferred.

(2A')

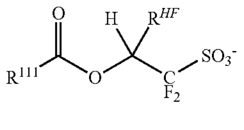

In formula (2A'), $R^{HF}$ is hydrogen or trifluoromethyl, preferably trifluoromethyl.

$R^{111}$ is a $C_1$-$C_{30}$ hydrocarbyl group which may contain a heteroatom. Of the hydrocarbyl groups, those of 6 to 30 carbon atoms are preferred because a high resolution is available in fine pattern formation. The hydrocarbyl group $R^{111}$ may be saturated or unsaturated and straight, branched or cyclic. Examples thereof include $C_1$-$C_{30}$ alkyl groups such as methyl, ethyl, propyl, isopropyl, butyl, isobutyl, sec-butyl, tert-butyl, pentyl, neopentyl, hexyl, heptyl, 2-ethylhexyl, nonyl, undecyl, tridecyl, pentadecyl, heptadecyl, and icosyl; $C_3$-$C_{30}$ cyclic saturated hydrocarbyl groups such as cyclopentyl, cyclohexyl, 1-adamantyl, 2-adamantyl, 1-adamantylmethyl, norbornyl, norbornylmethyl, tricyclodecanyl, tetracyclododecanyl, tetracyclododecanylmethyl, and dicyclohexylmethyl; $C_2$-$C_{30}$ unsaturated aliphatic hydrocarbyl groups such as allyl and 3-cyclohexenyl; $C_6$-$C_{30}$ aryl groups such as phenyl, 1-naphthyl and 2-naphthyl; $C_7$-$C_{30}$ aralkyl groups such as benzyl and diphenylmethyl; and combinations thereof.

In the hydrocarbyl group, some or all of the hydrogen atoms may be substituted by a moiety containing a heteroatom such as oxygen, sulfur, nitrogen or halogen, or some constituent —$CH_2$— may be replaced by a moiety containing a heteroatom such as oxygen, sulfur or nitrogen, so that the group may contain a hydroxy, fluorine, chlorine, bromine, iodine, cyano, carbonyl, ether bond, ester bond, sulfonic ester bond, carbonate bond, lactone ring, sultone ring, carboxylic anhydride (—C(═O)—O—C(═O)—) or haloalkyl moiety. Of the heteroatoms, oxygen is preferred. Examples of the heteroatom-containing hydrocarbyl group include tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl.

With respect to the synthesis of the sulfonium salt having an anion of formula (2A'), reference may be made to JP-A 2007-145797, JP-A 2008-106045, JP-A 2009-007327, and JP-A 2009-258695. Also useful are the sulfonium salts described in JP-A 2010-215608, JP-A 2012-041320, JP-A 2012-106986, and JP-A 2012-153644.

Examples of the anion having formula (2A) are shown below, but not limited thereto.

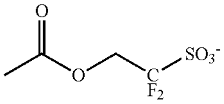
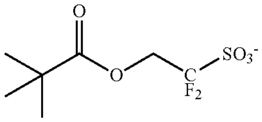
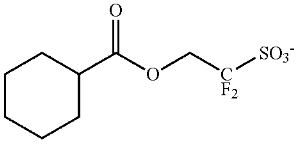
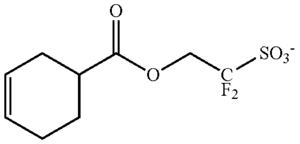
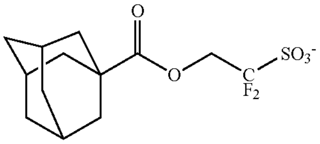
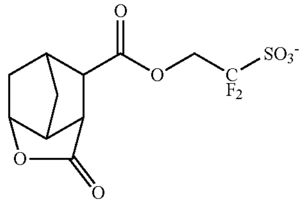
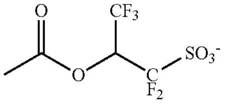
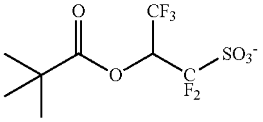
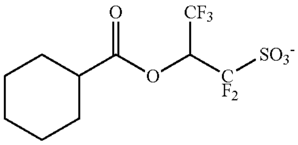
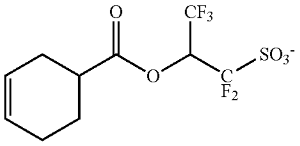
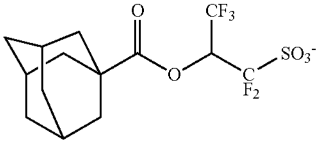
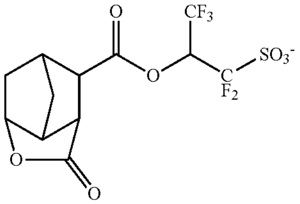
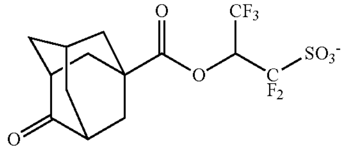
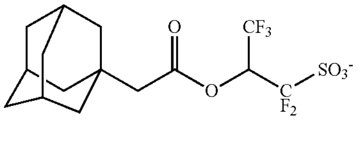
-continued
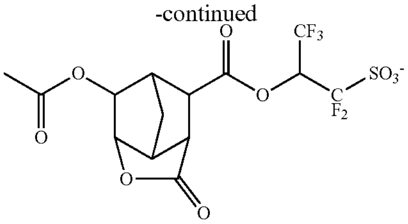
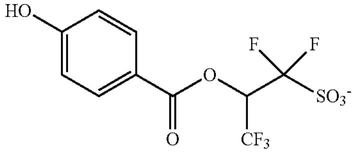
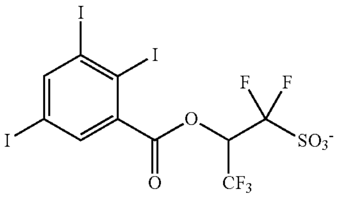
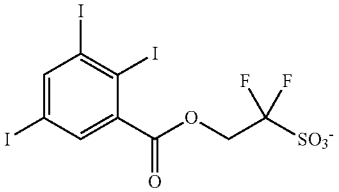
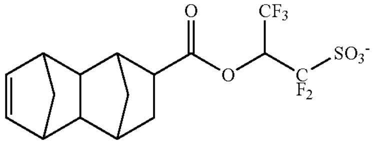
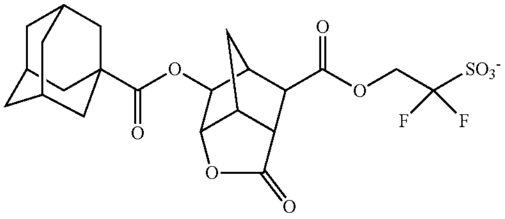
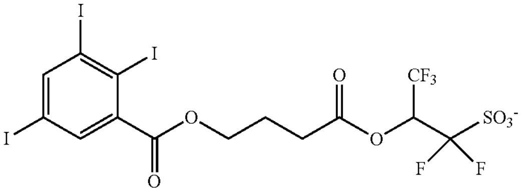
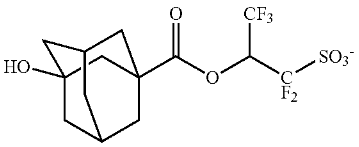
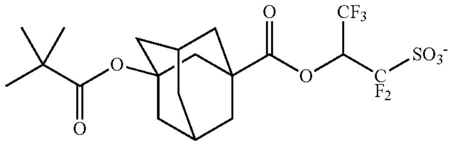
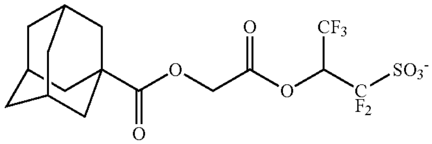

-continued

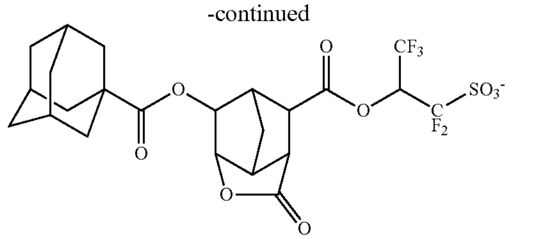

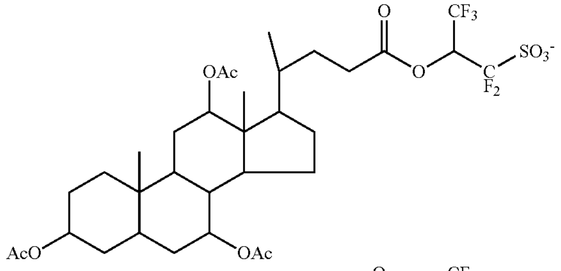

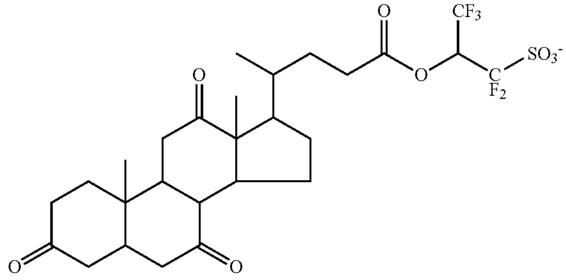

In formula (2B), $R^{fb1}$ and $R^{fb2}$ are each independently fluorine or a $C_1$-$C_{40}$ hydrocarbyl group which may contain a heteroatom. Examples of the hydrocarbyl group are as exemplified above for $R^{111}$ in formula (2A'). Preferably $R^{fb1}$ and $R^{fb2}$ are fluorine or $C_1$-$C_4$ straight fluorinated alkyl groups. Also, $R^{fb1}$ and $R^{fb2}$ may bond together to form a ring with the linkage: $—CF_2—SO_2—N^-—SO_2—CF_2—$ to which they are attached. It is preferred that a combination of $R^{fb1}$ and $R^{fb2}$ be a fluorinated ethylene or fluorinated propylene group.

In formula (2C), $R^{fc1}$, $R^{fc2}$ and $R^{fc3}$ are each independently fluorine or a $C_1$-$C_{40}$ hydrocarbyl group which may contain a heteroatom. Examples of the hydrocarbyl group are as exemplified for $R^{111}$. Preferably $R^{fc1}$, $R^{fc2}$ and $R^{fc3}$ are fluorine or $C_1$-$C_4$ straight fluorinated alkyl groups. Also, $R^{fc1}$ and $R^{fc2}$ may bond together to form a ring with the linkage: $—CF_2—SO_2—C^-—SO_2—CF_2—$ to which they are attached. It is preferred that a combination of $R^{fc1}$ and $R^{fc2}$ be a fluorinated ethylene or fluorinated propylene group.

In formula (2D), $R^{fd}$ is a $C_1$-$C_{40}$ hydrocarbyl group which may contain a heteroatom. The hydrocarbyl group may be saturated or unsaturated and straight, branched or cyclic. Examples thereof are as exemplified above for $R^{111}$.

With respect to the synthesis of the sulfonium salt having an anion of formula (2D), reference may be made to JP-A 2010-215608 and JP-A 2014-133723.

Examples of the anion having formula (2D) are shown below, but not limited thereto.

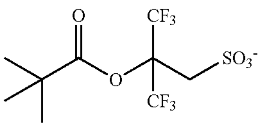

-continued

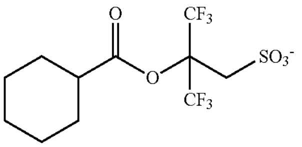

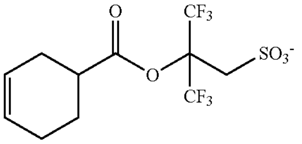

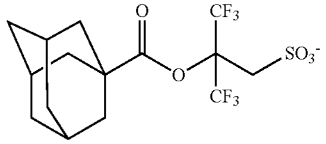

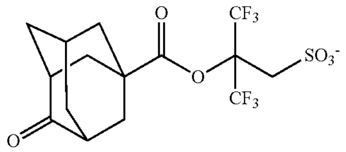

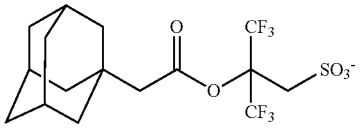

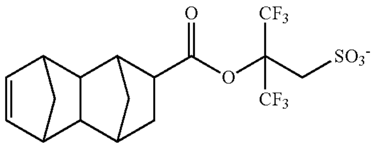

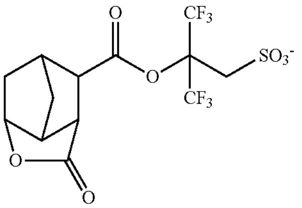

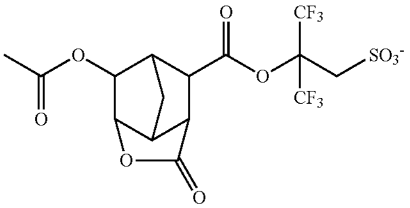

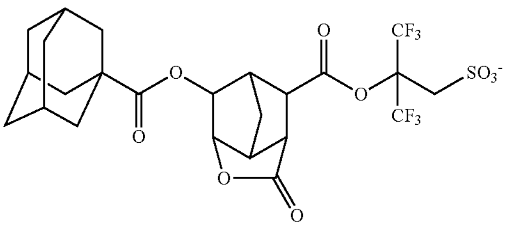

-continued

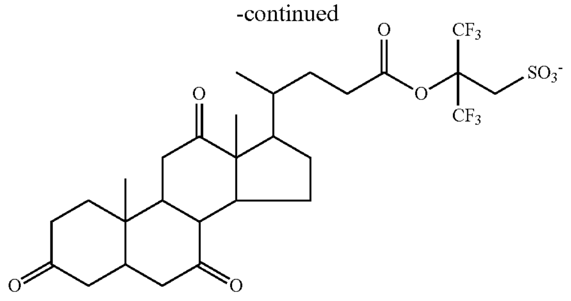

Notably, the compound having the anion of formula (2D) does not have fluorine at the α-position relative to the sulfo group, but two trifluoromethyl groups at the β-position. For this reason, it has a sufficient acidity to sever the acid labile groups in the base polymer. Thus the compound is an effective PAG.

Of the foregoing PAGs, those having an anion of formula (2A') or (2D) are especially preferred because of reduced acid diffusion and high solubility in solvents.

The other PAG (D) is added in an amount of 0 to 40 parts by weight per 80 parts by weight of the base polymer (B), and when used, in an amount of preferably 0.1 to 40 parts, and more preferably 0.1 to 20 parts by weight per 80 parts by weight of the base polymer (B). As long as the amount of the PAG is in the range, the risk of resolution being degraded or foreign particles being formed after development or during stripping of resist film is avoided. The other PAG may be used alone or in admixture.

(E) Quencher

The resist composition may further comprise (E) a quencher. As used herein, the quencher refers to a compound capable of trapping the acid generated by the PAG to suppress the diffusion rate of the acid which diffuses in the resist film.

The quencher is typically selected from conventional basic compounds. Conventional basic compounds include primary, secondary, and tertiary aliphatic amines, mixed amines, aromatic amines, heterocyclic amines, nitrogen-containing compounds with carboxy group, nitrogen-containing compounds with sulfonyl group, nitrogen-containing compounds with hydroxy group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxy group, ether bond, ester bond, lactone ring, cyano group, or sulfonic ester bond as described in JP-A 2008-111103, paragraphs [0146]-[0164], and compounds having a carbamate group as described in JP 3790649. Addition of a basic compound may be effective for further suppressing the diffusion rate of acid in the resist film or correcting the pattern profile.

Onium salts such as sulfonium, iodonium and ammonium salts of sulfonic acids which are not fluorinated at α-position as described in U.S. Pat. No. 8,795,942 (JP-A 2008-158339) and similar onium salts of carboxylic acid as described in JP 3991462 may also be used as the quencher, provided that the counter anion of the onium salt is a conjugated base of a weak acid. As used herein, the weak acid indicates an acidity insufficient to deprotect an acid labile group from an acid labile group-containing unit in the base polymer. The onium salt functions as a quencher when used in combination with an onium salt type PAG having a conjugated base of a strong acid (typically a sulfonic acid which is fluorinated at α-position) as the counter anion.

In a system using a mixture of an onium salt capable of generating a strong acid (e.g., α-position fluorinated sulfonic acid) and an onium salt capable of generating a weak acid (e.g., non-fluorinated sulfonic acid or carboxylic acid), if the strong acid generated from the PAG upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If a PAG capable of generating a strong acid is an onium salt, an exchange from the strong acid generated upon exposure to high-energy radiation to a weak acid as above can take place, but it rarely happens that the weak acid generated upon exposure to high-energy radiation collides with the unreacted onium salt capable of generating a strong acid to induce a salt exchange. This is because of a likelihood of an onium cation forming an ion pair with a stronger acid anion.

Examples of the quencher include a compound (onium salt of α-non-fluorinated sulfonic acid) having the formula (3) and a compound (onium salt of carboxylic acid) having the formula (4).

$$R^{201}\text{—}SO_3^-\ Mq^+ \quad (3)$$

$$R^{202}\text{—}CO_2^-\ Mq^+ \quad (4)$$

In formula (3), $R^{201}$ is hydrogen or a $C_1$-$C_{40}$ hydrocarbyl group which may contain a heteroatom, exclusive of the hydrocarbyl group in which the hydrogen bonded to the carbon atom at α-position of the sulfo group is substituted by fluorine or fluoroalkyl moiety.

The hydrocarbyl group may be saturated or unsaturated and straight, branched or cyclic. Examples thereof include $C_1$-$C_{40}$ alkyl groups such as methyl, ethyl, propyl, isopropyl, n-butyl, sec-butyl, tert-butyl, tert-pentyl, n-pentyl, n-hexyl, n-octyl, 2-ethylhexyl, n-nonyl, n-decyl; $C_3$-$C_{40}$ cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.$0^{2,6}$]decanyl, adamantyl, and adamantylmethyl; $C_2$-$C_{40}$ alkenyl groups such as vinyl, allyl, propenyl, butenyl and hexenyl; $C_3$-$C_{40}$ cyclic unsaturated aliphatic hydrocarbyl groups such as cyclohexenyl; $C_6$-$C_{40}$ aryl groups such as phenyl, naphthyl, alkylphenyl groups (e.g., 2-methylphenyl, 3-methylphenyl, 4-methylphenyl, 4-ethylphenyl, 4-tert-butylphenyl, 4-n-butylphenyl), dialkylphenyl groups (e.g., 2,4-dimethylphenyl and 2,4,6-triisopropylphenyl), alkylnaphthyl groups (e.g., methylnaphthyl and ethylnaphthyl), dialkylnaphthyl groups (e.g., dimethylnaphthyl and diethylnaphthyl); $C_7$-$C_{40}$ aralkyl groups such as benzyl, 1-phenylethyl and 2-phenylethyl; and combinations thereof.

In these hydrocarbyl groups, some or all hydrogen may be substituted by a moiety containing a heteroatom such as oxygen, sulfur, nitrogen or halogen, and some constituent $—CH_2—$ may be replaced by a moiety containing a heteroatom such as oxygen, sulfur or nitrogen, so that the group may contain a hydroxy moiety, fluorine, chlorine, bromine, iodine, cyano moiety, carbonyl moiety, ether bond, ester bond, sulfonic ester bond, carbonate bond, lactone ring, sultone ring, carboxylic anhydride (—C(═O)—O—C(═O)—), or haloalkyl moiety. Suitable heteroatom-containing hydrocarbyl groups include heteroaryl groups such as thienyl; alkoxyphenyl groups such as 4-hydroxyphenyl, 4-methoxyphenyl, 3-methoxyphenyl, 2-methoxyphenyl, 4-ethoxyphenyl, 4-tert-butoxyphenyl, 3-tert-butoxyphenyl; alkoxynaphthyl groups such as methoxynaphthyl, ethoxynaphthyl, n-propoxynaphthyl and n-butoxynaphthyl; dialkoxynaphthyl groups such as dimethoxynaphthyl and diethoxynaphthyl; and aryloxoalkyl groups, typically 2-aryl-2-oxoethyl groups such as 2-phenyl-2-oxoethyl, 2-(1-naphthyl)-2-oxoethyl and 2-(2-naphthyl)-2-oxoethyl.

In formula (4), $R^{202}$ is a $C_1$-$C_{40}$ hydrocarbyl group which may contain a heteroatom.

Examples of the hydrocarbyl group $R^{202}$ are as exemplified above for the hydrocarbyl group $R^{201}$. Also included are fluorinated alkyl groups such as trifluoromethyl, trifluoroethyl, 2,2,2-trifluoro-1-methyl-1-hydroxyethyl, 2,2,2-trifluoro-1-(trifluoromethyl)-1-hydroxyethyl, and fluorinated aryl groups such as pentafluorophenyl and 4-trifluoromethylphenyl.

An onium salt having a nitrogen-containing substituent may also be used in combination. This compound functions as a quencher in the unexposed region, but as a so-called photo-degradable base in the exposed region because it loses the quencher function in the exposed region due to neutralization thereof with the acid generated by itself. Using a photo-degradable base, the contrast between exposed and unexposed regions can be further enhanced. With respect to the photo-degradable base, reference may be made to JP-A 2009-109595 and JP-A 2012-046501, for example.

In formulae (3) and (4), $Mq^+$ is an onium cation. The onium cation is preferably selected from sulfonium, iodonium and ammonium cations, more preferably sulfonium and iodonium cations. Exemplary sulfonium and iodonium cations are as exemplified above for the sulfonium and iodonium cations represented by $Za^+$ and $Zb^+$ in formula (1).

A sulfonium salt of iodized benzene ring-containing carboxylic acid having the formula (5) is also useful as the quencher.

(5)

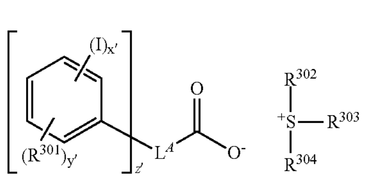

In formula (5), $R^{301}$ is hydroxy, fluorine, chlorine, bromine, amino, nitro, cyano, or a $C_1$-$C_6$ saturated hydrocarbyl, $C_1$-$C_6$ saturated hydrocarbyloxy, $C_2$-$C_6$ saturated hydrocarbylcarbonyloxy or $C_1$-$C_4$ saturated hydrocarbylsulfonyloxy group, in which some or all hydrogen may be substituted by halogen, or —N($R^{301A}$)—C(═O)—$R^{30}$1B or —N($R^{301A}$)—C(═O)—O—$R^{301B}$. $R^{301A}$ is hydrogen or a $C_1$-$C_6$ saturated hydrocarbyl group. $R^{301B}$ is a $C_1$-$C_6$ saturated hydrocarbyl or $C_2$-$C_8$ unsaturated aliphatic hydrocarbyl group.

In formula (5), x' is an integer of 1 to 5, y' is an integer of 0 to 3, and z' is an integer of 1 to 3. $L^A$ is a single bond, or a $C_1$-$C_{20}$ (z'+1)-valent linking group which may contain at least one moiety selected from ether bond, carbonyl moiety, ester bond, amide bond, sultone ring, lactam ring, carbonate bond, halogen, hydroxy moiety, and carboxy moiety. The saturated hydrocarbyl, saturated hydrocarbyloxy, saturated hydrocarbylcarbonyloxy, and saturated hydrocarbylsulfonyloxy groups may be straight, branched or cyclic. Groups $R^{301}$ may be the same or different when z' is 2 or 3.

In formula (5), $R^{302}$, $R^{303}$ and $R^{304}$ are each independently fluorine, chlorine, bromine, iodine, or a $C_1$-$C_{20}$ hydrocarbyl group which may contain a heteroatom. The hydrocarbyl group may be saturated or unsaturated and straight, branched or cyclic.

Examples thereof include $C_1$-$C_{20}$ alkyl, $C_2$-$C_{20}$ alkenyl, $C_6$-$C_{20}$ aryl, and $C_7$-$C_{20}$ aralkyl groups. In these groups, some or all hydrogen may be substituted by hydroxy, carboxy, halogen, oxo, cyano, nitro, sultone, sulfone, or sulfonium salt-containing moiety, or some —$CH_2$— may be replaced by an ether bond, ester bond, carbonyl moiety, amide bond, carbonate bond or sulfonic ester bond. Any two of $R^{302}$, $R^{303}$ and $R^{304}$ may bond together to form a ring with the sulfur atom to which they are attached.

Examples of the compound having formula (5) include those described in U.S. Pat. No. 10,295,904 (JP-A 2017-219836). Since iodine atoms are fully absorptive to EUV of wavelength 13.5 nm, they generate secondary electrons upon exposure. The energy of secondary electrons is transferred to the PAG to promote decomposition of the quencher for thereby enhancing sensitivity.

Also useful are quenchers of polymer type as described in U.S. Pat. No. 7,598,016 (JP-A 2008-239918). The polymeric quencher segregates at the resist film surface and thus enhances the rectangularity of resist pattern. When a protective film is applied as is often the case in the immersion lithography, the polymeric quencher is also effective for preventing a film thickness loss of resist pattern or rounding of pattern top.

When the resist composition contains the quencher (E), the quencher is preferably added in an amount of 0.001 to 12 parts, more preferably 0.01 to 8 parts by weight per 80 parts by weight of the base polymer. The quencher added within the range allows for easy adjustment of resist sensitivity, holds down the diffusion rate of acid within the resist film (with improved resolution), suppresses a sensitivity change after exposure, reduces substrate or environment dependency, and improves exposure latitude and pattern profile.

Also the addition of the quencher is effective for improving substrate adhesion. The quenchers may be used alone or in admixture.

(F) Surfactant

The resist composition may further include (F) a surfactant which is insoluble or substantially insoluble in water and soluble in alkaline developer, and/or a surfactant which is insoluble or substantially insoluble in water and alkaline developer. For the surfactant, reference should be made to those compounds described in JP-A 2010-215608 and JP-A 2011-016746.

While many examples of the surfactant which is insoluble or substantially insoluble in water and alkaline developer are described in the patent documents cited herein, preferred examples are surfactants FC-4430 (3M), Olfine® E1004 (Nissin Chemical Co., Ltd.), Surflon® S-381, KH-20 and KH-30 (AGC Seimi Chemical Co., Ltd.). Partially fluorinated oxetane ring-opened polymers having the formula (surf-1) are also useful.

(surf-1)

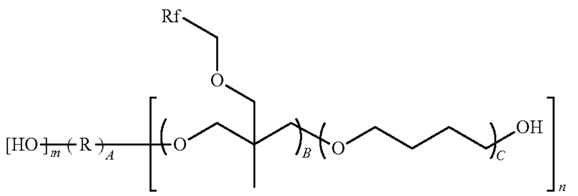

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent aliphatic groups include ethylene, 1,4-butylene, 1,2-propylene, 2,2-dimethyl-1,3-propylene and 1,5-pentylene. Exemplary tri- and tetra-valent groups are shown below.

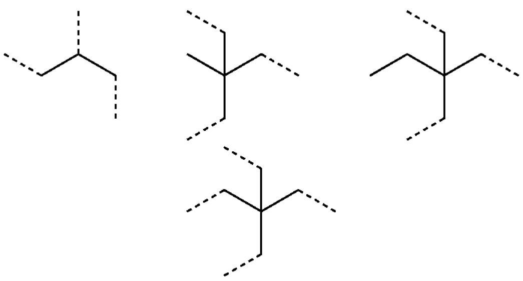

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. "A" is equal to 1, B is an integer of 2 to 25, and C is an integer of 0 to 10. Preferably, B is an integer of 4 to 20, and C is 0 or 1. Note that the formula (surf-1) does not prescribe the arrangement of respective constituent units while they may be arranged either blockwise or randomly. For the preparation of surfactants in the form of partially fluorinated oxetane ring-opened polymers, reference should be made to U.S. Pat. No. 5,650,483, for example.

The surfactant which is insoluble or substantially insoluble in water and soluble in alkaline developer is useful when ArF immersion lithography is applied to the resist composition in the absence of a resist protective film. In this embodiment, the surfactant has a propensity to segregate on the resist surface for achieving a function of minimizing water penetration or leaching. The surfactant is also effective for preventing water-soluble components from being leached out of the resist film for minimizing any damage to the exposure tool. The surfactant becomes solubilized during alkaline development following exposure and PEB, and thus forms few or no foreign particles which become defects. The preferred surfactant is a polymeric surfactant which is insoluble or substantially insoluble in water, but soluble in alkaline developer, also referred to as "hydrophobic resin" in this sense, and especially which is water repellent and enhances water sliding.

Suitable polymeric surfactants include those containing repeat units of at least one type selected from the formulae (6A) to (6E).

(6A)

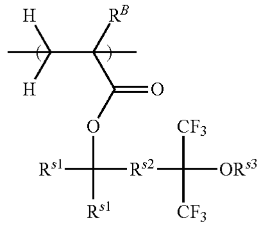

(6B)

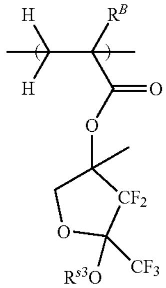

(6C)

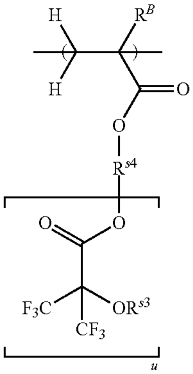

(6D)

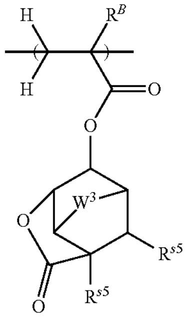

(6E)

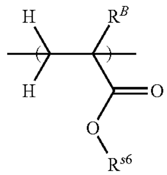

Herein, $R^B$ is hydrogen, fluorine, methyl or trifluoromethyl. $W^3$ is $—CH_2—$, $—CH_2CH_2—$ or —O—, or two separate —H. $R^{s1}$ is each independently hydrogen or a $C_1$-$C_{10}$ hydrocarbyl group. $R^{s2}$ is a single bond or a $C_1$-$C_5$ straight or branched hydrocarbylene group. $R^{s3}$ is each independently hydrogen, a $C_1$-$C_{15}$ hydrocarbyl or fluorinated hydrocarbyl group, or an acid labile group. When $R^{s3}$ is a hydrocarbyl or fluorinated hydrocarbyl group, an ether bond or carbonyl moiety may intervene in a carbon-carbon bond. $R^{s4}$ is a $C_1$-$C_{20}$ (u+1)-valent hydrocarbon or fluorinated hydrocarbon group, and u is an integer of 1 to 3. $R^{s5}$ is each independently hydrogen or a group: —C(═O)—O—$R^{s7}$ wherein $R^{s7}$ is a $C_1$-$C_{20}$ fluorinated hydrocarbyl group. $R^{s6}$ is a $C_1$-$C_{15}$ hydrocarbyl or fluorinated hydrocarbyl group in which an ether bond or carbonyl moiety may intervene in a carbon-carbon bond.

The hydrocarbyl group represented by $R^{s1}$ may be straight, branched or cyclic. Examples thereof include methyl, ethyl, n-propyl, isopropyl, cyclopropyl, n-butyl, isobutyl, sec-butyl, tert-butyl, cyclobutyl, n-pentyl, cyclopentyl, n-hexyl, cyclohexyl, n-heptyl, n-octyl, n-nonyl, n-decyl, adamantyl, and norbornyl. Inter alia, $C_1$-$C_6$ hydrocarbyl groups are preferred.

The hydrocarbylene group represented by $R^{s2}$ may be straight, branched or cyclic. Examples thereof include methylene, ethylene, propylene, butylene and pentylene.

The hydrocarbyl group represented by $R^{s3}$ or $R^{s6}$ may be straight, branched or cyclic. Examples thereof include alkyl, alkenyl and alkynyl groups, with the alkyl groups being preferred. Suitable alkyl groups include those exemplified for the hydrocarbyl group represented by $R^{s1}$ as well as n-undecyl, n-dodecyl, tridecyl, tetradecyl, and pentadecyl. Examples of the fluorinated hydrocarbyl group represented by $R^{s3}$ or $R^{s6}$ include the foregoing hydrocarbyl groups in which some or all carbon-bonded hydrogen atoms are substituted by fluorine atoms. In these groups, an ether bond or carbonyl moiety may intervene in a carbon-carbon bond as mentioned above.

Examples of the acid labile group represented by $R^{s3}$ include groups of the above formulae (AL-1) to (AL-3), $C_4$-$C_{20}$, preferably $C_4$-$C_{15}$ tertiary hydrocarbyl groups, trialkylsilyl groups in which each alkyl moiety has 1 to 6 carbon atoms, and $C_4$-$C_{20}$ oxoalkyl groups.

The (u+1)-valent hydrocarbon or fluorinated hydrocarbon group represented by $R^{s4}$ may be straight, branched or cyclic and examples thereof include the foregoing hydrocarbyl or fluorinated hydrocarbyl groups from which the number (u) of hydrogen atoms are eliminated.

The fluorinated hydrocarbyl group represented by $R^{s7}$ may be straight, branched or cyclic. Examples thereof include the foregoing hydrocarbyl groups in which some or all hydrogen atoms are substituted by fluorine atoms. Illustrative examples include trifluoromethyl, 2,2,2-trifluoroethyl, 3,3,3-trifluoro-1-propyl, 3,3,3-trifluoro-2-propyl, 2,2,3,3-tetrafluoropropyl, 1,1,1,3,3,3-hexafluoroisopropyl, 2,2,3,3,4,4,4-heptafluorobutyl, 2,2,3,3,4,4,5,5-octafluoropentyl, 2,2,3,3,4,4,5,5,6,6,7,7-dodecafluoroheptyl, 2-(perfluorobutyl)ethyl, 2-(perfluorohexyl)ethyl, 2-(perfluorooctyl)ethyl, and 2-(perfluorodecyl)ethyl.

Examples of the repeat units having formulae (6A) to (6E) are shown below, but not limited thereto. Herein $R^B$ is as defined above.

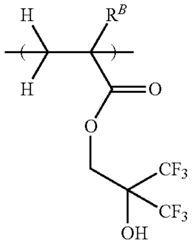
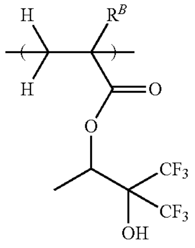

-continued

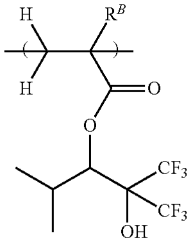
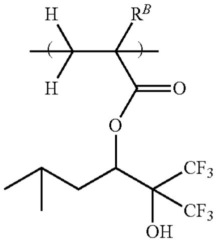
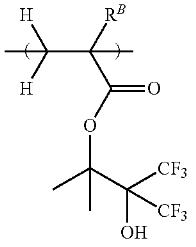
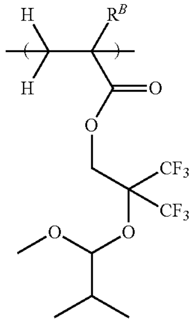
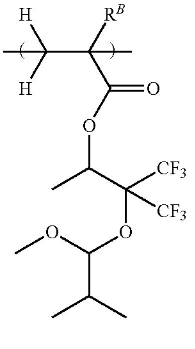
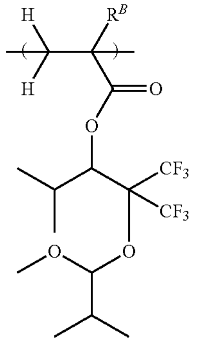
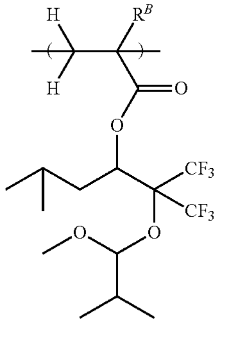
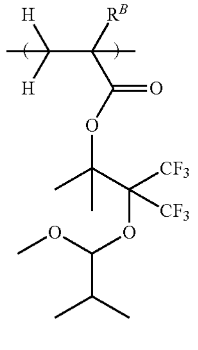
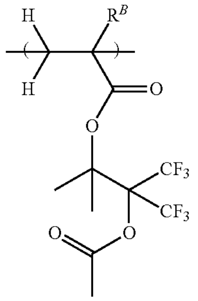
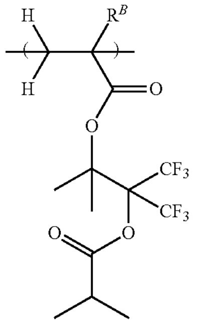

-continued
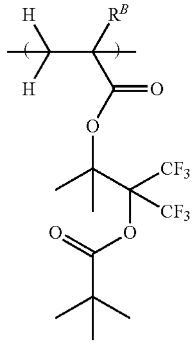
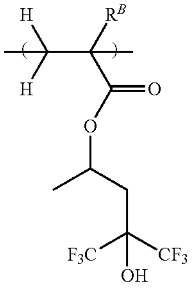
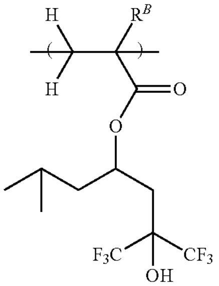
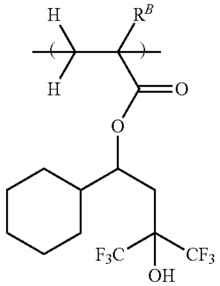
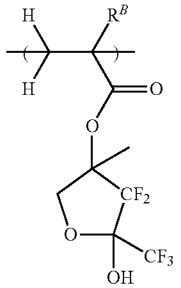
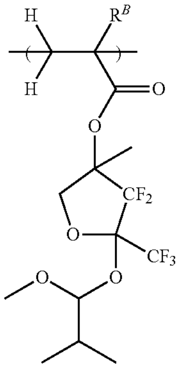
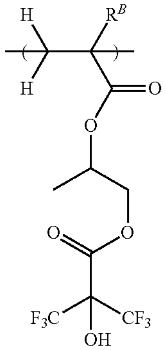
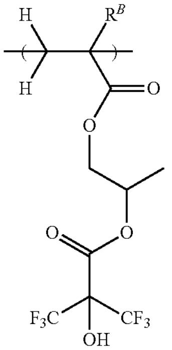
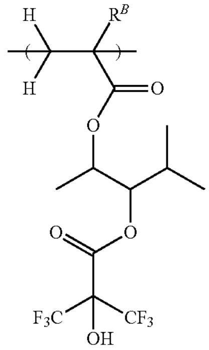
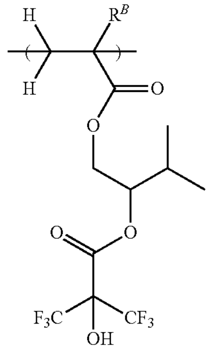
-continued
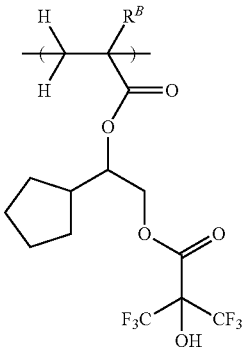
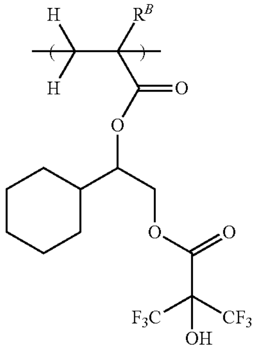
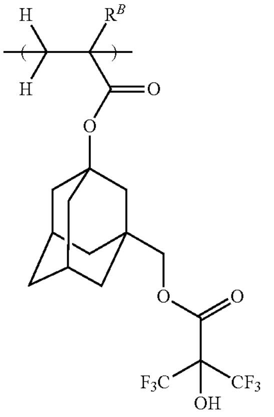
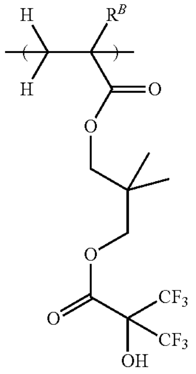
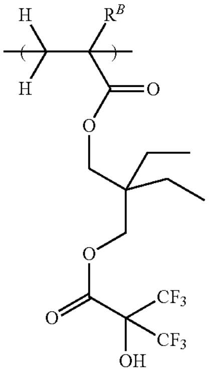
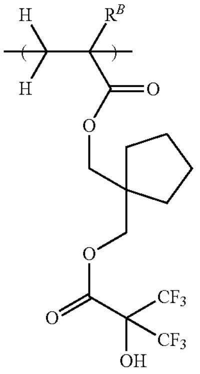
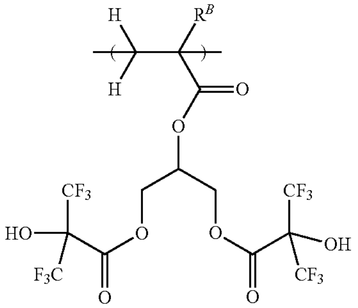

-continued
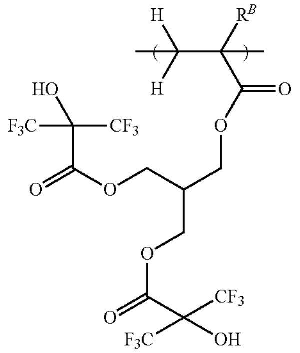
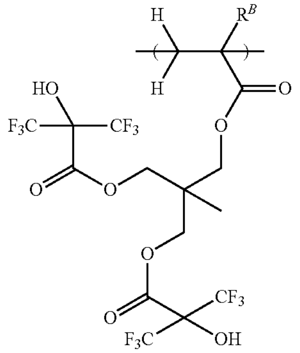
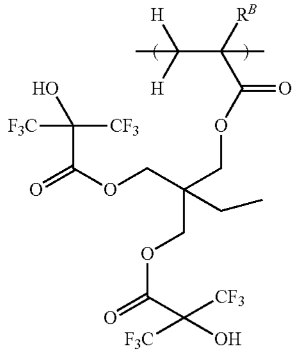
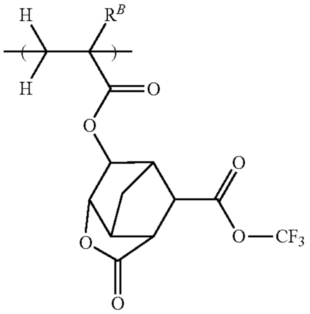
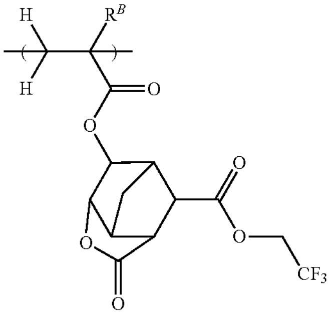
-continued
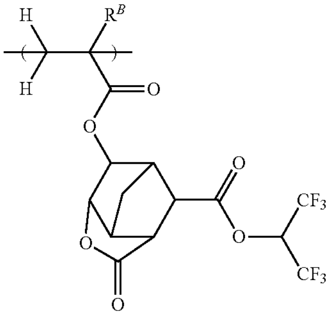
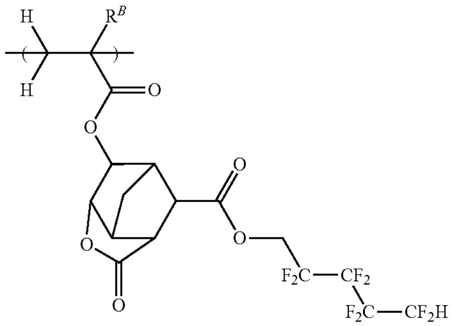
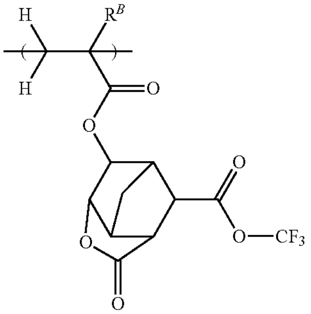
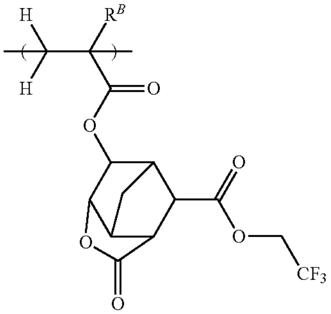
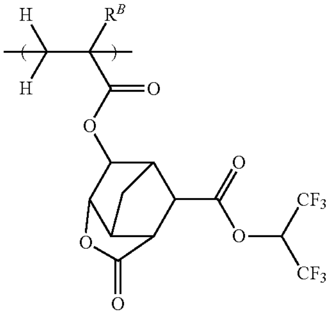

-continued
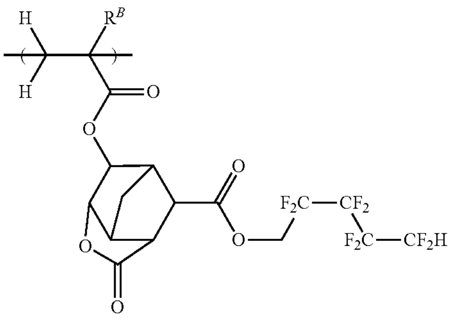
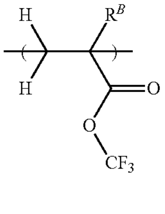
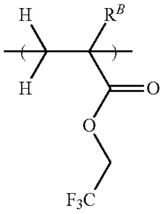
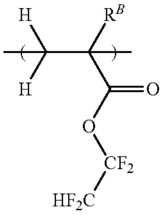
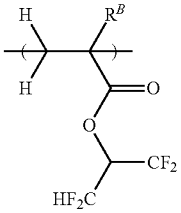
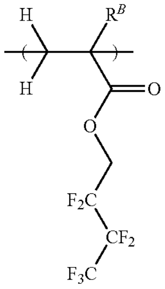
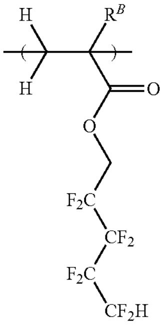
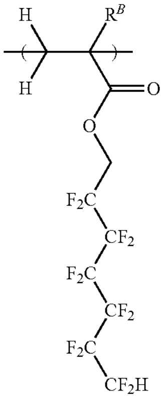
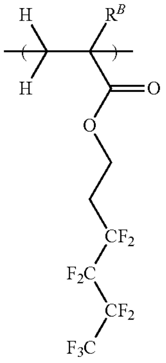
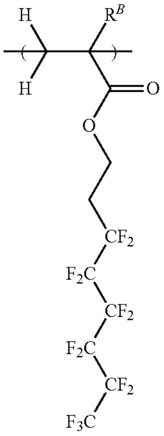
-continued
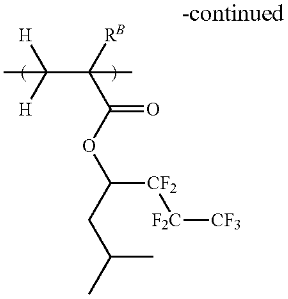
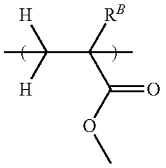
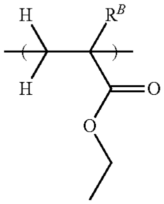
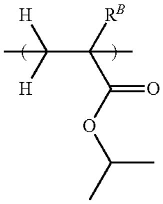
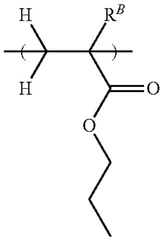
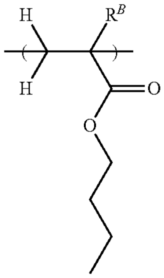
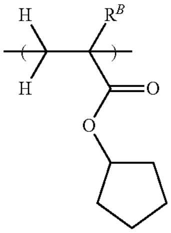
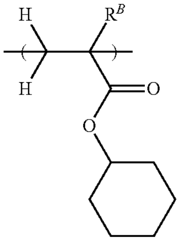
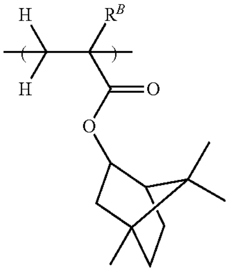
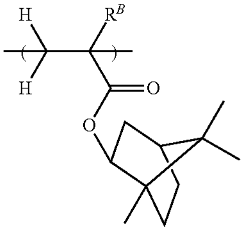
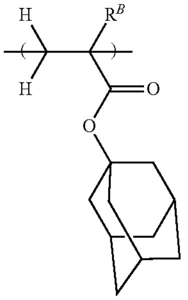
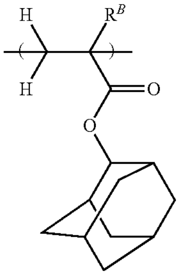
The polymeric surfactant may further contain repeat units other than the repeat units having formulae (6A) to (6E). Typical other repeat units are those derived from methacrylic acid and α-trifluoromethylacrylic acid derivatives. In the polymeric surfactant, the content of repeat units having formulae (6A) to (6E) is preferably at least 20 mol %, more preferably at least 60 mol %, most preferably 100 mol % of the overall repeat units.

The polymeric surfactant preferably has a Mw of 1,000 to 500,000, more preferably 3,000 to 100,000 and a Mw/Mn of 1.0 to 2.0, more preferably 1.0 to 1.6.

The polymeric surfactant may be synthesized by any desired method, for example, by dissolving an unsaturated bond-containing monomer or monomers providing repeat units having formula (6A) to (6E) and optionally other repeat units in an organic solvent, adding a radical initiator, and heating for polymerization. Suitable organic solvents used herein include toluene, benzene, THF, diethyl ether, and dioxane. Examples of the polymerization initiator used herein include AIBN, 2,2'-azobis(2,4-dimethylvaleronitrile), dimethyl 2,2-azobis(2-methylpropionate), benzoyl peroxide, and lauroyl peroxide. Preferably the reaction temperature is 50 to 100° C. and the reaction time is 4 to 24 hours. The acid labile group that has been incorporated in the monomer may be kept as such, or the polymer may be protected or partially protected therewith at the end of polymerization.

During the synthesis of polymeric surfactant, any known chain transfer agent such as dodecyl mercaptan or 2-mercaptoethanol may be added for molecular weight control purpose. The amount of chain transfer agent added is preferably 0.01 to 10 mol % based on the total moles of monomers to be polymerized.

When the resist composition contains a surfactant (F), the amount thereof is preferably 0.1 to 50 parts by weight, and more preferably 0.5 to 10 parts by weight per 80 parts by weight of the base polymer (B). At least 0.1 part of the surfactant is effective in improving the receding contact angle with water of the resist film at its surface. Up to 50 parts of the surfactant is effective in forming a resist film having a low rate of dissolution in a developer and capable of maintaining the height of a fine pattern formed therein.

(G) Other Components

The resist composition may further comprise (G) another component, for example, a compound which is decomposed with an acid to generate another acid (i.e., acid amplifier compound), an organic acid derivative, a fluorinated alcohol, a crosslinker, a compound having a Mw of up to 3,000 which changes its solubility in developer under the action of an acid (i.e., dissolution inhibitor), and an acetylene alcohol. Specifically, the acid amplifier compound is described in JP-A 2009-269953 and JP-A 2010-215608 and preferably used in an amount of 0 to 5 parts, more preferably 0 to 2 parts, even more preferably 0 to 1 part by weight per 80 parts by weight of the base polymer (B). An extra amount of the acid amplifier compound can make the acid diffusion control difficult and cause degradations to resolution and pattern profile. The addition of organic acid derivative, fluorinated alcohol, dissolution inhibitor and the like is optional. For these components, reference should be made to JP-A 2009-269953 and JP-A 2010-215608.

Process

A further embodiment of the invention is a process of forming a pattern from the resist composition defined above by lithography. The preferred process includes the steps of applying the resist composition onto a substrate to form a resist film thereon, exposing the resist film to high-energy radiation, and developing the exposed resist film in a developer. Any desired steps may be added to the process if necessary.

The substrate used herein may be a substrate for integrated circuitry fabrication, e.g., Si, $SiO_2$, SiN, SiON, TiN, WSi, BPSG, SOG, organic antireflective film, etc. or a substrate for mask circuitry fabrication, e.g., Cr, CrO, CrON, $MoSi_2$, $SiO_2$, etc.

The resist composition is applied onto a substrate by a suitable coating technique such as spin coating. The coating is prebaked on a hot plate preferably at a temperature of 60 to 180° C. for 10 to 600 seconds, more preferably at 70 to 150° C. for 15 to 300 seconds. The resulting resist film preferably has a thickness of 10 to 2,000 nm.

Then the resist film is exposed patternwise to high-energy radiation. On use of KrF excimer laser, ArF excimer laser or EUV of wavelength 13.5 nm, the resist film is exposed through a mask having a desired pattern, preferably in a dose of 1 to 200 $mJ/cm^2$, more preferably 10 to 100 $mJ/cm^2$. On use of EB, a pattern may be written directly or through a mask having the desired pattern, preferably in a dose of 1 to 300 $\mu C/cm^2$, more preferably 10 to 200 $\mu C/cm^2$.

The exposure may be performed by conventional lithography whereas the immersion lithography of holding a liquid having a refractive index of at least 1.0 between the resist film and the projection lens may be employed if desired. The liquid is typically water, and in this case, a protective film which is insoluble in water may be formed on the resist film.

While the water-insoluble protective film serves to prevent any components from being leached out of the resist film and to improve water sliding on the film surface, it is generally divided into two types. The first type is an organic solvent-strippable protective film which must be stripped, prior to alkaline development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

After the exposure, the resist film may be baked (PEB), for example, on a hotplate at 60 to 150° C. for 1 to 5 minutes, preferably at 80 to 140° C. for 1 to 3 minutes.

The resist film is then developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle and spray techniques. In the development step, the exposed region of resist film is dissolved away, and a desired resist pattern is formed on the substrate.

The process of forming a positive tone pattern using an alkaline aqueous solution as the developer is described in JP-A 2011-231312, paragraphs [0138]-[0146] whereas the process of forming a negative tone pattern using an organic solvent as the developer is described in JP-A 2015-214634, paragraphs [0173]-[0183].

Any desired step may be added to the pattern forming process. For example, after the resist film is formed, a step of rinsing with pure water (post-soaking) may be introduced to extract the acid generator or the like from the film surface or wash away particles. After exposure, a step of rinsing (post-soaking) may be introduced to remove any water remaining on the film after exposure.

Also, a double patterning version of pattern formation process may be used for allowing the ArF lithography to survive down to a size of 32 nm. The double patterning process includes a trench process of processing an underlay to a 1:3 trench pattern by a first step of exposure and etching, shifting the position, and forming a 1:3 trench pattern by a second step of exposure, for forming a 1:1 pattern; and a line process of processing a first underlay to a 1:3 isolated left pattern by a first step of exposure and etching, shifting the position, processing a second underlay formed below the first underlay by a second step of exposure through the 1:3 isolated left pattern, for forming a half-pitch 1:1 pattern.

Where a hole pattern is formed by negative tone development using organic solvent developer, exposure by double dipole illuminations of X- and Y-direction line patterns provides the highest contrast light. The contrast may be further increased by combining two dipole illuminations of X- and Y-direction line patterns with s-polarized illumination. These pattern forming processes are described in JP-A 2011-221513.

With respect to the developer in the pattern forming process, examples of the aqueous alkaline solution include TMAH aqueous solutions as mentioned above and aqueous alkaline solutions described in JP-A 2015-180748, paragraphs [0148]-[0149], preferably 2 to 3% by weight TMAH aqueous solutions.

The developer used in organic solvent development is preferably selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, butenyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate. These organic solvents may be used alone or in admixture of two or more.

A hole or trench pattern after development may be shrunk by the thermal flow, RELACS® (resolution enhancement lithography assisted by chemical shrink) or DSA (directed self-assembly) process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

When processed by photolithography, the chemically amplified resist composition comprising the onium salt having formula (1) as PAG forms a fine size pattern with improved lithography performance factors such as CDU, LWR and sensitivity.

EXAMPLES

Examples of the invention are given below by way of illustration and not by way of limitation. The abbreviation "pbw" is parts by weight. For all polymers, Mw and Mn are determined by GPC versus polystyrene standards using tetrahydrofuran (TIF) solvent. Analysis is made by IR spectroscopy, NMR spectroscopy, and time-of-flight mass spectrometry (TOF-MS) using analytic instruments as shown below.

IR: NICOLET 6700 by Thermo Fisher Scientific Inc.

$^1$H-NMR: ECA-500 by JEOL Ltd.

$^{19}$F-NMR: ECA-500 by JEOL Ltd.

MALDI TOF-MS: S3000 by JEOL Ltd.

[1] Synthesis of Photoacid Generators

Example 1-1

Synthesis of PAG-1

(1) Synthesis of Acid Chloride 1

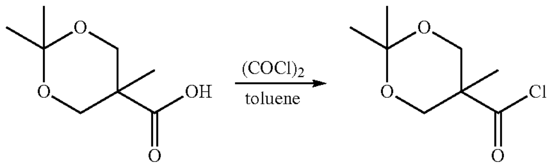

1

In nitrogen atmosphere, a flask was charged with 17.4 g of 2,2,5-trimethyl-1,3-dioxane-5-carboxylic acid and 135 g of toluene. With the flask held in an oil bath at 40° C., 15.2 g of oxalyl chloride was added dropwise. At the end of addition, the reaction system was stirred and aged at 40° C. for 16 hours. After the aging, the solvent was distilled off, obtaining Acid Chloride 1 as oily matter (amount 19.3 g).

(2) Synthesis of Intermediate 2

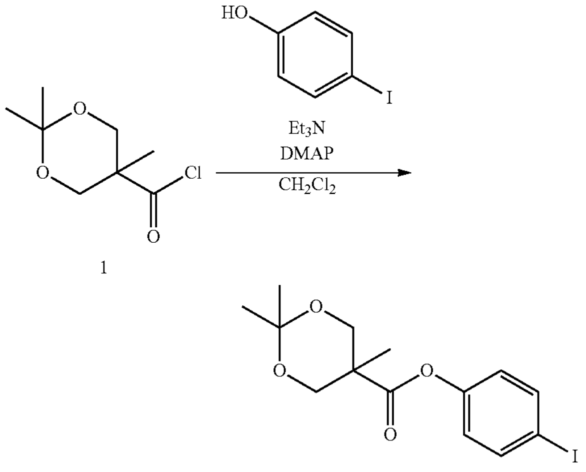

1

2

In nitrogen atmosphere, a flask was charged with 26.4 g of 4-iodophenol, 19.3 g of Acid Chloride 1, and 300 g of methylene chloride. Under ice cooling, 14.2 g of triethylamine, 1.2 g of dimethylaminopyridine, and 30 g of methylene chloride were added dropwise. At the end of addition, the reaction system was warmed up to room temperature and aged for 22 hours. At the end of aging, the reaction system was ice cooled, after which 100 g of saturated sodium bicarbonate aqueous solution was added dropwise to quench the reaction. This was followed by ordinary aqueous workup and solvent distillation. Diisopropyl ether, 60 g, was added to the residue, which was stirred for washing. The solvent was withdrawn, after which the remaining solvent was distilled off, obtaining Intermediate 2 as oily matter (amount 28.7 g, yield 76.3%).

(3) Synthesis of Diol A-1

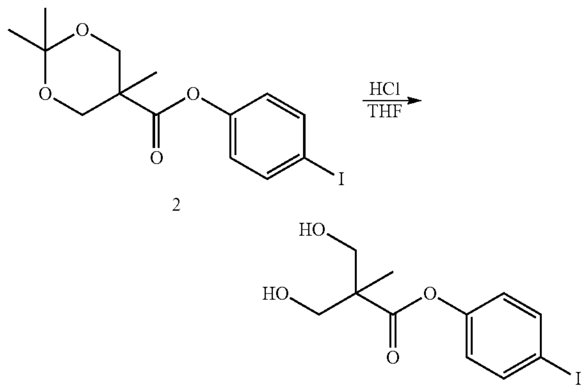

2

A-1

In nitrogen atmosphere, a flask was charged with 15.3 g of Intermediate 2, 50 g of 3 wt % hydrochloric acid, and 50 g of THF, which were stirred and aged at room temperature for 19 hours. After aging, the solvent was distilled off, after which 200 g of methylene chloride and 40 g of water were added for extraction. This was followed by ordinary aqueous work-up and solvent distillation. Diisopropyl ether, 150 g, was added to the residue, which was stirred for 1.5 hours. The resulting solid precipitate was collected by filtration and dried in vacuum for 2 hours, obtaining Diol A-1 as white solids (amount 9.5 g, yield 70.6%).

(4) Preparation of Acid Chloride 4

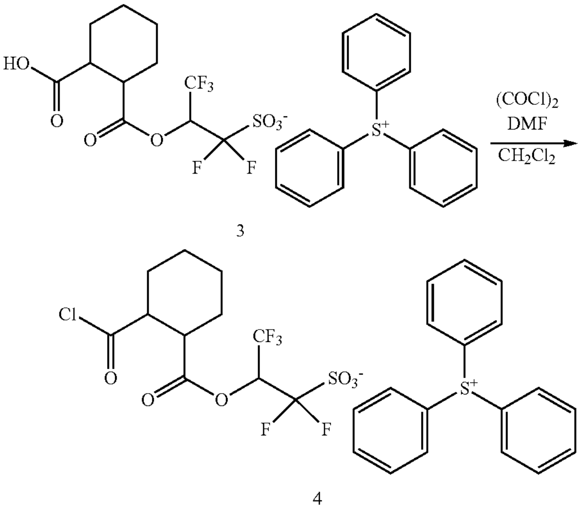

3

4

In nitrogen atmosphere, a flask was charged with 20.9 g of Intermediate 3, 0.2 g of dimethylformamide, and 100 g of methylene chloride. At room temperature, 4.9 g of oxalyl chloride was added dropwise. At the end of addition, the reaction system was aged for 16 hours. Thereafter, the solvent was distilled off, obtaining Acid Chloride 4 as oily matter (amount 21.5 g).

(5) Synthesis of PAG-1

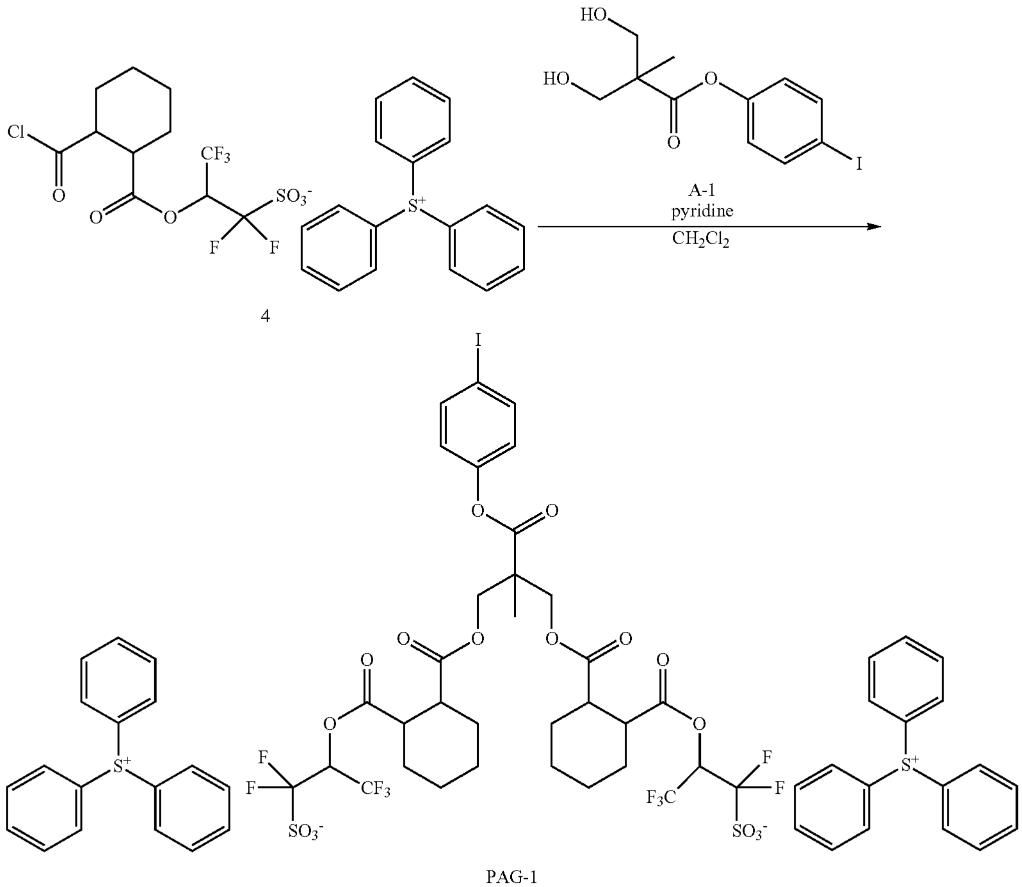

4

PAG-1

In nitrogen atmosphere, a flask was charged with 21.5 g of Acid Chloride 4, 4.2 g of Diol A-1, and 85 g of methylene chloride. Under ice cooling, 2.4 g of pyridine was added dropwise. At the end of addition, the reaction system was warmed up to room temperature and aged for 21 hours. After aging, the reaction system was ice cooled, after which 30 g of 5 wt % hydrochloric acid was added to quench the reaction. Thereafter, the organic layer was taken out by separatory operation, followed by ordinary aqueous work-up and solvent distillation.

The resulting oily matter was a mixture of the target compound and the acid anhydride originating from Acid Chloride 4. To the oily matter, 0.5 g of sodium bicarbonate, 0.1 g of dimethylaminopyridine, 35 g of THF, and 15 g of water were added to conduct hydrolysis at room temperature. The mixture was stirred for 1 hour, after which 150 g of methylene chloride and 35 g of water were added for extraction. This was followed by washing with 1 wt % hydrochloric acid, washing with saturated sodium bicarbonate aqueous solution, ordinary aqueous work-up, and solvent distillation. Thereafter, 70 g of diisopropyl ether was added to the residue, followed by stirring. The solid precipitate was collected by filtration, obtaining PAG-1 as solids (amount 17.0 g, yield 86.2%).

Figure 2:
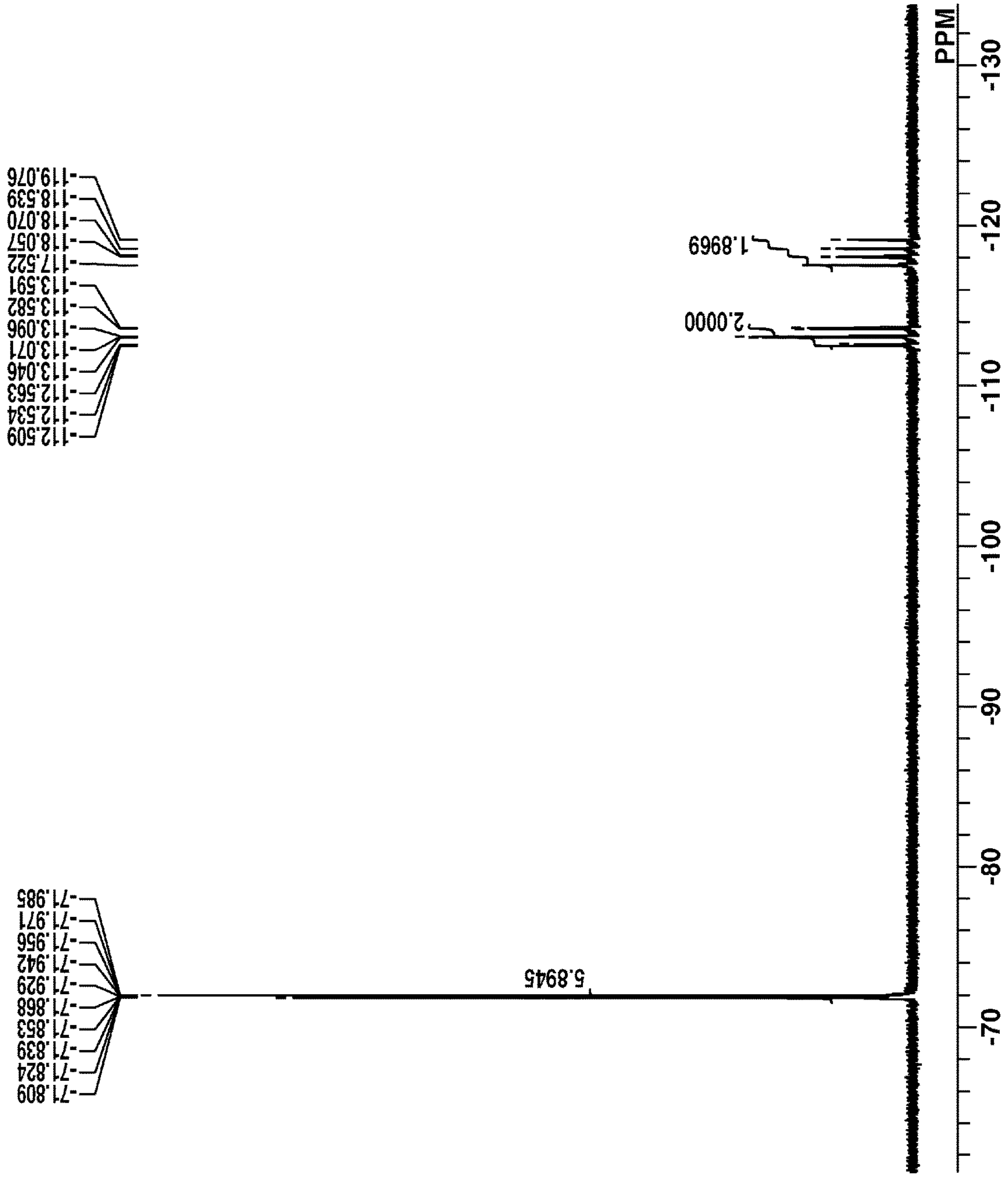
FIG. 2 is a $^{19}$F-NMR spectrum of PAG-1 synthesized in Example 1-1.

PAG-1 was analyzed by IR spectroscopy and TOF-MS, with the data shown below. FIGS. 1 and 2 are the $^1$H- and $^{19}$F-NMR/DMSO-$d_6$ spectrum of PAG-1, respectively.

IR (D-ATR): ν=3498, 3064, 2939, 2862, 1759, 1634, 1581, 1478, 1448, 1372, 1323, 1251, 1217, 1186, 1167, 1111, 1074, 1029, 1007, 996, 941, 905, 879, 837, 802, 750, 684, 641, 577, 552, 502 $cm^{-1}$

MALDI TOF-MS

Positive $M^+$ 263.1 (corresponding to $C_{18}H_{15}S^+$)

Negative $M^-$ 1329.0 (corresponding to $C_{51}H_{48}F_{10}IO_{16}S_3^-$)

Example 1-2

Synthesis of PAG-2

(1) Preparation of Acid Chloride 6

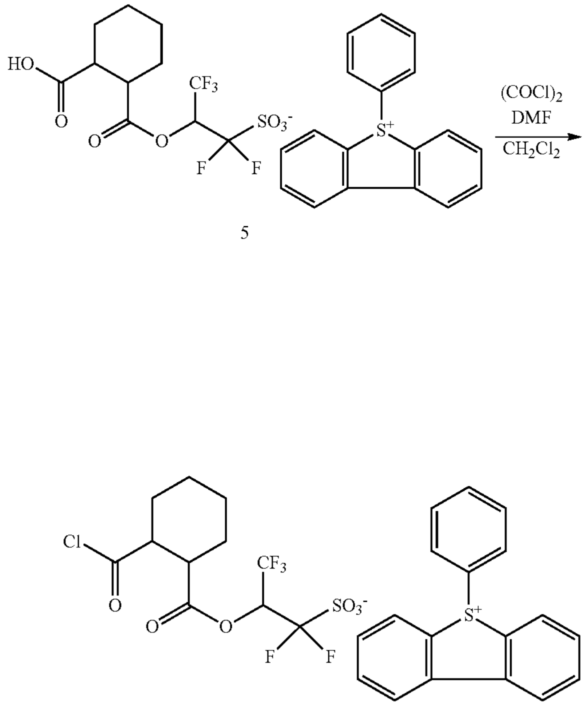

5

6

In nitrogen atmosphere, a flask was charged with 29.0 g of Intermediate 5, 0.2 g of dimethylformamide, and 150 g of methylene chloride. At room temperature, 6.9 g of oxalyl chloride was added dropwise. At the end of addition, the reaction system was aged for 16 hours. Thereafter, the solvent was distilled off, obtaining Acid Chloride 6 as oily matter (amount 29.8 g).

(2) Synthesis of PAG-2

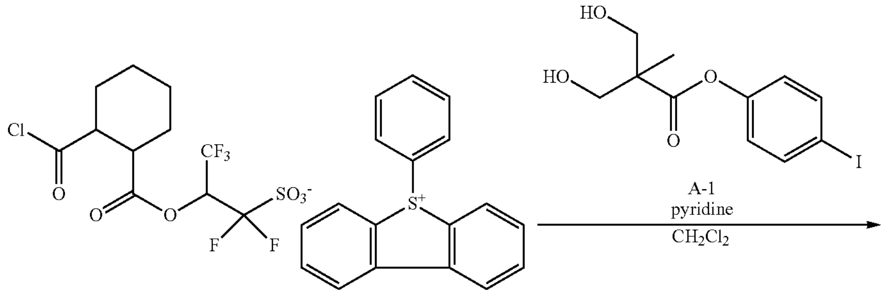

6

-continued

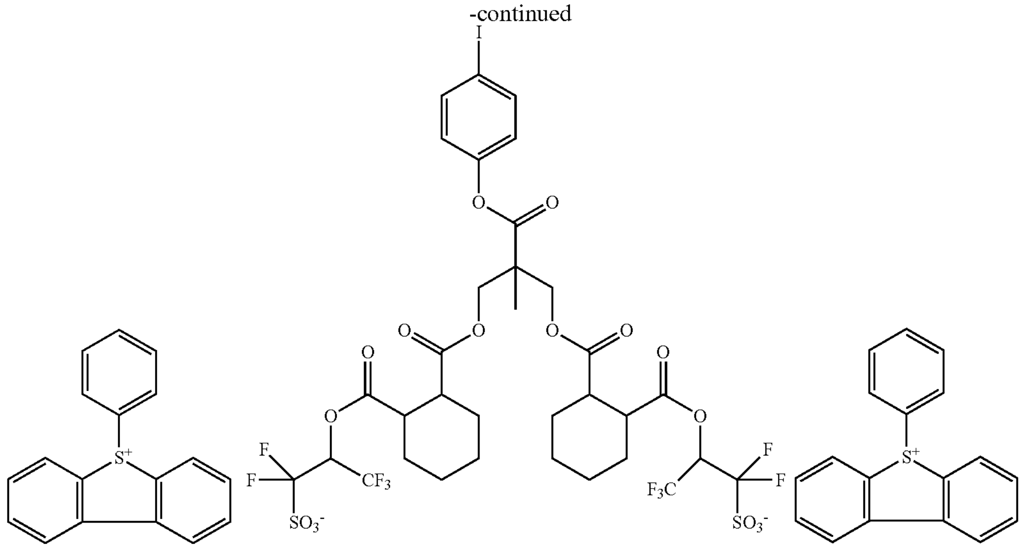

PAG-2

In nitrogen atmosphere, a flask was charged with 29.8 g of Acid Chloride 6, 5.8 g of Diol A-1, and 80 g of methylene chloride. Under ice cooling, 3.3 g of pyridine was added dropwise. At the end of addition, the reaction system was warmed up to room temperature and aged for 24 hours. After aging, the reaction system was ice cooled, after which 30 g of 5 wt % hydrochloric acid was added to quench the reaction. Thereafter, the organic layer was taken out by separatory operation, followed by ordinary aqueous work-up and solvent distillation.

The resulting oily matter was a mixture of the target compound and the acid anhydride originating from Acid Chloride 6. To the oily matter, 0.8 g of sodium bicarbonate, 0.1 g of dimethylaminopyridine, 50 g of THF, and 30 g of water were added to conduct hydrolysis at room temperature. The mixture was stirred for 1 hour, after which 100 g of methylene chloride and 30 g of water were added for extraction. This was followed by washing with 1 wt % hydrochloric acid, washing with saturated sodium bicarbonate aqueous solution, ordinary aqueous work-up, and solvent distillation. Thereafter, 200 g of hexane was added to the residue, followed by stirring. The solid precipitate was collected by filtration, obtaining PAG-2 as solids (amount 22.5 g, yield 82.0%).

Figure 3:
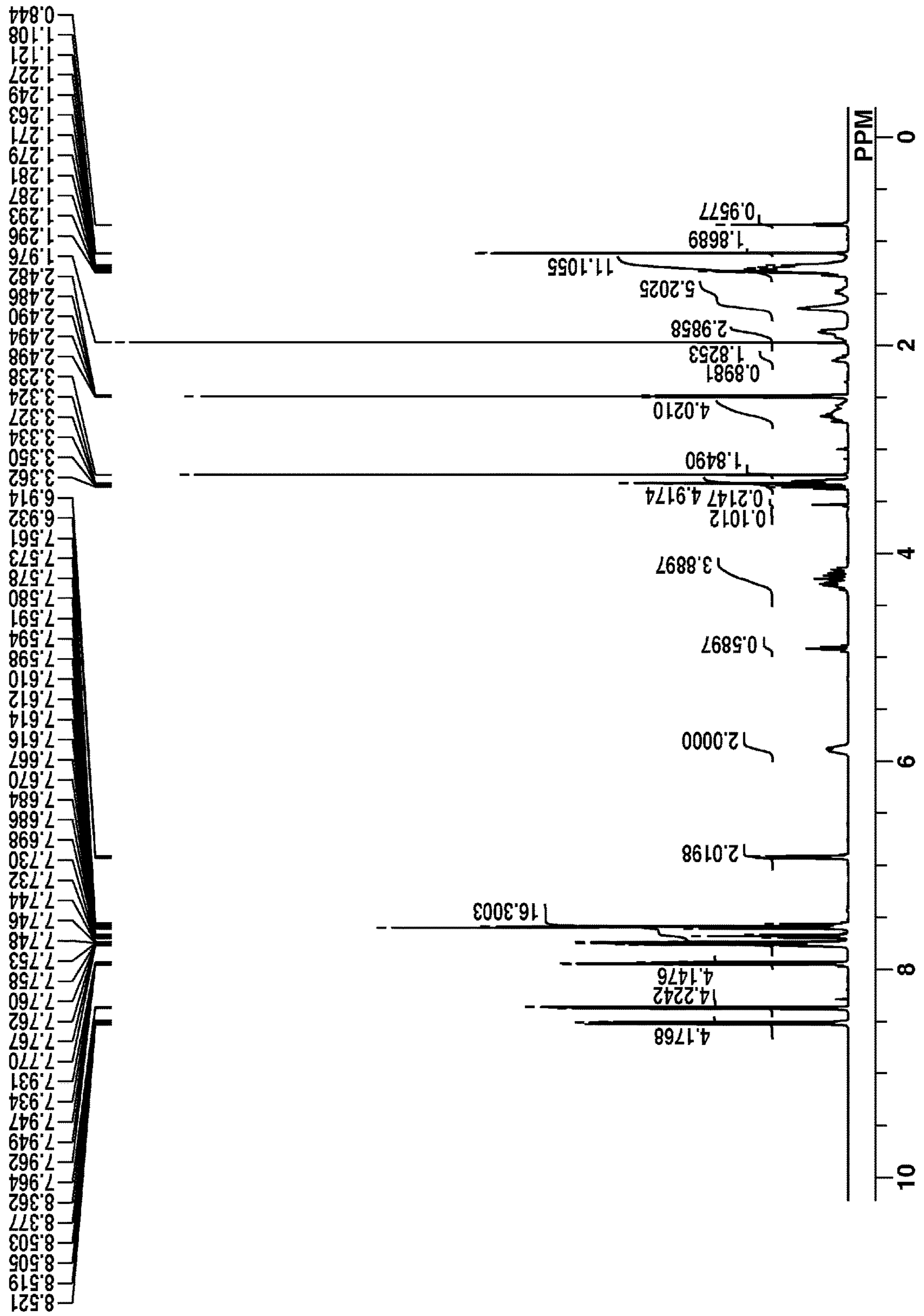
FIG. 3 is a $^1$H-NMR spectrum of PAG-2 synthesized in Example 1-2.
Figure 4:
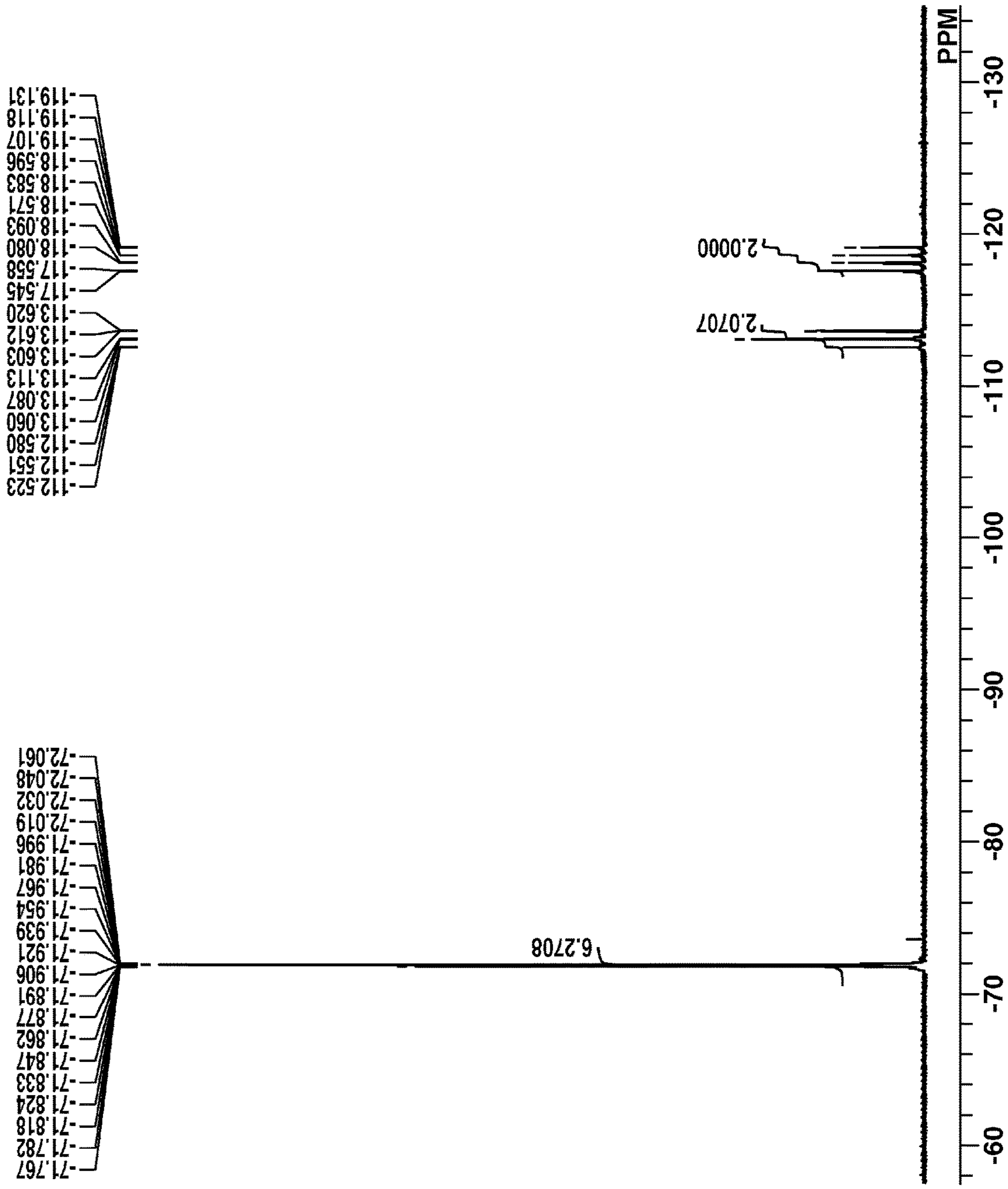
FIG. 4 is a $^{19}$F-NMR spectrum of PAG-2 synthesized in Example 1-2.

PAG-2 was analyzed by IR spectroscopy and TOF-MS, with the data shown below. FIGS. 3 and 4 are the $^{1}H$- and $^{19}F$-NMR/DMSO-$d_6$ spectrum of PAG-2, respectively.

IR (D-ATR): ν=3481, 3091, 2939, 2861, 1758, 1737, 1578, 1481, 1449, 1373, 1320, 1247, 1186, 1167, 1111, 1074, 1028, 994, 941, 904, 879, 837, 759, 707, 681, 641, 613, 576, 552, 525, 490, 423 $cm^{-1}$

MALDI TOF-MS

Positive $M^+$ 261.0 (corresponding to $C_{18}H_{13}S^+$)

Negative $M^-$ 1327.7 (corresponding to $C_{51}H_{46}F_{10}IO_{16}S_3^-$)

Example 1-3

Synthesis of PAG-3

(1) Preparation of Acid Chloride 8

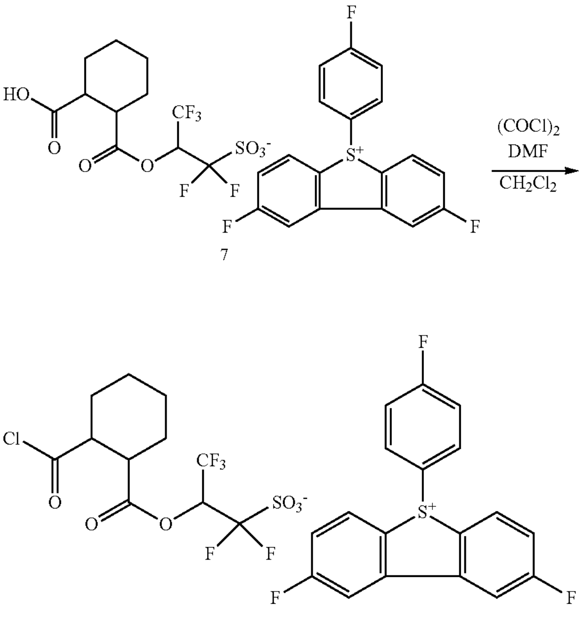

7

8

In nitrogen atmosphere, a flask was charged with 17.9 g of Intermediate 7, 0.2 g of dimethylformamide, and 80 g of methylene chloride. At room temperature, 4.2 g of oxalyl chloride was added dropwise. At the end of addition, the reaction system was aged for 17 hours. Thereafter, the solvent was distilled off, obtaining Acid Chloride 8 as oily matter (amount 19.6 g).

(2) Synthesis of PAG-3

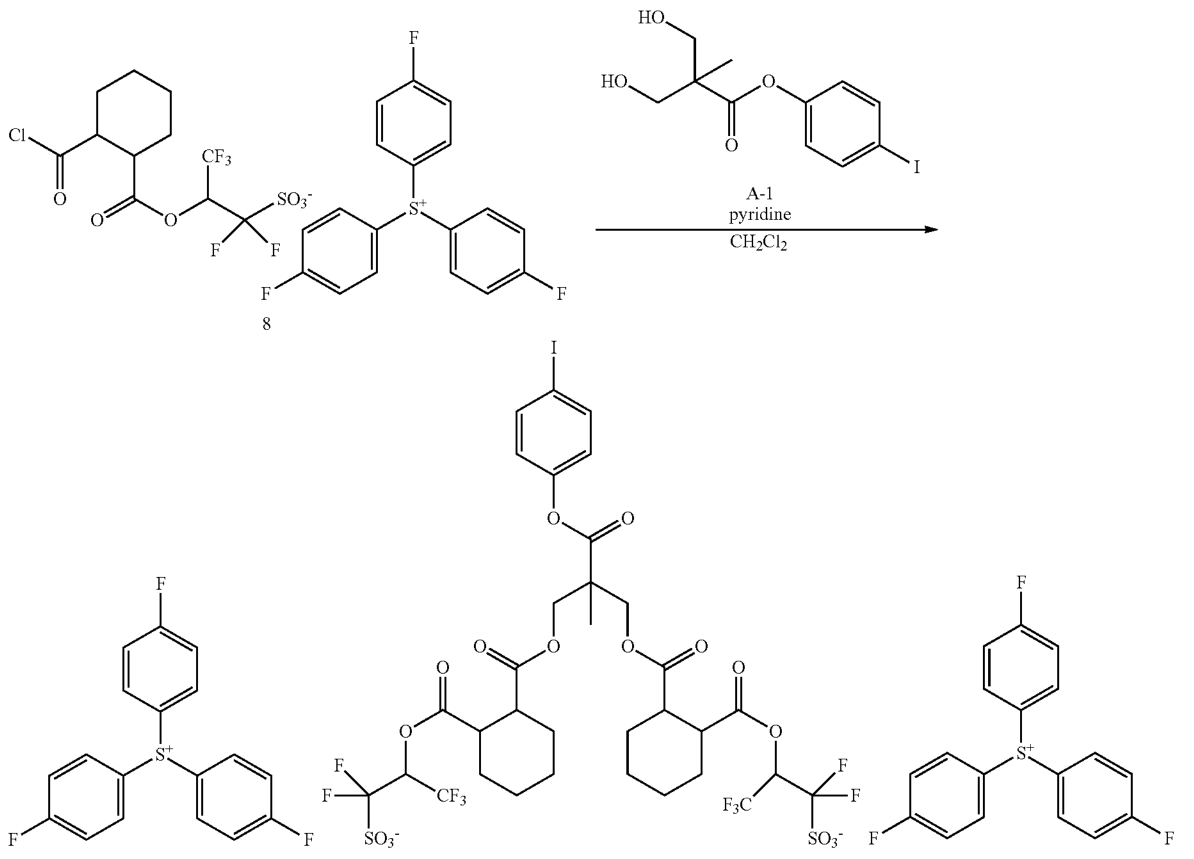

8

PAG-3

In nitrogen atmosphere, a flask was charged with 19.6 g of Acid Chloride 8, 3.5 g of Diol A-1, and 80 g of methylene chloride. Under ice cooling, 2.0 g of pyridine was added dropwise. At the end of addition, the reaction system was warmed up to room temperature and aged for 21 hours. After aging, the reaction system was ice cooled, after which 30 g of 5 wt % hydrochloric acid was added to quench the reaction. Thereafter, the organic layer was taken out by separatory operation, followed by ordinary aqueous work-up and solvent distillation.

The resulting oily matter was a mixture of the target compound and the acid anhydride originating from Acid Chloride 8. To the oily matter, 0.5 g of sodium bicarbonate, 0.1 g of dimethylaminopyridine, 35 g of THF, and 15 g of water were added to conduct hydrolysis at room temperature. The mixture was stirred for 1 hour, after which 100 g of methylene chloride and 30 g of water were added for extraction. This was followed by washing with 1 wt % hydrochloric acid, washing with saturated sodium bicarbonate aqueous solution, ordinary aqueous work-up, and solvent distillation. There was obtained PAG-3 as oily matter (amount 16.2 g, yield 91.1%).

Figure 5:
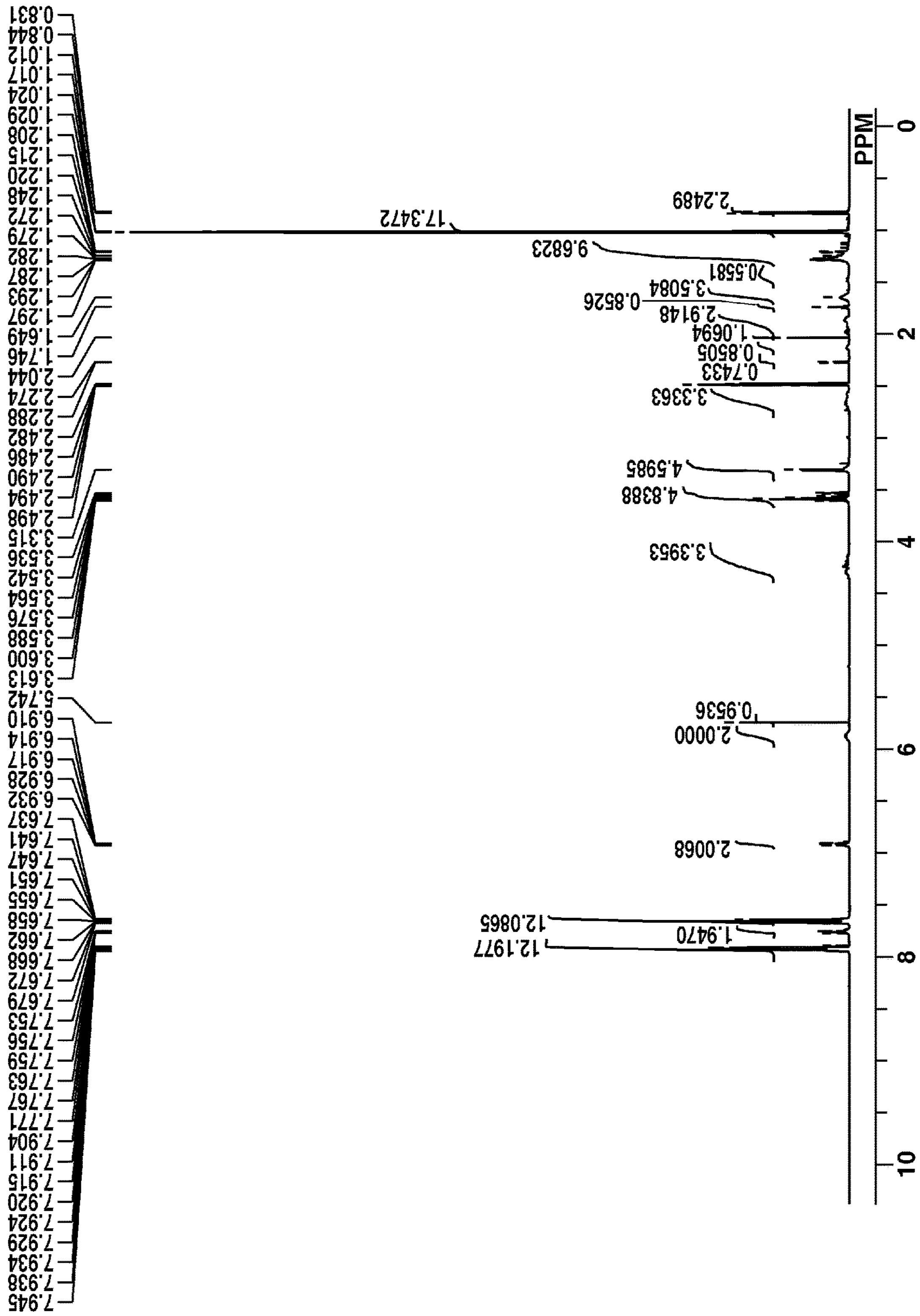
FIG. 5 is a $^1$H-NMR spectrum of PAG-3 synthesized in Example 1-3.
Figure 6:
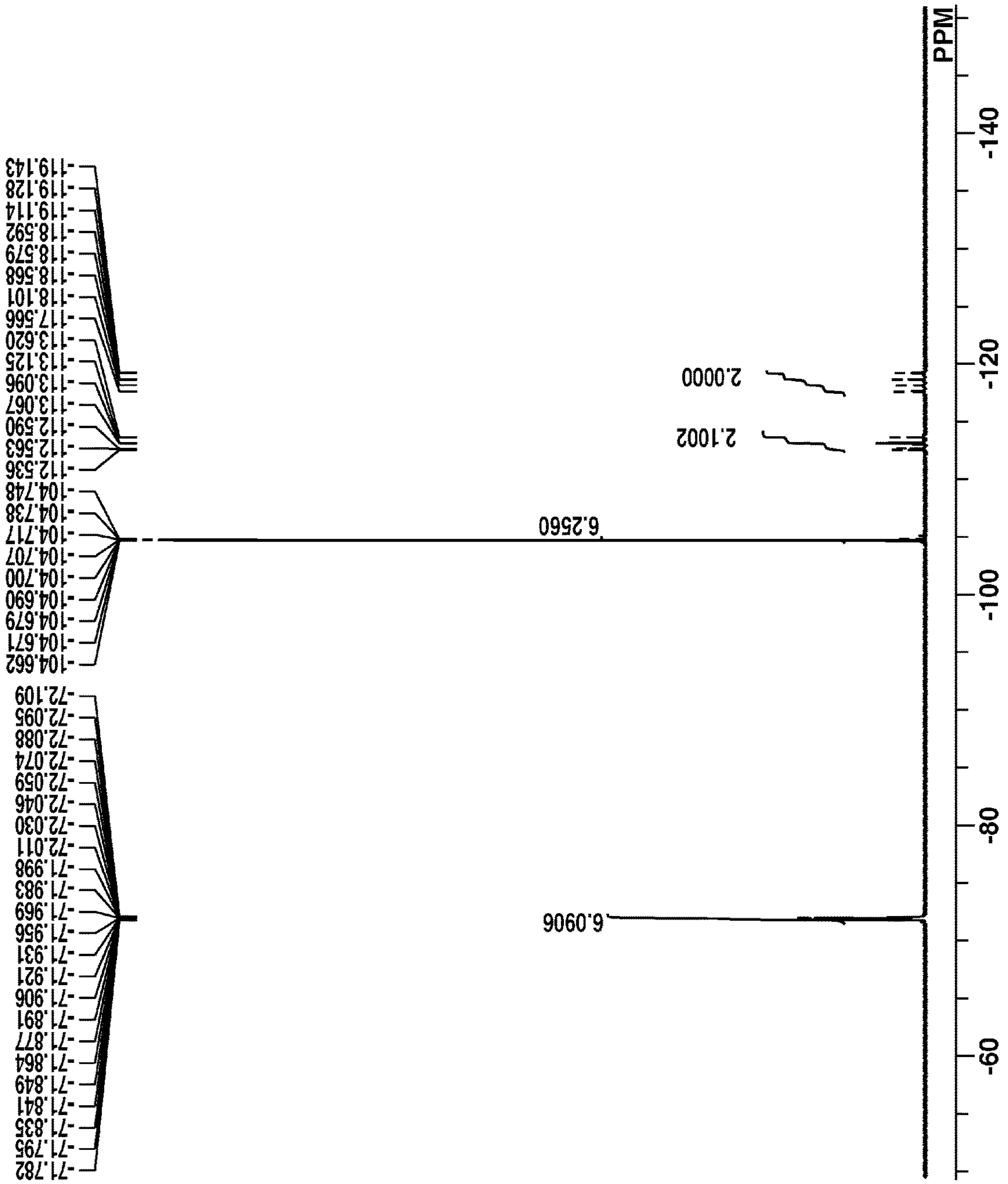
FIG. 6 is a $^{19}$F-NMR spectrum of PAG-3 synthesized in Example 1-3.

PAG-3 was analyzed by IR spectroscopy and TOF-MS, with the data shown below. FIGS. 5 and 6 are the $^1$H- and $^{19}$F-NMR/DMSO-$d_6$ spectrum of PAG-3, respectively.

IR (D-ATR): ν=3484, 3102, 3061, 2971, 2939, 2865, 1759, 1587, 1492, 1453, 1407, 1370, 1325, 1243, 1188, 1164, 1111, 1075, 1031, 1008, 993, 942, 903, 880, 839, 642, 577, 553, 520, 438 $cm^{-1}$

MALDI TOF-MS

Positive $M^+$ 317.1 (corresponding to $C_{18}H_{12}F_3S^+$)

Negative $M^-$ 1383.7 (corresponding to $C_{51}H_{45}F_{13}IO_{16}S_3^-$)

Example 1-4

Synthesis of PAG-4

(1) Preparation of Acid Chloride 9

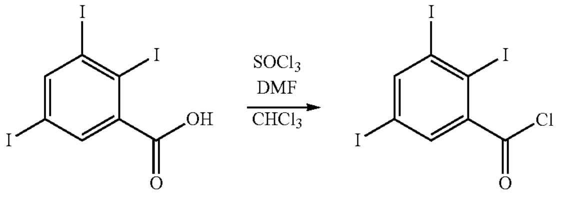

9

In nitrogen atmosphere, a flask was charged with 50.0 g of triiodobenzoic acid, 0.4 g of dimethylformamide, and 340 g of chloroform, which were stirred at 55° C. To the mixture, 23.8 g of thionyl chloride was added dropwise. At the end of addition, the reaction system was aged in an oil bath at 55°

C. for 20 hours. Thereafter, the solvent and the excess of thionyl chloride were distilled off, obtaining Acid Chloride 9 as solids.

(2) Synthesis of Intermediate 11

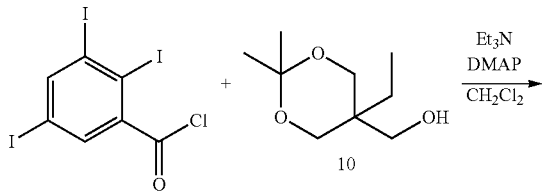

9 10

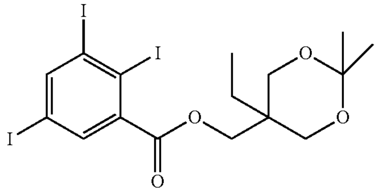

11

In nitrogen atmosphere, a flask was charged with 14.5 g of Alcohol 10, 11.8 g of triethylamine, 1.0 g of dimethylaminopyridine, and 300 g of methylene chloride. Under ice cooling, divided portions of Acid Chloride 9 were added. At the end of addition, the reaction system was warmed up to room temperature and aged for 20 hours. At the end of aging, the reaction system was ice cooled, after which 50 g of saturated sodium bicarbonate aqueous solution was added dropwise to quench the reaction. The organic layer was taken out by separatory operation, followed by ordinary aqueous work-up. After the solvent was distilled off, 200 g of diisopropyl ether was added to the residue, which was stirred. After 2 hours of stirring, the solid precipitate was collected by filtration and dried in vacuum for 2 hours, obtaining Intermediate 11 as white solids (amount 29.4 g, yield 54.0%).

(3) Synthesis of Diol A-2

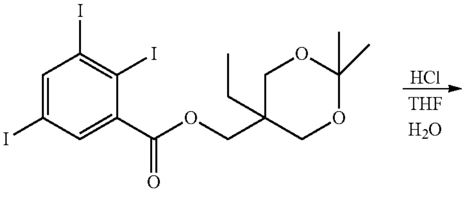

11

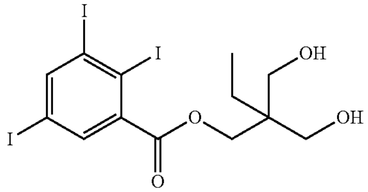

A-2

In nitrogen atmosphere, a flask was charged with 13.1 g of Intermediate 11, 30 g of 2.5 wt % hydrochloric acid, and 30 g of THF, which were aged at room temperature for 16 hours. At the end of aging, the solvent was distilled off. Then 80 g of methylene chloride and 30 g of water were added to the residue for extraction. This was followed by ordinary aqueous work-up and solvent distillation. 60 g of diisopropyl ether was added to the residue, which was stirred for 2 hours. The resulting solid precipitate was collected by filtration and dried in vacuum for 2 hours, obtaining Diol A-2 as white solids (amount 7.2 g, yield 58.6%).

(4) Synthesis of PAG-4

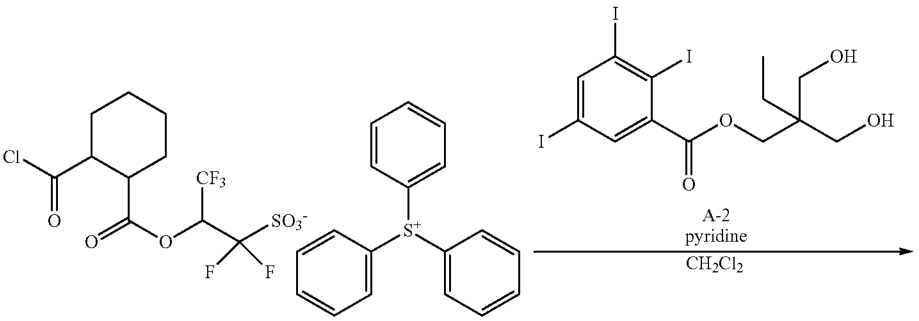

4

-continued

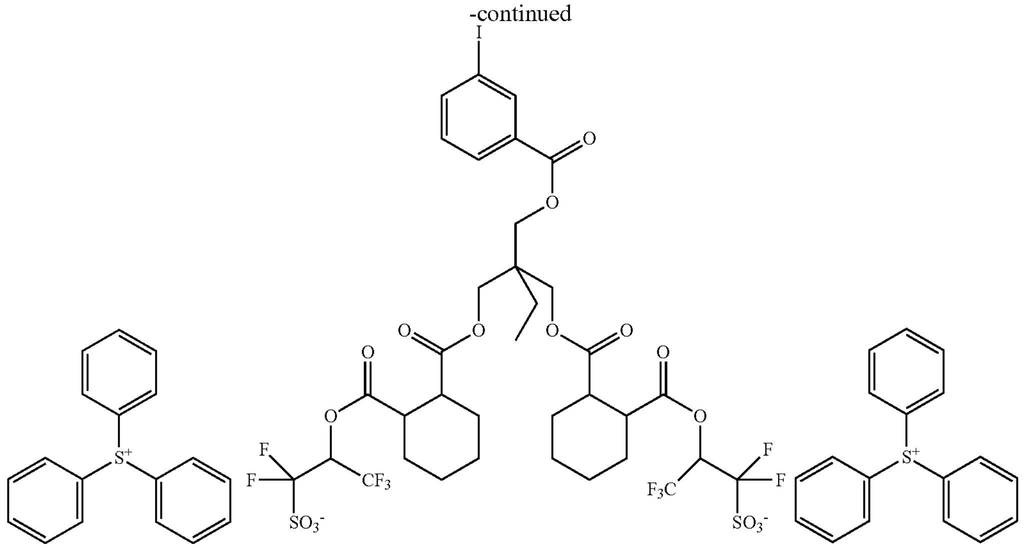

PAG-4

In nitrogen atmosphere, a flask was charged with 20.2 g of Acid Chloride 4, 7.2 g of Diol A-2, and 80 g of methylene chloride. Under ice cooling, 2.2 g of pyridine was added dropwise. At the end of addition, the reaction system was warmed up to room temperature and aged for 22 hours. After aging, the reaction system was ice cooled, after which 30 g of 5 wt % hydrochloric acid was added to quench the reaction. Thereafter, the organic layer was taken out by separatory operation, followed by ordinary aqueous work-up and solvent distillation.

The resulting oily matter was a mixture of the target compound and the acid anhydride originating from Acid Chloride 4. To the oily matter, 0.5 g of sodium bicarbonate, 0.1 g of dimethylaminopyridine, 35 g of THF, and 15 g of water were added to conduct hydrolysis at room temperature. The mixture was stirred for 1 hour, after which 100 g of methylene chloride and 15 g of water were added for extraction. This was followed by washing with 1 wt % hydrochloric acid, washing with saturated sodium bicarbonate aqueous solution, ordinary aqueous work-up, and solvent distillation. There was obtained PAG-4 as oily matter (amount 27.8 g, yield 100%).

Figure 7:
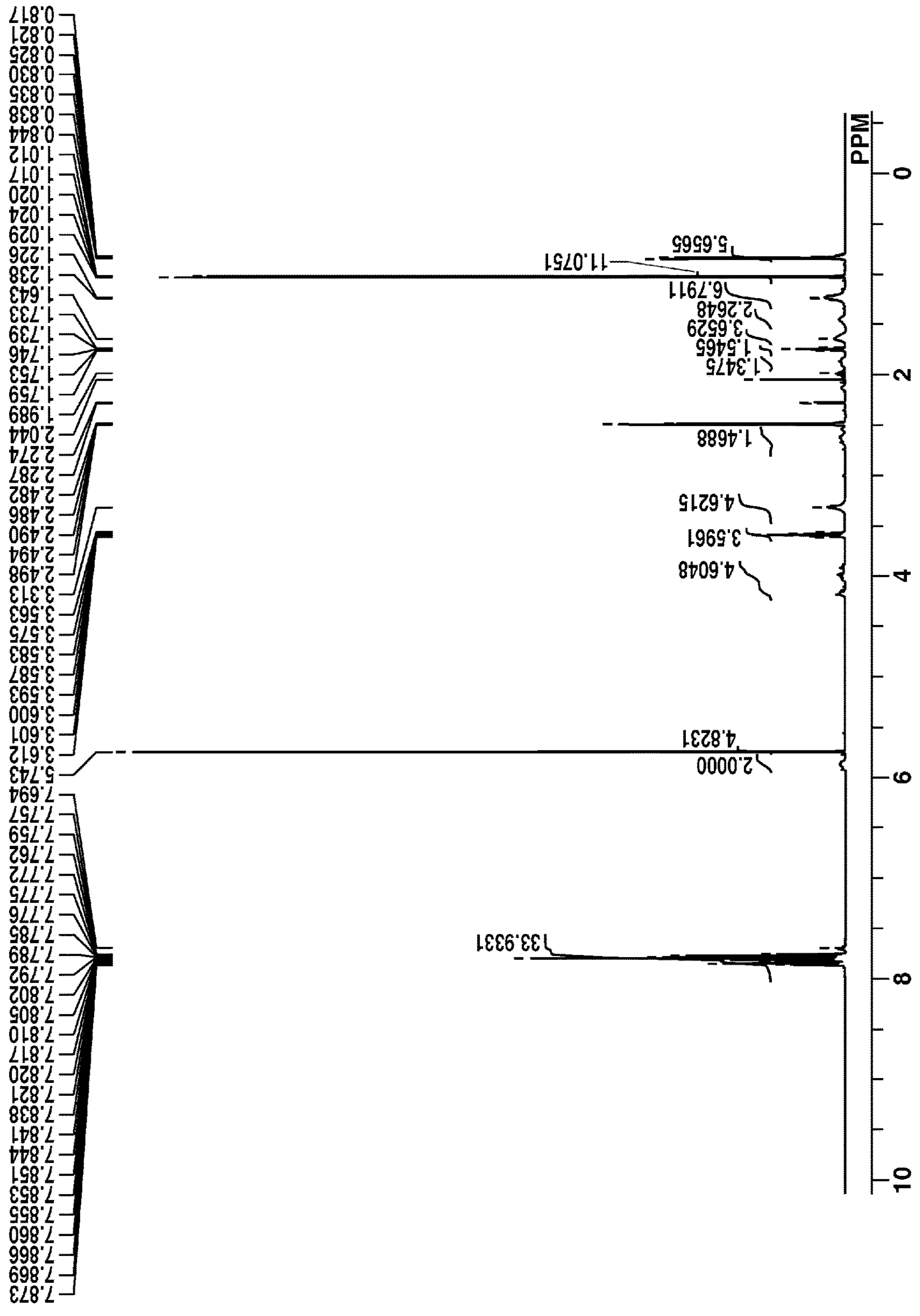
FIG. 7 is a $^1$H-NMR spectrum of PAG-4 synthesized in Example 1-4.
Figure 8:
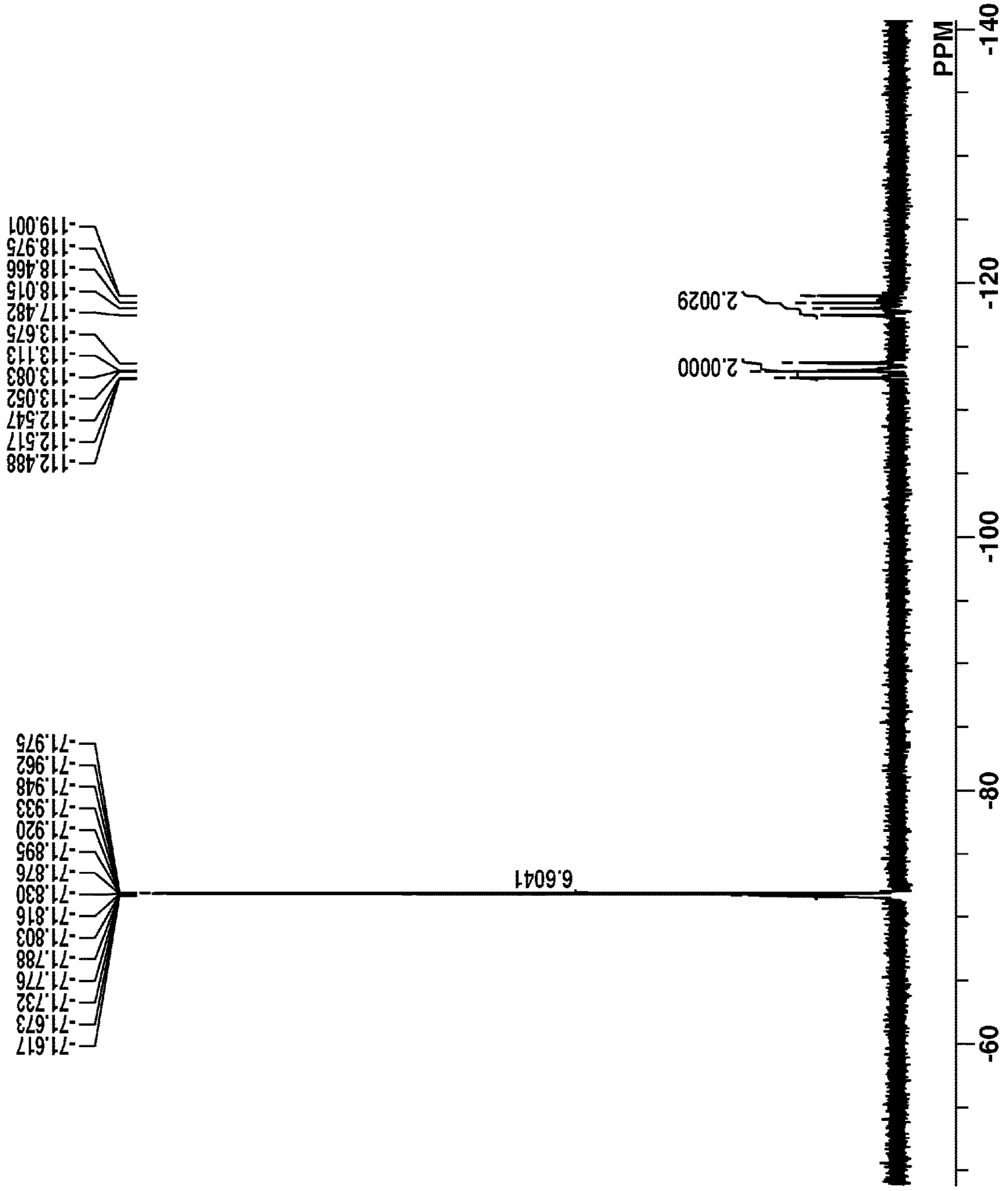
FIG. 8 is a $^{19}$F-NMR spectrum of PAG-4 synthesized in Example 1-4.

PAG-4 was analyzed by IR spectroscopy and TOF-MS, with the data shown below. FIGS. 7 and 8 are the $^{1}$H- and $^{19}$F-NMR/DMSO-$d_6$ spectrum of PAG-4, respectively.

IR (D-ATR): ν=3492, 3063, 2937, 2861, 1761, 1733, 1582, 1521, 1477, 1448, 1369, 1323, 1266, 1251, 1217, 1184, 1111, 1074, 1024, 996, 942, 912, 877, 837, 750, 685, 642, 578, 552, 503 $cm^{-1}$

MALDI TOF-MS

Positive $M^+$ 263.1 (corresponding to $C_{18}H_{15}S^+$)

Negative $M^-$ 1609.5, 383.2 (corresponding to $C_{53}H_{50}F_{10}I_3O_{16}S_3^-$)

Example 1-5

Synthesis of PAG-5

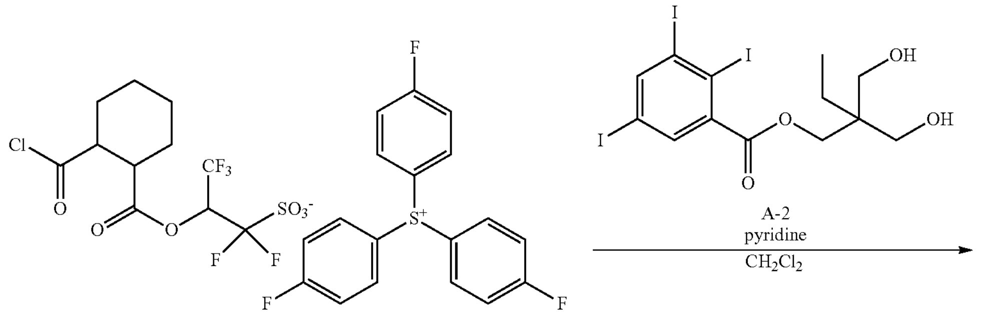

8

-continued

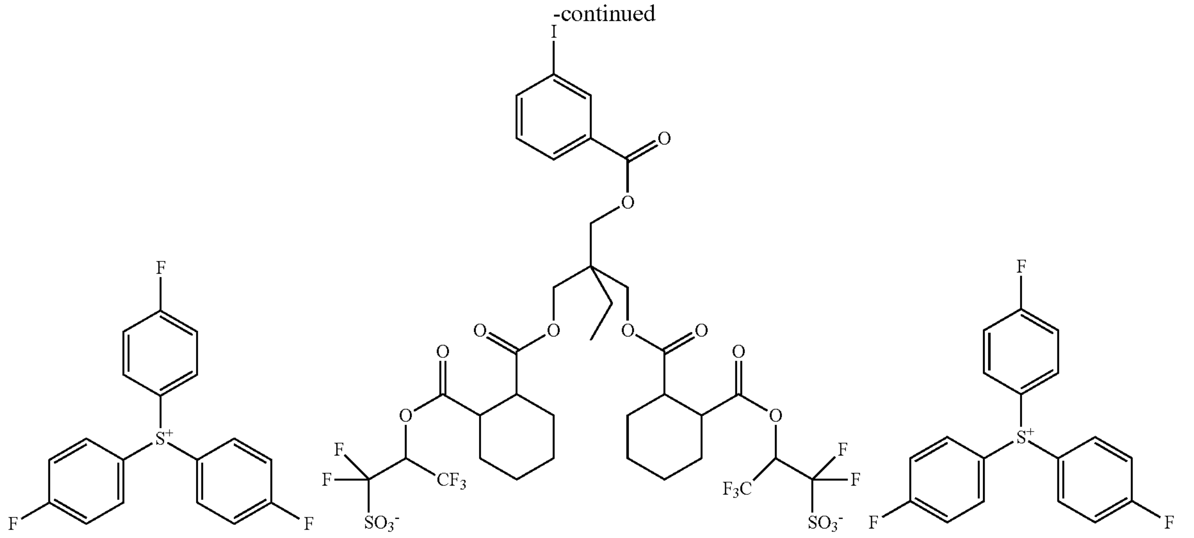

PAG-5

In nitrogen atmosphere, a flask was charged with 13.8 g of Acid Chloride 8, 4.6 g of Diol A-2, and 50 g of methylene chloride. Under ice cooling, 1.4 g of pyridine was added dropwise. At the end of addition, the reaction system was warmed up to room temperature and aged for 22 hours. After aging, the reaction system was ice cooled, after which 30 g of 5 wt % hydrochloric acid was added to quench the reaction. Thereafter, the organic layer was taken out by separatory operation, followed by ordinary aqueous work-up and solvent distillation.

The resulting oily matter was a mixture of the target compound and the acid anhydride originating from Acid Chloride 8. To the oily matter, 0.5 g of sodium bicarbonate, 0.1 g of dimethylaminopyridine, 35 g of THF, and 15 g of water were added to conduct hydrolysis at room temperature. The mixture was stirred for 1 hour, after which 100 g of methylene chloride and 15 g of water were added for extraction. This was followed by washing with 1 wt % hydrochloric acid, washing with saturated sodium bicarbonate aqueous solution, ordinary aqueous work-up, and solvent distillation. There was obtained PAG-5 as oily matter (amount 14.2 g, yield 96.8%).

Figure 9:
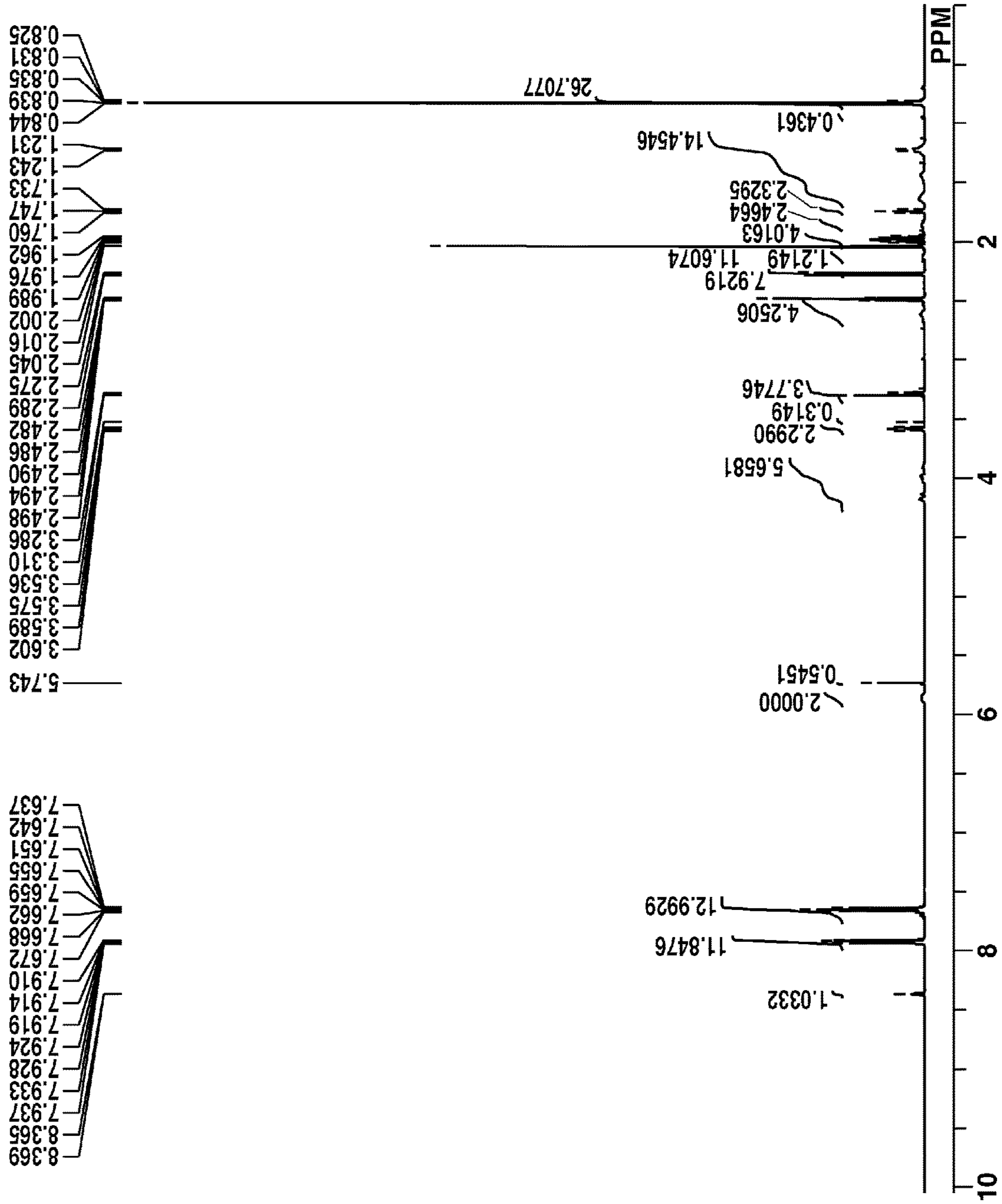
FIG. 9 is a $^1$H-NMR spectrum of PAG-5 synthesized in Example 1-5.
Figure 10:
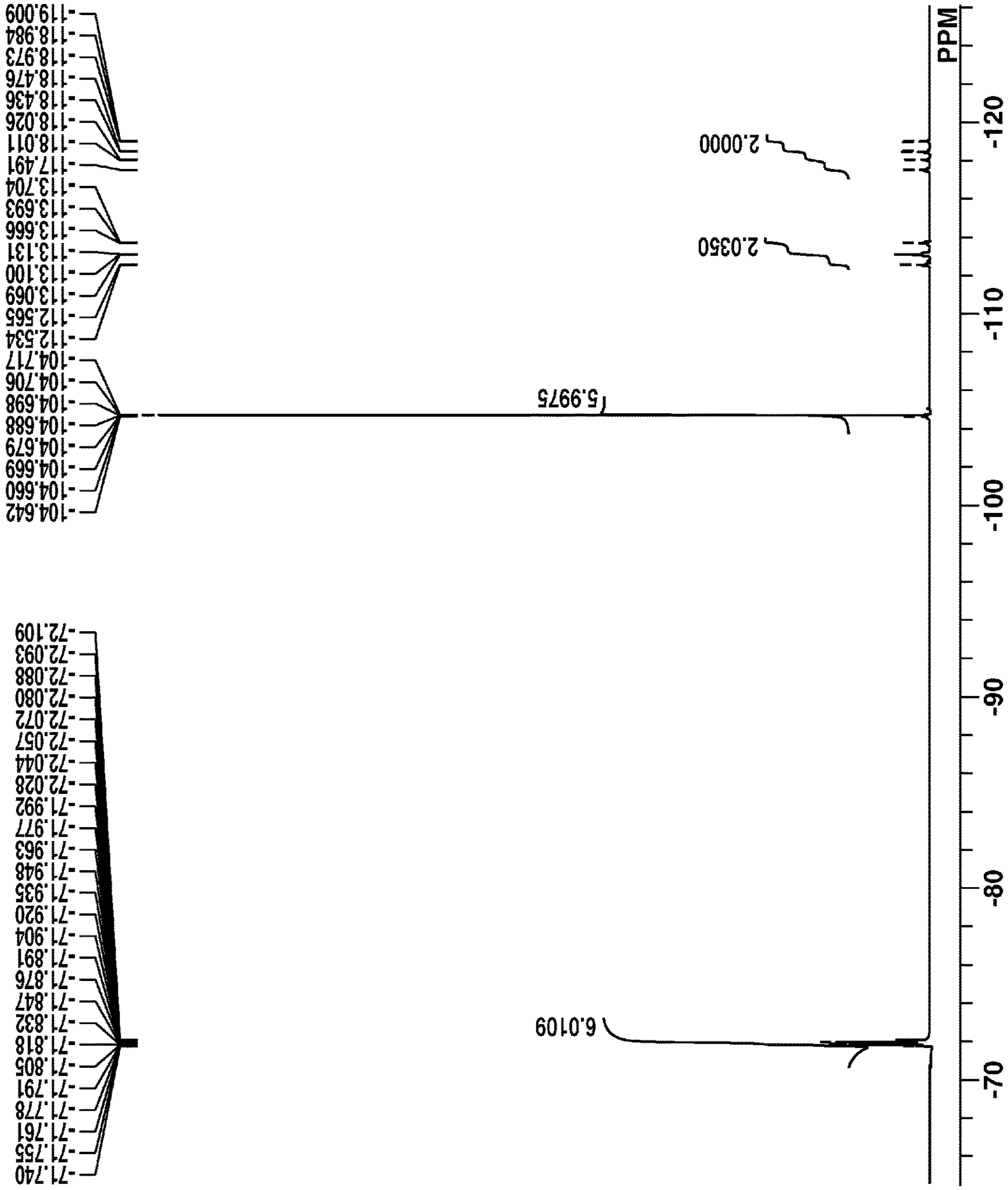
FIG. 10 is a $^{19}$F-NMR spectrum of PAG-5 synthesized in Example 1-5.

PAG-5 was analyzed by IR spectroscopy and TOF-MS, with the data shown below. FIGS. 9 and 10 are the $^{1}$H- and $^{19}$F-NMR/DMSO-$d_6$ spectrum of PAG-5, respectively.

IR (D-ATR): ν=3493, 3102, 3059, 2958, 2871, 1761, 1734, 1712, 1587, 1521, 1492, 1468, 1406, 1368, 1323, 1244, 1185, 1171, 1112, 1074, 1027, 1008, 992, 878, 840, 704, 642, 578, 553, 521, 438 $cm^{-1}$

MALDI TOF-MS

Positive $M^+$ 317.1 (corresponding to $C_{18}H_{12}F_3S^+$)

Negative $M^-$ 1663.4 (corresponding to $C_{53}H_{47}F_{13}I_3O_{16}S_3^-$)

Examples 1-6 to 1-11

Synthesis of PAG-6 to PAG-11

Bissulfonate salts as shown below were synthesized by a similar method with reference to the synthesis method in the above Examples, using corresponding reactants. It is noted that anion and cation reactants are commercially available compounds or synthesized by well-known methods.

PAG-6

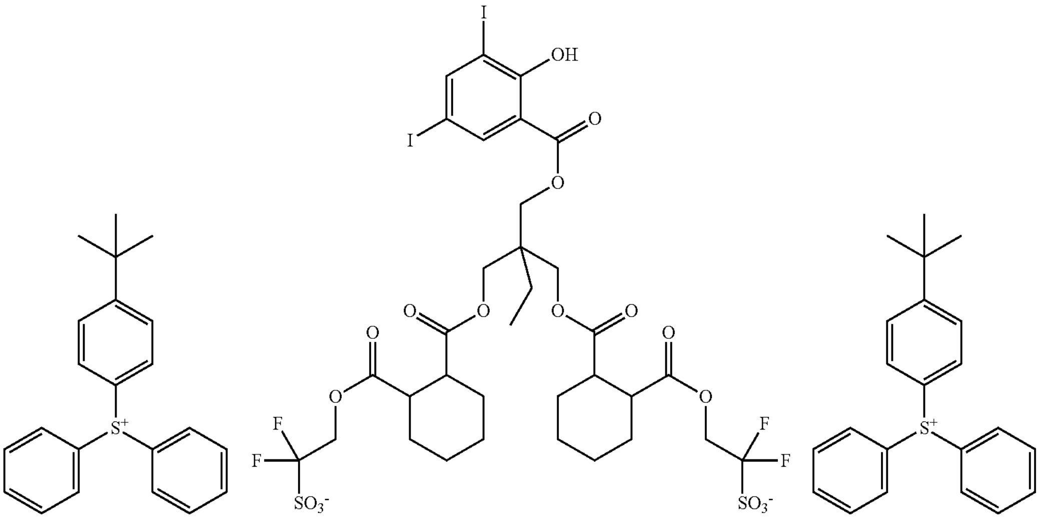

-continued
PAG-7
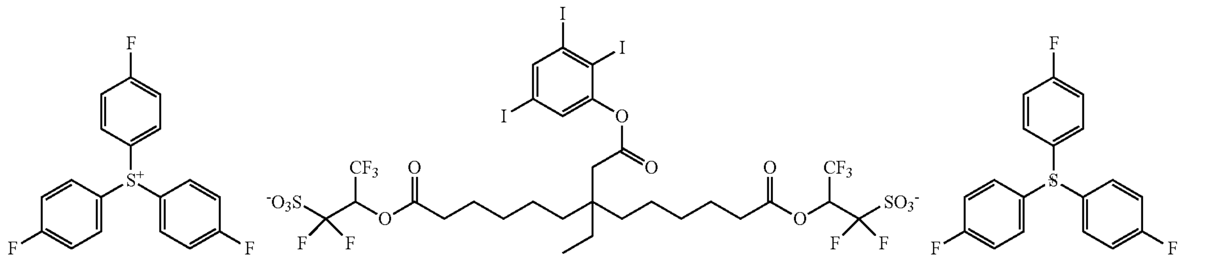
PAG-8
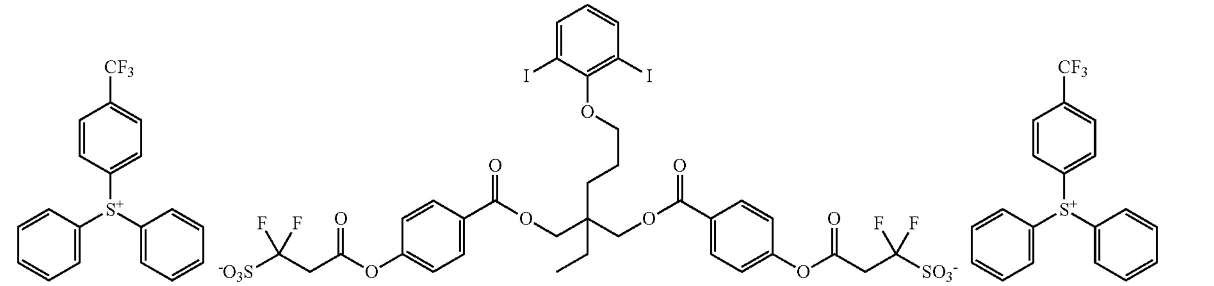
PAG-9
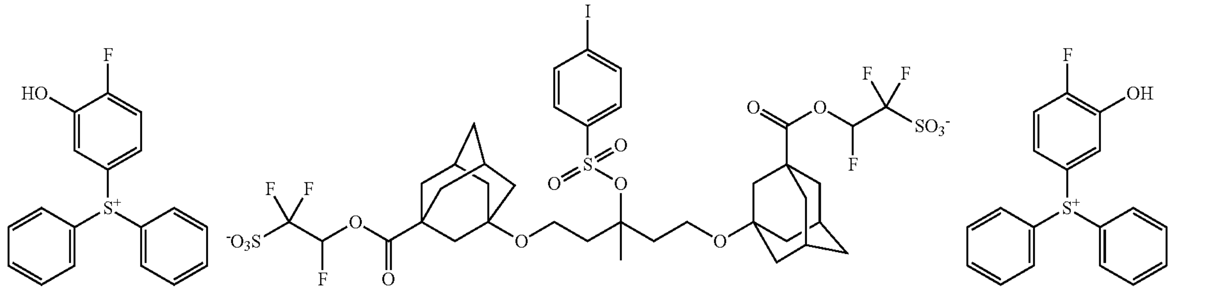
PAG-10
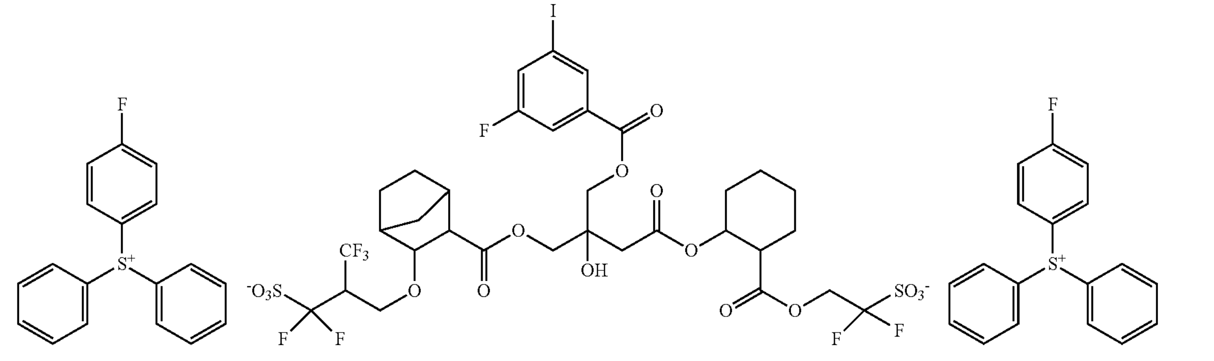
PAG-11
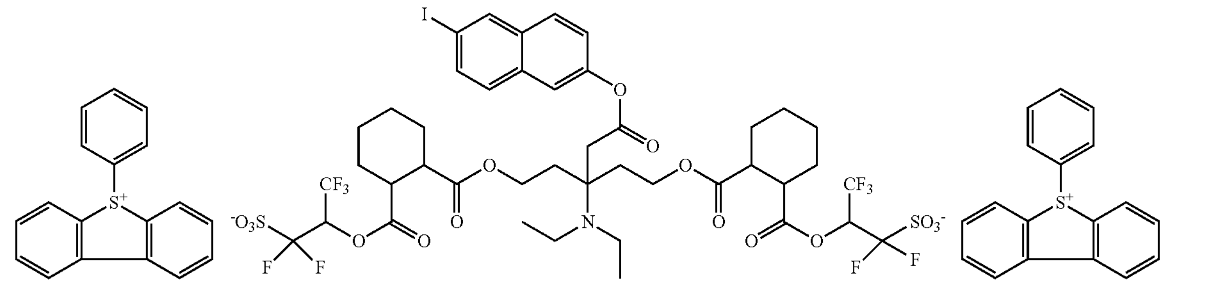

[2] Synthesis of Base Polymers

Synthesis Example 1

Synthesis of Polymer P-1

In nitrogen atmosphere, a flask was charged with 22 g of 1-tert-butylcyclopentyl methacrylate, 17 g of 2-oxotetrahydrofuran-3-yl methacrylate, 0.48 g of dimethyl 2,2'-azobis (2-methylpropionate) (V-601 by Fuji Film Wako Pure Chemical Industries, Ltd.), 0.41 g of 2-mercaptoethanol, and 50 g of methyl ethyl ketone (MEK) to form a monomer/initiator solution. In nitrogen atmosphere, another flask was charged with 23 g of MEK, which was heated at 80° C. with stirring. The monomer/initiator solution was added dropwise to the other flask over 4 hours. After the completion of dropwise addition, the polymerization solution was continuously stirred for 2 hours while maintaining its temperature at 80° C. The polymerization solution was cooled to room temperature and added dropwise to 640 g of methanol with vigorous stirring, whereupon a polymer precipitated. The precipitate was collected by filtration, washed twice with 240 g of methanol, and dried in vacuum at 50° C. for 20 hours, obtaining Polymer P-1 as white powder (amount 36 g, yield 90%). Polymer P-1 had a Mw of 8,200 and a Mw/Mn of 1.63.

P-1

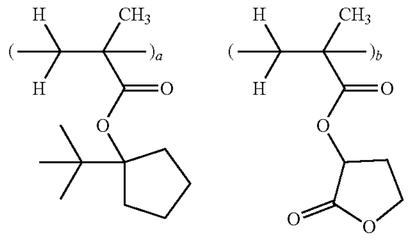

(a = 50, b = 50)
Mw = 8,200
Mw/Mn = 1.63

Synthesis Examples 2 to 4

Synthesis of Polymers P-2 to P-4

Polymers P-2 to P-4 were synthesized by the same procedure as Synthesis Example 1 except that the type and amount (mol %) of monomers were changed.

P-2

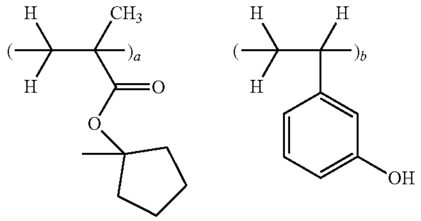

(a = 60, b = 40)
Mw = 9,300
Mw/Mn = 1.88

-continued

P-3

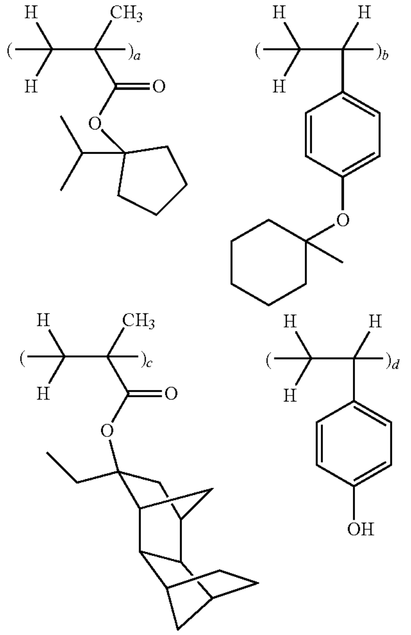

(a = 35, b = 15, c = 10, d = 40)
Mw = 9,900
Mw/Mn = 1.78

P-4

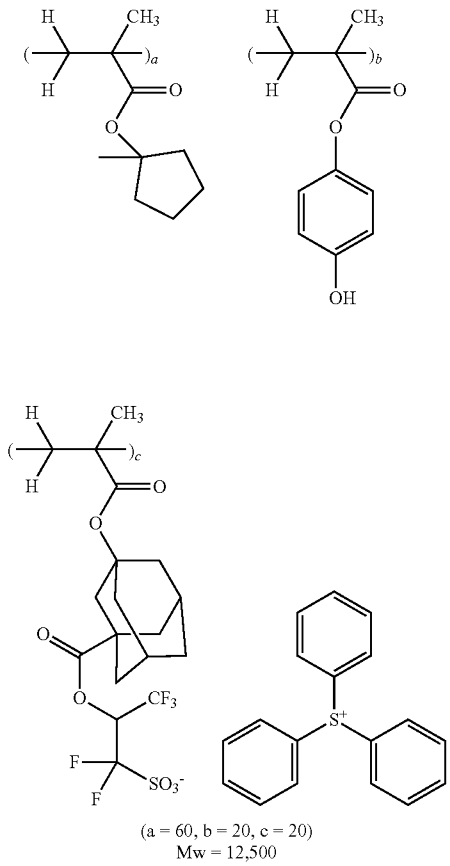

(a = 60, b = 20, c = 20)
Mw = 12,500
Mw/Mn = 1.79

[3] Preparation of Chemically Amplified Resist Composition

Examples 2-1 to 2-17 and Comparative Examples 1-1 to 1-12

A series of chemically amplified resist compositions were prepared by dissolving each of the photoacid generators synthesized in Examples 1-1 to 1-11, base polymer, photoacid generator (PAG-W, X, Y, and Z) other than the photoacid generators synthesized in Examples 1-1 to 1-11, quencher (Q-1, Q-2), and alkali-soluble surfactant (SF-1) in a solvent containing 0.01 wt % of surfactant A, and filtering through a Teflon® filter with a pore size of 0.2 μm. The formulation of the resist compositions is shown in Tables 1 and 2.

TABLE 1

| | | Resist composition | Base polymer (pbw) | Photoacid generator (pbw) | Quencher (pbw) | Surfactant (pbw) | Solvent 1 (pbw) | Solvent 2 (pbw) |
|---|---|---|---|---|---|---|---|---|
| Example | 2-1 | R-01 | P-1 (80) | PAG-1 (9.2) | Q-1 (1.7) | SF-1 (3.0) | PGMEA (1,728) | GBL (192) |
| | 2-2 | R-02 | P-1 (80) | PAG-4 (10.9) | Q-1 (1.7) | SF-1 (3.0) | PGMEA (1,728) | GBL (192) |
| | 2-3 | R-03 | P-1 (80) | PAG-1 (4.6) PAG-X (4.2) | Q-1 (1.7) | SF-1 (3.0) | PGMEA (1,728) | GBL (192) |
| | 2-4 | R-04 | P-1 (80) | PAG-6 (10.1) | Q-2 (3.7) | SF-1 (3.0) | PGMEA (1,728) | GBL (192) |
| | 2-5 | R-05 | P-2 (80) | PAG-2 (30.8) | Q-1 (1.2) | SF-1 (3.0) | PGMEA (1,728) | GBL (192) |
| | 2-6 | R-06 | P-2 (80) | PAG-3 (32.9) | Q-2 (9.1) | SF-1 (3.0) | PGMEA (1,728) | GBL (192) |
| | 2-7 | R-07 | P-2 (80) | PAG-5 (38.3) | Q-1 (4.2) | SF-1 (3.0) | PGMEA (1,728) | GBL (192) |
| | 2-8 | R-08 | P-3 (80) | PAG-2 (15.4) PAG-X (14.0) | Q-1 (4.2) | SF-1 (3.0) | PGMEA (1,728) | GBL (192) |
| | 2-9 | R-09 | P-4 (80) | PAG-2 (30.8) | Q-1 (4.2) | SF-1 (3.0) | PGMEA (1,728) | GBL (192) |
| | 2-10 | R-10 | P-4 (80) | PAG-3 (32.9) | Q-1 (4.2) | SF-1 (3.0) | PGMEA (1,728) | GBL (192) |
| | 2-11 | R-11 | P-4 (80) | PAG-5 (38.3) | Q-2 (9.1) | SF-1 (3.0) | PGMEA (1,728) | GBL (192) |
| | 2-12 | R-12 | P-2 (80) | PAG-6 (33.7) | Q-1 (1.2) | SF-1 (3.0) | PGMEA (1,728) | GBL (192) |
| | 2-13 | R-13 | P-2 (80) | PAG-7 (35.6) | Q-1 (1.2) | SF-1 (3.0) | PGMEA (1,728) | GBL (192) |
| | 2-14 | R-14 | P-2 (80) | PAG-8 (33.6) | Q-1 (1.2) | SF-1 (3.0) | PGMEA (1,728) | GBL (192) |
| | 2-15 | R-15 | P-2 (80) | PAG-9 (32.4) | Q-1 (1.2) | SF-1 (3.0) | PGMEA (1,728) | GBL (192) |
| | 2-16 | R-16 | P-2 (80) | PAG-10 (30.8) | Q-1 (1.2) | SF-1 (3.0) | PGMEA (1,728) | GBL (192) |
| | 2-17 | R-17 | P-2 (80) | PAG-11 (33.6) | Q-1 (1.2) | SF-1 (3.0) | PGMEA (1,728) | GBL (192) |

TABLE 2

| | | Resist composition | Base polymer (pbw) | Photoacid generator (pbw) | Quencher (pbw) | Surfactant (pbw) | Solvent 1 (pbw) | Solvent 2 (pbw) |
|---|---|---|---|---|---|---|---|---|
| Comparative Example | 1-1 | R-18 | P-1 (80) | PAG-X (8.4) | Q-1 (1.7) | SF-1 (3.0) | PGMEA (1,728) | GBL (192) |
| | 1-2 | R-19 | P-1 (80) | PAG-Y (6.4) | Q-1 (1.7) | SF-1 (3.0) | PGMEA (1,728) | GBL (192) |
| | 1-3 | R-20 | P-1 (80) | PAG-Z (5.7) | Q-2 (3.7) | SF-1 (3.0) | PGMEA (1,728) | GBL (192) |
| | 1-4 | R-21 | P-1 (80) | PAG-W (7.5) | Q-1 (1.7) | SF-1 (3.0) | PGMEA (1,728) | GBL (192) |
| | 1-5 | R-22 | P-2 (80) | PAG-X (28.0) | Q-1 (4.2) | SF-1 (3.0) | PGMEA (1,728) | GBL (192) |
| | 1-6 | R-23 | P-2 (80) | PAG-Y (21.2) | Q-1 (4.2) | SF-1 (3.0) | PGMEA (1,728) | GBL (192) |
| | 1-7 | R-24 | P-2 (80) | PAG-W (25.0) | Q-1 (4.2) | SF-1 (3.0) | PGMEA (1,728) | GBL (192) |
| | 1-8 | R-25 | P-3 (80) | PAG-Y (21.2) | Q-1 (4.2) | SF-1 (3.0) | PGMEA (1,728) | GBL (192) |

TABLE 2-continued

| | Resist composition | Base polymer (pbw) | Photoacid generator (pbw) | Quencher (pbw) | Surfactant (pbw) | Solvent 1 (pbw) | Solvent 2 (pbw) |
|---|---|---|---|---|---|---|---|
| 1-9 | R-26 | P-3 (80) | PAG-Z (18.9) | Q-1 (4.2) | SF-1 (3.0) | PGMEA (1,728) | GBL (192) |
| 1-10 | R-27 | P-4 (80) | PAG-X (28.0) | Q-1 (4.2) | SF-1 (3.0) | PGMEA (1,728) | GBL (192) |
| 1-11 | R-28 | P-4 (80) | PAG-Z (18.9) | Q-1 (4.2) | SF-1 (3.0) | PGMEA (1,728) | GBL (192) |
| 1-12 | R-29 | P-4 (80) | PAG-Z (18.9) | Q-2 (9.1) | SF-1 (3.0) | PGMEA (1,728) | GBL (192) |

The solvents, quenchers Q-1 and Q-2, alkali-soluble surfactant SF-1, other photoacid generators PAG-W, X, Y and Z, and surfactant A in Tables 1 and 2 are identified below.

Solvent:

PGMVEA (propylene glycol monomethyl ether acetate)

GBL (γ-butyrolactone)

Quencher: Q-1 and Q-2

Q-1

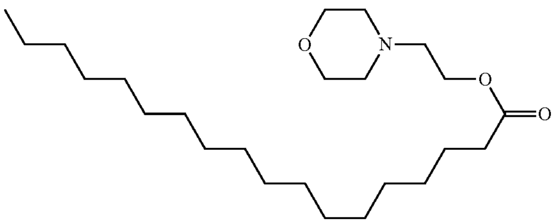

Q-2

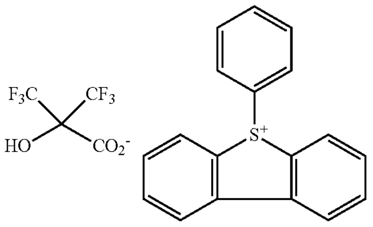

Other Photoacid Generator: PAG-W, X, Y and Z

PAG-W

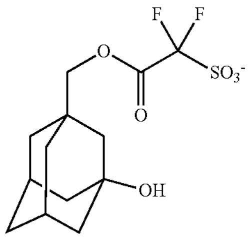

-continued

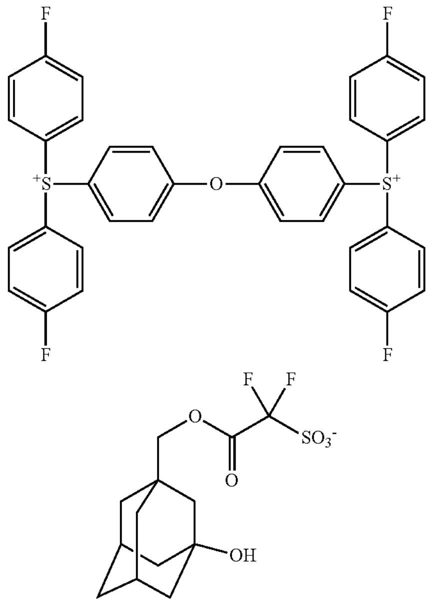

PAG-X

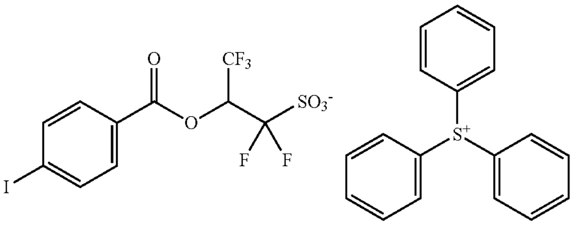

PAG-Y

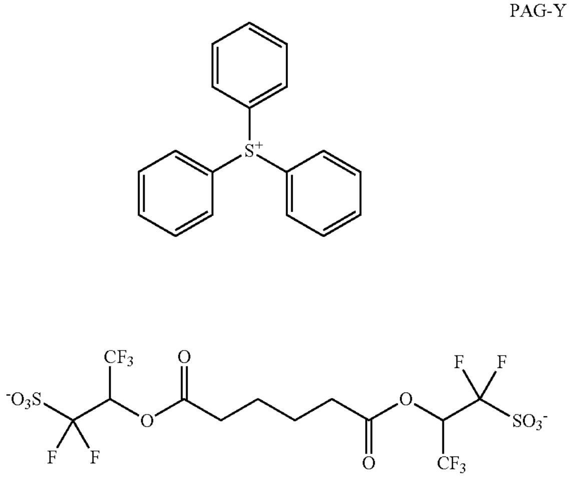

-continued

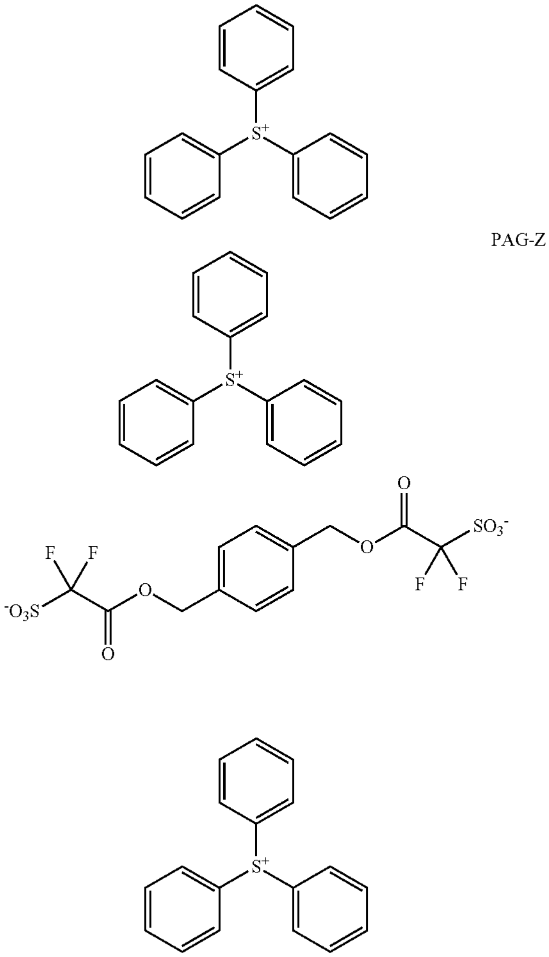

PAG-Z

Alkali-Soluble Surfactant SF-1:

poly(2,2,3,3,4,4,4-heptafluoro-1-isobutyl-1-butyl methacrylate/9-(2,2,2-trifluoro-1-trifluoroethyloxycarbonyl)-4-oxatricyclo[4.2.1.0$^{3,7}$]nonan-5-on-2-yl methacrylate)

SF-1

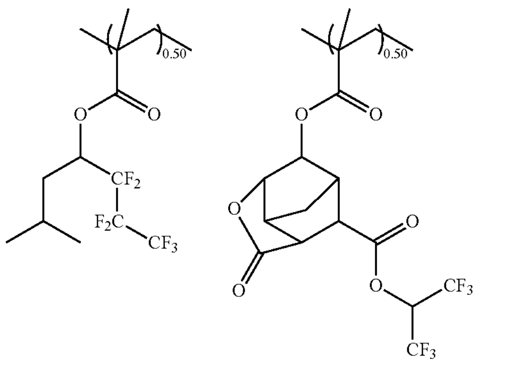

Mw = 7,700, Mw/Mn = 1.82

Surfactant A:

3-methyl-3-(2,2,2-trifluoroethoxymethyl)oxetane/tetrahydrofuran/2,2-dimethyl-1,3-propane diol copolymer (Omnova Solutions, Inc.)

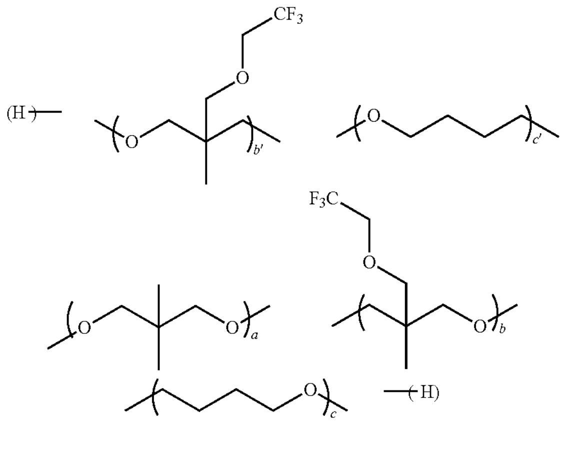

a:(b + b'):(c + c') = 1:4-7:0.01-1 (molar ratio)
Mw = 1,500

[4] Evaluation of Resist Composition: ArF Lithography Patterning Test 1

Examples 3-1 to 3-4 and Comparative Examples 2-1 to 2-4

On a silicon substrate, an antireflective coating solution (ARC-29A, Nissan Chemical Corp.) was coated and baked at 200° C. for 60 seconds to form an ARC of 100 nm thick. Each of the resist compositions (R-01 to R-04, R-18 to R-21) was spin coated on the ARC and prebaked on a hotplate at 90° C. for 60 seconds to form a resist film of 90 nm thick on the ARC. The wafer was exposed on an ArF excimer laser immersion lithography scanner (NSR-S610C by Nikon Corp., NA 1.30, quadrupole illumination) through a 6% halftone phase shift mask. The immersion liquid used herein was water. After exposure, the resist film was baked (PEB) at the temperature shown in Table 3 for 60 seconds and developed in a 2.38 wt % tetramethylammonium hydroxide (TMAH) aqueous solution for 60 seconds, forming a line-and-space (LS) pattern. The LS pattern was observed under CD-SEM (CG5000 by Hitachi High-Technologies Corp.), whereupon sensitivity, LWR, and MEF were evaluated by the following methods. The results are shown in Table 3.

Evaluation of Sensitivity

The optimum dose Eop is an exposure dose (mJ/cm2) which provides a 1:1 LS pattern having a line width of 40 nm and reported as an index of sensitivity. A smaller dose value indicates a higher sensitivity.

Evaluation of Line Width Roughness (LWR)

A LS pattern was formed by exposure in the optimum dose Eop. The line width was measured at longitudinally spaced apart 30 points, from which a 3-fold value (3σ) of standard deviation (σ) was determined and reported as LWR. A smaller value of LWR indicates a satisfactory line pattern with less fluctuation.

Evaluation of Mask Error Factor (MEF)

Exposure was made through a mask having a fixed pitch of 80 nm and a varying line width in a range from 38 nm to 42 nm by an increment of 1 nm, scaled as on-wafer size at the optimum dose. The size of the pattern transferred to the wafer was measured. With respect to the line width, the size of the transferred pattern is plotted relative to the mask design size, and a gradient is computed by linear approximation, and reported as MEF. A smaller MEF value, indicative of reduced influence of a finish error of the mask pattern, is better.

TABLE 3

| | | Resist composition | PEB temp. (° C.) | Eop ($mJ/cm^2$) | LWR (nm) | MEF |
|---|---|---|---|---|---|---|
| Example | 3-1 | R-01 | 90 | 44 | 3.1 | 2.4 |
| | 3-2 | R-02 | 90 | 48 | 3.2 | 2.2 |
| | 3-3 | R-03 | 90 | 43 | 3.0 | 2.4 |
| | 3-4 | R-04 | 90 | 43 | 3.0 | 2.4 |
| Comparative Example | 2-1 | R-18 | 90 | 40 | 3.9 | 3.6 |
| | 2-2 | R-19 | 90 | 42 | 4.1 | 3.2 |
| | 2-3 | R-20 | 90 | 41 | 3.9 | 3.4 |
| | 2-4 | R-21 | 90 | 41 | 4.3 | 3.4 |

As is evident from Table 3, the chemically amplified resist compositions within the scope of the invention exhibit improved values of LWR and MEF. The resist compositions are useful as the ArF immersion lithography material adapted for alkaline development.

[5] Evaluation of Resist Composition: ArF Lithography Test 2

Examples 4-1 to 4-4 and Comparative Examples 3-1 to 3-4

On a silicon wafer, a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, each of the resist compositions (R-01 to R-04, R-18 to R-21) was spin coated, then baked on a hot plate at 100° C. for 60 seconds to form a resist film of 90 nm thick. Using an ArF excimer laser immersion lithography scanner NSR-610C (Nikon Corp., NA 1.30, σ 0.98/0.74, cross-pole opening 35 deg.), pattern exposure was performed through a mask with a varying exposure dose and focus. The immersion liquid used herein was water. After exposure, the resist film was baked (PEB) at the temperature shown in Table 4 for 60 seconds and developed in butyl acetate for 30 seconds.

The mask used herein is a binary mask having an on-mask design corresponding to a 55 nm dot/90 nm pitch pattern (actual on-mask size is 4 times because of ¼ image reduction projection exposure). The hole pattern printed on the resist film through pattern reversal was observed under an electron microscope TD-SEM (S-9380 by Hitachi High-Technologies Corp.) whereupon sensitivity, CDU and MEF were evaluated by the following methods. The results are shown in Table 4.

Evaluation of Sensitivity

The optimum dose Eop is an exposure dose ($mJ/cm^2$) which provides a hole pattern of holes having an inner diameter of 50 nm and reported as an index of sensitivity. A smaller dose value indicates a higher sensitivity.

Evaluation of CDU

The size of 50 holes in the hole pattern printed at Eop was measured, from which a 3-fold value (36) of the standard deviation (6) was computed and reported as CDU. A smaller value of CDU is better.

Evaluation of MEF

Exposure was made through a mask having a fixed pitch and a varying dot size, scaled as on-wafer size at the optimum dose. The hole size of the pattern transferred to the wafer was measured. With respect to the hole size, the size of the transferred pattern is plotted relative to the mask design size, and a gradient is computed by linear approximation, and reported as MEF. A smaller MEF value, indicative of reduced influence of a finish error of the mask pattern, is better.

TABLE 4

| | | Resist composition | PEB temp. (° C.) | Eop ($mJ/cm^2$) | LWR (nm) | MEF |
|---|---|---|---|---|---|---|
| Example | 4-1 | R-01 | 90 | 42 | 4.5 | 3.8 |
| | 4-2 | R-02 | 90 | 46 | 4.7 | 4.0 |
| | 4-3 | R-03 | 90 | 41 | 4.6 | 4.1 |
| | 4-4 | R-04 | 90 | 42 | 4.3 | 3.9 |
| Comparative Example | 3-1 | R-18 | 90 | 39 | 7.0 | 5.2 |
| | 3-2 | R-19 | 90 | 40 | 7.2 | 5.1 |
| | 3-3 | R-20 | 90 | 39 | 7.1 | 4.9 |
| | 3-4 | R-21 | 90 | 39 | 7.4 | 5.0 |

As is evident from Table 4, the chemically amplified resist compositions within the scope of the invention exhibit improved values of CDU and MEF. The resist compositions are useful as the ArF immersion lithography material adapted for organic solvent development.

[6] Evaluation of Resist Compositions: EUV Lithography Test

Examples 5-1 to 5-13 and Comparative Examples 4-1 to 4-8

Each of the resist compositions (R-05 to R-17, R-22 to R-29) was spin coated on a silicon substrate having a 20-nm coating of silicon-containing spin-on hard mask SHB-A940 (silicon content 43 wt %, Shin-Etsu Chemical Co., Ltd.) and prebaked on a hotplate at 105° C. for 60 seconds to form a resist film of 50 nm thick. Using an EUV scanner NXE3400 (ASML, NA 0.33, σ 0.9/0.6, quadrupole illumination), the resist film was exposed to EUV through a mask bearing a hole pattern having a pitch 46 nm+20% bias (on-wafer size). The resist film was baked (PEB) on a hotplate at 85° C. for 60 seconds and developed in a 2.38 wt % TMAH aqueous solution for 30 seconds to form a hole pattern having a size of 23 nm.

The hole pattern as developed was observed under CD-SEM (CG-5000 by Hitachi High-Technologies Corp.) and evaluated for sensitivity and CDU by the following methods. The results are shown in Table 5.

Evaluation of Sensitivity

The optimum dose (Eop) is a dose ($mJ/cm^2$) which provides a hole pattern having a hole size of 23 nm and reported as sensitivity. A smaller value indicates a higher sensitivity.

Evaluation of CDU

For the hole pattern at the optimum dose (Eop), the size of 50 holes within the same dose shot was measured, from which a 3-fold value (36) of the standard deviation (6) was computed and reported as CDU. A smaller value of CDU indicates better dimensional uniformity of hole pattern.

TABLE 5

| | | Resist composition | PEB temperature (° C.) | Eop ($mJ/cm^2$) | CDU (nm) |
|---|---|---|---|---|---|
| Example | 5-1 | R-05 | 90 | 34 | 3.4 |
| | 5-2 | R-06 | 90 | 36 | 3.2 |
| | 5-3 | R-07 | 90 | 32 | 3.0 |
| | 5-4 | R-08 | 90 | 36 | 3.3 |
| | 5-5 | R-09 | 85 | 32 | 3.4 |
| | 5-6 | R-10 | 85 | 33 | 3.3 |
| | 5-7 | R-11 | 85 | 30 | 3.1 |
| | 5-8 | R-12 | 90 | 36 | 3.3 |
| | 5-9 | R-13 | 90 | 32 | 3.2 |
| | 5-10 | R-14 | 90 | 36 | 3.3 |
| | 5-11 | R-15 | 85 | 32 | 3.1 |
| | 5-12 | R-16 | 85 | 33 | 3.2 |
| | 5-13 | R-17 | 85 | 30 | 3.1 |
| Comparative Example | 4-1 | R-22 | 90 | 40 | 4.5 |
| | 4-2 | R-23 | 90 | 44 | 4.8 |
| | 4-3 | R-24 | 90 | 46 | 4.9 |
| | 4-4 | R-25 | 90 | 42 | 5.0 |
| | 4-5 | R-26 | 85 | 41 | 4.7 |
| | 4-6 | R-27 | 85 | 41 | 4.4 |
| | 4-7 | R-28 | 85 | 42 | 4.8 |
| | 4-8 | R-29 | 85 | 40 | 4.6 |

As is evident from Table 5, the chemically amplified resist compositions within the scope of the invention exhibit satisfactory values of sensitivity and CDU and are useful as the EUV lithography material.

Japanese Patent Application No. 2021-169695 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A photoacid generator in the form of an onium salt consisting of an anion containing an iodine-substituted aromatic group and two sulfonate groups and a sulfonium or iodonium cation.

2. The photoacid generator of claim 1 wherein the onium salt has the formula (1):

(1)

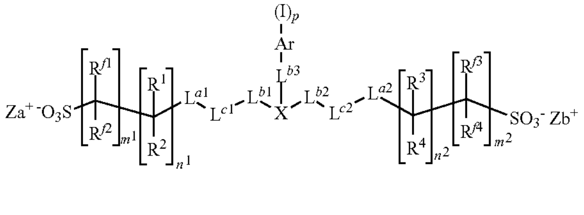

wherein X is a $C_1$-$C_{35}$ trivalent hydrocarbon group which may contain a heteroatom, $R^1$, $R^2$, $R^3$, and $R^4$ are each independently hydrogen or a $C_1$-$C_{10}$ hydrocarbyl group which may contain a heteroatom, $R^1$ and $R^2$ may bond together to form a ring with the carbon atom to which they are attached, $R^3$ and $R^4$ may bond together to form a ring with the carbon atom to which they are attached, $R^{f1}$, $R^{f2}$, $R^{f3}$, and $R^{f4}$ are each independently hydrogen, fluorine or trifluoromethyl, at least one of $R^{f1}$ and $R^{f2}$ is fluorine or trifluoromethyl, at least one of $R^{f3}$ and $R^{f4}$ is fluorine or trifluoromethyl, $m^1$ and $m^2$ are each independently an integer of 1 to 4, $n^1$ and $n^2$ are each independently an integer of 0 to 4, $L^{a1}$ and $L^{a2}$ are each independently an ether bond, ester bond, sulfonic ester bond or carbonate bond, $L^{c1}$ and $L^{c2}$ are each independently a single bond or a $C_1$-$C_{15}$ hydrocarbylene group in which some hydrogen may be substituted by a heteroatom-containing moiety and some constituent —$CH_2$— may be replaced by —O— or —C(=O)—, $L^{b1}$, $L^{b2}$ and $L^{b3}$ are each independently a single bond, ether bond, ester bond, sulfonic ester bond, carbonate bond or carbamate bond, Ar is a $C_3$-$C_{15}$ (p+1)-valent aromatic group in which some hydrogen may be substituted by fluorine, hydroxy or $C_1$-$C_{15}$ hydrocarbyl group, some hydrogen in the hydrocarbyl group may be substituted by a heteroatom-containing moiety and some constituent —$CH_2$— in the hydrocarbyl group may be replaced by —O—, —C(=O)— or —N($R^N$)—, $R^N$ is hydrogen or a $C_1$-$C_{10}$ hydrocarbyl group in which some hydrogen may be substituted by a heteroatom-containing moiety and some constituent —$CH_2$— may be replaced by —O—, —C(=O)— or —S(=O)$_2$—, p is an integer of 1 to 5, $Za^+$ and $Zb^+$ are each independently a sulfonium cation or iodonium cation.

3. The photoacid generator of claim 2 wherein the onium salt has the formula (1a):

(1a)

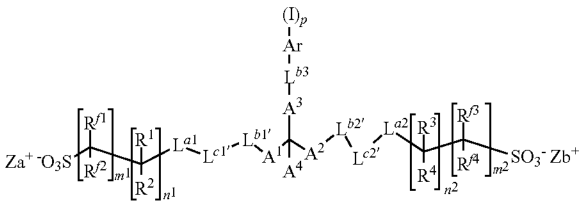

wherein $R^1$, $R^2$, $R^3$, $R^4$, $R^{f1}$, $R^{f2}$, $R^{f3}$, $R^{f4}$, $L^{a1}$, $L^{a2}$, $L^{b3}$, Ar, $m^1$, $m^2$, $n^1$, $n^2$, p, $Za^+$, and $Zb^+$ are as defined above, $A^1$, $A^2$, and $A^3$ are each independently a single bond or a $C_1$-$C_8$ hydrocarbylene group which may contain a heteroatom, in which some constituent —$CH_2$— may be replaced by —O— or —C(=O)—, $A^4$ is hydrogen, hydroxy, or a $C_1$-$C_{10}$ hydrocarbyl group which may contain a heteroatom, in which some constituent —$CH_2$— may be replaced by —O— or —C(=O)—, $L^{b1'}$ and $L^{b2'}$ are each independently an ether bond, ester bond, sulfonic ester bond, carbonate bond or carbamate bond, $L^{c1'}$ and $L^{c2'}$ are each independently a single bond or a $C_1$-$C_{10}$ hydrocarbylene group in which some hydrogen may be substituted by a heteroatom-containing moiety and some constituent —$CH_2$— may be replaced by —O— or —C(=O)—.

4. The photoacid generator of claim 3 wherein the onium salt has the formula (1b):

(1b)

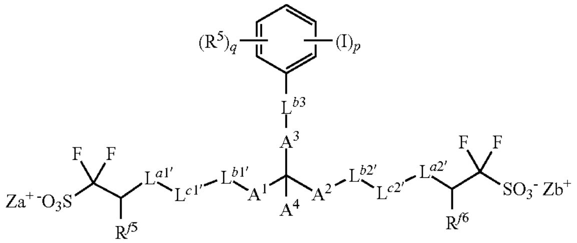

wherein $A^1$, $A^2$, $A^3$, $A^4$, $L^{b1'}$, $L^{b2'}$, $L^{b3}$, $Za^+$, and $Zb^+$ are as defined above, p is an integer of 1 to 5, q is an integer of 0 to 4, the sum of p and q is from 1 to 5, $R^{f5}$ and $R^{f6}$ are each independently hydrogen or trifluoromethyl, $L^{a1'}$ and $L^{a2'}$ are each independently an ether bond or ester bond, $R^5$ is hydroxy, fluorine, or a $C_1$-$C_{15}$ hydrocarbyl group in which some hydrogen may be substituted by a heteroatom-containing moiety and some constituent $-CH_2-$ may be replaced by $-O-$, $-C(=O)-$ or $-N(R^N)-$, $R^N$ is hydrogen or a $C_1$-$C_{10}$ hydrocarbyl group in which some hydrogen may be substituted by a heteroatom-containing moiety and some constituent $-CH_2-$ may be replaced by $-O-$, $-C(=O)-$ or $-S(=O)_2-$, when q is 2 or more, a plurality of $R^5$ may be the same or different and two $R^5$ may bond together to form a ring with the carbon atoms on the benzene ring to which they are attached.

5. The photoacid generator of claim 4 wherein the onium salt has the formula (1c):

(1c)

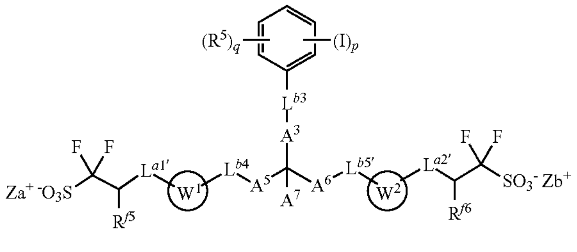

wherein $A^3$, $L^{a1'}$, $L^{a2'}$, $L^{b3}$, $R^5$, $R^{f5}$, $R^{f6}$, p, q, $Za^+$, and $Zb^+$ are as defined above, $L^{b4}$ and $L^{b5}$ are each independently an ether bond or ester bond, $A^5$ and $A^6$ are each independently a $C_1$-$C_4$ straight hydrocarbylene group, $A^7$ is hydrogen, hydroxy, or a $C_1$-$C_8$ alkyl group, the rings $W^1$ and $W^2$ are each independently a $C_3$-$C_{10}$ alicyclic hydrocarbon group which may contain a heteroatom.

6. The photoacid generator of claim 1 wherein $Za^+$ and $Zb^+$ are each independently a cation having the formula (Z-1) or (Z-2):

(Z-1)

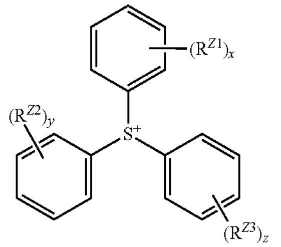

(Z-2)

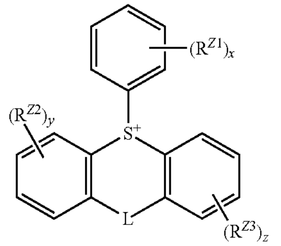

wherein $R^{Z1}$, $R^{Z2}$, and $R^{Z3}$ are each independently halogen, hydroxy or a $C_1$-$C_{15}$ hydrocarbyl group in which some hydrogen may be substituted by a heteroatom-containing moiety and some constituent $-CH_2-$ may be replaced by $-O-$, $-C(=O)-$, $-S-$, $-S(=O)-$, $-S(=O)_2-$, or $-N(R^N)-$, L is a single bond, $-CH_2-$, $-O-$, $-C(=O)-$, $-S-$, $-S(=O)-$, $-S(=O)_2-$, or $-N(R^N)-$, $R^N$ is hydrogen or a $C_1$-$C_{10}$ hydrocarbyl group in which some hydrogen may be substituted by a heteroatom-containing moiety and some constituent $-CH_2-$ may be replaced by $-O-$, $-C(=O)-$ or $-S(=O)_2-$, x, y and z are each independently an integer of 0 to 5, when x is 2 or more, a plurality of $R^{Z1}$ may be the same or different and two $R^{Z1}$ may bond together to form a ring with the carbon atoms on the benzene ring to which they are attached, when y is 2 or more, a plurality of $R^{Z2}$ may be the same or different and two $R^{Z2}$ may bond together to form a ring with the carbon atoms on the benzene ring to which they are attached, when z is 2 or more, a plurality of $R^{Z3}$ may be the same or different and two $R^{Z3}$ may bond together to form a ring with the carbon atoms on the benzene ring to which they are attached.

7. The photoacid generator of claim 2 wherein p is an integer of 1 to 3.

8. A chemically amplified resist composition comprising (A) the photoacid generator of claim 1, (B) a base polymer adapted to change its solubility in a developer under the action of acid, and (C) an organic solvent.

9. The resist composition of claim 8 wherein the base polymer comprises repeat units having the formula (a) or repeat units having the formula (b):

(a)

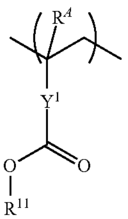

-continued (b)

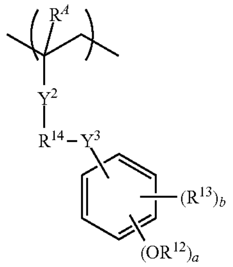

wherein $R^A$ is each independently hydrogen or methyl, $Y^1$ is a single bond, phenylene, naphthylene, or a $C_1$-$C_{12}$ linking group containing an ester bond and/or lactone ring, $Y^2$ is a single bond or ester bond, $Y^3$ is a single bond, ether bond or ester bond, $R^{11}$ and $R^{12}$ are each independently an acid labile group, $R^{13}$ is halogen, hydroxy, cyano, or a $C_1$-$C_6$ hydrocarbyl group in which some constituent —$CH_2$— may be replaced by —O— or —C(═O)—, $R^{14}$ is a single bond or a $C_1$-$C_6$ alkanediyl group in which some constituent —$CH_2$— may be replaced by an ether bond or ester bond, a is 1 or 2, b is an integer of 0 to 4, and the sum of a+b is from 1 to 5.

10. The resist composition of claim 9 wherein the base polymer further comprises repeat units of at least one type selected from repeat units having the formulae (g1) to (g3):

(g1)

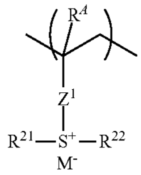

(g2)

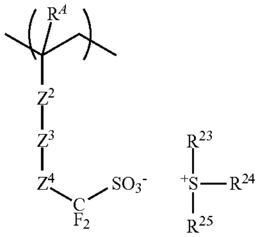

(g3)

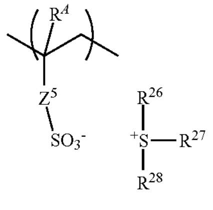

wherein $R^A$ is each independently hydrogen or methyl, $Z^1$ is a single bond, or a $C_1$-$C_6$ aliphatic hydrocarbylene group, phenylene group, naphthylene group, or a $C_7$-$C_{18}$ group obtained by combining the foregoing, or —O—$Z^{11}$—, —C(═O)—O—$Z^{11}$— or —C(═O)—NH—$Z^{11}$—, $Z^{11}$ is a $C_1$-$C_6$ aliphatic hydrocarbylene group, phenylene group, naphthylene group, or a $C_7$-$C_{18}$ group obtained by combining the foregoing, which may contain a carbonyl moiety, ester bond, ether bond or hydroxy moiety, $Z^2$ is a single bond or ester bond, $Z^3$ is a single bond, —$Z^{31}$—C(═O)—O—, —$Z^{31}$—O—, or —$Z^{31}$—O—C(═O)—, $Z^{31}$ is a $C_1$-$C_{12}$ aliphatic hydrocarbylene group, phenylene group or a $C_7$-$C_{18}$ group obtained by combining the foregoing, which may contain a carbonyl moiety, ester bond, ether bond, bromine or iodine, $Z^4$ is methylene, 2,2,2-trifluoro-1,1-ethanediyl or carbonyl, $Z^5$ is a single bond, methylene, ethylene, phenylene, fluorinated phenylene, trifluoromethyl-substituted phenylene group, —O—$Z^{51}$—, —C(═O)—O—$Z^{51}$— or —C(═O)—NH—$Z^{51}$—, $Z^{51}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond, halogen or hydroxy moiety, $R^{21}$ to $R^{28}$ are each independently halogen or a $C_1$-$C_{20}$ hydrocarbyl group which may contain a heteroatom, a pair of $R^{23}$ and $R^{24}$ or $R^{26}$ and $R^{27}$ may bond together to form a ring with the sulfur atom to which they are attached, and $M^-$ is a non-nucleophilic counter ion.

11. The resist composition of claim 8, further comprising a quencher.

12. The resist composition of claim 8, further comprising another photoacid generator other than the photoacid generator.

13. The resist composition of claim 8, further comprising a surfactant.

14. A pattern forming process comprising the steps of applying the chemically amplified resist composition of claim 8 onto a substrate to form a resist film thereon, exposing a selected region of the resist film to high-energy radiation, and developing the exposed resist film in a developer.

15. The process of claim 14 wherein the exposing step is carried out by the immersion lithography while a liquid having a refractive index of at least 1.0 is held between the resist film and a projection lens.

16. The process of claim 15, further comprising the step of forming a protective film on the resist film prior to the exposure step, wherein the immersion lithography is carried out while the liquid is held between the protective film and the projection lens.

17. The process of claim 14 wherein the high-energy radiation is KrF excimer laser radiation, ArF excimer laser radiation, EB, or EUV.

18. The process of claim 17 wherein the developing step uses an aqueous alkaline solution as the developer to form a positive tone pattern wherein the exposed region of resist film is dissolved away and the unexposed region of resist film is not dissolved.

19. The process of claim 17 wherein the developing step uses an organic solvent as the developer to form a negative tone pattern wherein the unexposed region of resist film is dissolved away and the exposed region of resist film is not dissolved.

20. The process of claim 19 wherein the developer is at least one organic solvent selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, butenyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

* * * * *